(12) United States Patent
Brown et al.

(10) Patent No.: US 7,294,691 B1
(45) Date of Patent: Nov. 13, 2007

(54) SOLUBLE SECRETED α2δ-2CALCIUM CHANNEL SUBUNIT POLYPEPTIDE

(75) Inventors: Jason Peter Brown, Cambridge (GB); Francois Bertelli, Canterbury (GB)

(73) Assignee: Warner Lambert Company, Ann Arbor, MI (US)

( * ) Notice: Subject to any disclaimer, the term of this patent is extended or adjusted under 35 U.S.C. 154(b) by 690 days.

(21) Appl. No.: 10/088,876

(22) PCT Filed: Sep. 18, 2000

(86) PCT No.: PCT/EP00/09137

§ 371 (c)(1),
(2), (4) Date: Jan. 16, 2003

(87) PCT Pub. No.: WO01/19870

PCT Pub. Date: Mar. 22, 2001

(51) Int. Cl.
*C07K 14/00* (2006.01)
*C12P 21/06* (2006.01)

(52) U.S. Cl. .................. 530/350; 435/69.1; 435/4; 536/23.5

(58) Field of Classification Search ............ None
See application file for complete search history.

(56) References Cited

U.S. PATENT DOCUMENTS

| | | | |
|---|---|---|---|
| 5,429,921 A | 7/1995 | Harpold et al. | ............. 435/4 |
| 5,846,757 A | 12/1998 | Harpold et al. | ............ 435/29 |
| 6,441,156 B1 * | 8/2002 | Lerman et al. | .......... 536/23.5 |

FOREIGN PATENT DOCUMENTS

| | | |
|---|---|---|
| WO | 9304083 | 3/1993 |
| WO | 9504822 | 2/1995 |
| WO | 0020450 | 4/2000 |

OTHER PUBLICATIONS

Mikayama et al., "Molecular cloning and functional expression of a cDNA encoding glycosylation-inhibiting factor", *Proc. Natl. Acad. Sci. USA*, vol. 90, pp. 10056-10060, 1993.
Voet et al., *Biochemistry*, 1990, John Wiley & Sons, Inc., pp. 126-128 and 228-234.
Kowalski et al., "Effects of anti-calcium channel $_\alpha$2-subunit antibodies on calsium flux and 1,4-dihydropridine binding", *Bochemical Society Transactions*, 1990, p. 890.
Gurnett et al., "Extracellular Interaction of the Voltage-dependent $Ca^{2+}0$ Channel $_{\alpha2\delta}$ and $_\alpha 1$ Subunits", *The Journal of Biological Chemistry*, vol. 272, No. 29, pp. 18508-18512, 1997.
Gurnett et al., "Dual Function of the Voltage-Dependent $Ca^{2+}$ Channel $_{\alpha 2\delta}$ Subunit Stimulation and Subunit Interaction", *Neuron*, vol. 16, pp. 431-440, 1996.
Felix et al., "Dissection of Functional Domains of the Voltage-Dependent $Ca^{2+}$ Channel $_{\alpha 2\delta}$ Subunit", *The Journal of Neuroscience*, vol. 17, No. 18, pp. 6884-6891, 1997.

Field et al., "Gabapentin (neurontin) and S-(+)-3-isobutylgaba represent a novel class of selective antihyperalgesic agents", *British Journal of Pharmacology*, vol. 121, pp. 1513-1522, 1977.
Klugbauer et al., "Molecular Diversity of the Calcium Channel $_{\alpha 2\delta}$ Subunit", *The Journal of Neuroscience*, vol. 19, No. 2, pp. 684-691, 1999.
Tokumaru et al., "Purification of the cardiac 1,4-dihydropyridine receptor using immunoaffinity chromatography with a monoclonal antibody against the $_{\alpha 2\delta}$ subunit of the skeletal muscle dihydropyridine receptor", *European Journal of Pharmacology—Molecular Pharmacology Section*, vol. 227, pp. 363-370, 1992.
Hill et al., "Localization of [$^3$H] gabapentin to a novel site in rat brain: autoradiographic studies", *European Journal of Pharmacology—Molecular Pharmacology Section*, vol. 244, pp. 303-309, 1993.
Dissnayake et al., "Spermine modulation of specific [$^3$H]-gabapentin binding to the detergent-solubilized porcine cerebral cortex $_{\alpha 2\delta}$ calcium channel subunit", *British Journal of Pharmacology*, vol. 120, pp. 833-840, 1997.
Brickley et al., "Use of site-directed antibodies to probe the topography of the $_{\alpha 2\delta}$ subunit of voltage-gated $Ca^{2+}$ channels", *FEBS Letters*, vol. 364, pp. 129-133, 1995.
Taylor et al., "Potent and stereospecific anticonvulsant activity of 3-isobutyl GABA relates to in vitro binding at a novel site labeled by tritiated gabapentin", *Epilepsy Research*, vol. 14, pp. 11-15, 1993.
Thurlow et al., "[$^3$ H]Gabapentin may label a system-L-like neutral amino acid carrier in brain", *European Journal of Pharmacology-Molecular Pharmacology Section*, vol. 247, pp. 341-345, 1993
Suman-Chauman et al., "Characterisation of [$^3$H]Gabapentin bindintg to a novel site in rat brain: homogenate binding studies", *European Journal of Pharmacology—Molecular Pharmacology Section*, vol. 244, pp. 293-301, 1993.
Ellis et al., "Sequence and Expression of mRNAs Encoding the $_\alpha 1$ and $_\alpha 2$ Subunits of a DHP-Sensitive Calcium Channel", *Science*, vol. 241, pp. 1661-1664, 1988.
DeJongh et al., "Subunits of Purified Calcium Channels", *The Journal of Biological Chemisty*, vol. 265, No. 25, pp. 14738-14741, 1990.
Jay et al., "Structural Characterization of the Dihydropyridine-sensitive Calcium Channel $_{\alpha 2}$-Subunit and the Associated $_\delta$Peptides", *The Journal of Biological Chemistry*, vol. 266, No. 5, pp. 3287-3293, 1991.

(Continued)

*Primary Examiner*—Gary Nickol
*Assistant Examiner*—Gyan Chandra
(74) *Attorney, Agent, or Firm*—Philip B. Polster, II

(57) ABSTRACT

The present invention relates to secreted soluble α2δ-2, α2δ-3 or α2δ-4 calcium channel subunit polypeptides and their preparation, corresponding nucleic acids, recombinant vectors and host cells, as well as screening assays using same.

9 Claims, 2 Drawing Sheets

OTHER PUBLICATIONS

Wiser et al., "The $_\alpha 2/\delta$ subunit of voltage sensitive $Ca^{2+}$ channels is a single transmembrane extracellular protein which is involved in regulatred secretion", *FEBS Letters*, vol. 379, pp. 15-20, 1996.

Brown et al., "Mechanisms of Action of Gabapentin", *Rev. Contemp, Pharmacother.*, vol. 7, pp. 203-214, 1996.

Brown et al., "Isolation of the [$^3$H]Gabapentin-Binding Protein/$_\alpha 2_\delta$ $Ca^{2+}$ Channel Subunit from Porcine Brain: Development of a Radioligand Binding Assay for $_\alpha 2_\delta$ Subunits Using [$^3$H]Leucine", *Analytical Biochemistry*, vol. 255, pp. 236-243, 1998.

Gee et al., "The Novel Anticonvulsant Drug, Gabapentin (Neurontin), Binds to the $_\alpha 2_\delta$ Subunit of a Calcium Channel", *The Journal of Biological Chemistry*, vol. 271, No. 10, pp. 5768-5776, 1996.

Brown and Gee, "Cloning and Deletion Mutagenesis of the $_\alpha 2_\delta$ Calcium Channel Subunit from Porcine Cerebral Cortex", *The Journal of Biological Chemistry*, vol. 273, No. 39, pp. 25458-25465, 1998.

\* cited by examiner

T — Total Binding
NSB — Non-Specific Binding

SOLUBLE SECRETED α2δ-2 CALCIUM CHANNEL SUBUNIT POLYPEPTIDE

FIELD OF THE INVENTION

The present invention relates to soluble α2δ-2, α2δ-3 or α2δ-4 calcium channel subunits and their preparation, corresponding nucleic acids, recombinant vectors and host cells comprising the same, as well as screening assays using same. The present invention relates to secreted soluble α2δ-2, α2δ-3 or α2δ-4 calcium channel subunit polypeptides and their preparation, corresponding nucleic acids, recombinant vectors and host cells, as well as screening assays using same

BACKGROUND OF THE INVENTION

Voltage-dependent $Ca^{2+}$ channels (VDCCs) are heteromultimeric complexes present in both neuronal and non-neuronal tissues, including heart and skeletal muscle. VDCCs are minimally composed of three subunits: a pore-forming transmembrane $\alpha_1$ subunit, a hydrophilic intracellular β subunit, and a membrane-associated $\alpha_2\delta$ subunit; a transmembrane γ subunit is also found in skeletal muscle tissue. Multiple subtypes and/or splice variants of the $\alpha_1$, β, and $\alpha_2\delta$ subunits have been found.

Gabapentin ((1-aminomethyl)cyclohexane acetic acid or Neurontin) is a structural analogue of GABA, which is mainly used as an adjunctive therapy for epilepsy. Recent research suggests that gabapentin may also have clinical utility for various indications including anxiety and pain. Although designed as a lipophilic GABA-mimetic, gabapentin does not have a high affinity for either $GABA_A$ or $GABA_B$ receptors, GABA uptake sites, or the GABA-degrading enzyme GABA-transaminase (EC 2.6.1.19).

A novel high affinity binding site for [$^3$H]gabapentin in rat, mouse, and porcin brains has been characterized. Recently, the [$^3$H]gabapentin-binding protein was isolated from pig brain and identified as the $\alpha_2\delta$-1 subunit of VDCCs. None of the prototypic anticonvulsant drugs displace [$^3$H]gabapentin binding from the $\alpha_2\delta$-1 subunit. [$^3$H] Gabapentin-binding is stereospecifically inhibited by two enantiomers of 3-isobutyl GABA. The rank order of potency of gabapentin, and S- and R-isobutyl GABA, at the [$^3$H] gabapentin binding site mirrors their anticonvulsant activity in mice. However, electrophysiological studies have yielded conflicting data on the action of gabapentin at VDCCs.

The $\alpha_2\delta$ subunit is derived from a single gene, the product of which is extensively post-translationally modified particularly through the cleavage of the signal sequence. The polypeptide is cleaved to form disulfide-bridged $\alpha_2$ and δ peptides, both of which are heavily glycosylated. Although it seems clear today that the $\alpha_2$ and δ peptides are membrane-associated peptides, it is unclear whether these peptides comprise one or several transmembrane domains. Furthermore, the location, size and structural configuration of these eventual transmembrane domains remains to be determined.

But in any event, the fact that $\alpha_2\delta$ is a membrane-associated protein, regardless of its precise structural configuration, renders its large scale expression in recombinant systems difficult. Indeed, as the $\alpha_2\delta$ protein is targeted to the membrane, it requires detergent solubilisation to release it for purification. This important drawback imposes considerable restrictions for any potential applications requiring large amounts of recombinant protein. Furthermore, the various subtypes of $\alpha_2\delta$ subunits are different proteins with very low homologies. It is therefore extremely difficult to predict their respective behaviors, for example in gene truncation experiments.

The only assay currently available for the screening of ligands that bind the $\alpha_2\delta$ subunit involves the use of pig membrane extracts as a source of the $\alpha_2\delta$ subunit. Such an assay presents major inconvenience. Firstly, because the assay material is a membrane extract, it is very difficult to accurately determine the protein composition from one assay preparation to another particularly with regard to the subtype. Also, the presence of various impurities in the assay preparation is a problem in small plate assays. Furthermore, as the protein preparation lacks homogeneity, the interaction between the targeted protein and the assay plate is often quite uneven. This renders the streamlining of the assay in a high throughput format almost impossible to achieve.

SUMMARY OF THE INVENTION

The invention relates to forms of calcium channel $\alpha_2\delta$ subunits that are soluble and retain the functional characteristics of the full-length or wild-type $\alpha_2\delta$ subunit from which they derive.

In particular, the invention relates to forms of calcium channel $\alpha_2\delta$-2, $\alpha_2\delta$-3 or $\alpha_2\delta$-4 subunits that are soluble and retain the functional characteristics of the full-length or wild-type $\alpha_2\delta$ subunit from which they derive.

In the context of the present invention, a calcium channel $\alpha_2\delta$ subunit, in particular a calcium channel $\alpha_2\delta$-2, $\alpha_2\delta$-3 or $\alpha_2\delta$-4 sub-unit, is preferably a mammalian calcium channel $\alpha_2\delta$ subunit, in particular human or porcine.

In the context of the present invention, a calcium channel is preferably of cerebral cortical origin and/or voltage-dependent.

In the context of the present invention, the inventors have found that it was possible to delete a portion of the nucleotide sequence encoding a eukaryotic, preferably a mammal cerebral cortical voltage-dependent calcium channel $\alpha_2\delta$ subunit to yield a soluble secreted protein which retains its affinity for [$^3$H]gabapentin.

Preferably, a "soluble form" means a form that is not membrane-associated. In particular, a "soluble form" means a form lacking membrane anchorage, a purified form, an isolated form, a free form and/or a secreted form.

Preferably, the "functional characteristics of the full-length or wild-type $\alpha_2\delta$ subunit" are the affinity for, the binding of or the interaction with ligands, especially [$^3$H] gabapentin, gabapentin and/or spermine.

The invention concerns:

1) A purified or isolated nucleic acid encoding a mammalian secreted soluble cerebral cortical voltage-dependent calcium channel $\alpha_2\delta$-2, $\alpha_2\delta$-3 or $\alpha_2\delta$-4 subunit polypeptide.

2) A purified or isolated nucleic acid according to 1), comprising a polynucleotide having at least 90% identity with the sequence encoding:
   from amino-acid 1 to between amino-acids 1027 and 1062 of SEQ ID No. 20 for $\alpha_2\delta$-2,
   from amino-acid 1 to between amino-acids 984 and 1019 of SEQ ID No. 22 for $\alpha_2\delta$-3.

3) A purified or isolated nucleic acid according to 1), having at least 90% identity with the sequence encoding:
   from amino-acid 1 to between amino-acids 1047 and 1062 of SEQ ID No. 20 for $\alpha_2\delta$-2,
   from amino-acid 1 to between amino-acids 1004 and 1019 of SEQ ID No. 22 for $\alpha_2\delta$-3.

4) A purified or isolated nucleotide sequence according to 1) wherein said sequence is the sequence of SEQ ID No. 1, SEQ ID No. 2, SEQ ID No. 3, SEQ ID No. 7, SEQ ID No. 8, SEQ ID No. 9, SEQ ID No. 13, SEQ ID No. 14, SEQ ID No. 15, SEQ ID No. 19 or SEQ ID No. 21.

5) A purified or isolated nucleic acid, having at least 90% identity with the nucleotide sequence of SEQ ID No. 19 or SEQ ID No. 21.

6) A purified or isolated polynucleotide comprising at least 10 consecutive nucleotides of the nucleotide sequence of SEQ ID N119 or SEQ ID No. 21.

7) A polynucleotide probe or primer hybridizing, under stringent conditions, with the nucleotide sequence of SEQ ID No. 19 or SEQ ID No. 21.

8) A method for the amplification of a nucleic acid encoding a mammalian secreted soluble cerebral cortical voltage-dependent calcium channel $\alpha_2\delta$-n subunit polypeptide wherein n is 2, 3 or 4, said method comprising the steps of:
  (a) contacting a test sample suspected of containing the target secreted soluble $\alpha_2\delta$-n subunit nucleic acid, or a sequence complementary thereto, with an amplification reaction reagent comprising a pair of amplification primers located on either side of the $\alpha_2\delta$-n subunit nucleic acid region to be amplified, and
  (b) optionally, detecting the amplification products.

9) A kit for the amplification of a nucleic acid encoding a secreted soluble $\alpha_2\delta$-n subunit polypeptide wherein n is 2, 3 or 4, or a complementary sequence thereto in a test sample, wherein said kit comprises:
  (a) a pair of oligonucleotide primers which can hybridize, under stringent conditions, to the secreted soluble $\alpha_2\delta$-n subunit nucleic acid region to be amplified;
  (b) optionally, the reagents necessary for performing the amplification reaction.

10) A recombinant vector comprising a nucleic acid according to any one of 1) to 6).

11) A recombinant host cell comprising a nucleic acid according to any one of 1) to 6) or a vector according to 10).

12) A method for producing a secreted soluble $\alpha_2\delta$-n subunit wherein n is 2, 3 or 4, and said method comprises the steps of:
  (a) inserting the nucleic acid encoding the desired $\alpha_2\delta$-n subunit polypeptide in an appropriate vector;
  (b) culturing, in an appropriate culture medium, a host cell previously transformed or transfected with the recombinant vector of step (a);
  (c) harvesting the culture medium thus obtained or lyse the host cell, for example by sonication or osmotic shock;
  (d) separating or purifying, from said culture medium, or from the pellet of the resultant host cell lysate, the thus produced $\alpha_2\delta$-n subunit polypeptide of interest.

13) A purified or isolated recombinant polypeptide comprising the amino acid sequence of a secreted soluble $\alpha_2\delta$-2, $\alpha_2\delta$-3 or $\alpha_2\delta$-4 subunit polypeptide.

14) A recombinant polypeptide according to 13), having at least 80% amino-acid identity with a polypeptide comprising:
  from amino acid 1 to between amino acids 1027 and 1062 of the amino acid sequence of SEQ ID No. 20, or
  from amino acid 1 to between amino acids 1019 and 1079 of the amino acid sequence of SEQ ID No. 22.

15) A recombinant polypeptide according to 14), wherein said recombinant polypeptide is selected from the group consisting of the amino acid sequences of SEQ ID No. 4, SEQ ID No. 5, SEQ ID No. 6, SEQ ID No. 10, SEQ ID No. 1, SEQ ID No. 12, SEQ ID No. 116, SEQ ID No. 17, SEQ ID No. 18, SEQ ID No. 23 and SEQ ID No. 24.

16) A method for the screening of ligands which bind a cerebral cortical voltage-dependent calcium channel $\alpha_2\delta$-n subunit wherein n is 2, 3 or 4, said method comprising the steps of:
  contacting a secreted soluble recombinant calcium channel $\alpha_2\delta$-n subunit polypeptide with:
    a ligand of interest; and
    a labelled compound which binds the $\alpha_2\delta$-n subunit; and
  measuring the level of binding of the labelled compound to the $\alpha_2\delta$-n subunit.

17) A method according to 16), wherein said method is a scintillation proximity assay.

18) A method according to 16), wherein said method is a flashplate assay.

19) A method according to 16), wherein said method is a filter binding assay.

20) A method according to 16), wherein said secreted soluble recombinant calcium channel $\alpha_2\delta$-n subunit polypeptide is selected from polypeptides having at least 80%, preferably 90%, more preferably 95%, and most preferably 98 or 99% amino-acid identity with the polypeptide comprising from amino acid 1 to between amino-acids 984 and 1063, preferably between amino-acids 994 and 1054, and most preferably between amino-acids 1019 and 1054 of SEQ ID No. 5 or SEQ ID No. 16.

21) A method according to 16), wherein said secreted soluble recombinant calcium channel $\alpha_2\delta$-n subunit polypeptide is selected from the group consisting of SEQ ID No. 4, 5, 6, 10, 11, 12, 16, 17 and 18, 22) A kit for the screening of ligands which bind a cerebral cortical voltage-dependent calcium channel $\alpha_2\delta$-n subunit wherein n is 2, 3 or 4, said kit comprising:
  a secreted soluble recombinant calcium channel $\alpha_2\delta$-n subunit; and
  a labelled compound which binds to the $\alpha_2\delta$-n subunit.

Hence, the invention concerns nucleotide sequence fragments of a cerebral cortical voltage dependent calcium channel $\alpha_2\delta$-2, $\alpha_2\delta$-3 or $\alpha_2\delta$-4 subunit cDNA encoding a soluble secreted $\alpha_2\delta$-2, $\alpha_2\delta$-3 or $\alpha_2\delta$-4 subunit polypeptide (hereinafter a $\alpha_2\delta$-2, $\alpha_2\delta$-3 or $\alpha_2\delta$-4 subunit). Preferably, these nucleotide sequences encode a soluble secreted $\alpha_2\delta$-2, $\alpha_2\delta$-3 or $\alpha_2\delta$-4 subunit polypeptide bearing a gabapentin or a [$^3$H]gabapentin binding site. More preferably, the soluble secreted $\alpha_2\delta$-2, $\alpha_2\delta$-3 or $\alpha_2\delta$-4 subunit nucleic acid is derived from a eukaryotic, preferably a mammal, more preferably a human $\alpha_2\delta$-2, $\alpha_2\delta$-3 or $\alpha_2\delta$-4 subunit.

bearing a gabapentin or a [$^3$H]gabapentin binding site

A further object of the present invention concerns recombinant vectors comprising a nucleic acid sequence encoding a soluble secreted $\alpha_2\delta$-2, $\alpha_2\delta$-3 or $\alpha_2\delta$-4 subunit polypeptide.

The invention also encompasses host cells and transgenic non-human mammals comprising said nucleic acid sequences or recombinant vectors.

The invention also concerns a soluble secreted $\alpha_2\delta$-2, $\alpha_2\delta$-3 or $\alpha_2\delta$-4 subunit polypeptide which is characterized in that it is a soluble secreted polypeptide having affinity for [$^3$H]gabapentin. Preferably, the soluble secreted polypeptide is derived from a mammal, more preferably a human $\alpha_2\delta$-2, $\alpha_2\delta$-3 or $\alpha_2\delta$-4 subunit.

The inventors have also found that it was possible to use a soluble secreted form of a voltage-dependant calcium channel $\alpha_2\delta$-2, $\alpha_2\delta$-3 or $\alpha_2\delta$-4 subunit polypeptide in an assay for the screening of ligands which bind the $\alpha_2\delta$-2, $\alpha_2\delta$-3 or $\alpha_2\delta$-4 subunit.

The invention therefore also concerns a method for the screening of ligands which bind a calcium channel $\alpha_2\delta$-2, $\alpha_2\delta$-3 or $\alpha_2\delta$-4 subunit.

The method comprises the steps of:
contacting a secreted soluble recombinant calcium channel $\alpha_2\delta$-2, $\alpha_2\delta$-3 or $\alpha_2\delta$-4 subunit polypeptide with:
a ligand of interest; and
a labelled compound which binds a $\alpha_2\delta$-2, $\alpha_2\delta$-3 or $\alpha_2\delta$-4 subunit; and
measuring the level of binding of the labelled compound to the secreted soluble $\alpha_2\delta$-2, $\alpha_2\delta$-3 or $\alpha_2\delta$-4 subunit.

The invention also concerns a kit for the screening of ligands which bind a calcium channel $\alpha_2\delta$-2, $\alpha_2\delta$-3 or $\alpha_2\delta$-4 subunit.

The kit comprises:
a secreted soluble recombinant calcium channel $\alpha_2\delta$-2, $\alpha_2\delta$-3 or $\alpha_2\delta$-4 subunit polypeptide; and
a labelled compound which binds a calcium channel $\alpha_2\delta$-2, $\alpha_2\delta$-3 or $\alpha_2\delta$-4 subunit.

The invention also concerns:

1) A calcium channel $\alpha_2\delta$ subunit that is soluble and retain the functional characteristics of the full-length or wild-type $\alpha_2\delta$ subunit from which it derives.

2) A calcium channel $\alpha_2\delta$ subunit according to 1) above wherein the full-length or wild-type $\alpha_2\delta$ subunit from which it derives is of mammalian origin.

3) A calcium channel $\alpha_2\delta$ subunit according to 2) above wherein the mammalian origin is a human, a porcine, a rat or a mouse origin.

4) A calcium channel $\alpha_2\delta$ subunit according to 3) above wherein the mammalian origin is a human origin.

5) A calcium channel $\alpha_2\delta$ subunit according to any one of 1) to 4) above, wherein the full-length or wild-type $\alpha_2\delta$ subunit from which it derives is naturally expressed in the cerebral cortical.

6) A calcium channel $\alpha_2\delta$ subunit according to any one of 1) to 5) above, wherein the full-length or wild-type $\alpha_2\delta$ subunit from which it derives is voltage-dependent.

7) A calcium channel $\alpha_2\delta$ subunit according to any one of 1) to 6) above, wherein the $\alpha_2\delta$ subunit is cleaved.

8) A calcium channel $\alpha_2\delta$ subunit according to any one of 1) to 7) above, wherein the $\alpha_2\delta$ subunit is cleaved into separate $\alpha_2$ and $\delta$ peptides.

9) A calcium channel $\alpha_2\delta$ subunit according to 8) above, wherein the $\alpha_2$ and $\delta$ peptides are disulfide-bridged.

10) A calcium channel $\alpha_2\delta$ subunit according to any one of 1) to 6) above, wherein the $\alpha_2\delta$ subunit is not cleaved.

11) A calcium channel $\alpha_2\delta$ subunit according to any one of 1) to 10) above characterized in that it is purified or isolated.

12) A calcium channel $\alpha_2\delta$ subunit according to any one of 1) to 11) above characterized in that it is processed as the full-length or wild-type $\alpha_2\delta$ subunit from which it derives is naturally processed.

13) A calcium channel $\alpha_2\delta$ subunit according to any one of 1) to 12) above characterized in that it is producible by the baculovirus/insect cells expression system.

14) A calcium channel $\alpha_2\delta$ subunit according to any one of 1) to 13) above characterized in that it is produced by the baculovirus/insect cells expression system.

15) A calcium channel $\alpha_2\delta$ subunit according to any one of 1) to 14) above characterized in that its $\delta$ peptide comprises at least the ligand-interacting part(s) of the complete $\delta$ peptide from which it originates 16) A calcium channel $\alpha_2\delta$ subunit according to any one of 1) to 15) above characterized in that its $\delta$ peptide has a C-terminal truncation with respect to the complete $\delta$ peptide from which it originates, said truncation being sufficient to render the truncated $\delta$ peptide soluble.

17) A calcium channel $\alpha_2\delta$ subunit according to any one of 1) to 16) above characterized in that its $\alpha_2$ peptide comprises at least the ligand-interacting part(s) of the complete $\alpha_2$ peptide from which it originates.

18) A calcium channel $\alpha_2\delta$ subunit according to any one of 15) or 17) above characterized in that ligand is gabapentin, L-Norleucine, L-Allo-Isoleucine, L-Methionine, L-Leucine, L-Isoleucine, L-Valine, Spermine or L-Phenylalanine.

19) A calcium channel $\alpha_2\delta$ subunit according to any one of 1) to 18) above characterized in that its $\alpha_2$ peptide comprises at least the ligand-interacting part(s) of the complete $\alpha_2$ peptide from which it originates, its $\delta$ peptide comprises at least the ligand-interacting part(s) of the complete $\delta$ peptide from which it originates and its $\delta$ peptide does not comprise a part of the transmembrane domain of the complete $\delta$ peptide from which it originates which renders said calcium channel insoluble.

20) A calcium channel $\alpha_2\delta$ subunit according to any one of 1) to 19) above wherein the full-length or wild-type $\alpha_2\delta$ subunit from which it derives or originates is $\alpha_2\delta$-2, $\alpha_2\delta$-3 or $\alpha_2\delta$-4.

21) A calcium channel $\alpha_2\delta$ subunit according to any one of 1) to 20) above wherein the full-length or wild-type $\alpha_2\delta$ subunit from which it derives or originates has the amino acid sequence of SEQ ID No. 20.

22) A calcium channel $\alpha_2\delta$ subunit according to 20) or 21) above characterized in that the amino acid sequence of its unprocessed form comprises or consists of SEQ ID No. 4, SEQ ID No. 5 or SEQ ID No. 6.

23) A calcium channel $\alpha_2\delta$ subunit according to any one of 20) to 22) above characterized in that the amino acid sequence of its unprocessed form comprises the region comprised between amino acid number 340 and amino acid number 1062 of SEQ ID No. 20.

24) A calcium channel $\alpha_2\delta$ subunit according to any one of 1) to 20) above wherein the full-length or wild-type $\alpha_2\delta$ subunit from which it derives or originates has the amino acid sequence of SEQ ID No. 21.

25) A calcium channel $\alpha_2\delta$ subunit according to 20) or 24) characterized in that the amino acid sequence of its unprocessed form comprises or consists of SEQ ID No. 10, SEQ ID No. 11 or SEQ ID No. 12.

26) A calcium channel $\alpha_2\delta$ subunit according to any one of 20), 24) or 25) above characterized in that the amino acid sequence of its unprocessed form comprises or consists of the region comprised between amino acid number 306 and amino acid number 1019 of SEQ ID No. 20.

27) A calcium channel $\alpha_2\delta$ subunit according to any one of 1) to 20) above wherein the full-length or wild-type $\alpha_2\delta$ subunit from which it derives or originates has the amino acid sequence of SEQ ID No. 55.

28) A calcium channel $\alpha_2\delta$ subunit according to 20) or 27) above characterized in that the amino acid sequence of its unprocessed form comprises or consists of SEQ ID No. 53, SEQ ID No. 54 or SEQ ID No. 55.

29) A calcium channel $\alpha_2\delta$ subunit according to any one of 20), 27) or 28) above characterized in that the amino acid sequence of its unprocessed form comprises or consists of the region comprised between amino acid number 302 and amino acid number 1050 of SEQ ID No. 55.

30) A calcium channel $\alpha_2\delta$ subunit according to any one of 1) to 20) above wherein the full-length or wild-type $\alpha_2\delta$ subunit from which it derives or originates has the amino acid sequence of SEQ ID No. 33 or SEQ ID No. 44.

31) A calcium channel $\alpha_2\delta$ subunit according to 20) or 30) above characterized in that the amino acid sequence of its unprocessed form comprises or consists of SEQ ID No. 34, SEQ ID No. 35, SEQ ID No. 36, SEQ ID No. 41, SEQ ID No. 42 or SEQ ID No. 43.

32) A calcium channel $\alpha_2\delta$ subunit according to any one of 20), 30) or 31) above characterized in that the amino acid sequence of its unprocessed form comprises or consists of the region comprised between amino acid number 302 and amino acid number 1018 of SEQ ID No. 33 or SEQ ID No. 44.

33) A calcium channel $\alpha_2\delta$ subunit according to any one of 20), 30) or 31) above characterized in that the amino acid sequence of its unprocessed form comprises or consists of the region comprised between amino acid number 302 and amino acid number 1018 of SEQ ID No. 33 or SEQ ID No. 44.

34) A calcium channel $\alpha_2\delta$ subunit according to any one of 20), 30), 31), 32) or 33) above characterized in that its $\alpha_2$ peptide comprises the region comprised between amino acid number 302 and amino acid number 946 or 997 of SEQ ID No. 33 or of SEQ ID No. 44 and its $\delta$ peptide comprises the region comprised between amino acid number 984 and amino acid number 1018 of SEQ ID No. 33 or of SEQ ID No. 44.

35) A calcium channel $\alpha_2\delta$ subunit characterized in that its $\alpha_2$ peptide and its $\delta$ peptide have 99%, 98%, 97%, 96%, or 95% homology or identity with the $\alpha_2$ peptide and the $\delta$ peptide respectively of a calcium channel $\alpha_2\delta$ subunit according to any one of 1) to 34) above.

36) A nucleic acid molecule characterized in that its nucleotide sequence comprises a nucleotide sequence which encodes a calcium channel $\alpha_2\delta$ subunit according to any one of 1) to 35) above.

37) A nucleic acid molecule characterized in that its nucleotide sequence comprises a nucleotide sequence which encodes the $\alpha_2$ peptide or the $\delta$ peptide of a calcium channel $\alpha_2\delta$ subunit according to any one of 1) to 35) above.

38) A nucleic acid molecule which hybridizes under stringent conditions with a nucleic acid molecule according to 36) or 37) above or 39) herebelow.

39) A nucleic acid molecule according to any one of 36) to 38) above which comprises SEQ ID No. 1, SEQ ID No. 2, SEQ ID No. 3, SEQ ID No. 7, SEQ ID No. 8, SEQ ID No. 9, SEQ ID No. 13, SEQ ID No. 14, SEQ ID No. 15, SEQ ID No. 30, SEQ ID No. 31, SEQ ID No. 32, SEQ ID No. 38, SEQ ID No. 39, SEQ ID No. 40, SEQ ID No. 50, SEQ ID No. 51, or SEQ ID No. 52.

40) A vector capable of expressing a nucleic acid molecule according to any one of 36) to 39) above.

41) An expression vector comprising a nucleic acid molecule according to any one of 36) to 39) above.

42) A vector according to 40) or 41) above which is a baculovirus vector.

43) A cell comprising a nucleic acid molecule according to any one of 36) to 39) above.

44) A cell comprising a vector according to 40), 41) or 42) above.

45) A cell according to 43) or 44) above which is a mammalian cell or an insect cell.

46) A composition comprising a calcium channel $\alpha_2\delta$ subunit according to any one of 7) to 9) above and a calcium channel $\alpha_2\delta$ subunit according to 10) above.

47) Screening assay using a calcium channel $\alpha_2\delta$ subunit according to any one of 1) to 35) above.

48) Screening assay according to 47) above which is an SPA assay, a Flashplate assay, a Nickel Flasplate assay, a Filter binding assay or a Wheat Germ Lectin flasplate assay.

49) Use of screening assay according to 47) or 48) above to detect or measure the binding or interaction of a ligand of a calcium channel $\alpha_2\delta$ subunit and a calcium channel $\alpha_2\delta$ subunit.

50) Use according to 49) above wherein the ligand is gabapentin, L-Norleucine, L-Allo-Isoleucine, L-Methionine, L-Leucine, L-Isoleucine, L-Valine, Spermine or L-Phenylalanine.

51) Kit to detect or measure the binding or interaction of a ligand of a calcium channel $\alpha_2\delta$ subunit and a calcium channel $\alpha_2\delta$ subunit comprising a calcium channel $\alpha_2\delta$ subunit according to any one of 1) to 35) above.

52) Kit according to 51) above wherein the ligand is gabapentin, L-Norleucine, L-Allo-Isoleucine, L-Methionine, L-Leucine, L-Isoleucine, L-Valine, Spermine or L-Phenylalanine.

53) Kit according to 51) or 52) above usable in an SPA assay, a Flashplate assay, a Nickel Flasplate assay, a Filter binding assay or a Wheat Germ Lectin flasplate assay.

DETAILED DESCRIPTION OF THE INVENTION

Figure 1:
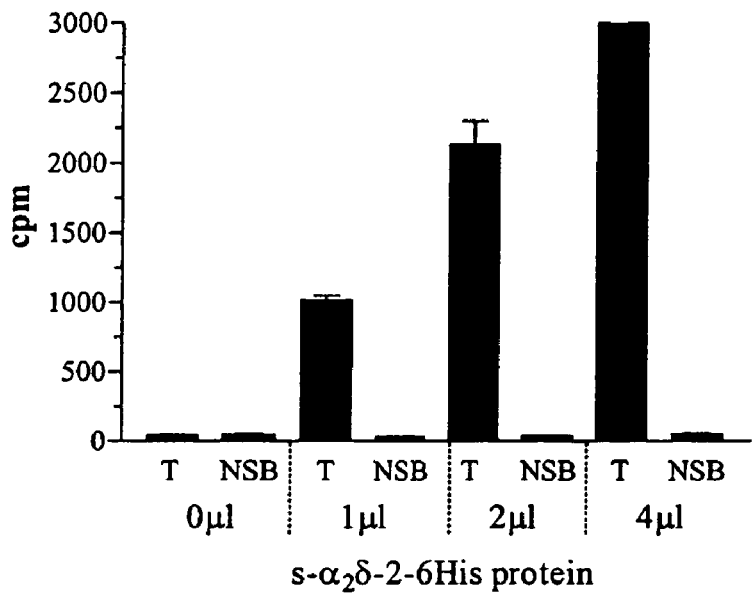
FIG. 1 illustrates the dose response nature of [$^3$H]gabapentin binding s-$\alpha_2\delta$-2-6His and the maintenance of a constant low-level of non-specific binding (around 30-60 cpm) independent of protein volume assayed.

The invention concerns truncated $\alpha_2\delta$-2, $\alpha_2\delta$-3 or $\alpha_2\delta$-4 subunit cDNA sequences. These truncated sequences encode soluble secreted polypeptides which retain their affinity for [$^3$H]gabapentin.

Throughout the present specification, the expression "nucleotide sequence" is used to designate indifferently a polynucleotide or a nucleic acid. More precisely, the expression "nucleotide sequence" encompasses the nucleic material and the sequence information and is not restricted to the sequence information (i.e. the succession of letters chosen among the four base letters) that biochemically characterizes a specific DNA or RNA molecule.

As used interchangeably herein, the terms "oligonucleotides", "nucleic acids" and "polynucleotides" include RNA, DNA, or RNA/DNA hybrid sequences of more than one nucleotide in either single chain or duplex form.

Further to its general meaning understood by the one skilled in the art, the term "nucleotide" is also used herein to encompass modified nucleotides which comprise at least one of the following modifications (a) an alternative linking group, (b) an analogous form of purine, (c) an analogous form of pyrimidine, or (d) an analogous sugar. For examples of analogous linking groups, purines, pyrimidines, and sugars, see for example PCT publication No. WO 95/04064.

The polynucleotide sequences of the invention may be prepared by any know method, including synthetic, recombinant, or a combination thereof as well as through any purification methods known in the art.

A) Secreted $\alpha_2\delta$-2, $\alpha_2\delta$-3 or $\alpha_2\delta$ Subunit Polypeptides The invention comprises polynucleotide sequences encoding a soluble secreted eukaryotic, preferably a soluble secreted mammal $\alpha_2\delta$-2, $\alpha_2\delta$-3 or $\alpha_2\delta$-4 subunit polypeptide. These sequences particularly include but are not restricted to 1) those sequences encoding a soluble secreted polypeptide of this $\alpha_2\delta$-2, $\alpha_2\delta$-3 or $\alpha_2\delta$-4 subunit which preferably retains its binding affinity for [$^3$H]gabapentin and 2) nucleotide fragments useful as nucleic acid primers or probes for amplification or detection purposes.

The expression "soluble secreted $\alpha_2\delta$-2, $\alpha_2\delta$-3 or $\alpha_2\delta$-4 subunit" is intended to designate polypeptide sequences which, when produced by a recombinant host cell, are secreted at least partially into the culture medium rather than remaining associated with the host cell membrane.

1) cDNA Fragments Encoding Soluble Secreted $\alpha_2\delta$-2, $\alpha_2\delta$-3, $\alpha_2\delta$ Subunit Polypeptides One of the important embodiments of the present invention concerns truncated nucleotide sequences of $\alpha_2\delta$-2, $\alpha_2\delta$-3 or $\alpha_2\delta$-4 subunit cDNAs which encode soluble secreted $\alpha_2\delta$-2, $\alpha_2\delta$-3 or $\alpha_2\delta$-4 subunit polypeptides. The inventors have found that it was possible to generate deletion mutants of $\alpha_2\delta$-2, $\alpha_2\delta$-3 or $\alpha_2\delta$-4 subunit cDNAs which, when expressed, produce a significant amount of soluble secreted proteins, preferably soluble secreted proteins, which retain their [$^3$H]gabapentin binding affinity. These truncated nucleotide sequences of the invention are of significant value to the skilled person as they now allow fast and reliable access to significant concentrations of selected soluble secreted $\alpha_2\delta$-2, $\alpha_2\delta$-3 or $\alpha_2\delta$-4 subunit polypeptides. To that end, the inventors have determined the minimal and optimal fragment lengths required to express a polypeptide which: 1) binds [$^3$H]gabapentin with sufficient affinity and; 2) is obtained in a soluble secreted form.

The discussion provided below provides comments on possible truncations, giving as an example the human $\alpha_2\delta$-2, $\alpha_2\delta$-3 or $\alpha_2\delta$-4 subunit. However, given the very substantial cross-species homology for $\alpha_2\delta$-2, $\alpha_2\delta$-3 or $\alpha_2\delta$-4 subunit sequences, the comments below can also be applied to other eukaryotic species, and more particularly other mammalian species such as rat, mouse, rabbit or pig. Their $\alpha_2\delta$-2, $\alpha_2\delta$-3 or $\alpha_2\delta$-4 subunit sequences, which for most are available in public databases, share a very substantial homology with the human $\alpha_2\delta$-2, $\alpha_2\delta$-3 or $\alpha_2\delta$-4 subunit sequences.

The inventors believe that the soluble secreted $\alpha_2\delta$-2 subunit polypeptides which are as close as possible to the native sequence and which are therefore more likely to retain their native folding and hence their [$^3$H]gabapentin binding properties are those corresponding to the native protein in which amino-acid stretch 1027 to the C-terminal end of the amino-acid sequence of SEQ ID No. 20 has been deleted. The skilled scientist can quite easily determine within this amino-acid stretch the optimal $\alpha_2\delta$-2 subunit polypeptides.

The inventors also believe that the soluble secreted $\alpha_2\delta$-3 subunit polypeptides which are as close as possible to the native sequence and which are therefore more likely to retain their native folding and hence thir [$^3$H]gabapentin binding properties are those corresponding to the native protein in which amino-acid stretch 984 to C-terminal end of the amino-acid sequence of SEQ ID No. 22 has been deleted. The skilled scientist can quite easily determine within this amino-acid stretch the optimal $\alpha_2\delta$-3 subunit polypeptides.

The invention therefore particularly concerns a nucleotide sequence encoding a polypeptide having at least 80% identity with the polypeptide comprising from amino-acid 1 to between amino-acids 1027 and 1145, preferably to between amino-acids 1062 and 1145 of SEQ ID No. 20.

Preferred nucleotide sequences include those of SEQ ID No. 1, SEQ ID No. 2 and SEQ ID No. 3.

The invention also concerns a nucleotide sequence encoding a polypeptide having at least 80% identity with the polypeptide comprising from amino-acid 1 to between amino-acids 984 and 1085, preferably to between amino-acids 1019 and 1085 of SEQ ID No. 22. Preferred nucleotide sequences include those of SEQ ID No. 7, SEQ ID No. 8 and SEQ ID No. 9.

The invention also encompasses isolated and/or purified nucleic acid molecules that hybridize under stringent conditions with the above nucleic acid sequences or a part thereof, and encode a soluble secreted $\alpha_2\delta$ subunit polypeptide having the ability to bind [$^3$H]gabapentin.

B) Amplification of the Soluble Secreted $\alpha_2\delta$-2, $\alpha_2\delta$-3 or $\alpha_2\delta$-4 Subunit Nucleotide Sequences Another object of the invention consists of a method for the amplification of a nucleic acid encoding a soluble secreted $\alpha_2\delta$-2, $\alpha_2\delta$-3 or $\alpha_2\delta$-4 subunit polypeptide, preferably a polypeptide bearing a [$^3$H]gabapentin binding site, said method comprising the steps of:

(a) contacting a test sample suspected of containing the target $\alpha_2\delta$-2, $\alpha_2\delta$-3 or $\alpha_2\delta$-4 subunit nucleic acid, a fragment or a variant thereof, or a sequence complementary thereto, with an amplification reaction reagent comprising a pair of amplification primers which can hybridize under stringent conditions, the $\alpha_2\delta$-2, $\alpha_2\delta$-3 or $\alpha_2\delta$-4 subunit nucleic acid region to be amplified, and (b) optionally, detecting the amplification products.

The expression [$^3$H]gabapentin binding site, when used herein is intended to designate a site which can bind either [$^3$H]gabapentin or other ligands such as (S+)-3-isobutyl gaba or (R—)-3-isobutyl gaba.

In a first preferred embodiment of the above method, the nucleic acid encodes a secreted soluble $\alpha_2\delta$-2, $\alpha_2\delta$-3 or $\alpha_2\delta$-4 subunit polypeptide of SEQ ID No. 4, SEQ ID No. 5, SEQ ID No. 6, SEQ ID No. 10, SEQ ID No. 11, SEQ ID No. 12, SEQ ID No. 16, SEQ ID No. 17 and SEQ ID No. 18.

In a second preferred embodiment of the above amplification method, the amplification product is detected by hybridization with a labelled probe having a sequence which is complementary to the amplified region.

C) Recombinant Vectors and Hosts Cells for the Expression of a Secreted Soluble $\alpha_2\delta$-2, $\alpha_2\delta$-3 or $\alpha_2\delta$ Subunit Polypeptide A most preferred system of expression of the calcium channel $\alpha_2\delta$ of the invention is the baculovirus/insect cell system. In fact, this system of expression allows to produce only the soluble form, is easy to use because the insect cells can be cultured without adherency and results in very high yield of production. Thus, this system allows mass-production of the calcium channel $\alpha_2\delta$ of the invention, provides an homogeneous production and is therefore particularly suitable for the preparation of this target for screening, in particular for high-throughput screening.

1) Recombinant vectors

The present invention also encompasses a family of recombinant vectors comprising any one of the nucleic acids described herein. Firstly, the invention deals with a recombinant vector comprising a nucleic acid selected from the group consisting of:

(a) a purified or isolated nucleic acid encoding a secreted soluble $\alpha_2\delta$-2, $\alpha_2\delta$-3 or $\alpha_2\delta$-4 subunit having at least 80% amino acid identity with the polypeptide of SEQ ID No. 20 or 22, or a sequence complementary thereto;

(b) a purified or isolated nucleic acid having at least 90% nucleotide identity with a polynucleotide selected from the group consisting of the nucleotide sequences of SEQ ID No. 1, SEQ ID No. 2, SEQ ID No. 3, SEQ ID No. 7, SEQ ID No. 8, SEQ ID No. 9, SEQ ID No. 13, SEQ ID No. 14, SEQ ID No. 15 or a sequence complementary thereto;

(c) a purified or isolated polynucleotide comprising at least 10 consecutive nucleotides of a nucleic acid described in (a) or (b) or a sequence complementary thereto.

In a first preferred embodiment a recombinant vector of the invention is used to amplify the inserted polynucleotide of the invention in a suitable host cell, this polynucleotide being amplified every time the recombinant vector replicates.

Recombinant expression vectors comprising a nucleic acid encoding secreted soluble $\alpha_2\delta$-2, $\alpha_2\delta$-3 or $\alpha_2\delta$-4 subunit polypeptides that are described in the present specification are also part of the invention. These include, but are not restricted to, nucleic acids encoding from amino-acid 1 to between amino-acids 1027 and 1145, preferably between amino-acids 1062 and 1145 of SEQ ID No. 20, as well as nucleic acids encoding from amino-acid 1 to between amino-acids 984 and 1085, preferably between amino-acids 1019 and 1085, of SEQ ID No. 22.

Another preferred embodiment of the recombinant vectors according to the invention consist of expression vectors comprising a nucleic acid encoding $\alpha_2\delta$-2, $\alpha_2\delta$-3 or $\alpha_2\delta$-4 subunit polypeptides of the invention, and more preferably a nucleic acid encoding a polypeptide selected from the group consisting of the amino acid sequences of SEQ ID No. 4, SEQ ID No. 5, SEQ ID No. 6, SEQ ID No. 10, SEQ ID No. 11, SEQ ID No. 12, SEQ ID No. 16, SEQ ID No. 17 and SEQ ID No. 18.

Within certain embodiments, expression vectors can be employed to express the secreted soluble $\alpha_2\delta$-2, $\alpha_2\delta$-3 or $\alpha_2\delta$-4 subunit polypeptides which can then be purified and for example, be used as a immunogen in order to raise specific antibodies directed against said secreted soluble $\alpha_2\delta$-2, $\alpha_2\delta$-3 or $\alpha_2\delta$-4 subunit polypeptides.

Preferred eukaryotic vectors of the invention are listed hereafter as illustrative but not limitative examples: pcDNA3, pFLAG, pCMV-Script, pIND, pMC1NEO, pHIL, pGAPZA, pMT/V5-His-TOPO, pMT/V5-His, pAc5.1/V5-HisA, pDS47/V5-His, pcDNA4, pcDNA6, pEF1, pEF4, pEF6, pUB6, pZeoSV2, pRc/CMv2, pcDM8, pCR3.1, pDisplay, pSecTag2, pVP22, pEMZ, pCMV/Zeo, pSinRep5, pCEP, pREP, pHook-1

Preferred bacteriophage recombinant vectors of the invention are P1 bacteriophage vectors such as described by Stemberg N. L. (1992; 1994).

A suitable vector for the expression of a soluble secreted $\alpha_2\delta$-2, $\alpha_2\delta$-3 or $\alpha_2\delta$-4 subunit polypeptide is a baculovirus vector that can be propagated in insect cells and in insect cell-lines. Specific suitable host vectors includes, but are not restricted to :pFastBac-1, pIZ/V5-His, pBacMan-1, pBlueBac4.5, pBlueBacHis2, pMelBacA, pVL1392, pVL1393

The recombinant expression vectors from the invention may also be derived from an adenovirus such as those described by Feldman and Steig. (1996) or Ohno et al. (1994). Another preferred recombinant adenovirus according to this specific embodiment of the present invention is the human adenovirus type two or five (Ad 2 or Ad 5) or an adenovirus of animal origin (French Patent Application No. FR93 05 954).

a) Regulatory expression sequences

Expression requires that appropriate signals are provided in the vectors, said signals including various regulatory elements such as enhancers/promoters from both viral and mammalian sources that drive expression of the genes of interest in host cells. The regulatory sequences of the expression vectors of the invention are operably linked to the nucleic acid encoding a soluble secreted $\alpha_2\delta$-2, $\alpha_2\delta$-3 or $\alpha_2\delta$-4 subunit polypeptide.

As used herein, the term "operably linked" refers to a linkage of polynucleotide elements in a functional relationship. For instance, a promoter or an enhancer is operably linked to a coding sequence if it affects the transcription of the coding sequence.

More precisely, two DNA molecules (such as a polynucleotide containing a promoter region and a polynucleotide encoding a desired polypeptide or polynucleotide) are said to be "operably linked" if the nature of the linkage between the two polynucleotides does not: (1) result in the introduction of a frame-shift mutation or (2) interfere with the ability of the polynucleotide containing the promoter to direct the transcription of the coding polynucleotide.

Generally, recombinant expression vectors include origins of replication, selectable markers permitting transformation of the host cell, and a promoter derived from a highly expressed gene to direct transcription of a downstream structural sequence. The heterologous structural sequence is assembled in an appropriate frame with the translation, initiation and termination sequences, and preferably a leader sequence capable of directing sequences of the translated protein into the periplasmic space or the extra-cellular medium.

In a specific embodiment wherein the vector is adapted for transfecting and expressing desired sequences in eukaryotic host cells, preferred vectors comprise an origin of replication from the desired host, a suitable promoter and an enhancer, and also any necessary ribosome binding sites, polyadenylation site, transcriptional termination sequences, and optionally 5'-flanking non-transcribed sequences. DNA sequences derived from the SV 40 viral genome, for example SV 40 origin early promoter, enhancer, and polyadenylation sites may be used to provide the required non-transcribed genetic elements.

b) Promoter sequences

Suitable promoter regions used in the expression vectors according to the invention are chosen taking into account the host cell in which the heterologous nucleic acids have to be expressed.

A suitable promoter may be heterologous with respect to the nucleic acid for which it controls the expression, or alternatively can be endogenous to the native polynucleotide containing the coding sequence to be expressed.

Additionally, the promoter is generally heterologous with respect to the recombinant vector sequences within which the construct promoter/coding sequence has been inserted.

Preferred eukaryotic promoters are the CMV, polyhidran or OPIE2.

2) Recombinant Host Cells

Host cells that have been transformed or transfected with one of the nucleic acids described herein, or with one of the recombinant vector, particularly recombinant expression vector, described herein are also part of the present invention.

Are included host cells that are transformed (prokaryotic cells) or are transfected (eukaryotic cells) with a recombinant vector such as one of those described above. Preferred host cells used as recipients for the expression vectors of the invention are the following:

(a) prokaryotic host cells: *Escherichia coli*, strains. (i.e. DH10 Bac strain) *Bacillus subtilis, Salmonella typhimurium* and strains from species such as *Pseudomonas, Streptomyces* and *Staphylococcus;*

(b) eukaryotic host cells: HeLa cells (ATCC No. CCL2; No. CCL2.1; No. CCL2.2), Cv 1 cells (ATCC No. CCL70), COS cells (ATCC No. CRL 1650; No. CRL 1651), Sf-9 cells (ATCC No. CRL 1711), C127 cells (ATCC No. CRL-1804), 3T3 cells (ATCC No. CRL-6361), CHO cells (ATCC No. CCL-61), human kidney 293 cells (ATCC No. 45504; No. CRL-1573), BHK (ECACC No. 84100 501; No. 84111301), sf 9, sf 21 and hi-5 cells.

D) Production of Recombinant Secreted Soluble $\alpha_2\delta$-2, $\alpha_2\delta$-3 or $\alpha_2\delta$-4 Subunit Polypeptides The present invention also concerns a method for producing one of the amino acid sequences described herein and especially a polypeptide selected from the group consisting of the aminoacid sequences of SEQ ID No. 4, SEQ ID No. 5, SEQ ID No. 6, SEQ ID No. 10, SEQ ID No. 11, SEQ ID No. 12, SEQ ID No. 16, SEQ ID No. 17 or SEQ ID n118 wherein said method comprises the steps of:

(a) inserting the nucleic acid encoding the desired amino acid sequence in an appropriate vector;

(b) culturing, in an appropriate culture medium, a host cell previously transformed or transfected with the recombinant vector of step (a);

(c) harvesting the culture medium thus obtained or lyse the host cell, for example by sonication or osmotic shock;

(d) separating or purifying, from said culture medium, or from the pellet of the resultant host cell lysate, the thus produced recombinant polypeptide of interest.

In some instances, it is required to tag the secreted soluble $\alpha_2\delta$-2, $\alpha_2\delta$-3 or $\alpha_2\delta$-4 subunit polypeptide prior to purification. The tag is then in most instances encoded into the nucleotide sequence that is needed to express the polypeptide. Examples of such tags include, but are not limited to sequences encoding C-myc, FLAG, a sequence of histidine residues, heamaglutin A, V5, Xpress or GST. Most of these tags can be incorporated directly into the sequence, for instance through PCR amplification by incorporating the appropriate coding sequence in one of the PCR amplification primers. However, the tag can also be introduced by other means such as covalent binding of the appropriate nucleic acid sequence encoding the tag moiety with the 3' or 5' end of the nucleic acid sequence encoding the polypeptide sequence. This is the case for GST.

Purification of the recombinant secreted soluble $\alpha_2\delta$-2, $\alpha_2\delta$-3, $\alpha_2\delta$-4 subunit polypeptides according to the present invention is then carried out by passage onto a nickel or copper affinity chromatography column, such as a Ni NTA column or a Q-Sepharose column.

In another embodiment of the above method, the polypeptide thus produced is further characterized, for example by binding onto an immuno-affinity chromatography column on which polyclonal or monoclonal antibodies directed to the secreted soluble $\alpha_2\delta$-2 subunit polypeptide of interest have been previously immobilised.

In another embodiment of the invention, the secreted soluble $\alpha_2\delta$-2, $\alpha_2\delta$-3, $\alpha_2\delta$-4 subunit polypeptide can be only partially purified. For instance, it can be purified along with other contaminating proteins using an appropriate chromatography matrix such as an ion-exchange chromatography column. In such instances, it is not required to tag the desired polypeptide of interest.

The most preferred embodiment contemplated by the inventors concerns the use of a purified tagged secreted soluble $\alpha_2\delta$-2, $\alpha_2\delta$-3 or $\alpha_2\delta$-4 subunit polypeptide. A particularly preferred tag is a nucleotide sequence encoding from 2 to 10, and preferably 6 histidine residues. Examples of such tagged polypeptides are depicted on SEQ ID No. 23 and 24.

With regard to the secreted soluble $\alpha_2\delta$-2, $\alpha_2\delta$-3 or $\alpha_2\delta$-4 subunit polypeptide used subsequently in the screening assay of the invention, several possibilities are also open to the skilled person.

In a first and preferred embodiment, the secreted soluble $\alpha_2\delta$-2, $\alpha_2\delta$-3 or $\alpha_2\delta$-4 subunit polypeptide comprises a tag moiety which can be selected among the tags referred to above. Such tagged polypeptides are particularly useful in SPA or flashplate assays. A preferred tag is the nucleotide sequence encoding histidine residues referred to above.

In a second embodiment, the secreted soluble $\alpha_2\delta$-2, $\alpha_2\delta$-3 or $\alpha_2\delta$-4 subunit polypeptide can be used without a tag. This is the case for instance in SPA or flashplate assays comprising beads or plates coated with wheat germ lectin. In such an embodiment, the tag is not needed as the carbohydrate moieties of the secreted soluble $\alpha_2\delta$-2, $\alpha_2\delta$-3 or $\alpha_2\delta$-4 subunit polypeptide bind directly to the wheat germ lectin-coated beads or plates.

E) Purified Recombinant Secreted Soluble $\alpha_2\delta$-2, $\alpha_2\delta$-3 or $\alpha_2\delta$ Polypeptides Another object of the present invention consists of a purified or isolated recombinant polypeptide comprising the amino acid sequence of a secreted soluble $\alpha_2\delta$-2, $\alpha_2\delta$-3 or $\alpha_2\delta$-4 subunit polypeptide.

Preferred isolated recombinant polypeptides of the invention include those having at least 80%, preferably 90%, more preferably 95, and most preferably 98 or 99%, amino-acid identity with polypeptides comprising from amino acid 1 to between amino-acids 1027 and 1145, preferably between amino-acids 1062 and 1145 of SEQ ID No. 20, as well as those having at least 80%, preferably 90%, more preferably 95, and most preferably 98 or 99%, amino-acid identity with polypeptides comprising from amino acid 1 to between amino-acids 984 and 1085, preferably between amino-acids 1019 and 1085 of SEQ ID No. 22.

In a further preferred embodiment, the polypeptide comprises an amino acid sequence having at least 80%, preferably 90%, more preferably 95%, and most preferably 98% or 99% amino acid identity with the amino acid sequence of SEQ ID No. 4, SEQ ID No. 5, SEQ ID No. 6, SEQ ID No. 10, SEQ ID No. 1, SEQ ID No. 12, SEQ ID No. 16, SEQ ID No. 17 and SEQ ID No. 18

More generally, the invention encompasses any secreted soluble α₂δ subunit polypeptide encoded by a nucleic acid of the present invention.

F) Modified Secreted Soluble α₂δ-2, α₂δ-3 or α₂δ Subunit Polypeptides

The invention also relates to secreted soluble α₂δ-2, α₂δ-3 or α₂δ-4 subunit polypeptide comprising amino acid changes ranging from 1, 2, 3, 4, 5, 10, 20, 25, 30, 35, 40 substitutions, additions or deletions of one amino acid as regards to polypeptides of anyone of the amino acid sequences of the present invention. Preferred sequences are those of SEQ ID No. 4, SEQ ID No. 5, SEQ ID No. 6, SEQ ID No. 10, SEQ ID No. 11, SEQ ID No. 12, SEQ ID No. 16, SEQ ID No. 17 and SEQ ID No. 18.

In the case of an amino acid substitution in the amino acid sequence of a polypeptide according to the invention, one or several consecutive or non-consecutive amino-acids are replaced by "equivalent" amino-acids. The expression "equivalent" amino acid is used herein to designate any amino acid that may be substituted for one of the amino-acids belonging to the native protein structure without decreasing the binding properties of the corresponding peptides to the antibodies raised against the polypeptides of the invention. In other words, the "equivalent" amino-acids are those which allow the generation or the synthesis of a polypeptide with a modified sequence when compared to the amino acid sequence of the secreted soluble α₂δ-2, α₂δ-3 or α₂δ-4 subunit polypeptides of interest, said modified polypeptide being able to bind to the antibodies raised against the secreted soluble α₂δ-2, α₂δ-3 or α₂δ-4 subunit polypeptide of interest and/or to induce antibodies recognizing the parent polypeptide.

Alternatively, amino acid changes encompassed are those which will not abolish the biological activity of the resulting modified polypeptide. These equivalent amino-acids may be determined either by their structural homology with the initial amino-acids to be replaced, by the similarity of their net charge or of their hydrophobicity, and optionally by the results of the cross-immunogenicity between the parent peptides and their modified counterparts.

The peptides containing one or several "equivalent" amino-acids must retain their specificity and affinity properties to the biological targets of the parent protein, as it can be assessed by a ligand binding assay or an ELISA assay.

Examples of amino-acids belonging to specific classes include Acidic (Asp, Glu), Basic (Lys, Arg, His), Non-polar (Ala, Val, Leu, Ile, Pro, Met, Phe, Trp) or uncharged Polar (Gly, Seu, Thr, lys, Tyr, Asn, Gln) amino-acids.

Preferably, a substitution of an amino acid in α₂δ-2, α₂δ-3 or α₂δ-4 subunit polypeptide of the invention, or in a peptide fragment thereof, consists in the replacement of an amino acid of a particular class for another amino acid belonging to the same class.

By an equivalent amino acid according to the present invention is also contemplated the replacement of a residue in the L-form by a residue in the D form or the replacement of a Glutamic acid (E) residue by a Pyro-glutamic acid compound. The synthesis of peptides containing at least one residue in the D-form is, for example, described by Koch (1977). A specific embodiment of a modified peptide of interest according to the present invention, includes, but is not limited to, a peptide molecule, which is resistant to proteolysis. This is a peptide in which the —CONH— peptide bond is modified and replaced by a (CH₂NH) reduced bond, a (NHCO) retro inverso bond, a (CH₂—O) methylene-oxy bond, a (CH₂S) thiomethylene bond, a (CH₂CH₂) carba bond, a (CO—CH₂) cetomethylene bond, a (CHOH—CH₂) hydroxyethylene bond), a (N—N) bound, a E-alcene bond or also a —CH═CH-bond.

The invention also encompasses secreted soluble α₂δ-2, α₂δ-3 or α₂δ-4 subunit polypeptide in which at least one peptide bond has been modified as described above. The polypeptides according to the invention may also be prepared by the conventional methods of chemical synthesis, either in a homogenous solution or in solid phase. As an illustrative embodiment of such chemical polypeptide synthesis techniques, it may be cited the homogenous solution technique described by Houbenweyl (1974).

The secreted soluble α₂δ-2, α₂δ-3 or α₂δ-4 subunit polypeptide of interest, or a fragment thereof may thus be prepared by chemical synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups.

For solid phase synthesis, the technique described by Merrifield (1965a; 1965b) may be used in particular.

G) Antibody Production

The secreted soluble α₂δ-2, α₂δ-3 or α₂δ-4 subunit polypeptides of the invention and their peptide fragments of interest can be used for the preparation of antibodies. Polyclonal antibodies may be prepared by immunization of a mammal, especially a mouse or a rabbit, with a polypeptide according to the invention that is combined with an adjuvant of immunity, and then by purifying the specific antibodies contained in the serum of the immunized animal on an affinity chromatography column on which has previously been immobilized the polypeptide that has been used as the antigen. Monoclonal antibodies may be prepared from hybridomas according to the technique described by Kohler and Milstein (1975).

The present invention also deals with antibodies produced by the trioma technique and by the human B-cell hybridoma technique, such as described by Kozbor et al. (1983). Antibodies of the invention also include chimeric single chain Fv antibody fragments (U.S. Pat. No. 4,946,778; Martineau et al., (1998), antibody fragments obtained through phage display libraries Ridder et al. (1995) and humanized antibodies (Leger et al., (1997)).

H) Screening Assays

The invention concerns a method for the screening of ligands which bind soluble secreted α₂δ-2, α₂δ-3 or α₂δ-4 subunit polypeptide. More particularly, the targeted α₂δ-2, α₂δ-3 or α₂δ-4 subunit binding site is preferably the [³H] gabapentin binding site. The various parameters of the method of the invention are described in further detail below.

1) Labelled Compounds which Bind the Secreted Soluble α₂δ-2, α₂δ-3 or α₂δ-4 Subunit Polypeptide In cases where the α₂δ-2, α₂δ-3 or α₂δ-4 binding site is the [³H]gabapentin binding site, the preferred labelled compound which can be used is of course gabapentin itself. However, gabapentin is not the only labelled compound which can be used in this context. Indeed, it has been previously demonstrated that saturation binding analyses on porcine synaptic plasma cerebral cortex membranes performed in the presence of L-leucine indicate a competitive interaction of the amino acid with the [³H]gabapentin binding site, significantly reducing [³H]gabapentin binding affinity for the site. The inventors believe that this competitive interaction is true across all the amino-acids listed in table 1 below.

TABLE 1

Binding affinities of selected amino acids ($IC_{50}$ < 500 nM) for the [$^3$H]gabapentin site in porcine cortical membranes

| COMPOUND | $IC_{50}$ (NM) ARITHMETIC MEAN (N = 3) ± S.E.M. |
|---|---|
| Gabapentin | 42.1 ± 5.5 |
| L-Norleucine | 23.6 ± 6.7 |
| L-Allo-Isoleucine | 32.8 ± 6.0 |
| L-Methionine | 49.6 ± 10.0 |
| L-Leucine | 61.3 ± 20.9 |
| L-Isoleucine | 68.8 ± 1.9 |
| L-Valine | 330 ± 18 |
| L-Phenylalanine | 351 ± 89 |

It is therefore possible to use commercially available labelled forms of these high affinity ligands in replacement of gabapentin. The utility of [$^3$H]L-leucine has been demonstrated in a filter binding assay and in a flashplate assay format. The inventors believe that labelled amino acids but also other compounds, with affinities preferably below 500 nM in the binding assay can be used as replacements of gabapentin.

With regard to the label, several embodiments can be used in the context of the invention. Preferred labels are of course radioactive labels, a list of which is provided further in this specification.

2) Assay Formats and Conditions

Several assay formats can be used to carry out the method of the present invention. Preferred assay formats include scintillation assays such as the scintillation proximity assay (SPA) or the flashplate assay. Other assay formats well known to those skilled in the arts such as the filter binding assay and the centrifugation assay are also contemplated in the present invention.

SPA and flashplate assays are preferred assay formats for the present invention. Additional details on these assays are provided below.

Scintillation Assay Format

Scintillation assays technology either involves the use of scintillant beads (for the SPA assay) or plates (for the flashplate assay). SPA beads are usually made from either cerium-doped yttrium ion silicate (y2SiO5:Ce) or polyvinyltoluene (PVT) containing an organic scintillant such as PPO. Flashplates commonly used are those such as Ni chelate flashplates although other flashplates can also be used, such as the Wheat Germ lectin flashplate.

Assays are usually carried out in aqueous buffers using radioisotopes such as $^3$H, $^{125}$I, $^{14}$C, $^{35}$S or $^{33}$P that emit low-energy radiation, the energy of which is easily dissipated in an aqueous environment. For example, the electrons emitted by $^3$H have an average energy of only 6 keV and have a very short path length (–1 ~tm) in water. If a molecule labelled with one of these isotopes is bound to the bead or flashplate surface, either directly or via interaction with another molecule previously coupled to the bead or flashplate, the emitted radiation will activate the scintillant and produce light. The amount of light produced, which is proportional to the amount of labelled molecules bound to the beads, can be measured conveniently with a liquid scintillation (LS) counter. If the labelled molecule is not attached to the bead or a flashplate surface, its radiation energy is absorbed by the surrounding aqueous solvent before it reaches the bead, and no light is produced. Thus, bound ligands give a scintillation signal, but free ligands do not, and the need for a time- consuming separation step, characteristic of conventional radioligand binding assays, is eliminated. The manipulations required in the assays are reduced to a few simple pipetting steps leading to better precision and reproducibility.

The conditions under which SPA and flashplate assays are performed in the context of the present invention are provided below.

Scintillation Assay Conditions a) SPA Assay

The SPA assays is first developed to optimize the conditions under which the radioligand binds the secreted soluble $\alpha_2\delta$-2, $\alpha_2\delta$-3 or $\alpha_2\delta$-4 subunit polypeptide. The parameters which can be varied to optimize radioligand binding in a typical SPA assay using Amersham beads include assay temperature, $\alpha_2\delta$-2, $\alpha_2\delta$-3 or $\alpha_2\delta$-4 subunit polypeptide interaction with the radioligand and the SPA beads, radioligand concentration as well as pH variations.

The temperature at which the assay can be carried out can vary from 1 to 30° C. Preferred temperatures range from 18 to 23° C., with 21° C. being the most preferred temperature. The interaction of the $\alpha_2\delta$ subunit polypeptide with the SPA beads can be optimized by adjusting the concentration of the polypeptide and by introducing a reagent which will favor this interaction. When 50 mg of Amersham SPA beads are used, the $\alpha_2\delta$-1 subunit polypeptide concentration may vary from 0.1 to 10 pmoles per well, with the optimal concentration being generally around 5 to 6 pmoles per well.

As for the reagent favoring the interaction between the secreted soluble $\alpha_2\delta$-2, $\alpha_2\delta$-3 or $\alpha_2\delta$-4 subunit polypeptide and the radioligand as well as the Amersham SPA beads, the inventors found that imidazole could be efficiently used for that purpose when the $\alpha_2\delta$-2, $\alpha_2\delta$-3 or $\alpha_2\delta$-4 subunit polypeptide is tagged with an amino acid sequence including 6 histidine residues. Furthermore, and more importantly, it was found that imidazole also enhanced binding of the radioligand to the $\alpha_2\delta$-2, $\alpha_2\delta$-3 or $\alpha_2\delta$-4 polypeptide.

The concentration of the radioligand is evaluated with respect to the concentration of secreted soluble $\alpha_2\delta$-2, $\alpha_2\delta$-3 or $\alpha_2\delta$-4 subunit polypeptide present in the assay medium. Generally, the concentration of radioligand varies from 1 nM to 100 nM. A preferred [$^3$H]gabapentin concentration is about 5 to 20 nM, with a most preferred concentration being about 10 nM. A preferred [$^3$H]leucine concentration is also about 5 to 20 nM, with a most preferred concentration being about 10 nM. It is to be noted that the concentration of other radioligands having affinities similar to those of [$^3$H]gabapentin and [$^3$H]leucine should also be in the range of about 5 to 20 nM.

Once the optimal radioligand binding conditions have been determined, a test ligand can be introduced in the assay medium to evaluate the level of displacement of the radioligand. The concentration of test ligand to be introduced in the assay medium usually varies from 0.1 nM to about 100 µM. A preferred test ligand concentration of about 10 µM is usually a starting point in a high throughput screening assay. Then, depending on the number of hits obtained, it may be lowered or increased.

It is to be noted that the parameters set forth above, which have been evaluated for a typical SPA assay using Amersham SPA beads can be adjusted by the skilled person, for example if SPA beads of a different type are used.

b) Flashplate Assay

Similarly to the SPA assays, the flashplate can first be developed in order to optimize the conditions under which the radioligand binds the $\alpha_2\delta$ subunit polypeptide. The parameters which can be varied to optimize radioligand binding in a typical flashplate assay using NEN Ni chelate flashplates or the Wheat Germ lectin flashplates also include assay temperature, secreted soluble $\alpha_2\delta$-2, $\alpha_2\delta$-3 or $\alpha_2\delta$-4 subunit polypeptide interaction with both the radioligand and the flashplates, radioligand concentration as well as pH variations.

The temperature at which the assay can be carried out can vary from 1 to 30° C. Preferred temperatures range from 18 to 23° C., with 21° C. being the most preferred temperature.

The interaction of the secreted soluble $\alpha_2\delta$-2, $\alpha_2\delta$-3 or $\alpha_2\delta$-4 subunit polypeptide with the flashplates can be optimized by adjusting the concentration of the polypeptide and by introducing a reagent which will favor this interaction. When a standard NEN Ni chelate flashplate is used, the secreted soluble $\alpha_2\delta$-2, $\alpha_2\delta$-3 or $\alpha_2\delta$-4 subunit polypeptide volume usually varies between 0.5 and 20 ul for a concentration of secreted soluble $\alpha_2\delta$-2, $\alpha_2\delta$-3 or $\alpha_2\delta$-4 subunit polypeptide of 0.6 pmol/µl. As the published maximum binding capacity of NEN p plates is about 6 pmol per well, the inventors consider that an optimal concentration of secreted soluble $\alpha_2\delta$-2, $\alpha_2\delta$-3 or $\alpha_2\delta$-4 subunit polypeptide is probably around 5 pmol per well at 8 µl.

With regard to the reagent favoring the interaction between the secreted soluble $\alpha_2\delta$-2, $\alpha_2\delta$-3 or $\alpha_2\delta$-4 subunit polypeptide and the radioligand as well as the flashplates, the inventors believe that imidazole could also be efficiently used for that purpose when the secreted soluble $\alpha_2\delta$-2, $\alpha_2\delta$-3 or $\alpha_2\delta$-4 subunit polypeptide is tagged with an amino acid sequence including 6 histidine residues. The inventors also believe that imidazole concentrations can substantially enhanced binding of the radioligand to the secreted soluble $\alpha_2\delta$-2, $\alpha_2\delta$-3 or $\alpha_2\delta$-4 polypeptide. The optimal concentration of imidazole used to enhance radioligand binding varies depending on the concentration of secreted soluble $\alpha_2\delta$-2, $\alpha_2\delta$-3 or $\alpha_2\delta$-4 subunit polypeptide used in the assay. For instance, when the volume of the $\alpha_2\delta$-1 subunit polypeptide is about 10 µl $\alpha_2\delta$-2, $\alpha_2\delta$-3 or $\alpha_2\delta$-4 polypeptide concentration of 0.6 pmol/µl), the optimal imidazole concentration can vary between 1 and 20 mM, with a concentration of about 10 mM being preferred. As mentioned previously, other compounds such as histidine as well as pH variations may be used to enhance radioligand binding.

The concentration of the radioligand is evaluated with respect to the concentration of $\alpha_2\delta$-2, $\alpha_2\delta$-3 or $\alpha_2\delta$-4 subunit polypeptide present in the assay medium. Generally, the concentration of radioligand varies from 1 nM to 100 nM. A preferred [$^3$H]gabapentin concentration is about 5 to 20 nM, with a most preferred concentration being about 10 nM. A preferred [$^3$H]leucine concentration is also about 5 to 20 nM, with a most preferred concentration being about 10 nM. It is to be noted that the concentration of other radioligands having affinities similar to those of [$^3$H]gabapentin and [$^3$H]leucine should also be in the range of about 5 to 20 nM.

Once the optimal radioligand binding conditions have been determined, a test ligand can be introduced in the assay medium to evaluate the level of displacement of the radioligand. The concentration of test ligand to be introduced in the assay medium usually varies from 0.1 nM to about 100 µM. A preferred test ligand concentration of about 10 µM is usually a starting point in a high throughput screening assay. Then, depending on the number of hits obtained, it may be lowered or increased.

The inventors have tested the displacement of a particular radioligand, [$^3$H]gabapentin, with (S+)-3-isobutyl gaba. The data provided in the examples which follow clearly shows that the assay can be used in high throughput competition studies.

The invention also resides in a product or ligand isolated, identified or selected using the above screening methods or kits, for use as a medicament or as a lead for further drug development purposes. As indicated above, the compounds are potentially useful for treating disorders of the nervous system, including epilepsy, pain and anxiety.

Further aspects and advantages of the present invention will be described in the following examples, which should be regarded as illustrative and not limiting the scope of the present application.

EXAMPLES

Example 1

Construction of a Nucleotide Sequence Encoding a Soluble Secreted Human $\alpha_2\delta$-2 Subunit Polypeptide Deletion Mutant of SEQ ID No. 23 a) Primer Design

PCR primers were designed to generate the secreted soluble human $\alpha_2\delta$-2 deletion mutant of SEQ ID No. 23 as follows:

5' PCR primer: This was designed to engineer in a KOZAK translation initiation consensus sequence prior to the coding sequence (Kozak JBC 266 19867-19870)

3' PCR primer: This was designed to engineer in six histidine residues followed by a stop-codon at the desired location in the coding sequence. In addition to the stop codon the $\alpha_2\delta$-2 primers also included an Eco RI restriction site.

The bold region in each primer sequence denotes the 'tagged' region; addition of sequences not present in the template. Primers were custom synthesized by Perkin Elmer Applied Biosystems UK to the ABI ready pure grade, supplied lyophilized then resuspended to 15 µM in 10 mM TE. JB197 and 198 were provided with 5' phosphate groups:

5' Primer JB197 (5'1-TCGCCACCATGGCGGTGCCG-GCTC-3', SEQ ID No. 25)

3' Primer JB198 (5'-TCGGAATTCCTCAGTGATGGT-GATGGTGATGGGCCCCGCGGCCACAGTC-3', SEQ ID No. 26)

b) Protocol for PCR Mediated 5' Kozak and 3' 6His Tagging of Human $\alpha_2\delta$-2

The full length human $\alpha_2\delta$-2 gene (Gen Bank Accession Number AF042792) in a pcDNA 3 vector as described in Brown, J. P. and Gee, N. S., (Cloning and deletion mutagenesis of the $\alpha_2\delta$ calcium channel subunit from porcine cerebral cortex, *The journal of biological chemistry*, 273 (39):25458-25465) was used as the template in the following PCR reaction.

The reagents were added in the following order in triplicate to a 96 well PCR plate:

|  | µl |
|---|---|
| 10x Pfx Amplification buffer | 5 |
| 10 mM dNTPs | 1.5 |
| 50 mM MgSO$_4$ | 1 |
| 15 µM JB197 | 1.5 |

-continued

| | μl |
|---|---|
| 15 μM JB198 | 1.5 |
| 100 ng/μl pcDNA3.1-humans-α$_2$δ-2 | 1 |
| 10x PCR Enhancer | 5 |
| H$_2$O | 32.7 |
| 2.5 UNITS/μL PFX POLYMERASE | 0.8 μL |

The plate was the cycled on an MJ Tetrad DNA engine according to the following cycling conditions:

| 94° C./2 mins followed by: | |
|---|---|
| for 30 cycles | 94° C./45 sec |
| | 58° C./45 sec |
| | 68° C./4 mins |
| followed by: | |
| 68° C./10 mins followed by: | |
| hold at 4° C. | |

The 3366 bp product was then gel purified from a 1% TAE agarose gel using QIAEX beads and eluted in approximately 50 μl TE.

Example 2

Cloning of the PCR Fragments of Example 1 into the Baculovirus Transfer Vector pFastBac1

The PCR products of Example 1 were cloned into Stu I digested, calf intestinal phosphatase dephosphorylated, phenol chloroform extracted and QIAEX gel purified pFastBac1 (Life Technologies) using the Rapid DNA ligation kit (Roche Diagnostics) transforming XL1-blue α$_2$δ-1b) E. Coli cells:

a) Screening for Positive Recombinants

Given that the PCR product was cloned by blunt-end ligation a screen was required to select a recombinant with the gene ligated in the positive orientation with respect to the polyhedrin promoter in pFastBac1. This was achieved by restriction digest of miniprep DNA (Qiagen miniprep kit) prepared from colony minicultures and analysis on a 1% TAE agarose gel. A positive clone was identified according to the following digest patterns:

| SEQ ID N° 23 in pFastBac1 Eco RI digest performed on miniprep DNA | |
|---|---|
| | Predicted fragments (bp) |
| PCR product cloned in a positive orientation | 4773 and 3368 |
| PCR product cloned in a negative orientation | 8127 and 14 | b) Sequencing Analysis of Selected Clones

One positive was selected for this clone and used to prepare a plasmid DNA stock of the desired construct (QIAGEN maxi kit). Confirmatory sequence reactions were performed using the Big Dye terminator sequencing kit and run on an ABI 310 Prism Genetic Analyzer. Sequence analysis of both coding strands was performed using a selection of sequencing oligonucleotide primers.

Example 3

Protocol for Establishing Baculovirus Banks for the Expression of the α$_2$δ-2 Deletion Mutant SEQ ID No. 23

Essentially, the protocol used to generate the baculovirus banks is that outlined in the Life Technologies Bac-to Bac™ baculovirus expression systems manual.

a) Transposition of DH10Bac E Coli Cells

One ng (5 μl) of the recombinant pFastBac-1 construct containing the nucleotide sequence encoding the porcine α$_2$δ-2 deletion mutant of SEQ ID No. 23 was added to 100 μl of DH10Bac cells thawed on ice. The cells were then mixed gently by tapping the tube then incubated on ice for 30 minutes before heat shock treatment by incubation in a 42° C. water bath for 45 seconds. The mixture was then chilled on ice for 2 minutes before the addition of 900 μl of S.O.C. medium. The mixture was then placed in a shaking incubator (200 rpm) at 37° C. for 4 hours. The cells were then serially diluted (10 fold dilutions from $10^{-1}$ to $10^{-3}$) and 10 μl of each dilution plated on LB agar plates containing 50 μg/ml kanamycin, 7 μg/ml gentamicin, 10 μg/ml tetracycline, 100 μg/ml Bluo-gal and 40 μg/ml IPTG. The plates were incubated at 37° C. for between 1 and 3 days until discrete colonies of blue and white colour were discernible.

b) Isolation of Recombinant DNA

White colonies (containing the recombinant bacmid) were picked and grown for 24 hours (to stationary phase) at 37° C. with shaking (200 rpm) in 2 ml of LB containing 50 μg/ml kanamycin, 7 μg/ml gentamicin and 10 μg/ml tetracycline. 1.5 ml of culture was then transferred to a microfuge tube and centrifuged at 14,000×g for 1 minute. The supernatant was removed and the cells resuspended gently in 0.3 ml of 15 mM Tris-HCl (pH8.0), 10 mM EDTA, 100 μg/ml RNase A. 0.3 ml of 0.2N NaOH, 1% SDS was then added and the mixture mixed gently before incubation at 22° C. for 5 minutes. Then 0.3 ml of 3M Potassium acetate (pH5.5) was added and the sample placed on ice for 10 minutes. After centrifugation at 14,000×g for 10 minutes the supernatant was transferred to a tube containing 0.8 ml of isopropanol, mixed then placed on ice for 10 minutes before centrifugation at 14,000×g for 10 minutes. The supernatant was then discarded and the pellet rinsed with 0.5 ml of 70% ethanol before centrifugation at 14,000×g for 5 minutes. This 70% ethanol rinse was then repeated before removing all of the supernatant and air drying the pellet for 10 minutes at room temperature. The pellet was finally resuspended in 40 μl of TE.

c) Transfection of sf9 Cells with the Recombinant Bacmid DNA

A 6-well tissue culture plate was seeded with 0.9×10$^6$ sf9 cells (cells at log phase having grown from a culture passaged at 0.3×10$^6$ cells/ml) per 35 mm well in 2 ml of Sf-900 II SFM media containing 50units/ml penicillin and 50 μg/ml streptomycin. Cells were left to attach at 27° C. for 1 hour. Bacmid DNA prepared as described above (5111) was added to 200 μl of Sf-900 II SFM media containing 6 μl of CELLFECTIN and mixed before incubation at room temperature for 45 minutes. The cells were washed once with 2 ml of Sf-900 II SFM media without antibiotics then 0.8 ml of Sf-900 II SFM media was added to each tube containing the lipid-DNA complex. The wash buffer was removed from the cells and the 1 ml of diluted lipid-DNA complex overlaid on the cells. The cells were incubated for 5 hours at 27° C. after which time the transfection mixture was removed and 2 ml of Sf-900 II SFM media containing 50 units/ml penicillin and 50 µg/ml streptomycin was added. The cells were then incubated for 72 hours.

After incubation for 72 hours the media was removed from the cells and centrifuged at 500×g for 5 minutes. The supernatant was then transferred to a fresh tube, this was labelled as the P0 bank and stored at 4° C. in the dark. The P1 bank was prepared by passaging sf9 cells at approx $5 \times 10^6$ cells/ml to $2 \times 10^6$ cells/ml (100 ml in a 250 ml Erlenmeyer flask) and adding 0.5 ml of the P0 bank harvested above. The cells were then incubated shaking (200 rpm) at 27° C. for 4 days. Under sterile conditions the culture was centrifuged at 500×g for 10 minutes and the supernatant 0.2 µM filtered (P1 bank). The P2 bank was prepared by adding 2 ml of P1 bank per 400 ml culture (in 1 L Erlenmeyer flasks) passaged as above to $2 \times 10^6$ cells/ml. The culture was incubated as before for 4 days and the supernatant harvested and filtered as described for the P1 bank. The supernatant was first pooled then aliquoted (10 ml) and stored at 4° C.

Example 4

Expression of the $\alpha_2\delta$-2 Deletion Mutant of SEQ ID No. 23

To sf9 cells passaged from ~$5 \times 10^6$ cells/ml to $2 \times 10^6$ cells/ml in Sf-900 II SFM media was added 0.1 ml virus per 100 ml of cells of the appropriate viral bank (400 ml volumes in 1L Erlenmeyer flasks). The cells were then cultured for 4-5 days at 27° C. with 110 rpm shaking. Expression of the protein was confirmed by SDS-PAGE and Western blotting using an anti penta-His monoclonal antibody (Qiagen) and was detected in the culture supernatant and cell lysate.

Example 5

Purification of $\alpha_2\delta$-2 Deletion Mutant of SEQ ID No. 23

The-$\alpha_2\delta$-2 deletion mutant of SEQ ID No. 23 was purified from the cell lysate following the purification strategy outlined below:

The culture was centrifuged at 6,000×g for 10 minutes and the supernatant removed. The weight of the cell pellet was determined before re-suspension in 20 mM Tris pH8.0, 100 mMKCl, 1% P40-Nonidet (100 ml per 20 g of wet cells). A protease inhibitor cocktail (Sigma, Cat# P8849), 1 ml/L, was added to the mixture. The solution was then stirred for 10 minutes before centrifugation for 1 hour at 30,000×g and 4° C. The supernatant was concentrated (30 kDa cut off) to approx. ~300 ml then centrifuged for 1 hour at 100,000×g. Supernatant containing the soluble proteins was diluted 1:3 in 10 mM Tris-HCl pH8.0 (equilibration buffer) and loaded onto a pre-equilibrated Q-Sepharose column (2.5 cm i.d.×30 cm h.) at a flow rate of 900 ml/h. After washing with equilibration buffer until a stable $A_{280nm}$ baseline had been achieved, protein was eluted with 20 mM Tris-HCl pH8.0, 0.5M KCl, 10 mM Imidazole.

The eluate was then loaded onto a Ni-NTA (Qiagen) column (2.5 cm i.d.×6 cm h.) pre-equilibrated in 20 mM Tris pH8.0, 0.5M KCl, 10 mM Imidazole at a flow rate of 2 ml/min. The column was washed successively with buffer A (20 mM Tris pH8.0, 0.5M KCl, 20 mM Imidazole), buffer B (100 mM Tris-HCl pH8.0, 1M KCl), and buffer A again. Elution was performed with buffer C (20 mM Tris-HCl pH8.0, 100 mM KCl, 0.5M Imidazole). The Ni-NTA eluate (~50 ml) was concentrated (30 kDa cut-off) to 2 ml and applied at 1 ml/min and in 0.2 ml aliquots, to an FPLC Superdex-200 column equilibrated in 10 mM HEPES, pH7.4, 150 mM NaCl. Fractions containing the polypeptide of SEQ ID No. 23 were pulled.

Example 6

SPA Assay of [$^3$H]Gabapentin Binding to the Secreted Soluble Human$\alpha_2\delta$-2 Subunit of SEQ ID No. 23

The assay is carried out at 21° C. Assay components are added in the following order (all reagents are diluted in 10 mM HEPES (pH 7.4 at 21° C.) to 96-well Optiplates:

| | |
|---|---|
| 25 µl | imidazole at various concentrations (diluted from a 1 M stock pH 8.0, see assay details) |
| 50 µl | 10 mM HEPES pH 7.4 |
| 25 µl | (50 mg) SPA beads (Amersham) |
| 100 µl | s-$\alpha_2\delta$-2 subunit polypeptide of SEQ ID No 23 (2 µl protein diluted to 100 µl) |
| 25 µl | radioligand ([$^3$H]gabapentin obtained from example 5 |

Immediately after adding radioligand, the optiplates were loaded in the Packard Top Count scintillation counter to follow the binding time course. Imidazole was first used in the assay to optimize the specific interaction of the protein's 6His tag with the SPA bead. Imidazole itself (up to 100 mM) in the filtration assay has no effect on [$^3$H]gabapentin binding (n=1).

Example 7

Ni Flashplate Assay of [$^3$H]Gabapentin Binding to Secreted Soluble Human $\alpha_2\delta$-2 (SEQ ID No. 23)

Assays are carried out at 21° C. in a final volume of 250 µl in 96-well NEN Ni chelate flash plates. Assay components are added in the following order (all reagents were diluted in 10 mM HEPES (pH 7.4 at 21° C.)):

| | |
|---|---|
| 25 µl | 10 mM HEPES pH 7.4 |
| 25 µl | imidazole at various concentrations (diluted from a 1 M stock pH 8.0, see assay details) |
| 75 µl | 10 mM HEPES pH 7.4 |
| 100 µl | s-$\alpha_2\delta$-2-6His (2µl protein diluted to 100 µl) obtained from example 5 |
| 25 µl | radioligand ([$^3$H]gabapentin (65Ci/mmole) |

Immediately after adding the radioligand, flash plates are loaded in the Packard Top Count scintillation counter to follow the binding time course. The '[$^3$H] flash plate' programme (cpm) is used to monitor activity. Imidazole is first used in the assay to optimize the specific interaction of the protein's 6His tag with the Ni flashplate.

Example 8

Ni Flashplate Assay of [$^3$H]Leucine Binding to Secreted Soluble Human $\alpha_2\delta$-2-6His The procedure described in example 7 is repeated, except that [$^3$H]gabapentin is replaced by 25 µl (10.1 nM) of [$^3$H]Leucine (141 Ci/mmole).

Example 9

Ni Flashplate Assay Studying Competitive Binding of [$^3$H] gabapentin and (S+)-3-Isobutyl GABA to Human $\alpha_2\delta$-2-6His (SEQ ID No. 23).

Assays are carried out at 21° C. in a final volume of 250 µl in 96-well NEN Ni chelate flash plates. Wells are set up for both 'total' and 'non-specific' binding. Specific binding is defined as that remaining after subtraction of the average of the 'non-specific binding' values from the average of the 'total' binding values. Assay components are added in the following order (all reagents were diluted in 10 mM HEPES (pH 7.4 at 21° C.)):

|  |  |  |
|---|---|---|
|  | 25 µl | 10 mM HEPES pH 7.4 or 25 µl of the test compound at the appropriate concentration in HEPES |
|  | 25 µl | 200 mM imidazole (diluted from a 1 M stock pH 8.0, see assay details) |
| Total binding | 75 µl | 10 mM HEPES pH 7.4 |
| Non-specific binding | 50 µl | 10 mM HEPES pH 7.4 and 25 µl 100 µM (S+)-3-isobutyl GABA |
|  | 100 µl | $\alpha_2\delta$-2-6His (2µl protein* diluted to 100 µl) |
|  | 25 µl | radioligand ([$^3$H]gabapentin or [$^3$H]Leucine) |

*The source of $\alpha_2\delta$-2-6His is that purified by fplc Superdex-200 gel filtration (see example 5)

Immediately after adding radioligand, flash plates are loaded in the Packard Top Count scintillation counter to follow the binding time course. Incubation time before the assay is 3 hours. The '[$^3$H] flash plate' programme (cpm) is used to monitor activity Competition studies are compared across the flash-plate and filter binding methodologies in order to validate the new assay technology with the established filter binding methodology.

GraphPad Prism software is used to process competition curve data and determine IC$_{50}$ and hill slope values. Twelve point competition curves with half log dilution steps of test compounds are used in the experiments.

Example 10

Filter Binding Assay of [$^3$H]gabapentin Binding to the Recombinant Polypeptide of SEQ ID No. 23

Assays were carried out at 21° C. in a final volume of 250 µl in 96-deep well plates. Assay components were (all reagents were diluted in 10 mM HEPES (pH 7.4 at 21° C.)):

|  |  |
|---|---|
| 25 µl | compound to test |
| 200 µl | Polypeptide of SEQ ID N° 23 (3 µl protein diluted to 200 µl) |
| 25 µl | radioligand ([$^3$H]gabapentin (65Ci/mmole) |

Plates were incubated at room temperature for 1h prior to filtering on to 96-well GF/B Unifilter plates pre-soaked in 0.3% polyethylenimine. Filters were washed with 3×1 ml 50 mM Tris-HCl (pH 7.4 at 4° C.), and dried over-night. Scintillant (Microscint O, 50 µl) was added and the plates counted using a Packard Top Count scintillation counter. Specific binding was ~98% of the 'total' value. In [$^3$H]gabapentin saturation studies, the K$_D$ (nM) obtained was about 10.62.

[$^3$H]Gabapentin Saturation Studies.

Data shown represent the mean±SEM determined in 3 separate experiments. Saturation experiments were performed with 12 duplicate data points, [$^3$H]gabapentin concentration ranged from ~1-350 nM. data was analysed using KEL-RADLIG Human s-$\alpha_2\delta$-2-6His K$_D$ in the Filtration Assay 28.55±3.08 nM

TABLE 2

Binding affinities of key compounds in the [$^3$H]gabapentin binding assay using s-$\alpha_2\delta$-2-6His

| Compound | Ki (nM) and range (n = 3) Filtration assay |
|---|---|
| Gabapentin | 20 (19-23) |
| (S+)-3-isobutyl GABA | 11 (9.5-13) |
| (R−)-3-isobutyl GABA | 296 (282-310) |

N.B. Ki = IC$_{50}$/(1 + [L]/K$_D$)

Competition curves were generated with 10 duplicate data points from 10 µM to 1 nM and analyzed on GraphPad prism.

Example 11

Binding of [$^3$H]gabapentin to the Recombinant Polypeptide of SEQ ID No. 23 using Various Flashplates Assay Formats and Conditions a) Preparation of Protein Stocks:

Protein was expressed as described in Example 4 except that the cells were infected at 1×10$^6$ cells/ml. Additionally, the cells were cultured in 20 liter Applikon fermentation vessels (18L culture volume). The culture was maintained at 27° C. and 60% dO2 (100% dO$_2$ equates to [O$_2$] when media—without cells—has been saturated with air at 27° C.) with single marine impeller stirring at 125 rpm. The protein was expressed in either Sf-900 II SFM (LTI Inc) or ESF-921 (Expression Systems Inc.) media.

b) Purification of s-$\alpha_2\delta$-2-6His Protein from Cell Culture Supernatants:

On the harvest day (day 4-7 post-infection with virus) the cell culture was centrifuged at 9,000×g for 20 minutes to remove the cellular debris, and the supernatant concentrated to approximately 3 liters using a pellicon tangential-flow filtration system employing 10 kDa cut-off cassettes. The concentrated sample was re-centrifuged at 9,000×g for 20 minutes then diluted with 2 volumes of 10 mM Tris pH9.0. The diluted sample was then loaded at 10 ml/min onto a Q-sepharose column (5 cm i.d.×50 cm h.) which was washed with 20 mM Tris-HCl (pH8.0) and eluted with 20 mM Tris-HCl (pH8.0), 0.5M KCl, 10 mM Imidazole.

The eluate was then loaded at 10 ml/min onto a Ni-superflow (Qiagen) column (2.5 cm i.d.×6 cm h.) pre-equilibrated in 20 mM Tris (pH8.0), 0.1M KCl, 10 mM Imidazole. The column was washed successively with buffer A (20 mM Tris pH8.0, 0.5M KCl, 20 mM Imidazole), 20 mM Tris-HCl (pH8.0), 100 mM KCl, and buffer A again at 10 mM/min. Elution was performed with a gradient of buffer C (20 mM Tris-HCl (pH8.0), 100 mM KCl, 0.5M Imidazole) against buffer B at 2 ml/min. Fractions from the gradient elution were assayed for [$^3$H]gabapentin binding activity and the active fractions pooled then dialysed at 4° C. four times (each for 24 hours) against 10 mM HEPES, 150 mM NaCl at a ratio of 1:60 (sample:dialysate). The dialysed material was then aliquoted and frozen for use in the assays as described below.

c) Preparation of Protein Cocktails for Filter, Wheat Germ Lectin and Ni Chelate Assays (volumes in µl):

|  | cocktail | | | |
| --- | --- | --- | --- | --- |
|  | x1 | | x23 | |
|  | s-α$_2$δ-2-6His | HBS | s-α$_2$δ-2-6His | HBS |
| 0 µl | 0 | 75 | 0 | 1,725 |
| 1 µl | 1 | 74 | 23 | 1,702 |
| 2 µl | 2 | 73 | 46 | 1,679 |
| 4 µl | 4 | 71 | 92 | 1,633 | s-α$_2$δ-2-6His protein was sourced from the aliquots generated above.

d) Filter and Wheat Germ Lectin Flashplate Assays

The reagents were added in the following order to each well of either a 96-well Wheat Germ Lectin flashplate or a 96-deep well plate. Conditions were prepared in triplicate for both 'total' and 'non-specific' binding (20 µl H$_2$O added for total binding and 20 µl of 100 µM (S+)-3-isobutyl GABA to define non-specific binding) for each of the four volumes of protein tested.

Assay Set-Up Per Well:

| | |
| --- | --- |
| 100 µM (S+)-3-isobutyl GABA/H$_2$O | 20 µl |
| *100 nM [$^3$H]Gabapentin | 20 µl |
| 235 mM HEPES (pH 7.3) | 85 µl |
| s-α$_2$δ-2-6His (0, 1, 2 or 4 µl – x23 cocktail) | 75 µl |

*20 µl aliquots of the [$^3$H]gabapentin stock added to each well were counted on a liquid β-scintillation counter (Beckman LS 5000TD) to determine the actual concentration of [$^3$H]gabapentin achieved in each well. For these experiments this value was calculated as 10.8 nM.

Figure 3:
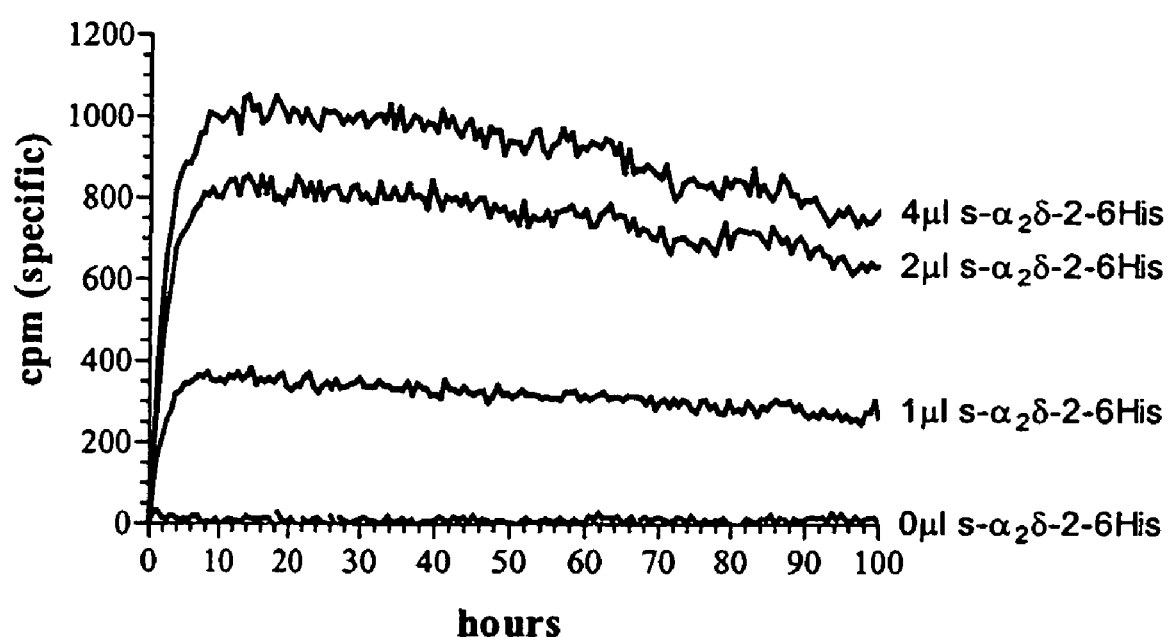
FIG. 3 illustrates the dose response nature of [$^3$H]gabapentin binding s-$\alpha_2\delta$-2-6His in the Wheat Germ lectin flashplate assay. Once again the level of non-specific binding is low (around 50-70 cpm) and stable, independent of the volume of protein assayed or the point analysed on the time-course. The window is relatively stable over an extended period of time with just a gradual decline from the 15-hour time point (approximately 10% of the window every 24 hours).

The Wheat Germ flashplate was then counted under continuous cycling conditions on a Packard Top Count Microplate scintillation counter. The plate was counted on the '[$^3$H]flashplate' programme with a count delay and count time of 1 minute. Data for the wheat germ lectin assay was plotted as 'specific' binding (i.e. 'total' minus 'non-specific' binding'), see FIG. 3.

In the Filter assay, the binding reaction in the deep-well plate was left for 1 hour at 22° C. then filtered with three 1 ml washes of 4° C. 50 mM Tris (pH 7.4 at 4° C.) onto a 96-well GF/B filter plate pre-soaked for 1 hour in 0.3% Polyethylenemine at 4° C. After leaving at 22° C. to dry overnight 45 µl of Microscint-O (Packard) was added to each filter well and the plate sealed and counted in the Packard Top Count Microplate Scintillation counter on the '[$^3$H]Microscint' programme with a count delay and count time of 1 minute. The mean of the 'total' and 'non-specific' binding is presented in FIG. 1.

e) Nickel Flashplate Assay 2.35×Nickel Flashplate Buffer:

| | |
| --- | --- |
| 4.7 ml | 1 M HEPES (pH 7.3) |
| 0.118 ml | 10% BSA (Sigma A7906, Fraction V (98%), Lot 57H1088) in H$_2$O |
| 1.175 ml | 0.2 M Imidazole pH 7.3 (NaOH) |
| 14.007 ml | H$_2$O |

Assay Set-Up Per Well:

| | |
| --- | --- |
| 100 µM (S+)-3-isobutyl GABA/H$_2$O | 20 µl |
| *100 nM [$^3$H]Gabapentin | 20 µl |
| 2.35x Nickel Flashplate buffer | 85 µl |
| s-α$_2$δ-2-6His (0, 1, 2 or 4 µl of the x23 cocktail) | 75 µl |

*20 µl aliquots of the [$^3$H]gabapentin stock added to each well were counted on a liquid β-scintillation counter (Beckman LS5000TD) to determine the actual concentration of [$^3$H]gabapentin reached in the each well. For these experiments this value was calculated as 10.8 nM.

Figure 2:
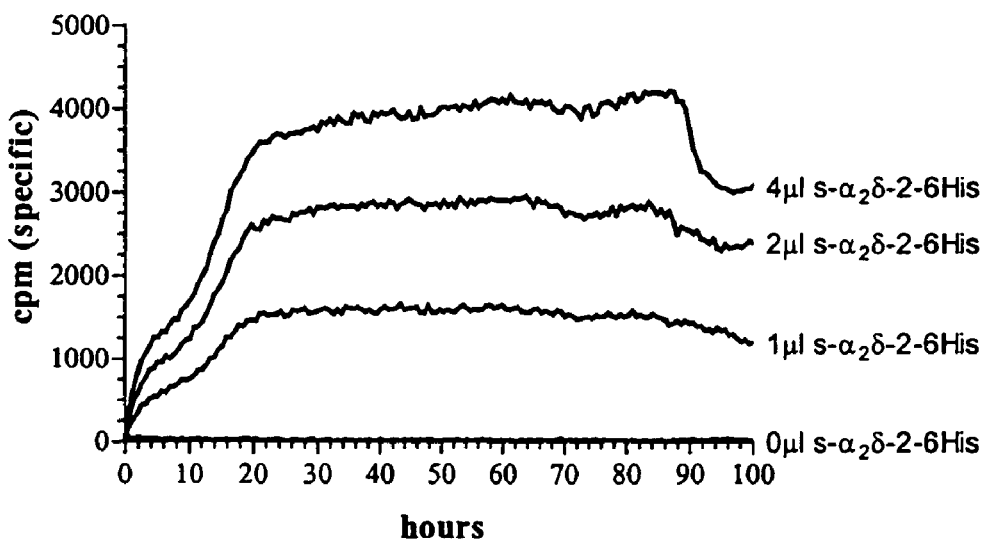
FIG. 2 illustrates the dose response nature of [$^3$H]gabapentin binding s-$\alpha_2\delta$-2-6His in the Nickel flashplate assay. As in the filter-binding assay, the level of non-specific binding is low (around 70-100 cpm) and stable, independent of the volume of protein assayed or the point analysed on the time-course. A stable window is maintained for a period of at least 50 hours (between ~20 and 70 hours on the time-course)

The Nickel flashplate was then counted under continuous cycling conditions on the Packard Top Count Microplate scintillation counter. The plate was counted on the '[$^3$H]flashplate' programme with a count delay and count time of 1 minute (FIG. 2).

The data described demonstrates that it is possible to assay [$^3$H]gabapentin binding to recombinantly expressed freely soluble and purified s-α$_2$δ-2-6His in either a filter assay or an homogenous flashplate assay in either the Nickel chelate or the Wheat germ lectin format. The data demonstrates the extended stability of the flashplate assay over time, which is crucial if the assay format is to be used for mass-screening purposes, thus enabling the stacking of plates into counters (ideally with appropriate controls on each plate along with test compound wells in order to confirm signal stability across individual plates).

The data presented also demonstrate that it is possible to use the Wheat Germ lectin flashplate assay, as a primary assay or as a secondary screen to further refine and screen ligands identified or selected using the Ni flashplate assay or another format of this invention.

Example 12

Construction of a Nucleotide Sequence Encoding a Soluble Secreted Mouse α$_2$δ-3 Deletion Mutant of SEQ ID No. 24 as follows.

a) Primer Design

PCR primers were designed to generate the secreted soluble mouse α$_2$δ-3 deletion mutant of SEQ ID No. 24 as follows:

5' PCR primer: This was designed to engineer in a KOZAK translation initiation consensus sequence prior to the coding sequence (Kozak JBC 266 19867-19870)

3' PCR primer: This was designed to engineer in six histidine residues followed by a stop-codon at the desired location in the coding sequence. In addition to the stop codon the α$_2$δ-3 primers also included an Eco RI restriction site.

The bold region in each primer sequence denotes the 'tagged' region; addition of sequences not present in the template. Primers were custom synthesized by Perkin Elmer Applied Biosystems UK to the ABI ready pure grade, supplied lyophilized then resuspended to 15 µM in 10 mM TE. JB201 and 202 were provided with 5' phosphate groups:

5' Primer JB201 (5'-TCGCCACCATGGCCGGGC-CGGGC-3', SEQ ID No. 27)

3' Primer JB202 (5'-TCTCAGTGATGGTGATGGTGAT-GCGATGCACCCCCACACTCTC-3', SEQ ID No. 28)

b) Protocol for PCR Mediated 5' Kozak and 3' 6His Tagging of Mouse α$_2$δ-3

The full length mouse α$_2$δ-3 gene (Gen Bank Accession number AJ010949) in the pcDNA3 vector as described in Brown, J. P. and Gee, N. S., (Cloning and deletion mutagenesis of the α₂δ calcium channel subunit from porcine cerebral cortex, *The journal of biological chemistry*, 273 (39):25458-25465) was used as the template in the following PCR reaction.

The reagents were added in the following order in triplicate to a 96 well PCR plate:

|  | μl |
| --- | --- |
| 10x Pfx Amplification buffer | 5 |
| 10 mM dNTPs | 1.5 |
| 50 mM MgSO₄ | 1 |
| 15 μM JB201 | 1.5 |
| 15 μM JB202 | 1.5 |
| 100 ng/μl pcDNA3-mouse-α₂δ-3 | 1 |
| 10x PCR Enhancer | 5 |
| H₂O | 32.7 |
| 2.5 UNITS/μL PFX POLYMERASE | 0.8 μL |

The plate was the cycled on an MJ Tetrad DNA engine according to the following cycling conditions:

| 94° C./2 mins followed by: |  |
| --- | --- |
| for 30 cycles | 94° C./45 sec |
|  | 60° C./45 sec |
|  | 68° C./4 mins |
| followed by: |  |
| 68° C./10 mins followed by: |  |
| hold at 4° C. |  |

The 3244 bp product was then gel purified from a 1% TAE agarose gel using QIAEX beads and eluted in approximately 50 μl.

The truncated protein of SEQ ID No. 24 was expressed such the procedure of example 2,3 and 4.

REFERENCES

Perez-Reyes, E., and Schneider, T. (1994) *Drug Dev. Res.* 33, 295-318

Catterall, W. A. (1995) *Annu. Rev. Biochem.* 64, 493-531

Birnbaumer, L., Campbell, K. P., Catterall, W. A., Harpold, M. M., Hofmann, F., Home, W. A., Mori, Y., Schwartz, A., Snutch, T. P., Tanabe, T., and Tsien, R. W. (1994) *Neuron* 13, 505-506

Brust, P. F., Simerson, S., McCue, A. F., Deal, C. R., Schoonmaker, S., Williams, M. E., Velicelebi, G., Johnson, E. C., Harpold, M. M., and Ellis, S. B. (1993) *Neuropharmacology* 32, 1089-1102

Itagaki, K., Koch, W. J., Bodi, L, Klockner, U., Slish, D. F., and Schwartz, A. (1992) *FEBS Lett.* 297, 221-225

Mikami, A., Imoto, F_Tanabe, T., Niidome, T., Mori, Y., Takeshima, H., Narumiya, S., and Numa, S. (1989) *Nature* 340, 230-233

Mori, Y., Friedrich, T., Kim, M. S., Mikami, A., Nakai, J., Ruth, P., Bosse, E., Hofmann, F., Flockerzi, V., Furuichi, T., Mikoshiba, K., Imoto, K, Tanabe, T., and Numa, S. (1991) *Nature* 350, 398-402

Singer, D., Biel, M., Lotan, I., Flockerzi, V., Hofmann, F., and Dascal, N. (1991) *Science* 253, 1553-1657

Ramsay, R. E. (1994) *Neurology* 44, Suppl. 5, 23-30

Watson, W. P., and Little, H. J. (1995) *Br. J. Pharmacol.* 116, 33P (abstr.)

Singh, L., Field, M. J., Ferris, P., Hunter, J. C., Oles, R. J., Williams, R. G., and Woodruff, G. N. (1996) *Psychopharmacology* 127, 1-9

Xiao, W. H., and Bennet, G. L (1995) *Soc. Neurosci.* 21, 897 (abstr.)

Mellick, G. A., Mellicy, L. B., and Mellick, L. B. (1995) *J Pain Symptom Manage.* 10, 265-266

Shimoyama, N., Shimoyama, M., Davis, A. M., Inturrisi, C. E., and Elliott, K. J. (1997) *Neurosci. Lett.* 222, 65-67

SegaL A. Z., and Rordorf, G. (1996) *Neurology* 46, 1175-1176

Mellick, G. A., and Mellick, L. B. (1996) *Sleep* 19, 224-226

Patel, J., and Naritoku, D. K (1996) *Clin. Neuropharmacol.* 19, 185-188

Suman Chauhan, N., Webdale, L., Hill, D. R., and Woodruff, G. N. (1993) *Eur. J. Pharmacol.* 244, 293-301

Macdonald, R. L., and Kelly, F_M. (1993) *Epilepsia* 34, Suppl. 5, S1-S8

Taylor, C. P. (1994) *Neurology* 44, Suppl. 5, 10-16

Gotz, E., Feuerstein, T. J., Lais, A., and Meyer, D. K (1993) *Arzneimittelforschung* 43, 636-638

Loscher, W., Honack, D., and Taylor, C. P. (1991) *Neurosci. Lett.* 128, 150-154

Honmou, 0., Knesis, J. D., and Richerson, G. B. (1995) *Epilepsy Res.* 20, 193-202

Honmou, 0., Oyelese, A. A., and Kocsis, J. D. (1995) *Brain Res.* 692, 273-277

Petroff, 0. A. C., Rothman, D. L., Behar, K. L., Lamoureux, D., and Mattson, R. H. (1996) *Ann. Neurol.* 39, 95-99

Reimann, W. (1983) *Eur. J. Pharmacol.* 94, 341-344

Dooley, D. J., Bartoszyk, G. D., Hartenstein, J., Reimann, W., Rock, D. M., and Satzinger, G. (1986) *Golden Jubilee Conference and Northern European Epilepsy Meeting.* Abstracts, University of York, UK, September 1986 (Abstract 8).

Thurlow, R. J., Brown, J. P., Gee, N. S., Hill, D. R., and Woodruff, G. N. (1993) *Eur. J. Pharmacol.* 247, 341-345

Gee, N. S., Brown, J. P., Dissanayake, V. U. I, Offord, J., Thurlow, R., and Woodruff, G. N. (1996) *J. Biol. Chem.* 271, 5768-5776

Dissanayake, V. U. I-, Gee, N. S., Brown, J. P., and Woodruff, G. N. (1997) *Br. J. Pharmacol.* 120, 833-840

Taylor, C. P., Vartanian, M. G., Yuen, P. W., Bigge, C., Suman Chauhan, N., and Hill, D. R. (1993) *Epilepsy Res.* 14, 11-15

Rock, D. M., Kelly, K. M., and Macdonald, R. L. (1993) *Epilepsy Res.* 16, 89-98

Wamil, A. W., Mclean, M. J., Nashville, T. N., and Taylor, C. P. (1991) *Neurology* 41, Suppl. 1, 140 (abstr.)

De Jongh, K S., Warner, C., and Catterall, W. A. (1990) *J. Biol. Chem.* 265, 14738-14741

Jay, S . D., Sharp, A. H., Kahl, S. D., Vedvick, T. S., Harpold, M. M., and Campbell, K. P. (1991) *J. Biol. Chem.* 266, 3287-3293

Burgess, A. J., and Norman, R. 1. (1988) *Eur. J. Biochem.* 178, 527-533

Ellis, S. B., Williams, M. E., Ways, N. R., Brenner, R., Sharp, A. H., Leung, A. T., Campbell, K. P., McKenna, E., Koch, W. J., Hai, A., Schwartz, A., and Harpold, M. M. (1988) *Science* 241, 1661-1664

Brickley, K., Campbell, V., Berrow, N., Leach, R., Norman, R. I., Wray, D., Dolphin, A. C., and Baldwin, S. A- (1995) *FEBS Lett.* 364, 129-133

Brice, N. L., Berrow, N. S., Campbell, V., Page, K. M., Brickley, K., Tedder, I., Dolphin, A C. (1997) *Eur. J. Neurosci.* 9, 749-759

Wiser, 0., Trus, M., Tobi, D., Halevi, S., Giladi, E., and Atlas, D. (1996) *FEBS Lett.* 379, 15-20

Xu, X., and Arnason, U. (1994) *Gene* (Amst.) 148, 357-362

Williams, M. E., Feldman, D. H., McCue, A. F., Brenner, R., Velicelebi, G., Ellis, S. B., and Harpold, M. M. (1992) *Neuron* 8, 71-84

Kim, H. L., Kim, H., Lee, P., King, R. G., and Chin, H. (1992) *Proc. Natl. Acad. Sci. U. S. A.* 89, 3251-3255

Brown, J. P., Dissanayake, V. U. K., Briggs, A. R., Milic, M. R., and Gee, N. S. (1998) *Anal. Biochem.* 255, 236-243

Higuchi, R. (1990) in *PCR Protocols: A Guide to Methods and Applications* (Innis, M. A., Gelfand, D. H., Sninsky, J. J., and White, T. J. eds) pp. 177-183, Academic Press, Ltd., London Bradford, M. M. (1976) *Anal. Biochem.* 72, 248-252

Kyte, J., and Doolittle, F. (1982) *J. Mol. Biol.* 157, 105-132

Summers, M. F., Henderson, L. E., Chance, M. R., Bess, J. W., Jr., South, T. L., Blake, P. R., Sagi, I., Perez-Alvarado, G., Sowder, R. C., Hare, D. R., and Arthur, L. 0. (1992) *Protein Sci.* 1, 563-574

Klug, A. and Rhodes, D. (1987) *Trends. Biochem. Sci.* 12, 464-469

Pieler, T., and Bellefroid, E. (1994) *Mol. Biol. Rep.* 20, 1-8

Preston, R. A., Manolson, M. F., Becherer, M, Weidenhammer, E., Kirkpatrick, D., Wright, R., and Jones, E. W. (1991) *Mol. Cell, Biol.* 11, 5801-5812

Tan, X., Waterham, H. R., Veenhuis, M., and Cregg, J. M. (1995) *J. Cell Biol.* 128, 307-319

Scotland, P. B., Colledge, M., Melnikova, I., Dai, Z., and Froehner, S. C. (1993) *J. Cell Biol.* 123, 719-728

Henderson, L. E., Copeland, T. D., Sowder, R. C., Smythers, G. W., and Oroszlan, S. (1981) *J. Biol. Chem.* 256, 8400-8406

Beaucage et al., *Tetrahedron Lett* (1981) 22: 1859-1862.

Brown El., Belagaje R, Ryan M J, Khorana H G, *Methods Enzymol* (1979); 68, 109-151.

Feldman and Steg, (1996) *Medecine/Sciences, synthese,* 12, 47-55.

Houbenweyl, (1974), in *Meuthode der Organischen Chemie,* E. Wunsch Ed., Volume 15-I et 15-II, Thieme, Stuttgart.

Koch Y. (1977), *Biochem. Biophys. Res. Commun.,* 74, 488-491.

Kohler G. and Milstein C., (1975) *Nature,* 256, 495.

Kozbor et al., (1983) *Hybridoma,* 2(1), 7-16.

Leger O J, et al. (1997) *Hum Antibodies,* 8(1), 3-16.

Martineau P, Jones P, Winter G. (1998), *J Mol Biol,* 280(1), 117-127.

Merrifield R B, 1965a, *Nature,* 207(996), 522-523.

Merrifield R B, 1965b, *Nature,* 207 (996), 22-523.

Narang S A, Hsiung H M, Brousseau R, *Methods Enzymol* 1979, 68, 90-98.

Ohno et al., (1994), *Science,* 265, 781-784.

O'Reilly et al., (1992) Baculovirus expression vectors: a Laboratory Manual. W.H. Freeman and Co., New York.

Ridder R. Schmitz R, Legay F, Gram H, (1995) *Biotechnology* (NY), 13(3), 255-260.

Smith et al., (1983), *Mol. Cell. Biol.,* 3, 2156-2165.

Stemberg N. L. (1992), *Trends Genet,* 8, 1-16.

Stemberg N. L. (1994) *Mamm. Genome,* 5, 397-404.

Sambrook, J. Fritsch, E. F. and T. Maniatis (1989). Molecular cloning: a laboratory manual, 2ed. Cold Spring Harbor Laboratory, Cold Spring Harbor, N.Y.

Sanchez-Pescador R., (1988), *J. Clin. Microbiol.,* 26(10), 1934-1938.

Urdea et al., MS (1988) *Nucleic Acids Research,* 11, 4937-4957.

Urdea et al., MS (1991) *Nucleic Acids Symp Ser.,* 24, 197-200.

---

The invention claimed is:

1. An isolated calcium channel $\alpha_2\delta_2$ subunit wherein:
   (a) it is soluble and retains the functional characteristics of the full-length human $\alpha_2\delta_2$ subunit from which it derives;
   (b) its $\delta_2$ peptide has a C-terminal truncation with respect to the full-length human $\alpha_2\delta_2$ peptide, wherein said C-terminal truncation consists of SEQ ID NO: 4, SEQ ID NO: 5 or SEQ ID NO: 6; and
   (c) its $\alpha_2$ peptide comprises at least the ligand-interacting part(s) of the full-length human $\alpha_2\delta_2$ peptide from which it derives.

2. A calcium channel $\alpha_2\delta_2$ subunit according to claim 1, wherein the $\alpha_2\delta_2$ subunit is expressed in the cerebral cortical.

3. A calcium channel $\alpha_2\delta_2$ subunit according to claim 1, wherein the $\alpha_2\delta_2$ subunit is voltage-dependent.

4. A calcium channel $\alpha_2\delta_2$ subunit according to claim 1, wherein the $\alpha_2\delta_2$ subunit is cleaved.

5. A calcium channel $\alpha_2\delta_2$ subunit according to claim 1, wherein the $\alpha_2\delta_2$ subunit is cleaved into separate $\alpha_2$ and $\delta_2$ peptides.

6. A calcium channel $\alpha_2\delta_2$ subunit according to claim 1, wherein the $\alpha 2$ and $\delta_2$ peptides are disulfide-bridged.

7. A calcium channel $\alpha_2\delta_2$ subunit according to claim 1, wherein the $\alpha_2\delta_2$ subunit is not cleaved.

8. A calcium channel $\alpha_2\delta_2$ subunit according to claim 1, wherein said calcium channel is produced by a baculovirus/insect cells expression system.

9. A calcium channel $\alpha_2\delta_2$ subunit according to claim 1, characterized in that ligand is gabapentin, L-Norleucine, L-Allo-Isoleucine, L-Methionine, L-Leucine, L-Isoleucine, L-Valine, Spermine or L-Phenylalanine.

* * * * *

SEQUENCE LISTING

<160> NUMBER OF SEQ ID NOS: 55

<210> SEQ ID NO 1
<211> LENGTH: 3186
<212> TYPE: DNA
<213> ORGANISM: Homo sapiens

<400> SEQUENCE: 1

```
atggcggtgc cggctcggac ctgcggcgcc tctcggcccg gcccagcgcg gactgcgcgc      60
ccctggcccg gctgcggccc ccaccctggc cccggcaccc ggcgcccgac gtccgggccc     120
ccgcgcccgc tgtggctgct gctgccgctt ctaccgctgc tcgccgcccc cggcgcctct     180
gcctacagct tcccccagca gcacacgatg cagcactggg cccggcgtct ggagcaggag     240
gtcgacggcg tgatgcggat ttttggaggc gtccagcagc tccgtgagat ttacaaggac     300
aaccggaacc tgttcgaggt acaggagaat gagcctcaga agttggtgga gaaggtggca     360
ggggacattg agagccttct ggacaggaag gtgcaggccc tgaagagact ggctgatgct     420
gcagagaact tccagaaagc acaccgctgg caggacaaca tcaaggagga agacatcgtg     480
tactatgacg ccaaggctga cgctgagctg gacgaccctg agagtgagga tgtggaaagg     540
gggtctaagg ccagcaccct aaggctggac ttcatcgagg acccaaactt caagaacaag     600
gtcaactatt catacgcggc tgtacagatc cctacggaca tctacaaagg ctccactgtc     660
```

-continued

```
atcctcaatg agctcaactg gacagaggcc ctggagaatg tgttcatgga aaaccgcaga    720
caagacccca cactgctgtg gcaggtcttc ggcagcgcca caggagtcac tcgctactac    780
ccggccaccc cgtggcgagc ccccaagaag atcgacctgt acgatgtccg aaggagaccc    840
tggtatatcc aggggcctc gtcacccaaa gacatggtca tcatcgtgga tgtgagtggc    900
agtgtgagcg gcctgaccct gaagctgatg aagacatctg tctgcgagat gctggacacg    960
ctgtctgatg atgactatgt gaatgtggcc tcgttcaacg agaaggcaca gcctgtgtca   1020
tgcttcacac acctggtgca ggccaatgtg cgcaacaaga aggtgttcaa ggaagctgtg   1080
cagggcatgg tggccaaggg caccacaggc tacaaggccg gctttgagta tgcctttgac   1140
cagctgcaga actccaacat cactcgggcc aactgcaaca agatgatcat gatgttcacg   1200
gatggtggtg aggaccgcgt gcaggacgtc tttgagaagt acaattggcc aaaccggacg   1260
gtgcgcgtgt ttactttctc cgtggggcag cataactatg acgtcacacc gctgcagtgg   1320
atggcctgtg ccaacaaagg ctactatttt gagatcccct ccatcggagc catccgcatc   1380
aacacacagg aatatctaga tgtgttgggc aggcccatgg tgctggcagg caaggaggcc   1440
aagcaggttc agtggaccaa cgtgtatgag gatgcactgg gactggggtt ggtggtaaca   1500
gggaccctcc ctgttttcaa cctgacacag gatggccctg ggaaaagaa gaaccagctg   1560 atcctgggcg tgatgggcat tgacgtggct ctgaatgaca tcaagaggct gaccccaac    1620 tacacgcttg gagccaacgg ctatgtgttt gccattgacc tgaacggcta cgtgttgctg   1680 cacccccaatc tcaagcccca gaccaccaac ttccgggagc ctgtgactct ggacttcctg   1740
gatgcggagc tagaggatga gaacaaggaa gagatccgtc ggagcatgat tgatggcaac   1800
aagggccaca agcagatcag aacgttggtc aagtccctgg atgagaggta catagatgag   1860
gtgacacgga actacacctg ggtgcctata aggagcacta actacagcct ggggctggtg   1920 ctcccacccct acagcacctt ctacctccaa gccaatctca gtgaccagat cctgcaggtc   1980
aagtattttg agttcctgct ccccagcagc tttgagtctg aaggacacgt tttcattgct   2040
cccagagagt actgcaagga cctgaatgcc tcagacaaca caccgagtt cctgaaaaac   2100 tttattgagc tcatggagaa agtgactcca gactccaagc agtgcaacaa cttccttctg   2160
cacaacctga tcttggacac gggcatcacg cagcagctgg tagagcgtgt gtggagggac   2220
caggatctca acacgtacag cctactggcc gtgttcgctg ccacagacgg tggcatcacc   2280
cgagtcttcc ccaacaaggc agctgaggac tggacagaga ccctgagcc cttcaatgcc   2340 agcttctacc gccgcagcct ggataaccac ggttatgtct tcaagccccc acaccaggat   2400
gccctgttaa ggccgctgga gctggagaat gacactgtgg gcatcctcgt cagcacagct   2460
gtggagctca gcctaggcag gcgcacactg aggccagcag tggtgggcgt caagctggac   2520
ctagaggctt gggctgagaa gttcaaggtg ctagccagca accgtaccca ccaagaccag   2580
cctcagaagt gcggccccaa cagccactgt gagatggact gcgaggttaa caatgaggac   2640
ttactctgtg tcctcattga tgatggagga ttcctggtgc tgtcaaacca gaaccatcag   2700
tgggaccagg tgggcaggtt cttcagtgag gtggatgcca acctgatgct ggcactctac   2760
aataactcct tctacacccg caaggagtcc tatgactatc aggcagcctg tgcccctcag   2820 cccccctggca acctgggtgc tgcaccccgg ggtgtctttg tgcccaccgt tgcagatttc   2880
cttaacctgg cctggtggac ctctgctgcc gcctggtccc tgttccagca gcttctctac   2940
ggcctcatct accacagctg gttccaagca gaccccgcgg aggccgaggg gagccccgag   3000
```

-continued

| | |
|---|---|
| acgcgcgaga gcagctgcgt catgaaacag acccagtact acttcggctc ggtaaacgcc | 3060 |
| tcctacaacg ccatcatcga ctgcggaaac tgctccaggc tgttccacgc gcagagactg | 3120 |
| accaacacca atcttctctt tgtggtggcc gagaagccgc tgtgcagcca gtgcgaggct | 3180 |
| ggccgg | 3186 |

<210> SEQ ID NO 2
<211> LENGTH: 3248
<212> TYPE: DNA
<213> ORGANISM: Homo sapiens

<400> SEQUENCE: 2

| | |
|---|---|
| atggcggtgc cggctcggac ctgcggcgcc tctcggcccg cccagcgcg gactgcgcgc | 60 |
| ccctggcccg gctgcggccc ccaccctggc cccggcaccc ggcgcccgac gtccgggccc | 120 |
| ccgcgcccgc tgtggctgct gctgccgctt ctaccgctgc tcgccgcccc cggcgcctct | 180 |
| gcctacagct cccccagca gcacgcgatg cagcactggg cccggcgtct ggagcaggag | 240 |
| gtcgacggcg tgatgcggat ttttggaggc gtccagcagc tccgtgagat ttacaaggac | 300 |
| aaccggaacc tgttcgaggt acaggagaat gagcctcaga agttggtgga aaggtggca | 360 |
| ggggacattg agagccttct ggacaggaag gtgcaggccc tgaagagact ggctgatgct | 420 |
| gcagagaact tccagaaagc acaccgctgg caggacaaca tcaaggagga agacatcgtg | 480 |
| tactatgacg ccaaggctga cgctgagctg gacgaccctg agagtgagga tgtggaaagg | 540 |
| gggtctaagg ccagcaccct aaggctggac ttcatcgagg acccaaactt caagaacaag | 600 |
| gtcaactatt catacgcggc tgtacagatc cctacggaca tctacaaagg ctccactgtc | 660 |
| atcctcaatg agctcaactg gacagaggcc tggagaatg tgttcatgga aaaccgcaga | 720 |
| caagacccca cactgctgtg gcaggtcttc ggcagcgcca caggagtcac tcgctactac | 780 |
| ccggccaccc cgtggcgagc ccccaagaag atcgacctgt acgatgtccg aaggagaccc | 840 |
| tggtatatcc agggggcctc gtcacccaaa gacatggtca tcatcgtgga tgtgagtggc | 900 |
| agtgtgagcg gcctgacccc gaagctgatg aagacatctg tctgcgagat gctggacacg | 960 |
| ctgtctgatg atgactatgt gaatgtggcc tcgttcaacg agaaggcaca gcctgtgtca | 1020 |
| tgcttcacac acctggtgca ggccaatgtg cgcaacaaga aggtgttcaa ggaagctgtg | 1080 |
| cagggcatgg tggccaaggg caccacaggc tacaaggccg gctttgagta tgcctttgac | 1140 |
| cagctgcaga actccaacat cactcgggcc aactgcaaca agatgatcat gatgttcacg | 1200 |
| gatggtggtg aggaccgcgt gcaggacgtc tttgagaagt acaattggcc aaaccggacg | 1260 |
| gtgcgcgtgt ttactttctc cgtggggcag cataactatg acgtcacacc gctgcagtgg | 1320 |
| atggcctgtg ccaacaaagg ctactatttt gagatcccct ccatcggagc catccgcatc | 1380 |
| aacacacagg aatatctaga tgtgttgggc aggcccatgg tgctggcagg caaggaggcc | 1440 |
| aagcaggttc agtggaccaa cgtgtatgag gatgcactgg gactggggtt ggtggtaaca | 1500 |
| gggaccctcc ctgttttcaa cctgacacag gatggccctg ggaaaagaa gaaccagctg | 1560 |
| atcctgggcg tgacgggcat tgacgtggct ctgaatgaca tcaagaggct gaccccccaac | 1620 |
| tacacgcttg gagccaacgg ctatgtgttt gccattgacc tgaacggcta cgtgttgctg | 1680 |
| cacccccaatc tcaagcccca gaccaccaac ttccgggagc tgtgactct ggacttcctg | 1740 |
| gatgcggagc tagaggatga gaacaaggaa gagatccgtc ggagcatgat tgatggcaac | 1800 |
| aagggccaca gcagatcag aacgttggtc aagtccctgg atgagaggta catagatgag | 1860 |
| gtgacacgga actacacctg ggtgcctata aggagcacta actacagcct ggggctggtg | 1920 |

-continued

```
ctcccaccct acagcacctt ctacctccaa gccaatctca gtgaccagat cctgcaggtc     1980
aagtattttg agttcctgct ccccagcagc tttgagtctg aaggacacgt tttcattgct     2040
cccagagagt actgcaagga cctgaatgcc tcagacaaca acaccgagtt cctgaaaaac     2100
tttattgagc tcatggagaa agtgactcca gactccaagc agtgcaacaa cttccttctg     2160
cacaacctga tcttggacac gggcatcacg cagcagctgg tagagcgtgt gtggagggac     2220
caggatctca acacgtacag cctactggcc gtgttcgctg ccacagacgg tggcatcacc     2280
cgagtcttcc ccaacaaggc agctgaggac tggacagaga ccctgagcc cttcaatgcc     2340 agcttctacc gccgcagcct ggataaccac ggttatgtct tcaagccccc acaccaggat     2400
gccctgttaa ggccgctgga gctggagaat gacactgtgg catcctcgt cagcacagct     2460 gtggagctca gcctaggcag gcgcacactg aggccagcag tggtgggcgt caagctggac     2520
ctagaggctt gggctgagaa gttcaaggtg ctagccagca accgtaccca ccaagaccag     2580
cctcagaagt gcggccccaa cagccactgt gagatggact gcgaggttaa caatgaggac     2640
ttactctgtg tcctcattga tgatggagga ttcctggtgc tgtcaaacca gaaccatcag     2700
tgggaccagg tgggcaggtt cttcagtgag gtggatgcca acctgatgct ggcactctac     2760
aataactcct tctacacccg caaggagtcc tatgactatc aggcagcctg tgcccctcag     2820
ccccctggca acctgggtgc tgcaccccgg ggtgtctttg tgcccaccgt tgcagatttc     2880
cttaacctgg cctggtggac ctctgctgcc gcctggtccc tgttccagca gcttctctac     2940
ggcctcatct accacagctg gttccaagca gaccccgcgg aggccgaggg gagccccgag     3000
acgcgcgaga gcagctgcgt catgaaacag acccagtact acttcggctc ggtaaacgcc     3060
tcctacaacg ccatcatcga ctgcggaaac tgctccaggc tgttccacgc gcagagactg     3120
accaacacca atcttctctt tgtggtggcc gagaagccgc tgtgcagcca gtgcgaggct     3180
ggccggctgc tgcagaagga gacgcactgc ccagcggacg gcccggagca gtgtgagcta     3240
gtgcagag                                                             3248
```

<210> SEQ ID NO 3
<211> LENGTH: 3327
<212> TYPE: DNA
<213> ORGANISM: Homo sapiens

<400> SEQUENCE: 3

```
atggcggtgc cggctcggac ctgcggcgcc tctcggcccg gccagcgcg gactgcgcgc       60 ccctggcccg gctgcggccc ccaccctggc cccggcaccc ggcgcccgac gtccgggccc      120
ccgcgcccgc tgtggctgct gctgccgctt ctaccgctgc tcgccgcccc cggcgcctct      180
gcctacagct tcccccagca gcacacgatg cagcactggg cccggcgtct ggagcaggag      240
gtcgacggcg tgatgcggat ttttggaggc gtccagcagc tccgtgagat ttacaaggac      300
aaccggaacc tgttcgaggt acaggagaat gagcctcaga agttggtgga aggtggca       360 ggggacattg agagccttct ggacaggaag gtgcaggccc tgaagagact ggctgatgct      420
gcagagaact tccagaaagc acaccgctgg caggacaaca tcaaggagga agacatcgtg      480
tactatgacg ccaaggctga cgctgagctg acgaccctg agagtgagga tgtgaaagg        540 gggtctaagg ccagcaccct aaggctggac ttcatcgagg cccaaacttt caagaacaag      600
gtcaactatt catacgcggc tgtacagatc cctacggaca tctacaaagg ctccactgtc      660
atcctcaatg agctcaactg gacagaggcc ctggagaatg tgttcatgga aaaccgcaga      720
```

```
caagacccca cactgctgtg gcaggtcttc ggcagcgcca caggagtcac tcgctactac    780
ccggccaccc cgtggcgagc ccccaagaag atcgacctgt acgatgtccg aaggagaccc    840
tggtatatcc aggggccctc gtcacccaaa gacatggtca tcatcgtgga tgtgagtggc    900
agtgtgagcg gcctgaccct gaagctgatg aagacatctg tctgcgagat gctggacacg    960
ctgtctgatg atgactatgt gaatgtggcc tcgttcaacg agaaggcaca gcctgtgtca   1020
tgcttcacac acctggtgca ggccaatgtg cgcaacaaga aggtgttcaa ggaagctgtg   1080
cagggcatgg tggccaaggg caccacaggc tacaaggccg gctttgagta tgcctttgac   1140
cagctgcaga actccaacat cactcgggcc aactgcaaca agatgatcat gatgttcacg   1200
gatggtggtg aggaccgcgt gcaggacgtc tttgagaagt acaattggcc aaaccggacg   1260
gtgcgcgtgt ttactttctc cgtggggcag cataactatg acgtcacacc gctgcagtgg   1320
atggcctgtg ccaacaaagg ctactatttt gagatcccct tccatcggag catccgcatc   1380
aacacacagg aatatctaga tgtgttgggc aggcccatgg tgctggcagg caaggaggcc   1440
aagcaggttc agtggaccaa cgtgtatgag gatgcactgg gactgggggtt ggtggtaaca   1500
gggaccctcc ctgttttcaa cctgacacag gatggccctg gggaaaagaa gaaccagctg   1560
atcctgggcg tgatgggcat tgacgtggct ctgaatgaca tcaagaggct gaccccccaac   1620
tacacgcttg gagccaacgg ctatgtgttt gccattgacc tgaacggcta cgtgttgctg   1680
caccccaatc tcaagcccca gaccaccaac ttccgggagc ctgtgactct ggacttcctg   1740
gatgcggagc tagaggatga gaacaaggaa gagatccgtc ggagcatgat tgatggcaac   1800
aagggccaca agcagatcag aacgttggtc aagtccctgg atgagaggta catagatgag   1860
gtgacacgga actacacctg ggtgcctata aggagcacta actacagcct ggggctggtg   1920
ctcccaccct acagcacctt ctacctccaa gccaatctca gtgaccagat cctgcaggtc   1980
aagtattttg agttcctgct ccccagcagc tttgagtctg aaggacacgt tttcattgct   2040
cccagagagt actgcaagga cctgaatgcc tcagacaaca caccgagtt cctgaaaaac   2100
tttattgagc tcatggagaa agtgactcca gactccaagc agtgcaacaa cttccttctg   2160
cacaacctga tcttggacac gggcatcacg cagcagctgg tagagcgtgt gtggagggac   2220
caggatctca acacgtacag cctactggcc gtgttcgctg ccacagacgg tggcatcacc   2280
cgagtcttcc ccaacaaggc agctgaggac tggacagaga cccctgagcc cttcaatgcc   2340
agcttctacc gccgcagcct ggataaccac ggttatgtct tcaagccccc acaccaggat   2400
gccctgttaa ggccgctgga gctggagaat gacactgtgg gcatcctcgt cagcacagct   2460
gtggagctca gcctaggcag cgcacactg aggccagcag tggtgggcgt caagctggac   2520
ctagaggctt gggctgagaa gttcaaggtg ctagccagca ccgtaccca ccaagaccag   2580
cctcagaagt gcggccccaa cagccactgt gagatggact gcgaggttaa caatgaggac   2640
ttactctgtg tcctcattga tgatggagga ttcctggtgc tgtcaaacca gaaccatcag   2700
tgggaccagg tgggcaggtt cttcagtgag gtggatgcca acctgatgct ggcactctac   2760
aataactcct tctacacccg caaggagtcc tatgactatc aggcagcctg tgcccctcag   2820
ccccctggca acctgggtgc tgcaccccgg ggtgtctttg tgcccaccgt tgcagatttc   2880
cttaacctgg cctggtggac ctctgctgcc gcctggtccc tgttccagca gcttctctac   2940
ggcctcatct accacagctg gttccaagca gaccccgcgg aggccgaggg gagccccgag   3000
acgcgcgaga gcagctgcgt catgaaacag acccagtact acttcggctc ggtaaacgcc   3060
tcctacaacg ccatcatcga ctgcggaaac tgctccaggc tgttccacgc gcagagactg   3120
```

```
accaacacca atcttctctt tgtggtggcc gagaagccgc tgtgcagcca gtgcgaggct    3180
ggccggctgc tgcagaagga gacgcactgc ccagcggacg gcccggagca gtgtgagcta    3240
gtgcagagac cgcgataccg gagaggcccg cacatctgct tcgactacaa cgcgacagaa    3300
gatacctcag actgtggccg cggggcc                                        3327
```

<210> SEQ ID NO 4
<211> LENGTH: 1062
<212> TYPE: PRT
<213> ORGANISM: Homo sapiens

<400> SEQUENCE: 4

```
Met Ala Val Pro Ala Arg Thr Cys Gly Ala Ser Arg Pro Gly Pro Ala
  1               5                  10                  15

Arg Thr Ala Arg Pro Trp Pro Gly Cys Gly Pro His Pro Gly Pro Gly
                 20                  25                  30

Thr Arg Arg Pro Thr Ser Gly Pro Arg Pro Leu Trp Leu Leu Leu
         35                  40                  45

Pro Leu Leu Pro Leu Leu Ala Ala Pro Gly Ala Ser Ala Tyr Ser Phe
 50                  55                  60

Pro Gln Gln His Thr Met Gln His Trp Ala Arg Arg Leu Glu Gln Glu
 65                  70                  75                  80

Val Asp Gly Val Met Arg Ile Phe Gly Gly Val Gln Gln Leu Arg Glu
                 85                  90                  95

Ile Tyr Lys Asp Asn Arg Asn Leu Phe Glu Val Gln Glu Asn Glu Pro
                100                 105                 110

Gln Lys Leu Val Glu Lys Val Ala Gly Asp Ile Glu Ser Leu Leu Asp
            115                 120                 125

Arg Lys Val Gln Ala Leu Lys Arg Leu Ala Asp Ala Ala Glu Asn Phe
        130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
        195                 200                 205

Gln Ile Pro Thr Asp Ile Tyr Lys Gly Ser Thr Val Ile Leu Asn Glu
    210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Arg Pro Trp Tyr Ile Gln Gly Ala Ser Ser
        275                 280                 285

Pro Lys Asp Met Val Ile Ile Val Asp Val Ser Gly Ser Val Ser Gly
    290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                325                 330                 335
```

```
Gln Pro Val Ser Cys Phe Thr His Leu Val Gln Ala Asn Val Arg Asn
            340                 345                 350

Lys Lys Val Phe Lys Glu Ala Val Gln Gly Met Val Ala Lys Gly Thr
            355                 360                 365

Thr Gly Tyr Lys Ala Gly Phe Glu Tyr Ala Phe Asp Gln Leu Gln Asn
            370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
            420                 425                 430

Tyr Asp Val Thr Pro Leu Gln Trp Met Ala Cys Ala Asn Lys Gly Tyr
            435                 440                 445

Tyr Phe Glu Ile Pro Ser Ile Gly Ala Ile Arg Ile Asn Thr Gln Glu
            450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
            500                 505                 510

Pro Gly Glu Lys Lys Asn Gln Leu Ile Leu Gly Val Met Gly Ile Asp
            515                 520                 525

Val Ala Leu Asn Asp Ile Lys Arg Leu Thr Pro Asn Tyr Thr Leu Gly
530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
            565                 570                 575

Leu Asp Phe Leu Asp Ala Glu Leu Glu Asp Glu Asn Lys Glu Glu Ile
            580                 585                 590

Arg Arg Ser Met Ile Asp Gly Asn Lys Gly His Lys Gln Ile Arg Thr
            595                 600                 605

Leu Val Lys Ser Leu Asp Glu Arg Tyr Ile Asp Glu Val Thr Arg Asn
            610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
            645                 650                 655

Ile Leu Gln Val Lys Tyr Phe Glu Phe Leu Leu Pro Ser Ser Phe Glu
            660                 665                 670

Ser Glu Gly His Val Phe Ile Ala Pro Arg Glu Tyr Cys Lys Asp Leu
            675                 680                 685

Asn Ala Ser Asp Asn Asn Thr Glu Phe Leu Lys Asn Phe Ile Glu Leu
            690                 695                 700

Met Glu Lys Val Thr Pro Asp Ser Lys Gln Cys Asn Asn Phe Leu Leu
705                 710                 715                 720

His Asn Leu Ile Leu Asp Thr Gly Ile Thr Gln Gln Leu Val Glu Arg
            725                 730                 735

Val Trp Arg Asp Gln Asp Leu Asn Thr Tyr Ser Leu Leu Ala Val Phe
            740                 745                 750
```

```
Ala Ala Thr Asp Gly Gly Ile Thr Arg Val Phe Pro Asn Lys Ala Ala
        755                 760                 765
Glu Asp Trp Thr Glu Asn Pro Glu Pro Phe Asn Ala Ser Phe Tyr Arg
        770                 775                 780
Arg Ser Leu Asp Asn His Gly Tyr Val Phe Lys Pro His Gln Asp
785                 790                 795                 800
Ala Leu Leu Arg Pro Leu Glu Leu Asn Asp Thr Val Gly Ile Leu
                805                 810                 815
Val Ser Thr Ala Val Glu Leu Ser Leu Gly Arg Arg Thr Leu Arg Pro
                820                 825                 830
Ala Val Val Gly Val Lys Leu Asp Leu Glu Ala Trp Ala Glu Lys Phe
                835                 840                 845
Lys Val Leu Ala Ser Asn Arg Thr His Gln Asp Gln Pro Gln Lys Cys
        850                 855                 860
Gly Pro Asn Ser His Cys Glu Met Asp Cys Glu Val Asn Asn Glu Asp
865                 870                 875                 880
Leu Leu Cys Val Leu Ile Asp Asp Gly Gly Phe Leu Val Leu Ser Asn
                885                 890                 895
Gln Asn His Gln Trp Asp Gln Val Gly Arg Phe Phe Ser Glu Val Asp
                900                 905                 910
Ala Asn Leu Met Leu Ala Leu Tyr Asn Asn Ser Phe Tyr Thr Arg Lys
        915                 920                 925
Glu Ser Tyr Asp Tyr Gln Ala Ala Cys Ala Pro Gln Pro Gly Asn
930                 935                 940
Leu Gly Ala Ala Pro Arg Gly Val Phe Val Pro Thr Val Ala Asp Phe
945                 950                 955                 960
Leu Asn Leu Ala Trp Trp Thr Ser Ala Ala Trp Ser Leu Phe Gln
                965                 970                 975
Gln Leu Leu Tyr Gly Leu Ile Tyr His Ser Trp Phe Gln Ala Asp Pro
                980                 985                 990
Ala Glu Ala Glu Gly Ser Pro Glu Thr Arg Glu Ser Ser Cys Val Met
        995                 1000                1005
Lys Gln Thr Gln Tyr Tyr Phe Gly Ser Val Asn Ala Ser Tyr Asn Ala
    1010                1015                1020
Ile Ile Asp Cys Gly Asn Cys Ser Arg Leu Phe His Ala Gln Arg Leu
1025                1030                1035                1040
Thr Asn Thr Asn Leu Leu Phe Val Val Ala Gly Lys Pro Leu Cys Ser
                1045                1050                1055
Gln Cys Glu Ala Gly Arg
        1060

<210> SEQ ID NO 5
<211> LENGTH: 1082
<212> TYPE: PRT
<213> ORGANISM: Homo sapiens

<400> SEQUENCE: 5

Met Ala Val Pro Ala Arg Thr Cys Gly Ala Ser Arg Pro Gly Pro Ala
1               5                   10                  15
Arg Thr Ala Arg Pro Trp Pro Gly Cys Gly Pro His Pro Gly Pro Gly
                20                  25                  30
Thr Arg Arg Pro Thr Ser Gly Pro Arg Pro Leu Trp Leu Leu Leu
                35                  40                  45
Pro Leu Leu Pro Leu Leu Ala Ala Pro Gly Ala Ser Ala Tyr Ser Phe
        50                  55                  60
```

-continued

```
Pro Gln Gln His Thr Met Gln His Trp Ala Arg Arg Leu Glu Gln Glu
65                  70                  75                  80

Val Asp Gly Val Met Arg Ile Phe Gly Gly Val Gln Gln Leu Arg Glu
                85                  90                  95

Ile Tyr Lys Asp Asn Arg Asn Leu Phe Glu Val Gln Glu Asn Glu Pro
            100                 105                 110

Gln Lys Leu Val Glu Lys Val Ala Gly Asp Ile Glu Ser Leu Leu Asp
        115                 120                 125

Arg Lys Val Gln Ala Leu Lys Arg Leu Ala Asp Ala Ala Glu Asn Phe
    130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
        195                 200                 205

Gln Ile Pro Thr Asp Ile Tyr Lys Gly Ser Thr Val Ile Leu Asn Glu
    210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Pro Trp Tyr Ile Gln Gly Ala Ser Ser
        275                 280                 285

Pro Lys Asp Met Val Ile Ile Val Asp Val Ser Gly Ser Val Ser Gly
    290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                325                 330                 335

Gln Pro Val Ser Cys Phe Thr His Leu Val Gln Ala Asn Val Arg Asn
            340                 345                 350

Lys Lys Val Phe Lys Glu Ala Val Gln Gly Met Val Ala Lys Gly Thr
        355                 360                 365

Thr Gly Tyr Lys Ala Gly Phe Glu Tyr Ala Phe Asp Gln Leu Gln Asn
    370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
            420                 425                 430

Tyr Asp Val Thr Pro Leu Gln Trp Met Ala Cys Ala Asn Lys Gly Tyr
        435                 440                 445

Tyr Phe Glu Ile Pro Ser Ile Gly Ala Ile Arg Ile Asn Thr Gln Glu
    450                 455                 460

Tyr Leu Asp Val Leu Gly Arg Pro Met Val Leu Ala Gly Lys Glu Ala
465                 470                 475                 480
```

```
Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
                500                 505                 510

Pro Gly Glu Lys Lys Asn Gln Leu Ile Leu Gly Val Met Gly Ile Asp
                515                 520                 525

Val Ala Leu Asn Asp Ile Lys Arg Leu Thr Pro Asn Tyr Thr Leu Gly
530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
                565                 570                 575

Leu Asp Phe Leu Asp Ala Glu Leu Glu Asp Glu Asn Lys Glu Glu Ile
                580                 585                 590

Arg Arg Ser Met Ile Asp Gly Asn Lys Gly His Lys Gln Ile Arg Thr
                595                 600                 605

Leu Val Lys Ser Leu Asp Glu Arg Tyr Ile Asp Glu Val Thr Arg Asn
                610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
                645                 650                 655

Ile Leu Gln Val Lys Tyr Phe Glu Phe Leu Leu Pro Ser Ser Phe Glu
                660                 665                 670

Ser Glu Gly His Val Phe Ile Ala Pro Arg Glu Tyr Cys Lys Asp Leu
                675                 680                 685

Asn Ala Ser Asp Asn Asn Thr Glu Phe Leu Lys Asn Phe Ile Glu Leu
                690                 695                 700

Met Glu Lys Val Thr Pro Asp Ser Lys Gln Cys Asn Asn Phe Leu Leu
705                 710                 715                 720

His Asn Leu Ile Leu Asp Thr Gly Ile Thr Gln Gln Leu Val Glu Arg
                725                 730                 735

Val Trp Arg Asp Gln Asp Leu Asn Thr Tyr Ser Leu Leu Ala Val Phe
                740                 745                 750

Ala Ala Thr Asp Gly Gly Ile Thr Arg Val Phe Pro Asn Lys Ala Ala
                755                 760                 765

Glu Asp Trp Thr Glu Asn Pro Glu Pro Phe Asn Ala Ser Phe Tyr Arg
770                 775                 780

Arg Ser Leu Asp Asn His Gly Tyr Val Phe Lys Pro Pro His Gln Asp
785                 790                 795                 800

Ala Leu Leu Arg Pro Leu Glu Leu Glu Asn Asp Thr Val Gly Ile Leu
                805                 810                 815

Val Ser Thr Ala Val Glu Leu Ser Leu Gly Arg Arg Thr Leu Arg Pro
                820                 825                 830

Ala Val Val Gly Val Lys Leu Asp Leu Glu Ala Trp Ala Glu Lys Phe
                835                 840                 845

Lys Val Leu Ala Ser Asn Arg Thr His Gln Asp Gln Pro Gln Lys Cys
850                 855                 860

Gly Pro Asn Ser His Cys Glu Met Asp Cys Glu Val Asn Asn Glu Asp
865                 870                 875                 880

Leu Leu Cys Val Leu Ile Asp Asp Gly Gly Phe Leu Val Leu Ser Asn
                885                 890                 895

Gln Asn His Gln Trp Asp Gln Val Gly Arg Phe Phe Ser Glu Val Asp
```

-continued

```
                900               905                910
Ala Asn Leu Met Leu Ala Leu Tyr Asn Asn Ser Phe Tyr Thr Arg Lys
        915                 920                 925

Glu Ser Tyr Asp Tyr Gln Ala Ala Cys Ala Pro Gln Pro Pro Gly Asn
        930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Trp Ser Leu Phe Gln
                965                 970                 975

Gln Leu Leu Tyr Gly Leu Ile Tyr His Ser Trp Phe Gln Ala Asp Pro
            980                 985                 990

Ala Glu Ala Glu Gly Ser Pro Glu Thr Arg Glu Ser Ser Cys Val Met
        995                1000                1005

Lys Gln Thr Gln Tyr Tyr Phe Gly Ser Val Asn Ala Ser Tyr Asn Ala
        1010                1015                1020

Ile Ile Asp Cys Gly Asn Cys Ser Arg Leu Phe His Ala Gln Arg Leu
1025                1030                1035                1040

Thr Asn Thr Asn Leu Leu Phe Val Val Ala Glu Lys Pro Leu Cys Ser
                1045                1050                1055

Gln Cys Glu Ala Gly Arg Leu Leu Gln Lys Glu Thr His Cys Pro Ala
            1060                1065                1070

Asp Gly Pro Glu Gln Cys Glu Leu Val Gln
        1075                1080
```

<210> SEQ ID NO 6
<211> LENGTH: 1109
<212> TYPE: PRT
<213> ORGANISM: Homo sapiens

<400> SEQUENCE: 6

```
Met Ala Val Pro Ala Arg Thr Cys Gly Ala Ser Arg Pro Gly Pro Ala
1               5                  10                  15

Arg Thr Ala Arg Pro Trp Pro Gly Cys Gly Pro His Pro Gly Pro Gly
            20                  25                  30

Thr Arg Arg Pro Thr Ser Gly Pro Pro Arg Pro Leu Trp Leu Leu Leu
        35                  40                  45

Pro Leu Leu Pro Leu Leu Ala Ala Pro Gly Ala Ser Ala Tyr Ser Phe
50                  55                  60

Pro Gln Gln His Thr Met Gln His Trp Ala Arg Arg Leu Glu Gln Glu
65                  70                  75                  80

Val Asp Gly Val Met Arg Ile Phe Gly Gly Val Gln Gln Leu Arg Glu
                85                  90                  95

Ile Tyr Lys Asp Asn Arg Asn Leu Phe Glu Val Gln Glu Asn Glu Pro
            100                 105                 110

Gln Lys Leu Val Glu Lys Val Ala Gly Asp Ile Glu Ser Leu Leu Asp
        115                 120                 125

Arg Lys Val Gln Ala Leu Lys Arg Leu Ala Asp Ala Glu Asn Phe
        130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Pro Glu Ser Glu
                165                 170                 175

Asp Val Glu Arg Gly Ser Lys Ala Ser Thr Leu Arg Leu Asp Phe Ile
            180                 185                 190
```

-continued

```
Glu Asp Pro Asn Phe Lys Asn Lys Val Asn Tyr Ser Tyr Ala Ala Val
    195                 200                 205

Gln Ile Pro Thr Asp Ile Tyr Lys Gly Ser Thr Val Ile Leu Asn Glu
    210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Pro Trp Tyr Ile Gln Gly Ala Ser Ser
    275                 280                 285

Pro Lys Asp Met Val Ile Ile Val Asp Val Ser Gly Ser Val Ser Gly
    290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                325                 330                 335

Gln Pro Val Ser Cys Phe Thr His Leu Val Gln Ala Asn Val Arg Asn
            340                 345                 350

Lys Lys Val Phe Lys Glu Ala Val Gln Gly Met Val Ala Lys Gly Thr
    355                 360                 365

Thr Gly Tyr Lys Ala Gly Phe Glu Tyr Ala Phe Asp Gln Leu Gln Asn
    370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
            420                 425                 430

Tyr Asp Val Thr Pro Leu Gln Trp Met Ala Cys Ala Asn Lys Gly Tyr
    435                 440                 445

Tyr Phe Glu Ile Pro Ser Ile Gly Ala Ile Arg Ile Asn Thr Gln Glu
    450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
            500                 505                 510

Pro Gly Glu Lys Lys Asn Gln Leu Ile Leu Gly Val Met Gly Ile Asp
    515                 520                 525

Val Ala Leu Asn Asp Ile Lys Arg Leu Thr Pro Asn Tyr Thr Leu Gly
    530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
                565                 570                 575

Leu Asp Phe Leu Asp Ala Glu Leu Glu Asp Glu Asn Lys Glu Glu Ile
            580                 585                 590

Arg Arg Ser Met Ile Asp Gly Asn Lys Gly His Lys Gln Ile Arg Thr
    595                 600                 605

Leu Val Lys Ser Leu Asp Glu Arg Tyr Ile Asp Glu Val Thr Arg Asn
```

-continued

```
                610                 615                 620
Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
                645                 650                 655

Ile Leu Gln Val Lys Tyr Phe Glu Phe Leu Pro Ser Ser Phe Glu
                660                 665                 670

Ser Glu Gly His Val Phe Ile Ala Pro Arg Glu Tyr Cys Lys Asp Leu
                675                 680                 685

Asn Ala Ser Asp Asn Asn Thr Glu Phe Leu Lys Asn Phe Ile Glu Leu
690                 695                 700

Met Glu Lys Val Thr Pro Asp Ser Lys Gln Cys Asn Asn Phe Leu Leu
705                 710                 715                 720

His Asn Leu Ile Leu Asp Thr Gly Ile Thr Gln Gln Leu Val Glu Arg
                725                 730                 735

Val Trp Arg Asp Gln Asp Leu Asn Thr Tyr Ser Leu Leu Ala Val Phe
                740                 745                 750

Ala Ala Thr Asp Gly Gly Ile Thr Arg Val Phe Pro Asn Lys Ala Ala
                755                 760                 765

Glu Asp Trp Thr Glu Asn Pro Glu Pro Phe Asn Ala Ser Phe Tyr Arg
770                 775                 780

Arg Ser Leu Asp Asn His Gly Tyr Val Phe Lys Pro Pro His Gln Asp
785                 790                 795                 800

Ala Leu Leu Arg Pro Leu Glu Leu Glu Asn Asp Thr Val Gly Ile Leu
                805                 810                 815

Val Ser Thr Ala Val Glu Leu Ser Leu Gly Arg Arg Thr Leu Arg Pro
                820                 825                 830

Ala Val Val Gly Val Lys Leu Asp Leu Glu Ala Trp Ala Glu Lys Phe
                835                 840                 845

Lys Val Leu Ala Ser Asn Arg Thr His Gln Asp Gln Pro Gln Lys Cys
850                 855                 860

Gly Pro Asn Ser His Cys Glu Met Asp Cys Glu Val Asn Asn Glu Asp
865                 870                 875                 880

Leu Leu Cys Val Leu Ile Asp Asp Gly Gly Phe Leu Val Leu Ser Asn
                885                 890                 895

Gln Asn His Gln Trp Asp Gln Val Gly Arg Phe Phe Ser Glu Val Asp
                900                 905                 910

Ala Asn Leu Met Leu Ala Leu Tyr Asn Asn Ser Phe Tyr Thr Arg Lys
                915                 920                 925

Glu Ser Tyr Asp Tyr Gln Ala Ala Cys Ala Pro Gln Pro Gly Asn
930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Trp Ser Leu Phe Gln
                965                 970                 975

Gln Leu Leu Tyr Gly Leu Ile Tyr His Ser Trp Phe Gln Ala Asp Pro
                980                 985                 990

Ala Glu Ala Glu Gly Ser Pro Glu Thr Arg Glu Ser Ser Cys Val Met
                995                 1000                1005

Lys Gln Thr Gln Tyr Tyr Phe Gly Ser Val Asn Ala Ser Tyr Asn Ala
    1010                1015                1020

Ile Ile Asp Cys Gly Asn Cys Ser Arg Leu Phe His Ala Gln Arg Leu
1025                1030                1035                1040
```

```
Thr Asn Thr Asn Leu Leu Phe Val Val Ala Glu Lys Pro Leu Cys Ser
            1045                1050                1055
Gln Cys Glu Ala Gly Arg Leu Leu Gln Lys Glu Thr His Cys Pro Ala
        1060                1065                1070
Asp Gly Pro Glu Gln Cys Glu Leu Val Gln Arg Pro Arg Tyr Arg Arg
    1075                1080                1085
Gly Pro His Ile Cys Phe Asp Tyr Asn Ala Thr Glu Asp Thr Ser Asp
  1090                1095                1100
Cys Gly Arg Gly Ala
1105

<210> SEQ ID NO 7
<211> LENGTH: 3057
<212> TYPE: DNA
<213> ORGANISM: Homo sapiens

<400> SEQUENCE: 7
atggccgggc cgggctcgcc gcgccgcgcg tcccgggggg cctcggcgct tctcgctgcc    60
gcgcttctct acgccgcgct gggggacgtg gtgcgctcgg agcagcagat accgctctcc   120
gtggtgaagc tctgggcctc ggcttttggt ggggagataa aatccattgc tgctaagtac   180
tccggttccc agcttctgca aaagaaatac aaagagtatg agaaagacgt tgccatagaa   240
gaaattgatg cctccaact ggtaaagaag ctggcaaaga catggaaga gatgtttcac    300 aagaagtctg aggccgtcag gcgtctggtg gaggctgcag aagaagcaca cctgaaacat   360
gaatttgatg cagacttaca gtatgaatac ttcaatgctg tgctgataaa tgaaagggac   420
aaagacggga atttttggga gctgggaaag gaattcatct tagccccaaa tgaccatttt   480
aataatttgc ctgtgaacat cagtctaagt gacgtccaag taccaacgaa catgtacaac   540
aaagaccctg caattgtcaa tggggtttat tggtctgaat ctctaaacaa gttttttgta   600
gataactttg accgtgaccc atctctcata tggcagtact ttggaagtgc aaagggcttt   660
tttaggcagt atccggggat taaatgggaa ccagatgaga atggagtcat tgccttcgac   720
tgcaggaacc gaaatggta catccaggca gcaacttctc cgaaagacgt ggtcatttta   780
gttgacgtca gtggcagcat gaaaggactc cgtctgacta tcgcgaagca aacagtctca   840 tccatttttgg atacacttgg ggatgatgac ttcttcaaca taattgctta taatgaggag   900
cttcactatg tggaaccttg cctgaatgga actttggtgc aagccgacag gacaaacaaa   960
gagcacttca gggagcatct ggacaaactt ttcgccaaag gaattggaat gttggatata  1020
gctctgaatg aggccttcaa cattctgagt gatttcaacc acacgggaca aggaagtatc  1080
tgcagtcagg ccatcatgct cataactgat ggggcggtgg acacctatga tacaatctttt  1140 gcaaaataca attggccaga tcgaaaggtt cgcatcttca catacctcat ggacgagag   1200 gctgcgtttg cagacaatct aaagtggatg gcctgtgcca acaaggatt ttttacccag   1260 atctccacct ggctgatgt gcaggagaat gtcatggaat ccttcacgt gcttagccgg   1320 cccaaagtca tcgaccagga gcatgatgtg tgtggaccg aagcttacat tgacagcact   1380
ctgactgatg atcagggccc cgtcctgatg accactgtag ccatgcctgt gtttagtaag   1440
cagaacgaaa ccagatcgaa gggcattctt ctgggagtgg ttggcacaga tgtcccagtg   1500
aaagaacttc tgaagaccat ccccaaatac aagttaggga ttcacggtta tgcctttgca   1560
atcacaaata tatggrtatat cctgacgcat ccggaactca ggctgctgta cgaagaagga  1620
aaaaagcgaa ggaaacctaa ctatagtagc gttgacctct ctgaggtgga gtgggaagac  1680
```

| | |
|---|---|
| cgagatgacg tgttgagaaa tgctatggtg aatcgaaaga cggggaagtt ttccatggag | 1740 |
| gtgaagaaga cagtggacaa agggaaacgg ttttggtga tgacaaatga ctactattat | 1800 |
| acagacatca agggtactcc tttcagttta ggtgtggcgc tttccagagg tcatgggaaa | 1860 |
| tatttcttcc gagggaatgt aaccatcgaa gaaggcctgc atgacttaga acatcccgat | 1920 |
| gtgtccttgg cagatgaatg gtcctactgc aacactgacc tacaccctga gcaccgccat | 1980 |
| ctgtctcagt tagaagcgat taagctctac ctaaaaggca agaacctct gctccagtgt | 2040 |
| gataaagaat tgatccaaga agtccttttt gacgcggtgg tgagtgcccc cattgaagcg | 2100 |
| tattggacca gcctggccct caacaaatct gaaaattctg acaagggcgt ggaggttgcc | 2160 |
| ttcctcggca ctcgcacggg cctctccaga atcaacctgt ttgtcggggc tgagcagctc | 2220 |
| accaatcagg acttcctgaa agctggcgac aaggagaaca tttttaacgc agaccatttc | 2280 |
| cctctctggt accgaagagc cgctgagcag attccaggga gcttcgtcta ctcgatccca | 2340 |
| ttcagcactg gaccagtcaa taaaagcaat gtggtgacag caagtacatc catccagctc | 2400 |
| ctggatgaac ggaaatctcc tgtggtggca gctgtaggca ttcagatgaa acttgaattt | 2460 |
| ttccaaagga agttctggac tgccagcaga cagtgtgctt ccctggatgg caaatgctcc | 2520 |
| atcagctgtg atgatgagac tgtgaattgt tacctcatag acaataatgg atttattttg | 2580 |
| gtgtctgaag actacacaca gactggagac ttttttggtg agatcgaggg agctgtgatg | 2640 |
| aacaaattgc taacaatggg ctcctttaaa agaattaccc tttatgacta ccaagccatg | 2700 |
| tgtagagcca acaaggaaag cagcgatggc gcccatggcc tcctggatcc ttataatgcc | 2760 |
| ttcctctctg cagtaaaatg gatcatgaca gaacttgtct tgttcctggt ggaatttaac | 2820 |
| ctctgcagtt ggtggcactc cgatatgaca gctaaagccc agaaattgaa acagaccctg | 2880 |
| gagccttgtg atactgaata tccagcattc gtctctgagc gcaccatcaa ggagactaca | 2940 |
| gggaatattg cttgtgaaga ctgctccaag tcctttgtca tccagcaaat cccaagcagc | 3000 |
| aacctgttca tggtggtggt ggacagcagc tgcctctgtg aatctgtggc ccccatc | 3057 |

<210> SEQ ID NO 8
<211> LENGTH: 3114
<212> TYPE: DNA
<213> ORGANISM: Homo sapiens

<400> SEQUENCE: 8

| | |
|---|---|
| atggccgggc cgggctcgcc gcgccgcgcg tcccgggggg cctcggcgct ttctcgctgcc | 60 |
| gcgcttctct acgccgcgct gggggacgtg gtgcgctcgg agcagcagat accgctctcc | 120 |
| gtggtgaagc tctgggcctc ggcttttggt ggggagataa aatccattgc tgctaagtac | 180 |
| tccggttccc agcttctgca aaagaaatac aaagagtatg agaaagacgt tgccatagaa | 240 |
| gaaattgatg gcctccaact ggtaaagaag ctggcaaaga acatggaaga gatgtttcac | 300 |
| aagaagtctg aggccgtcag gcgtctggtg gaggctgcag aagaagcaca cctgaaacat | 360 |
| gaatttgatg cagacttaca gtatgaatac ttcaatgctg tgctgataaa tgaaagggac | 420 |
| aaagacggga attttttgga gctgggaaag gaattcatct tagccccaaa tgaccatttt | 480 |
| aataatttgc ctgtgaacat cagtctaagt gacgtccaag taccaacgaa catgtacaac | 540 |
| aaagaccctg caattgtcaa tggggtttat tggtctgaat ctctaaacaa agttttttgta | 600 |
| gataactttg accgtgaccc atctctcata tggcagtact ttggaagtgc aaagggcttt | 660 |
| tttaggcagt atccggggat taaatgggaa ccagatgaga atggagtcat tgccttcgac | 720 |

```
tgcaggaacc gaaaatggta catccaggca gcaacttctc cgaaagacgt ggtcatttta    780
gttgacgtca gtggcagcat gaaaggactc cgtctgacta tcgcgaagca aacagtctca    840
tccattttgg atacacttgg ggatgatgac ttcttcaaca taattgctta taatgaggag    900
cttcactatg tggaaccttg cctgaatgga actttggtgc aagccgacag gacaaacaaa    960
gagcacttca gggagcatct ggacaaactt ttcgccaaag gaattggaat gttggatata   1020
gctctgaatg aggccttcaa cattctgagt gatttcaacc acacgggaca aggaagtatc   1080
tgcagtcagg ccatcatgct cataactgat ggggcggtgg acacctatga tacaatcttt   1140
gcaaaataca attggccaga tcgaaaggtt cgcatcttca catacctcat tggacgagag   1200
gctgcgtttg cagacaatct aaagtggatg gcctgtgcca acaaaggatt ttttacccag   1260
atctccacct ggctgatgt gcaggagaat gtcatgaat accttcacgt gcttagccgg   1320
cccaaagtca tcgaccagga gcatgatgtg tgtgtggaccg aagcttacat tgacagcact   1380
ctgactgatg atcagggccc cgtcctgatg accactgtag ccatgcctgt gtttagtaag   1440
cagaacgaaa ccagatcgaa gggcattctt ctgggagtgg ttggcacaga tgtcccagtg   1500
aaagaacttc tgaagaccat ccccaaatac aagttaggga ttcacggtta tgcctttgca   1560
atcacaaata atggrtatat cctgacgcat ccggaactca ggctgctgta cgaagaagga   1620
aaaaagcgaa ggaaacctaa ctatagtagc gttgacctct ctgaggtgga gtgggaagac   1680
cgagatgacg tgttgagaaa tgctatggtg aatcgaaaga cggggaagtt ttccatggag   1740
gtgaagaaga cagtggacaa agggaaacgg ttttggtga tgacaaatga ctactattat   1800
acagacatca agggtactcc tttcagttta ggtgtggcgc tttccagagg tcatgggaaa   1860
tatttcttcc gagggaatgt aaccatcgaa gaaggcctgc atgacttaga acatcccgat   1920
gtgtccttgg cagatgaatg gtcctactgc aacactgacc tacaccctga gcaccgccat   1980
ctgtctcagt tagaagcgat taagctctac ctaaaaggca aagaacctct gctccagtgt   2040
gataaagaat tgatccaaga agtccttttt gacgcggtgg tgagtgcccc cattgaagcg   2100
tattggacca gcctggccct caacaaatct gaaaattctg acaagggcgt ggaggttgcc   2160
ttcctcggca ctcgcacggg cctctccaga atcaacctgt ttgtcggggc tgagcagctc   2220
accaatcagg acttcctgaa agctggcgac aaggagaaca tttttaacgc agaccatttc   2280
cctctctggt accgaagagc cgctgagcag attccaggga gcttcgtcta ctcgatccca   2340
ttcagcactg gaccagtcaa taaaagcaat gtggtgacag caagtacatc catccagctc   2400
ctggatgaac ggaaatctcc tgtggtggca gctgtaggca ttcagatgaa acttgaattt   2460
ttccaaagga agttctggac tgccagcaga cagtgtgctt ccctggatgg caaatgctcc   2520
atcagctgtg atgatgagac tgtgaattgt tacctcatag acaataatgg atttatttg   2580
gtgtctgaag actacacaca gactggagac tttttggtg agatcgaggg agctgtgatg   2640
aacaaattgc taacaatggg ctcctttaaa agaattaccc tttatgacta ccaagccatg   2700
tgtagagcca acaaggaaag cagcgatggc gcccatggcc tcctggatcc ttataatgcc   2760
ttcctctctg cagtaaaatg gatcatgaca gaacttgtct tgttcctggt ggaatttaac   2820
ctctgcagtt ggtggcactc cgatatgaca gctaaagccc agaaattgaa acagaccctg   2880
gagccttgtg atactgaata tccagcattc gtctctgagc gcaccatcaa ggagactaca   2940
gggaatattg cttgtgaaga ctgctccaag tcctttgtca tccagcaaat cccaagcagc   3000
aacctgttca tggtggtggt ggacagcagc tgcctctgtg aatctgtggc ccccatcacc   3060
atggcaccca ttgaaatcag gtataatgaa tcccttaagt gtgaacgtct aaag        3114
```

<210> SEQ ID NO 9
<211> LENGTH: 3213
<212> TYPE: DNA
<213> ORGANISM: Homo sapiens

<400> SEQUENCE: 9

| | | | | | |
|---|---|---|---|---|---|
| atggccgggc | cgggctcgcc | cgccgcgcg | tcccgggggg | cctcggcgct | tctcgctgcc | 60 |
| gcgcttctct | acgccgcgct | ggggacgtg | gtgcgctcgg | agcagcagat | accgctctcc | 120 |
| gtggtgaagc | tctgggcctc | ggcttttggt | ggggagataa | aatccattgc | tgctaagtac | 180 |
| tccggttccc | agcttctgca | aaagaaatac | aaagagtatg | agaaagacgt | tgccatagaa | 240 |
| gaaattgatg | gcctccaact | ggtaaagaag | ctggcaaaga | acatggaaga | gatgtttcac | 300 |
| aagaagtctg | aggccgtcag | gcgtctggtg | gaggctgcag | aagaagcaca | cctgaaacat | 360 |
| gaatttgatg | cagacttaca | gtatgaatac | ttcaatgctg | tgctgataaa | tgaaagggac | 420 |
| aaagacggga | atttttttgga | gctgggaaag | gaattcatct | tagccccaaa | tgaccatttt | 480 |
| aataatttgc | ctgtgaacat | cagtctaagt | gacgtccaag | taccaacgaa | catgtacaac | 540 |
| aaagaccctg | caattgtcaa | tggggtttat | tggtctgaat | ctctaaacaa | agttttttgta | 600 |
| gataactttg | accgtgaccc | atctctcata | tggcagtact | ttggaagtgc | aaagggcttt | 660 |
| tttaggcagt | atccggggat | taaatgggaa | ccagatgaga | atggagtcat | tgccttcgac | 720 |
| tgcaggaacc | gaaaatggta | catccaggca | gcaacttctc | gaaagacgt | ggtcatttta | 780 |
| gttgacgtca | gtgcagcat | gaaaggactc | cgtctgacta | tcgcgaagca | aacagtctca | 840 |
| tccattttgg | atacacttgg | ggatgatgac | ttcttcaaca | taattgctta | taatgaggag | 900 |
| cttcactatg | tggaaccttg | cctgaatgga | actttggtgc | aagccgacag | gacaaacaaa | 960 |
| gagcacttca | gggagcatct | ggacaaactt | ttcgccaaag | gaattggaat | gttggatata | 1020 |
| gctctgaatg | aggccttcaa | cattctgagt | gatttcaacc | acacgggaca | aggaagtatc | 1080 |
| tgcagtcagg | ccatcatgct | cataactgat | ggggcggtgg | acacctatga | tacaatctttt | 1140 |
| gcaaaataca | attggccaga | tcgaaaggtt | cgcatcttca | catacctcat | tggacgagag | 1200 |
| gctgcgtttg | cagacaatct | aaagtggatg | gcctgtgcca | acaaaggatt | ttttacccag | 1260 |
| atctccacct | tggctgatgt | gcaggagaat | gtcatggaat | accttcacgt | gcttagccgg | 1320 |
| cccaaagtca | tcgaccagga | gcatgatgtg | tgtgtggaccg | aagcttacat | tgacagcact | 1380 |
| ctgactgatg | atcagggccc | cgtcctgatg | accactgtag | ccatgcctgt | gtttagtaag | 1440 |
| cagaacgaaa | ccagatcgaa | gggcattctt | ctgggagtgg | ttggcacaga | tgtcccagtg | 1500 |
| aaagaacttc | tgaagaccat | ccccaaatac | aagttaggga | ttcacggtta | tgcctttgca | 1560 |
| atcacaaata | atggrtatat | cctgacgcat | ccggaactca | ggctgctgta | cgaagaagga | 1620 |
| aaaaagcgaa | ggaaacctaa | ctatagtagc | gttgacctct | ctgaggtgga | gtgggaagac | 1680 |
| cgagatgacg | tgttgagaaa | tgctatggtg | aatcgaaaga | cggggaagtt | ttccatggag | 1740 |
| gtgaagaaga | cagtggacaa | agggaaacgg | ttttggtga | tgacaaatga | ctactattat | 1800 |
| acagacatca | agggtactcc | tttcagttta | ggtgtggcgc | tttccagagg | tcatgggaaa | 1860 |
| tatttcttcc | gagggaatgt | aaccatcgaa | gaaggcctgc | atgacttaga | acatcccgat | 1920 |
| gtgtccttgg | cagatgaatg | gtcctactgc | aacactgacc | tacaccctga | gcaccgccat | 1980 |
| ctgtctcagt | tagaagcgat | taagctctac | ctaaaaggca | aagaacctct | gctccagtgt | 2040 |
| gataaagaat | tgatccaaga | agtcctttttt | gacgcggtgg | tgagtgcccc | cattgaagcg | 2100 |

-continued

```
tattggacca gcctggccct caacaaatct gaaaattctg acaagggcgt ggaggttgcc      2160
ttcctcggca ctcgcacggg cctctccaga atcaacctgt tgtcggggc tgagcagctc       2220 accaatcagg acttcctgaa agctggcgac aaggagaaca ttttaacgc agaccatttc       2280 cctctctggt accgaagagc cgctgagcag attccaggga gcttcgtcta ctcgatccca     2340
ttcagcactg gaccagtcaa taaaagcaat gtggtgacag caagtacatc catccagctc    2400
ctggatgaac ggaaatctcc tgtggtggca gctgtaggca ttcagatgaa acttgaattt    2460
ttccaaagga agttctggac tgccagcaga cagtgtgctt ccctggatgg caaatgctcc    2520
atcagctgtg atgatgagac tgtgaattgt tacctcatag acaataatgg atttattttg    2580
gtgtctgaag actacacaca gactggagac tttttggtg agatcgaggg agctgtgatg     2640
aacaaattgc taacaatggg ctcctttaaa agaattaccc tttatgacta ccaagccatg    2700
tgtagagcca acaaggaaag cagcgatggc gcccatggcc tcctggatcc ttataatgcc   2760
ttcctctctg cagtaaaatg gatcatgaca gaacttgtct tgttcctggt ggaatttaac    2820
ctctgcagtt ggtggcactc cgatatgaca gctaaagccc agaaattgaa acagaccctg    2880
gagccttgtg atactgaata tccagcattc gtctctgagc gcaccatcaa ggagactaca    2940
gggaatattg cttgtgaaga ctgctccaag tcctttgtca tccagcaaat cccaagcagc    3000
aacctgttca tggtggtggt ggacagcagc tgcctctgtg aatctgtggc ccccatcacc    3060
atggcaccca ttgaaatcag gtataatgaa tcccttaagt gtgaacgtct aaaggcccag   3120
aagatcagaa gggcccagaa gatcagaagg cgcccagaat cttgtcatgg cttccatcct   3180
gaggagaatg caagggagtg tgggggtgcg ccg                                 3213
```

<210> SEQ ID NO 10
<211> LENGTH: 1019
<212> TYPE: PRT
<213> ORGANISM: Homo sapiens

<400> SEQUENCE: 10

```
Met Ala Gly Pro Gly Ser Pro Arg Arg Ala Ser Arg Gly Ala Ser Ala
 1               5                  10                  15

Leu Leu Ala Ala Ala Leu Leu Tyr Ala Ala Leu Gly Asp Val Val Arg
                20                  25                  30

Ser Glu Gln Gln Ile Pro Leu Ser Val Val Lys Leu Trp Ala Ser Ala
         35                  40                  45

Phe Gly Gly Glu Ile Lys Ser Ile Ala Ala Lys Tyr Ser Gly Ser Gln
     50                  55                  60

Leu Leu Gln Lys Lys Tyr Lys Glu Tyr Glu Lys Asp Val Ala Ile Glu
 65                  70                  75                  80

Glu Ile Asp Gly Leu Gln Leu Val Lys Lys Leu Ala Lys Asn Met Glu
                 85                  90                  95

Glu Met Phe His Lys Lys Ser Glu Ala Val Arg Arg Leu Val Glu Ala
                100                 105                 110

Ala Glu Glu Ala His Leu Lys His Glu Phe Asp Ala Asp Leu Gln Tyr
            115                 120                 125

Glu Tyr Phe Asn Ala Val Leu Ile Asn Glu Arg Asp Lys Asp Gly Asn
        130                 135                 140

Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr
                165                 170                 175
```

-continued

```
Asn Met Tyr Asn Lys Asp Pro Ala Ile Val Asn Gly Val Tyr Trp Ser
        180                 185                 190
Glu Ser Leu Asn Lys Val Phe Val Asp Asn Phe Asp Arg Asp Pro Ser
            195                 200                 205
Leu Ile Trp Gln Tyr Phe Gly Ser Ala Lys Gly Phe Phe Arg Gln Tyr
        210                 215                 220
Pro Gly Ile Lys Trp Glu Pro Asp Glu Asn Gly Val Ile Ala Phe Asp
225                 230                 235                 240
Cys Arg Asn Arg Lys Trp Tyr Ile Gln Ala Ala Thr Ser Pro Lys Asp
                245                 250                 255
Val Val Ile Leu Val Asp Val Ser Gly Ser Met Lys Gly Leu Arg Leu
            260                 265                 270
Thr Ile Ala Lys Gln Thr Val Ser Ser Ile Leu Asp Thr Leu Gly Asp
        275                 280                 285
Asp Asp Phe Phe Asn Ile Ile Ala Tyr Asn Glu Glu Leu His Tyr Val
290                 295                 300
Glu Pro Cys Leu Asn Gly Thr Leu Val Gln Ala Asp Arg Thr Asn Lys
305                 310                 315                 320
Glu His Phe Arg Glu His Leu Asp Lys Leu Phe Ala Lys Gly Ile Gly
                325                 330                 335
Met Leu Asp Ile Ala Leu Asn Glu Ala Phe Asn Ile Leu Ser Asp Phe
            340                 345                 350
Asn His Thr Gly Gln Gly Ser Ile Cys Ser Gln Ala Ile Met Leu Ile
        355                 360                 365
Thr Asp Gly Ala Val Asp Thr Tyr Asp Thr Ile Phe Ala Lys Tyr Asn
370                 375                 380
Trp Pro Asp Arg Lys Val Arg Ile Phe Thr Tyr Leu Ile Gly Arg Glu
385                 390                 395                 400
Ala Ala Phe Ala Asp Asn Leu Lys Trp Met Ala Cys Ala Asn Lys Gly
                405                 410                 415
Phe Phe Thr Gln Ile Ser Thr Leu Ala Asp Val Gln Glu Asn Val Met
            420                 425                 430
Glu Tyr Leu His Val Leu Ser Arg Pro Lys Val Ile Asp Gln Glu His
        435                 440                 445
Asp Val Val Trp Thr Glu Ala Tyr Ile Asp Ser Thr Leu Thr Asp Asp
450                 455                 460
Gln Gly Pro Val Leu Met Thr Thr Val Ala Met Pro Val Phe Ser Lys
465                 470                 475                 480
Gln Asn Glu Thr Arg Ser Lys Gly Ile Leu Leu Gly Val Val Gly Thr
                485                 490                 495
Asp Val Pro Val Lys Glu Leu Leu Lys Thr Ile Pro Lys Tyr Lys Leu
            500                 505                 510
Gly Ile His Gly Tyr Ala Phe Ala Ile Thr Asn Asn Gly Tyr Ile Leu
        515                 520                 525
Thr His Pro Glu Leu Arg Leu Leu Tyr Glu Glu Gly Lys Lys Arg Arg
530                 535                 540
Lys Pro Asn Tyr Ser Ser Val Asp Leu Ser Glu Val Glu Trp Glu Asp
545                 550                 555                 560
Arg Asp Asp Val Leu Arg Asn Ala Met Val Asn Arg Lys Thr Gly Lys
                565                 570                 575
Phe Ser Met Glu Val Lys Lys Thr Val Asp Lys Gly Lys Arg Val Leu
            580                 585                 590
Val Met Thr Asn Asp Tyr Tyr Tyr Thr Asp Ile Lys Gly Thr Pro Phe
```

-continued

```
                595                 600                 605
Ser Leu Gly Val Ala Leu Ser Arg Gly His Gly Lys Tyr Phe Phe Arg
            610                 615                 620
Gly Asn Val Thr Ile Glu Glu Gly Leu His Asp Leu Glu His Pro Asp
625                 630                 635                 640
Val Ser Leu Ala Asp Glu Trp Ser Tyr Cys Asn Thr Asp Leu His Pro
                645                 650                 655
Glu His Arg His Leu Ser Gln Leu Glu Ala Ile Lys Leu Tyr Leu Lys
            660                 665                 670
Gly Lys Glu Pro Leu Leu Gln Cys Asp Lys Glu Leu Ile Gln Glu Val
            675                 680                 685
Leu Phe Asp Ala Val Val Ser Ala Pro Ile Glu Ala Tyr Trp Thr Ser
            690                 695                 700
Leu Ala Leu Asn Lys Ser Glu Asn Ser Asp Lys Gly Val Glu Val Ala
705                 710                 715                 720
Phe Leu Gly Thr Arg Thr Gly Leu Ser Arg Ile Asn Leu Phe Val Gly
                725                 730                 735
Ala Glu Gln Leu Thr Asn Gln Asp Phe Leu Lys Ala Gly Asp Lys Glu
            740                 745                 750
Asn Ile Phe Asn Ala Asp His Phe Pro Leu Trp Tyr Arg Arg Ala Ala
            755                 760                 765
Glu Gln Ile Pro Gly Ser Phe Val Tyr Ser Ile Pro Phe Ser Thr Gly
            770                 775                 780
Pro Val Asn Lys Ser Asn Val Val Thr Ala Ser Thr Ser Ile Gln Leu
785                 790                 795                 800
Leu Asp Glu Arg Lys Ser Pro Val Val Ala Ala Val Gly Ile Gln Met
                805                 810                 815
Lys Leu Glu Phe Phe Gln Arg Lys Phe Trp Thr Ala Ser Arg Gln Cys
            820                 825                 830
Ala Ser Leu Asp Gly Lys Cys Ser Ile Ser Cys Asp Asp Glu Thr Val
            835                 840                 845
Asn Cys Tyr Leu Ile Asp Asn Asn Gly Phe Ile Leu Val Ser Glu Asp
850                 855                 860
Tyr Thr Gln Thr Gly Asp Phe Phe Gly Glu Ile Glu Gly Ala Val Met
865                 870                 875                 880
Asn Lys Leu Leu Thr Met Gly Ser Phe Lys Arg Ile Thr Leu Tyr Asp
                885                 890                 895
Tyr Gln Ala Met Cys Arg Ala Asn Lys Glu Ser Ser Asp Gly Ala His
            900                 905                 910
Gly Leu Leu Asp Pro Tyr Asn Ala Phe Leu Ser Ala Val Lys Trp Ile
            915                 920                 925
Met Thr Glu Leu Val Leu Phe Leu Val Glu Phe Asn Leu Cys Ser Trp
            930                 935                 940
Trp His Ser Asp Met Thr Ala Lys Ala Gln Lys Leu Lys Gln Thr Leu
945                 950                 955                 960
Glu Pro Cys Asp Thr Glu Tyr Pro Ala Phe Val Ser Glu Arg Thr Ile
                965                 970                 975
Lys Glu Thr Thr Gly Asn Ile Ala Cys Glu Asp Cys Ser Lys Ser Phe
            980                 985                 990
Val Ile Gln Gln Ile Pro Ser Ser Asn Leu Phe Met Val Val Val Asp
            995                 1000                1005
Ser Ser Cys Leu Cys Glu Ser Val Ala Pro Ile
     1010                1015
```

<210> SEQ ID NO 11
<211> LENGTH: 1038
<212> TYPE: PRT
<213> ORGANISM: Homo sapiens

<400> SEQUENCE: 11

```
Met Ala Gly Pro Gly Ser Pro Arg Arg Ala Ser Arg Gly Ala Ser Ala
 1               5                   10                  15

Leu Leu Ala Ala Ala Leu Leu Tyr Ala Ala Leu Gly Asp Val Val Arg
            20                  25                  30

Ser Glu Gln Gln Ile Pro Leu Ser Val Val Lys Leu Trp Ala Ser Ala
        35                  40                  45

Phe Gly Gly Glu Ile Lys Ser Ile Ala Ala Lys Tyr Ser Gly Ser Gln
    50                  55                  60

Leu Leu Gln Lys Lys Tyr Lys Glu Tyr Glu Lys Asp Val Ala Ile Glu
65                  70                  75                  80

Glu Ile Asp Gly Leu Gln Leu Val Lys Lys Leu Ala Lys Asn Met Glu
                85                  90                  95

Glu Met Phe His Lys Lys Ser Glu Ala Val Arg Arg Leu Val Glu Ala
            100                 105                 110

Ala Glu Glu Ala His Leu Lys His Glu Phe Asp Ala Asp Leu Gln Tyr
        115                 120                 125

Glu Tyr Phe Asn Ala Val Leu Ile Asn Glu Arg Asp Lys Asp Gly Asn
    130                 135                 140

Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr
                165                 170                 175

Asn Met Tyr Asn Lys Asp Pro Ala Ile Val Asn Gly Val Tyr Trp Ser
            180                 185                 190

Glu Ser Leu Asn Lys Val Phe Val Asp Asn Phe Asp Arg Asp Pro Ser
        195                 200                 205

Leu Ile Trp Gln Tyr Phe Gly Ser Ala Lys Gly Phe Phe Arg Gln Tyr
    210                 215                 220

Pro Gly Ile Lys Trp Glu Pro Asp Glu Asn Gly Val Ile Ala Phe Asp
225                 230                 235                 240

Cys Arg Asn Arg Lys Trp Tyr Ile Gln Ala Ala Thr Ser Pro Lys Asp
                245                 250                 255

Val Val Ile Leu Val Asp Val Ser Gly Ser Met Lys Gly Leu Arg Leu
            260                 265                 270

Thr Ile Ala Lys Gln Thr Val Ser Ser Ile Leu Asp Thr Leu Gly Asp
        275                 280                 285

Asp Asp Phe Phe Asn Ile Ile Ala Tyr Asn Glu Glu Leu His Tyr Val
    290                 295                 300

Glu Pro Cys Leu Asn Gly Thr Leu Val Gln Ala Asp Arg Thr Asn Lys
305                 310                 315                 320

Glu His Phe Arg Glu His Leu Asp Lys Leu Phe Ala Lys Gly Ile Gly
                325                 330                 335

Met Leu Asp Ile Ala Leu Asn Glu Ala Phe Asn Ile Leu Ser Asp Phe
            340                 345                 350

Asn His Thr Gly Gln Gly Ser Ile Cys Ser Gln Ala Ile Met Leu Ile
        355                 360                 365

Thr Asp Gly Ala Val Asp Thr Tyr Asp Thr Ile Phe Ala Lys Tyr Asn
```

-continued

```
            370                 375                 380
Trp Pro Asp Arg Lys Val Arg Ile Phe Thr Tyr Leu Ile Gly Arg Glu
385                 390                 395                 400

Ala Ala Phe Ala Asp Asn Leu Lys Trp Met Ala Cys Ala Asn Lys Gly
                405                 410                 415

Phe Phe Thr Gln Ile Ser Thr Leu Ala Asp Val Gln Glu Asn Val Met
                420                 425                 430

Glu Tyr Leu His Val Leu Ser Arg Pro Lys Val Ile Asp Gln Glu His
            435                 440                 445

Asp Val Val Trp Thr Glu Ala Tyr Ile Asp Ser Thr Leu Thr Asp Asp
        450                 455                 460

Gln Gly Pro Val Leu Met Thr Thr Val Ala Met Pro Val Phe Ser Lys
465                 470                 475                 480

Gln Asn Glu Thr Arg Ser Lys Gly Ile Leu Leu Gly Val Val Gly Thr
                485                 490                 495

Asp Val Pro Val Lys Glu Leu Leu Lys Thr Ile Pro Lys Tyr Lys Leu
                500                 505                 510

Gly Ile His Gly Tyr Ala Phe Ala Ile Thr Asn Asn Gly Tyr Ile Leu
            515                 520                 525

Thr His Pro Glu Leu Arg Leu Leu Tyr Glu Glu Gly Lys Lys Arg Arg
        530                 535                 540

Lys Pro Asn Tyr Ser Ser Val Asp Leu Ser Glu Val Glu Trp Glu Asp
545                 550                 555                 560

Arg Asp Asp Val Leu Arg Asn Ala Met Val Asn Arg Lys Thr Gly Lys
                565                 570                 575

Phe Ser Met Glu Val Lys Lys Thr Val Asp Lys Gly Lys Arg Val Leu
                580                 585                 590

Val Met Thr Asn Asp Tyr Tyr Tyr Thr Asp Ile Lys Gly Thr Pro Phe
            595                 600                 605

Ser Leu Gly Val Ala Leu Ser Arg Gly His Gly Lys Tyr Phe Phe Arg
        610                 615                 620

Gly Asn Val Thr Ile Glu Glu Gly Leu His Asp Leu Glu His Pro Asp
625                 630                 635                 640

Val Ser Leu Ala Asp Glu Trp Ser Tyr Cys Asn Thr Asp Leu His Pro
                645                 650                 655

Glu His Arg His Leu Ser Gln Leu Glu Ala Ile Lys Leu Tyr Leu Lys
                660                 665                 670

Gly Lys Glu Pro Leu Leu Gln Cys Asp Lys Glu Leu Ile Gln Glu Val
            675                 680                 685

Leu Phe Asp Ala Val Val Ser Ala Pro Ile Glu Ala Tyr Trp Thr Ser
        690                 695                 700

Leu Ala Leu Asn Lys Ser Glu Asn Ser Asp Lys Gly Val Glu Val Ala
705                 710                 715                 720

Phe Leu Gly Thr Arg Thr Gly Leu Ser Arg Ile Asn Leu Phe Val Gly
                725                 730                 735

Ala Glu Gln Leu Thr Asn Gln Asp Phe Leu Lys Ala Gly Asp Lys Glu
                740                 745                 750

Asn Ile Phe Asn Ala Asp His Phe Pro Leu Trp Tyr Arg Arg Ala Ala
            755                 760                 765

Glu Gln Ile Pro Gly Ser Phe Val Tyr Ser Ile Pro Phe Ser Thr Gly
        770                 775                 780

Pro Val Asn Lys Ser Asn Val Val Thr Ala Ser Thr Ser Ile Gln Leu
785                 790                 795                 800
```

-continued

```
Leu Asp Glu Arg Lys Ser Pro Val Ala Ala Val Gly Ile Gln Met
            805                 810                 815

Lys Leu Glu Phe Phe Gln Arg Lys Phe Trp Thr Ala Ser Arg Gln Cys
        820                 825                 830

Ala Ser Leu Asp Gly Lys Cys Ser Ile Ser Cys Asp Asp Glu Thr Val
        835                 840                 845

Asn Cys Tyr Leu Ile Asp Asn Asn Gly Phe Ile Leu Val Ser Glu Asp
        850                 855                 860

Tyr Thr Gln Thr Gly Asp Phe Phe Gly Glu Ile Glu Gly Ala Val Met
865                 870                 875                 880

Asn Lys Leu Leu Thr Met Gly Ser Phe Lys Arg Ile Thr Leu Tyr Asp
                885                 890                 895

Tyr Gln Ala Met Cys Arg Ala Asn Lys Glu Ser Ser Asp Gly Ala His
                900                 905                 910

Gly Leu Leu Asp Pro Tyr Asn Ala Phe Leu Ser Ala Val Lys Trp Ile
                915                 920                 925

Met Thr Glu Leu Val Leu Phe Leu Val Glu Phe Asn Leu Cys Ser Trp
        930                 935                 940

Trp His Ser Asp Met Thr Ala Lys Ala Gln Lys Leu Lys Gln Thr Leu
945                 950                 955                 960

Glu Pro Cys Asp Thr Glu Tyr Pro Ala Phe Val Ser Glu Arg Thr Ile
                965                 970                 975

Lys Glu Thr Thr Gly Asn Ile Ala Cys Glu Asp Cys Ser Lys Ser Phe
                980                 985                 990

Val Ile Gln Gln Ile Pro Ser Ser Asn Leu Phe Met Val Val Asp
            995                 1000                1005

Ser Ser Cys Leu Cys Glu Ser Val Ala Pro Ile Thr Met Ala Pro Ile
    1010                1015                1020

Glu Ile Arg Tyr Asn Glu Ser Leu Lys Cys Glu Arg Leu Lys
1025                1030                1035
```

<210> SEQ ID NO 12
<211> LENGTH: 1065
<212> TYPE: PRT
<213> ORGANISM: Homo sapiens

<400> SEQUENCE: 12

```
Met Ala Gly Pro Gly Ser Pro Arg Arg Ala Ser Arg Gly Ala Ser Ala
  1               5                  10                  15

Leu Leu Ala Ala Ala Leu Leu Tyr Ala Ala Leu Gly Asp Val Val Arg
                20                  25                  30

Ser Glu Gln Gln Ile Pro Leu Ser Val Val Lys Leu Trp Ala Ser Ala
            35                  40                  45

Phe Gly Gly Glu Ile Lys Ser Ile Ala Ala Lys Tyr Ser Gly Ser Gln
        50                  55                  60

Leu Leu Gln Lys Lys Tyr Lys Glu Tyr Glu Lys Asp Val Ala Ile Glu
65                  70                  75                  80

Glu Ile Asp Gly Leu Gln Leu Val Lys Lys Leu Ala Lys Asn Met Glu
                85                  90                  95

Glu Met Phe His Lys Lys Ser Glu Ala Val Arg Arg Leu Val Glu Ala
                100                 105                 110

Ala Glu Glu Ala His Leu Lys His Glu Phe Asp Ala Asp Leu Gln Tyr
            115                 120                 125

Glu Tyr Phe Asn Ala Val Leu Ile Asn Glu Arg Asp Lys Asp Gly Asn
```

-continued

```
            130                 135                 140
Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr
                165                 170                 175

Asn Met Tyr Asn Lys Asp Pro Ala Ile Val Asn Gly Val Tyr Trp Ser
                180                 185                 190

Glu Ser Leu Asn Lys Val Phe Val Asp Asn Phe Asp Arg Asp Pro Ser
                195                 200                 205

Leu Ile Trp Gln Tyr Phe Gly Ser Ala Lys Gly Phe Phe Arg Gln Tyr
210                 215                 220

Pro Gly Ile Lys Trp Glu Pro Asp Glu Asn Gly Val Ile Ala Phe Asp
225                 230                 235                 240

Cys Arg Asn Arg Lys Trp Tyr Ile Gln Ala Ala Thr Ser Pro Lys Asp
                245                 250                 255

Val Val Ile Leu Val Asp Val Ser Gly Ser Met Lys Gly Leu Arg Leu
                260                 265                 270

Thr Ile Ala Lys Gln Thr Val Ser Ser Ile Leu Asp Thr Leu Gly Asp
                275                 280                 285

Asp Asp Phe Phe Asn Ile Ile Ala Tyr Asn Glu Glu Leu His Tyr Val
                290                 295                 300

Glu Pro Cys Leu Asn Gly Thr Leu Val Gln Ala Asp Arg Thr Asn Lys
305                 310                 315                 320

Glu His Phe Arg Glu His Leu Asp Lys Leu Phe Ala Lys Gly Ile Gly
                325                 330                 335

Met Leu Asp Ile Ala Leu Asn Glu Ala Phe Asn Ile Leu Ser Asp Phe
                340                 345                 350

Asn His Thr Gly Gln Gly Ser Ile Cys Ser Gln Ala Ile Met Leu Ile
                355                 360                 365

Thr Asp Gly Ala Val Asp Thr Tyr Asp Thr Ile Phe Ala Lys Tyr Asn
                370                 375                 380

Trp Pro Asp Arg Lys Val Arg Ile Phe Thr Tyr Leu Ile Gly Arg Glu
385                 390                 395                 400

Ala Ala Phe Ala Asp Asn Leu Lys Trp Met Ala Cys Ala Asn Lys Gly
                405                 410                 415

Phe Phe Thr Gln Ile Ser Thr Leu Ala Asp Val Gln Glu Asn Val Met
                420                 425                 430

Glu Tyr Leu His Val Leu Ser Arg Pro Lys Val Ile Asp Gln Glu His
                435                 440                 445

Asp Val Val Trp Thr Glu Ala Tyr Ile Asp Ser Thr Leu Thr Asp Asp
450                 455                 460

Gln Gly Pro Val Leu Met Thr Thr Val Ala Met Pro Val Phe Ser Lys
465                 470                 475                 480

Gln Asn Glu Thr Arg Ser Lys Gly Ile Leu Leu Gly Val Val Gly Thr
                485                 490                 495

Asp Val Pro Val Lys Glu Leu Leu Lys Thr Ile Pro Lys Tyr Lys Leu
                500                 505                 510

Gly Ile His Gly Tyr Ala Phe Ala Ile Thr Asn Asn Gly Tyr Ile Leu
                515                 520                 525

Thr His Pro Glu Leu Arg Leu Leu Tyr Glu Glu Gly Lys Lys Arg Arg
                530                 535                 540

Lys Pro Asn Tyr Ser Ser Val Asp Leu Ser Glu Val Glu Trp Glu Asp
545                 550                 555                 560
```

```
Arg Asp Asp Val Leu Arg Asn Ala Met Val Asn Arg Lys Thr Gly Lys
                565                 570                 575

Phe Ser Met Glu Val Lys Lys Thr Val Asp Lys Gly Lys Arg Val Leu
                580                 585                 590

Val Met Thr Asn Asp Tyr Tyr Thr Asp Ile Lys Gly Thr Pro Phe
                595                 600             605

Ser Leu Gly Val Ala Leu Ser Arg Gly His Gly Lys Tyr Phe Phe Arg
        610                 615                 620

Gly Asn Val Thr Ile Glu Glu Gly Leu His Asp Leu Glu His Pro Asp
625                 630                 635                 640

Val Ser Leu Ala Asp Glu Trp Ser Tyr Cys Asn Thr Asp Leu His Pro
                645                 650                 655

Glu His Arg His Leu Ser Gln Leu Glu Ala Ile Lys Leu Tyr Leu Lys
                660                 665                 670

Gly Lys Glu Pro Leu Leu Gln Cys Asp Lys Glu Leu Ile Gln Glu Val
            675                 680                 685

Leu Phe Asp Ala Val Val Ser Ala Pro Ile Glu Ala Tyr Trp Thr Ser
690                 695                 700

Leu Ala Leu Asn Lys Ser Glu Asn Ser Asp Lys Gly Val Glu Val Ala
705                 710                 715                 720

Phe Leu Gly Thr Arg Thr Gly Leu Ser Arg Ile Asn Leu Phe Val Gly
                725                 730                 735

Ala Glu Gln Leu Thr Asn Gln Asp Phe Leu Lys Ala Gly Asp Lys Glu
                740                 745                 750

Asn Ile Phe Asn Ala Asp His Phe Pro Leu Trp Tyr Arg Arg Ala Ala
            755                 760                 765

Glu Gln Ile Pro Gly Ser Phe Val Tyr Ser Ile Pro Phe Ser Thr Gly
            770                 775                 780

Pro Val Asn Lys Ser Asn Val Val Thr Ala Ser Thr Ser Ile Gln Leu
785                 790                 795                 800

Leu Asp Glu Arg Lys Ser Pro Val Val Ala Val Gly Ile Gln Met
                805                 810                 815

Lys Leu Glu Phe Phe Gln Arg Lys Phe Trp Thr Ala Ser Arg Gln Cys
                820                 825                 830

Ala Ser Leu Asp Gly Lys Cys Ser Ile Ser Cys Asp Asp Glu Thr Val
            835                 840                 845

Asn Cys Tyr Leu Ile Asp Asn Asn Gly Phe Ile Leu Val Ser Glu Asp
850                 855                 860

Tyr Thr Gln Thr Gly Asp Phe Phe Gly Glu Ile Glu Gly Ala Val Met
865                 870                 875                 880

Asn Lys Leu Leu Thr Met Gly Ser Phe Lys Arg Ile Thr Leu Tyr Asp
                885                 890                 895

Tyr Gln Ala Met Cys Arg Ala Asn Lys Glu Ser Ser Asp Gly Ala His
            900                 905                 910

Gly Leu Leu Asp Pro Tyr Asn Ala Phe Leu Ser Ala Val Lys Trp Ile
            915                 920                 925

Met Thr Glu Leu Val Leu Phe Leu Val Glu Phe Asn Leu Cys Ser Trp
            930                 935                 940

Trp His Ser Asp Met Thr Ala Lys Ala Gln Lys Leu Lys Gln Thr Leu
945                 950                 955                 960

Glu Pro Cys Asp Thr Glu Tyr Pro Ala Phe Val Ser Glu Arg Thr Ile
                965                 970                 975
```

-continued

```
Lys Glu Thr Thr Gly Asn Ile Ala Cys Glu Asp Cys Ser Lys Ser Phe
            980                 985                 990
Val Ile Gln Gln Ile Pro Ser Ser Asn Leu Phe Met Val Val Asp
        995                 1000                1005
Ser Ser Cys Leu Cys Glu Ser Val Ala Pro Ile Thr Met Ala Pro Ile
    1010                1015                1020
Glu Ile Arg Tyr Asn Glu Ser Leu Lys Cys Glu Arg Leu Lys Ala Gln
1025                1030                1035                1040
Lys Ile Arg Arg Arg Pro Glu Ser Cys His Gly Phe His Pro Glu Glu
                1045                1050                1055
Asn Ala Arg Glu Cys Gly Gly Ala Pro
            1060                1065
```

<210> SEQ ID NO 13
<211> LENGTH: 912
<212> TYPE: DNA
<213> ORGANISM: Homo sapiens

<400> SEQUENCE: 13

| | |
|---|---|
| agtggcctcc tgagaagcag cttgttcgtg ggctccgaga aggtctccga caggaagttc | 60 |
| ctgacacctg aggacgaggc cagcgtgttc accctggacc gcttcccgct gtggtaccgc | 120 |
| caggcctcag agcatcctgc tggcagcttc gtcttcaacc tccgctgggc agaaggacca | 180 |
| gaaagtgcgg gtgaacccat ggtggtgacg gcaagcacag ctgtggcggt gaccgtggac | 240 |
| aagaggacag ccattgctgc agccgcgggc gtccaaatga agctggaatt cctccagcgc | 300 |
| aaattctggg cggcaacgcg gcagtgcagc actgtggatg ggccgtgcac acagagctgc | 360 |
| gaggacagtg atctggactg cttcgtcatc gacaacaacg ggttcattct gatctccaag | 420 |
| aggtcccgag agacgggaag atttctgggg gaggtggatg tgctgtcct gacccagctg | 480 |
| ctcagcatgg gggtgttcag ccaagtgact atgtatgact atcaggccat gtgcaaaccc | 540 |
| tcgagtcacc accacagtgc agcccagccc ctggtcagcc caatttctgc cttcttgacg | 600 |
| gcgaccaggt ggctgctgca ggagctggtg ctgttcctgc tggagtggag tgtctggggc | 660 |
| tcctggtacg acagagggc cgaggccaaa agtgtcttcc atcactccca caaacacaag | 720 |
| aagcaggacc cgctgcagcc ctgcgacacg gagtaccccg tgttcgtgta ccagccggcc | 780 |
| atccgggagg ccaacgggat cgtggagtgc gggccctgcc agaaggtatt tgtggtgcag | 840 |
| cagattccca acagtaacct cctcctcctg gtgacagacc ccacctgtga ctgcagcatc | 900 |
| ttcccaccag tg | 912 |

<210> SEQ ID NO 14
<211> LENGTH: 969
<212> TYPE: DNA
<213> ORGANISM: Homo sapiens

<400> SEQUENCE: 14

| | |
|---|---|
| agtggcctcc tgagaagcag cttgttcgtg ggctccgaga aggtctccga caggaagttc | 60 |
| ctgacacctg aggacgaggc cagcgtgttc accctggacc gcttcccgct gtggtaccgc | 120 |
| caggcctcag agcatcctgc tggcagcttc gtcttcaacc tccgctgggc agaaggacca | 180 |
| gaaagtgcgg gtgaacccat ggtggtgacg gcaagcacag ctgtggcggt gaccgtggac | 240 |
| aagaggacag ccattgctgc agccgcgggc gtccaaatga agctggaatt cctccagcgc | 300 |
| aaattctggg cggcaacgcg gcagtgcagc actgtggatg ggccgtgcac acagagctgc | 360 |
| gaggacagtg atctggactg cttcgtcatc gacaacaacg ggttcattct gatctccaag | 420 |

```
aggtcccgag agacgggaag atttctgggg gaggtggatg gtgctgtcct gacccagctg      480
ctcagcatgg gggtgttcag ccaagtgact atgtatgact atcaggccat gtgcaaaccc      540
tcgagtcacc accacagtgc agcccagccc tggtcagcc  caatttctgc cttcttgacg      600
gcgaccaggt ggctgctgca ggagctggtg ctgttcctgc tggagtggag tgtctggggc      660
tcctggtacg acagagggc  cgaggccaaa agtgtcttcc atcactccca caaacacaag      720
aagcaggacc cgctgcagcc ctgcgacacg gagtacccccg tgttcgtgta ccagccggcc     780
atccgggagg ccaacgggat cgtggagtgc gggccctgcc agaaggtatt tgtggtgcag      840
cagattccca acagtaacct cctcctcctg gtgacagacc ccacctgtga ctgcagcatc      900
ttcccaccag tgctgcagga ggcgacagaa gtcaaatata atgcctctgt caaatgtgac      960
cggatgcgc                                                              969

<210> SEQ ID NO 15
<211> LENGTH: 1050
<212> TYPE: DNA
<213> ORGANISM: Homo sapiens

<400> SEQUENCE: 15
agtggcctcc tgagaagcag cttgttcgtg ggctccgaga aggtctccga caggaagttc       60
ctgacacctg aggacgaggc cagcgtgttc accctggacc gcttcccgct gtggtaccgc      120
caggcctcag agcatcctgc tggcagcttc gtcttcaacc tccgctgggc agaaggacca      180
gaaagtgcgg gtgaacccat ggtggtgacg gcaagcacag ctgtggcggt gaccgtggac      240
aagaggacag ccattgctgc agccgcgggc gtccaaatga agctggaatt cctccagcgc      300
aaattctggg cggcaacgcg gcagtgcagc actgtggatg ggccgtgcac acagagctgc      360
gaggacagtg atctggactg cttcgtcatc gacaacaacg ggttcattct gatctccaag      420
aggtcccgag agacgggaag atttctgggg gaggtggatg gtgctgtcct gacccagctg      480
ctcagcatgg gggtgttcag ccaagtgact atgtatgact atcaggccat gtgcaaaccc      540
tcgagtcacc accacagtgc agcccagccc tggtcagcc  caatttctgc cttcttgacg      600
gcgaccaggt ggctgctgca ggagctggtg ctgttcctgc tggagtggag tgtctggggc      660
tcctggtacg acagagggc  cgaggccaaa agtgtcttcc atcactccca caaacacaag      720
aagcaggacc cgctgcagcc ctgcgacacg gagtacccccg tgttcgtgta ccagccggcc     780
atccgggagg ccaacgggat cgtggagtgc gggccctgcc agaaggtatt tgtggtgcag      840
cagattccca acagtaacct cctcctcctg gtgacagacc ccacctgtga ctgcagcatc      900
ttcccaccag tgctgcagga ggcgacagaa gtcaaatata atgcctctgt caaatgtgac      960
cggatgcgct cccagaagct ccgccggcga ccagactcct gccacgcctt ccatccagag     1020
gagaatgccc aggactgcgg cggcgcctcg                                      1050

<210> SEQ ID NO 16
<211> LENGTH: 304
<212> TYPE: PRT
<213> ORGANISM: Homo sapiens

<400> SEQUENCE: 16

Ser Gly Leu Leu Arg Ser Ser Leu Phe Val Gly Ser Glu Lys Val Ser
 1               5                  10                  15

Asp Arg Lys Phe Leu Thr Pro Glu Asp Glu Ala Ser Val Phe Thr Leu
            20                  25                  30
```

-continued

```
Asp Arg Phe Pro Leu Trp Tyr Arg Gln Ala Ser Glu His Pro Ala Gly
         35                  40                  45

Ser Phe Val Phe Asn Leu Arg Trp Ala Glu Gly Pro Glu Ser Ala Gly
 50                  55                  60

Glu Pro Met Val Val Thr Ala Ser Thr Ala Val Ala Val Thr Val Asp
 65                  70                  75                  80

Lys Arg Thr Ala Ile Ala Ala Ala Gly Val Gln Met Lys Leu Glu
                 85                  90                  95

Phe Leu Gln Arg Lys Phe Trp Ala Ala Thr Arg Gln Cys Ser Thr Val
                100                 105                 110

Asp Gly Pro Cys Thr Gln Ser Cys Glu Asp Ser Asp Leu Asp Cys Phe
            115                 120                 125

Val Ile Asp Asn Asn Gly Phe Ile Leu Ile Ser Lys Arg Ser Arg Glu
130                 135                 140

Thr Gly Arg Phe Leu Gly Glu Val Asp Gly Ala Val Leu Thr Gln Leu
145                 150                 155                 160

Leu Ser Met Gly Val Phe Ser Gln Val Thr Met Tyr Asp Tyr Gln Ala
                165                 170                 175

Met Cys Lys Pro Ser Ser His His His Ser Ala Ala Gln Pro Leu Val
                180                 185                 190

Ser Pro Ile Ser Ala Phe Leu Thr Ala Thr Arg Trp Leu Leu Gln Glu
            195                 200                 205

Leu Val Leu Phe Leu Leu Glu Trp Ser Val Trp Gly Ser Trp Tyr Asp
210                 215                 220

Arg Gly Ala Glu Ala Lys Ser Val Phe His His Ser His Lys His Lys
225                 230                 235                 240

Lys Gln Asp Pro Leu Gln Pro Cys Asp Thr Glu Tyr Pro Val Phe Val
                245                 250                 255

Tyr Gln Pro Ala Ile Arg Glu Ala Asn Gly Ile Val Glu Cys Gly Pro
                260                 265                 270

Cys Gln Lys Val Phe Val Val Gln Gln Ile Pro Asn Ser Asn Leu Leu
            275                 280                 285

Leu Leu Val Thr Asp Pro Thr Cys Asp Cys Ser Ile Phe Pro Pro Val
290                 295                 300
```

<210> SEQ ID NO 17
<211> LENGTH: 323
<212> TYPE: PRT
<213> ORGANISM: Homo sapiens

<400> SEQUENCE: 17

```
Ser Gly Leu Leu Arg Ser Ser Leu Phe Val Gly Ser Glu Lys Val Ser
 1               5                  10                  15

Asp Arg Lys Phe Leu Thr Pro Glu Asp Glu Ala Ser Val Phe Thr Leu
                 20                  25                  30

Asp Arg Phe Pro Leu Trp Tyr Arg Gln Ala Ser Glu His Pro Ala Gly
         35                  40                  45

Ser Phe Val Phe Asn Leu Arg Trp Ala Glu Gly Pro Glu Ser Ala Gly
 50                  55                  60

Glu Pro Met Val Val Thr Ala Ser Thr Ala Val Ala Val Thr Val Asp
 65                  70                  75                  80

Lys Arg Thr Ala Ile Ala Ala Ala Gly Val Gln Met Lys Leu Glu
                 85                  90                  95

Phe Leu Gln Arg Lys Phe Trp Ala Ala Thr Arg Gln Cys Ser Thr Val
                100                 105                 110
```

-continued

```
Asp Gly Pro Cys Thr Gln Ser Cys Glu Asp Ser Asp Leu Asp Cys Phe
            115                 120                 125

Val Ile Asp Asn Asn Gly Phe Ile Leu Ile Ser Lys Arg Ser Arg Glu
    130                 135                 140

Thr Gly Arg Phe Leu Gly Glu Val Asp Gly Ala Val Leu Thr Gln Leu
145                 150                 155                 160

Leu Ser Met Gly Val Phe Ser Gln Val Thr Met Tyr Asp Tyr Gln Ala
                165                 170                 175

Met Cys Lys Pro Ser Ser His His Ser Ala Ala Gln Pro Leu Val
            180                 185                 190

Ser Pro Ile Ser Ala Phe Leu Thr Ala Thr Arg Trp Leu Leu Gln Glu
            195                 200                 205

Leu Val Leu Phe Leu Leu Glu Trp Ser Val Trp Gly Ser Trp Tyr Asp
    210                 215                 220

Arg Gly Ala Glu Ala Lys Ser Val Phe His His Ser His Lys His Lys
225                 230                 235                 240

Lys Gln Asp Pro Leu Gln Pro Cys Asp Thr Glu Tyr Pro Val Phe Val
                245                 250                 255

Tyr Gln Pro Ala Ile Arg Glu Ala Asn Gly Ile Val Glu Cys Gly Pro
                260                 265                 270

Cys Gln Lys Val Phe Val Val Gln Gln Ile Pro Asn Ser Asn Leu Leu
                275                 280                 285

Leu Leu Val Thr Asp Pro Thr Cys Asp Cys Ser Ile Phe Pro Pro Val
            290                 295                 300

Leu Gln Glu Ala Thr Glu Val Lys Tyr Asn Ala Ser Val Lys Cys Asp
305                 310                 315                 320

Arg Met Arg
```

<210> SEQ ID NO 18
<211> LENGTH: 350
<212> TYPE: PRT
<213> ORGANISM: Homo sapiens

<400> SEQUENCE: 18

```
Ser Gly Leu Leu Arg Ser Ser Leu Phe Val Gly Ser Glu Lys Val Ser
  1               5                  10                  15

Asp Arg Lys Phe Leu Thr Pro Glu Asp Glu Ala Ser Val Phe Thr Leu
                 20                  25                  30

Asp Arg Phe Pro Leu Trp Tyr Arg Gln Ala Ser Glu His Pro Ala Gly
             35                  40                  45

Ser Phe Val Phe Asn Leu Arg Trp Ala Glu Gly Pro Glu Ser Ala Gly
         50                  55                  60

Glu Pro Met Val Val Thr Ala Ser Thr Ala Val Ala Val Thr Val Asp
 65                  70                  75                  80

Lys Arg Thr Ala Ile Ala Ala Ala Gly Val Gln Met Lys Leu Glu
                 85                  90                  95

Phe Leu Gln Arg Lys Phe Trp Ala Ala Thr Arg Gln Cys Ser Thr Val
                100                 105                 110

Asp Gly Pro Cys Thr Gln Ser Cys Glu Asp Ser Asp Leu Asp Cys Phe
            115                 120                 125

Val Ile Asp Asn Asn Gly Phe Ile Leu Ile Ser Lys Arg Ser Arg Glu
    130                 135                 140

Thr Gly Arg Phe Leu Gly Glu Val Asp Gly Ala Val Leu Thr Gln Leu
145                 150                 155                 160
```

Leu Ser Met Gly Val Phe Ser Gln Val Thr Met Tyr Asp Tyr Gln Ala
            165                 170                 175

Met Cys Lys Pro Ser Ser His His Ser Ala Ala Gln Pro Leu Val
            180                 185                 190

Ser Pro Ile Ser Ala Phe Leu Thr Ala Thr Arg Trp Leu Leu Gln Glu
            195                 200                 205

Leu Val Leu Phe Leu Leu Glu Trp Ser Val Trp Gly Ser Trp Tyr Asp
        210                 215                 220

Arg Gly Ala Glu Ala Lys Ser Val Phe His Ser His Lys His Lys
225                 230                 235                 240

Lys Gln Asp Pro Leu Gln Pro Cys Asp Thr Glu Tyr Pro Val Phe Val
                245                 250                 255

Tyr Gln Pro Ala Ile Arg Glu Ala Asn Gly Ile Val Glu Cys Gly Pro
                260                 265                 270

Cys Gln Lys Val Phe Val Gln Gln Ile Pro Asn Ser Asn Leu Leu
            275                 280                 285

Leu Leu Val Thr Asp Pro Thr Cys Asp Cys Ser Ile Phe Pro Pro Val
290                 295                 300

Leu Gln Glu Ala Thr Glu Val Lys Tyr Asn Ala Ser Val Lys Cys Asp
305                 310                 315                 320

Arg Met Arg Ser Gln Lys Leu Arg Arg Arg Pro Asp Ser Cys His Ala
                325                 330                 335

Phe His Pro Glu Glu Asn Ala Gln Asp Cys Gly Gly Ala Ser
                340                 345                 350

<210> SEQ ID NO 19
<211> LENGTH: 5482
<212> TYPE: DNA
<213> ORGANISM: Homo sapiens

<400> SEQUENCE: 19
cgggcagcgc agcccgcaga ggcgctgcgg cccgtgcagc cccggaggcc cctcgcggag    60
aaggcggcgg cggaggagag gccgagttac cgcccgccgc ccgcgccccc caacccccgc   120
cgccgccgcc gccgccgcca ctgccccccc tccccgcggc gccgcatctt gaatggaaac   180
atggcggtgc cggctcggac ctgcggcgcc tctcggcccg gccagcgcg gactgcgcgc   240
ccctggcccg gctgcggccc ccaccctggc cccggcaccc ggcgcccgac gtccgggccc   300
ccgcgcccgc tgtggctgct gctgccgctt ctaccgctgc tcgccgcccc cggcgcctct   360
gcctacagct tcccccagca gcacacgatg cagcactggg cccggcgtct ggagcaggag   420
gtcgacggcg tgatgcggat ttttggaggc gtccagcagc tccgtgagat ttacaaggac   480
aaccggaacc tgttcgaggt acaggagaat gagcctcaga agttggtgga aggtggca    540
ggggacattg agagccttct ggacaggaag gtgcaggccc tgaagagact ggctgatgct   600
gcagagaact tccagaaagc acaccgctgg caggacaaca tcaaggagga agacatcgtg   660
tactatgacg ccaaggctga cgctgagctg acgaccctg agagtgagga tgtggaaagg   720
gggtctaagg ccagcaccct aaggctggac ttcatcgagg acccaaactt caagaacaag   780
gtcaactatt catacgcggc tgtacagatc cctacggaca tctacaaagg ctccactgtc   840
atcctcaatg agctcaactg gacagaggcc ctggagaatg tgttcatgga aaaccgcaga   900
caagacccca cactgctgtg gcaggtcttc ggcagcgcca caggagtcac tcgctactac   960
ccggccaccc cgtggcgagc ccccaagaag atcgacctgt acgatgtccg aaggagaccc  1020

-continued

```
tggtatatcc aggggcctc gtcacccaaa gacatggtca tcatcgtgga tgtgagtggc      1080
agtgtgagcg gcctgaccct gaagctgatg aagacatctg tctgcgagat gctggacacg      1140
ctgtctgatg atgactatgt gaatgtggcc tcgttcaacg agaaggcaca gcctgtgtca      1200
tgcttcacac acctggtgca ggccaatgtg cgcaacaaga aggtgttcaa ggaagctgtg      1260
cagggcatgg tggccaaggg caccacaggc tacaaggccg gctttgagta tgcctttgac      1320
cagctgcaga actccaacat cactcgggcc aactgcaaca agatgatcat gatgttcacg      1380
gatggtggtg aggaccgcgt gcaggacgtc tttgagaagt acaattggcc aaaccggacg      1440
gtgcgcgtgt ttactttctc cgtggggcag cataactatg acgtcacacc gctgcagtgg      1500
atggcctgtg ccaacaaagg ctactatttt gagatcccct ccatcggagc catccgcatc      1560
aacacacagg aatatctaga tgtgttgggc aggcccatgg tgctggcagg caaggaggcc      1620
aagcaggttc agtggaccaa cgtgtatgag gatgcactgg gactggggtt ggtggtaaca      1680
gggaccctcc ctgttttcaa cctgacacag gatggccctg gggaaaagaa gaaccagctg      1740
atcctgggcg tgatgggcat tgacgtggct ctgaatgaca tcaagaggct gaccccaac      1800 tacacgcttg gagccaacgg ctatgtgttt gccattgacc tgaacggcta cgtgttgctg      1860
caccccaatc tcaagcccca gaccaccaac ttccgggagc ctgtgactct ggacttcctg      1920
gatgcggagc tagaggatga gaacaaggaa gagatccgtc ggagcatgat tgatggcaac      1980
aagggccaca agcagatcag aacgttggtc aagtccctgg atgagaggta catagatgag      2040
gtgacacgga actacacctg ggtgcctata aggagcacta actacagcct ggggctggtg      2100
ctcccaccct acagcacctt ctacctccaa gccaatctca gtgaccagat cctgcaggtc      2160
aagtattttg agttcctgct ccccagcagc tttgagtctg aaggacacgt tttcattgct      2220
cccagagagt actgcaagga cctgaatgcc tcagacaaca caccgagtt cctgaaaaac      2280 tttattgagc tcatggagaa agtgactcca gactccaagc agtgcaacaa cttccttctg      2340
cacaacctga tcttggacac gggcatcacg cagcagctgg tagagcgtgt gtggagggac      2400
caggatctca acacgtacag cctactggcc gtgttcgctg ccacagacgg tggcatcacc      2460
cgagtcttcc ccaacaaggc agctgaggac tggacagaga cccctgagcc cttcaatgcc      2520
agcttctacc gccgcagcct ggataaccac ggttatgtct tcaagccccc acaccaggat      2580
gccctgttaa ggccgctgga gctggagaat gacactgtgg gcatcctcgt cagcacagct      2640
gtggagctca gcctaggcag gcgcacactg aggccagcag tggtgggcgt caagctggac      2700
ctagaggctt gggctgagaa gttcaaggtg ctagccagca ccgtaccca ccaagaccag      2760 cctcagaagt gcggccccaa cagccactgt gagatggact gcgaggttaa caatgaggac      2820
ttactctgtg tcctcattga tgatggagga ttcctggtgc tgtcaaacca gaaccatcag      2880
tgggaccagg tgggcaggtt cttcagtgag gtggatgcca acctgatgct ggcactctac      2940
aataactcct tctacacccg caaggagtcc tatgactatc aggcagcctg tgcccctcag      3000 cccccctggca acctgggtgc tgcaccccgg ggtgtctttg tgcccaccgt tgcagatttc      3060
cttaacctgg cctggtggac ctctgctgcc gcctggtccc tgttccagca gcttctctac      3120
ggcctcatct accacagctg gttccaagca gacccgcgg aggccgaggg gagccccgag      3180
acgcgcgaga gcagctgcgt catgaaacag acccagtact acttcggctc ggtaaacgcc      3240
tcctacaacg ccatcatcga ctgcggaaac tgctccaggc tgttccacgc gcagagactg      3300
accaacacca tcttctcttt tgtggtggcc gagaagccgc tgtgcagcca gtgcgaggct      3360
ggccggctgc tgcagaagga gacgcactgc ccagcggacg gcccggagca gtgtgagcta      3420
```

-continued

| | | | | | |
|---|---|---|---|---|---|
| gtgcagagac | cgcgataccg | gagaggcccg | cacatctgct | tcgactacaa | cgcgacagaa | 3480 |
| gataccatcag | actgtggccg | cggggcctcc | ttcccgccgt | cgctgggcgt | cctggtctcc | 3540 |
| ctgcaactgc | tgctcctcct | gggcctgccg | ccccggccgc | agcctcaagt | cctcgtccac | 3600 |
| gcctctcgcc | gcctctgagc | accctgcccc | accccacctc | cactcccacc | tcacccggcc | 3660 |
| tcttcgcctt | tcccaccctc | ctgccccaca | ctccccgcct | tagagcctcg | tccctccctc | 3720 |
| actgaaggac | ctgagctggc | caggccctga | gagtctggtc | tgcgccttgg | gatggggagt | 3780 |
| cccaaagcgg | gacgccgcag | gtgtttggca | cccaaatcac | atctcacctc | cgaactgttc | 3840 |
| aagtgtcccc | agaccttct | tgcctgctgg | gctcccccca | gtgggatggg | acagggaggc | 3900 |
| cacacgcact | ggtgccaaaa | ccaggcctct | gctgccgccc | ttcctggagg | ctgcctatgt | 3960 |
| tgggggggac | cctgcctcag | ctgacccggc | ctctctgccc | cacccaagcc | caaacttggt | 4020 |
| ttctgtgaga | atagtggagg | aaggtgagat | ggccagtttg | aagcctgtgc | ctcccagctt | 4080 |
| aaatcctagc | aggagagagg | ctctggggca | gcccccatgg | gctcctgccc | ctttcaggcc | 4140 |
| tacagccaca | tccccaagcc | caccaggtgt | caggatagtc | acagtgatac | cagttcagac | 4200 |
| actacccat | atacacctgg | aacattgagg | atggaaactg | gactcacatt | cgacataccc | 4260 |
| cactgggcac | acgcacaaac | acacacacta | tgggtgggg | tgggtgtagg | ggcttacaaa | 4320 |
| gccttacaca | gggcgagggg | ttggtgggag | ggttggcacc | tgcacactcc | atctcctgct | 4380 |
| caccacctgc | ctctaatctg | agctgcagcc | tggctggtcc | tcccatttct | aaagctgaat | 4440 |
| gtcaaacagt | gccaaatgct | ggggcagggg | gtgaagaacc | ctctgtccca | ccctagcca | 4500 |
| ccagtgtcct | ccaagtgccc | cctcacctct | ccaggtgctc | attgtaacca | tttctcacta | 4560 |
| gtgtcaggcc | cccagtggga | ccacatgcca | ctgcctgcac | ctttcggcag | aggaaccccc | 4620 |
| accagacatc | acccttgcc | ttagcagggg | tgactttgtc | tctcctggct | gggccatcct | 4680 |
| tccgccaatc | tggcccttac | acactcaggc | ctgtgcccac | tccctatctc | cttcccaccc | 4740 |
| ctacacacac | actccctgct | tgcaggaggc | caaactgtcc | ctcccttgct | gaacacacac | 4800 |
| acacacacac | acacacaggt | ggggactggg | cacagctctt | cacaccattc | attctggtca | 4860 |
| tttcccccaa | aggcatccca | gcctgggggc | cagtgggaa | ctgagggcaa | ggggatatag | 4920 |
| tgatggggct | cagatggact | gggaggaggg | ggagggtgat | gcattaatta | atggcttcgt | 4980 |
| taattaatgt | catgttgctt | gtcgctttct | cagtgtgtgt | gtgtggtcca | tgcccactgc | 5040 |
| tggtgccagg | gtgggtgtcc | atgtgcaccc | ggcctggatg | ccagctgtgt | ccttcggggg | 5100 |
| cgtgcgtgta | actgtagtgt | agtcaggtgc | tcaatggaga | atataaacat | atacagaaaa | 5160 |
| atatatattt | taagtttaaa | aaacagaaaa | acagacaaaa | caatccccat | caggtagctg | 5220 |
| tctaaccccc | agctgggtct | aatccttctc | attacccacc | cgacctggct | gcccctcacc | 5280 |
| ttgggctggg | ggactggggg | gccatttcct | tttctctgcc | cttttttttgt | tgttctattt | 5340 |
| tgtacagaca | agttggaaaa | acaacagcga | caaaaaagtc | aagaaacttt | gtaaaatatc | 5400 |
| gtgtgtgtga | ttccttgtaa | aatattttca | aatggtttat | tacagaagat | cagttattaa | 5460 |
| ataatgttca | tattttcact | tc | | | | 5482 |

<210> SEQ ID NO 20
<211> LENGTH: 1145
<212> TYPE: PRT
<213> ORGANISM: Homo sapiens

<400> SEQUENCE: 20

```
Met Ala Val Pro Ala Arg Thr Cys Gly Ala Ser Arg Pro Gly Pro Ala
 1               5                  10                  15

Arg Thr Ala Arg Pro Trp Pro Gly Cys Gly Pro His Pro Gly Pro Gly
            20                  25                  30

Thr Arg Arg Pro Thr Ser Gly Pro Pro Arg Pro Leu Trp Leu Leu Leu
        35                  40                  45

Pro Leu Leu Pro Leu Leu Ala Ala Pro Gly Ala Ser Ala Tyr Ser Phe
    50                  55                  60

Pro Gln Gln His Thr Met Gln His Trp Ala Arg Arg Leu Glu Gln Glu
65                  70                  75                  80

Val Asp Gly Val Met Arg Ile Phe Gly Gly Val Gln Gln Leu Arg Glu
                85                  90                  95

Ile Tyr Lys Asp Asn Arg Asn Leu Phe Glu Val Gln Glu Asn Glu Pro
                100                 105                 110

Gln Lys Leu Val Glu Lys Val Ala Gly Asp Ile Glu Ser Leu Leu Asp
            115                 120                 125

Arg Lys Val Gln Ala Leu Lys Arg Leu Ala Asp Ala Ala Glu Asn Phe
        130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
                180                 185                 190

Glu Asp Pro Asn Phe Lys Asn Lys Val Asn Tyr Ser Tyr Ala Ala Val
            195                 200                 205

Gln Ile Pro Thr Asp Ile Tyr Lys Gly Ser Thr Val Ile Leu Asn Glu
        210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Arg Pro Trp Tyr Ile Gln Gly Ala Ser Ser
        275                 280                 285

Pro Lys Asp Met Val Ile Ile Val Asp Val Ser Gly Ser Val Ser Gly
    290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                325                 330                 335

Gln Pro Val Ser Cys Phe Thr His Leu Val Gln Ala Asn Val Arg Asn
            340                 345                 350

Lys Lys Val Phe Lys Glu Ala Val Gln Gly Met Val Ala Lys Gly Thr
        355                 360                 365

Thr Gly Tyr Lys Ala Gly Phe Glu Tyr Ala Phe Asp Gln Leu Gln Asn
    370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
```

-continued

```
                420                 425                 430
Tyr Asp Val Thr Pro Leu Gln Trp Met Ala Cys Ala Asn Lys Gly Tyr
                435                 440                 445
Tyr Phe Glu Ile Pro Ser Ile Gly Ala Ile Arg Ile Asn Thr Gln Glu
    450                 455                 460
Tyr Leu Asp Val Leu Gly Arg Pro Met Val Leu Ala Gly Lys Glu Ala
465                 470                 475                 480
Lys Gln Val Gln Trp Thr Asn Val Tyr Glu Asp Ala Leu Gly Leu Gly
                485                 490                 495
Leu Val Val Thr Gly Thr Leu Pro Val Phe Asn Leu Thr Gln Asp Gly
                500                 505                 510
Pro Gly Glu Lys Lys Asn Gln Leu Ile Leu Gly Val Met Gly Ile Asp
                515                 520                 525
Val Ala Leu Asn Asp Ile Lys Arg Leu Thr Pro Asn Tyr Thr Leu Gly
            530                 535                 540
Ala Asn Gly Tyr Val Phe Ala Ile Asp Leu Asn Gly Tyr Val Leu Leu
545                 550                 555                 560
His Pro Asn Leu Lys Pro Gln Thr Thr Asn Phe Arg Glu Pro Val Thr
                565                 570                 575
Leu Asp Phe Leu Asp Ala Glu Leu Glu Asp Glu Asn Lys Glu Glu Ile
                580                 585                 590
Arg Arg Ser Met Ile Asp Gly Asn Lys Gly His Lys Gln Ile Arg Thr
                595                 600                 605
Leu Val Lys Ser Leu Asp Glu Arg Tyr Ile Asp Glu Val Thr Arg Asn
            610                 615                 620
Tyr Thr Trp Val Pro Ile Arg Ser Thr Asn Tyr Ser Leu Gly Leu Val
625                 630                 635                 640
Leu Pro Pro Tyr Ser Thr Phe Tyr Leu Gln Ala Asn Leu Ser Asp Gln
                645                 650                 655
Ile Leu Gln Val Lys Tyr Phe Glu Phe Leu Leu Pro Ser Ser Phe Glu
                660                 665                 670
Ser Glu Gly His Val Phe Ile Ala Pro Arg Glu Tyr Cys Lys Asp Leu
                675                 680                 685
Asn Ala Ser Asp Asn Asn Thr Glu Phe Leu Lys Asn Phe Ile Glu Leu
            690                 695                 700
Met Glu Lys Val Thr Pro Asp Ser Lys Gln Cys Asn Asn Phe Leu Leu
705                 710                 715                 720
His Asn Leu Ile Leu Asp Thr Gly Ile Thr Gln Gln Leu Val Glu Arg
                725                 730                 735
Val Trp Arg Asp Gln Asp Leu Asn Thr Tyr Ser Leu Leu Ala Val Phe
                740                 745                 750
Ala Ala Thr Asp Gly Gly Ile Thr Arg Val Phe Pro Asn Lys Ala Ala
            755                 760                 765
Glu Asp Trp Thr Glu Asn Pro Glu Pro Phe Asn Ala Ser Phe Tyr Arg
            770                 775                 780
Arg Ser Leu Asp Asn His Gly Tyr Val Phe Lys Pro Pro His Gln Asp
785                 790                 795                 800
Ala Leu Leu Arg Pro Leu Glu Leu Glu Asn Asp Thr Val Gly Ile Leu
                805                 810                 815
Val Ser Thr Ala Val Glu Leu Ser Leu Gly Arg Arg Thr Leu Arg Pro
            820                 825                 830
Ala Val Val Gly Val Lys Leu Asp Leu Glu Ala Trp Ala Glu Lys Phe
            835                 840                 845
```

```
Lys Val Leu Ala Ser Asn Arg Thr His Gln Asp Gln Pro Gln Lys Cys
    850                 855                 860

Gly Pro Asn Ser His Cys Glu Met Asp Cys Glu Val Asn Asn Glu Asp
865                 870                 875                 880

Leu Leu Cys Val Leu Ile Asp Asp Gly Gly Phe Leu Val Leu Ser Asn
                    885                 890                 895

Gln Asn His Gln Trp Asp Gln Val Gly Arg Phe Phe Ser Glu Val Asp
                900                 905                 910

Ala Asn Leu Met Leu Ala Leu Tyr Asn Asn Ser Phe Tyr Thr Arg Lys
            915                 920                 925

Glu Ser Tyr Asp Tyr Gln Ala Ala Cys Ala Pro Gln Pro Pro Gly Asn
        930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Trp Ser Leu Phe Gln
                    965                 970                 975

Gln Leu Leu Tyr Gly Leu Ile Tyr His Ser Trp Phe Gln Ala Asp Pro
                980                 985                 990

Ala Glu Ala Glu Gly Ser Pro Glu Thr Arg Glu Ser Ser Cys Val Met
            995                 1000                1005

Lys Gln Thr Gln Tyr Tyr Phe Gly Ser Val Asn Ala Ser Tyr Asn Ala
    1010                1015                1020

Ile Ile Asp Cys Gly Asn Cys Ser Arg Leu Phe His Ala Gln Arg Leu
1025                1030                1035                1040

Thr Asn Thr Asn Leu Leu Phe Val Val Ala Glu Lys Pro Leu Cys Ser
                1045                1050                1055

Gln Cys Glu Ala Gly Arg Leu Leu Gln Lys Glu Thr His Cys Pro Ala
                1060                1065                1070

Asp Gly Pro Glu Gln Cys Glu Leu Val Gln Arg Pro Arg Tyr Arg Arg
        1075                1080                1085

Gly Pro His Ile Cys Phe Asp Tyr Asn Ala Thr Glu Asp Thr Ser Asp
    1090                1095                1100

Cys Gly Arg Gly Ala Ser Phe Pro Pro Ser Leu Gly Val Leu Val Ser
1105                1110                1115                1120

Leu Gln Leu Leu Leu Leu Leu Gly Leu Pro Pro Arg Pro Gln Pro Gln
                1125                1130                1135

Val Leu Val His Ala Ser Arg Arg Leu
            1140                1145

<210> SEQ ID NO 21
<211> LENGTH: 3770
<212> TYPE: DNA
<213> ORGANISM: Homo sapiens

<400> SEQUENCE: 21 tactatagggc ggccgcgaa ttcggcacga ggcggcgcgg agcggagcag gcagccccgc      60
gcgctcgccc accgcccgct ccgcgcagct ccccgcggcc gctctcgtcg ccgccgcagc     120
gggcgcgtcg gagggagccc agcatggccg gccgggctc gccgcgccgc gcgtcccggg      180
gggcctcggc gcttctcgct gccgcgcttc tctacgccgc gctgggggac gtggtgcgct     240
cggagcagca gataccgctc tccgtggtga agctctgggc ctcggctttt ggtggggaga     300
taaaatccat tgctgctaag tactccggtt cccagcttct gcaaaagaaa tacaaagagt     360
atgagaaaga cgttgccata gaagaaattg atggcctcca actggtaaag aagctggcaa     420
```

-continued

```
agaacatgga agagatgttt cacaagaagt ctgaggccgt caggcgtctg gtggaggctg       480
cagaagaagc acacctgaaa catgaatttg atgcagactt acagtatgaa tacttcaatg       540
ctgtgctgat aaatgaaagg gacaaagacg ggaattttt ggagctggga aaggaattca        600
tcttagcccc aaatgaccat tttaataatt tgcctgtgaa catcagtcta agtgacgtcc       660
aagtaccaac gaacatgtac aacaaagacc ctgcaattgt caatgggtt tattggtctg        720
aatctctaaa caaagttttt gtagataact ttgaccgtga cccatctctc atatggcagt      780
actttggaag tgcaaagggc ttttttaggc agtatccggg gattaaatgg gaaccagatg      840
agaatggagt cattgccttc gactgcagga accgaaaatg gtacatccag gcagcaactt      900
ctccgaaaga cgtggtcatt ttagttgacg tcagtggcag catgaaagga ctccgtctga      960
ctatcgcgaa gcaaacagtc tcatccattt tggatacact tggggatgat gacttcttca     1020
acataattgc ttataatgag gagcttcact atgtggaacc ttgcctgaat ggaactttgg      1080
tgcaagccga caggacaaac aaagagcact tcagggagca tctggacaaa cttttcgcca     1140
aaggaattgg aatgttggat atagctctga atgaggcctt caacattctg agtgatttca     1200
accacacggg acaaggaagt atctgcagtc aggccatcat gctcataact gatggggcgg     1260
tggacaccta tgatacaatc tttgcaaaat acaattggcc agatcgaaag gttcgcatct     1320
tcacatacct cattggacga gaggctgcgt ttgcagacaa tctaaagtgg atggcctgtg     1380
ccaacaaagg attttttacc cagatctcca ccttggctga tgtgcaggag aatgtcatgg     1440
aataccttca cgtgcttagc cggcccaaag tcatcgacca ggagcatgat gtggtgtgga     1500
ccgaagctta cattgacagc actctgactg atgatcaggg ccccgtcctg atgaccactg     1560
tagccatgcc tgtgtttagt aagcagaacg aaaccagatc gaagggcatt cttctgggag     1620
tggttggcac agatgtccca gtgaaagaac ttctgaagac catccccaaa tacaagttag     1680
ggattcacgg ttatgccttt gcaatcacaa ataatggrta tatcctgacg catccggaac     1740
tcaggctgct gtacgaagaa ggaaaaaagc gaaggaaacc taactatagt agcgttgacc     1800
tctctgaggt ggagtgggaa gaccgagatg acgtgttgag aaatgctatg gtgaatcgaa     1860
agacggggaa gttttccatg gaggtgaaga agacagtgga caaagggaaa cgggttttgg    1920
tgatgacaaa tgactactat tatacagaca tcaagggtac tcctttcagt ttaggtgtgg     1980
cgctttccag aggtcatggg aaatatttct tccgagggaa tgtaaccatc gaagaaggcc     2040
tgcatgactt agaacatccc gatgtgtcct ggcagatga atggtcctac tgcaacactg      2100
acctacaccc tgagcaccgc catctgtctc agttagaagc gattaagctc tacctaaaag     2160
gcaaagaacc tctgctccag tgtgataaag aattgatcca agaagtcctt tttgacgcgg     2220
tggtgagtgc ccccattgaa gcgtattgga ccagcctggc cctcaacaaa tctgaaaatt     2280
ctgacaaggg cgtggaggtt gccttcctcg gcactcgcac gggcctctcc agaatcaacc     2340
tgtttgtcgg ggctgagcag ctcaccaatc aggacttcct gaaagctggc gacaaggaga     2400
acattttaa cgcagaccat ttccctctct ggtaccgaag agccgctgag cagattccag     2460
ggagcttcgt ctactcgatc ccattcagca ctggaccagt caataaaagc aatgtggtga     2520
cagcaagtac atccatccag ctcctggatg aacggaaatc tcctgtggtg gcagctgtag     2580
gcattcagat gaaacttgaa ttttccaaa ggaagttctg gactgccagc agacagtgtg     2640
cttccctgga tggcaaatgc tccatcagct gtgatgatga actgtgaat tgttacctca     2700
tagacaataa tggatttatt ttggtgtctg aagactacac acagactgga gactttttg     2760
```

-continued

```
gtgagatcga gggagctgtg atgaacaaat tgctaacaat gggctccttt aaaagaatta    2820 cccttttatga ctaccaagcc atgtgtagag ccaacaagga aagcagcgat ggcgcccatg    2880
gcctcctgga tccttataat gccttcctct ctgcagtaaa atggatcatg acagaacttg    2940
tcttgttcct ggtggaattt aacctctgca gttggtggca ctccgatatg acagctaaag    3000
cccagaaatt gaaacagacc ctggagcctt gtgatactga atatccagca ttcgtctctg    3060
agcgcaccat caaggagact acagggaata ttgcttgtga agactgctcc aagtcctttg    3120
tcatccagca aatcccaagc agcaacctgt tcatggtggt ggtggacagc agctgcctct    3180
gtgaatctgt ggcccccatc accatggcac ccattgaaat caggtataat gaatccctta    3240
agtgtgaacg tctaaaggcc cagaagatca gaaggcgccc agaatcttgt catggcttcc    3300
atcctgagga gaatgcaagg gagtgtgggg gtgcgccgag tctccaagcc cagacagtcc    3360
tccttctgct ccctctgctt ttgatgctct tctcaaggtg acactgactg agatgttctc    3420
ttactgactg agatgttctc ttggcatgct aaatcatgga taaactgtga accaaaatat    3480
ggtgcaacat acgagacatg aatatagtcc aaccatcagc atctcatcat gattttaaac    3540
tgtgcgtgat ataaactctt aaagatatgt tgacaaaaag ttatctatca tcttttttact    3600 ttgccagtca tgcaaatgtg agtttgccac atgataatca cccttcatca gaaatgggac    3660
cgcaagtggt aggcagtgtc ccttctgctt gaaacctatt gaaaccaatt taaaactgtg    3720 tacttttttaa ataaagtata ttaaaatcat aaaaaaaaaa aaaaaaaaaa              3770
```

<210> SEQ ID NO 22
<211> LENGTH: 1085
<212> TYPE: PRT
<213> ORGANISM: Homo sapiens

<400> SEQUENCE: 22

```
Met Ala Gly Pro Gly Ser Pro Arg Arg Ala Ser Arg Gly Ala Ser Ala
 1               5                  10                  15

Leu Leu Ala Ala Ala Leu Leu Tyr Ala Ala Leu Gly Asp Val Val Arg
            20                  25                  30

Ser Glu Gln Gln Ile Pro Leu Ser Val Val Lys Leu Trp Ala Ser Ala
        35                  40                  45

Phe Gly Gly Glu Ile Lys Ser Ile Ala Ala Lys Tyr Ser Gly Ser Gln
    50                  55                  60

Leu Leu Gln Lys Lys Tyr Lys Glu Tyr Glu Lys Asp Val Ala Ile Glu
65                  70                  75                  80

Glu Ile Asp Gly Leu Gln Leu Val Lys Lys Leu Ala Lys Asn Met Glu
                85                  90                  95

Glu Met Phe His Lys Lys Ser Glu Ala Val Arg Arg Leu Val Glu Ala
            100                 105                 110

Ala Glu Glu Ala His Leu Lys His Glu Phe Asp Ala Asp Leu Gln Tyr
        115                 120                 125

Glu Tyr Phe Asn Ala Val Leu Ile Asn Glu Arg Asp Lys Asp Gly Asn
    130                 135                 140

Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr
                165                 170                 175

Asn Met Tyr Asn Lys Asp Pro Ala Ile Val Asn Gly Val Tyr Trp Ser
            180                 185                 190

Glu Ser Leu Asn Lys Val Phe Val Asp Asn Phe Asp Arg Asp Pro Ser
```

```
                195                 200                 205
Leu Ile Trp Gln Tyr Phe Gly Ser Ala Lys Gly Phe Phe Arg Gln Tyr
    210                 215                 220
Pro Gly Ile Lys Trp Glu Pro Asp Glu Asn Gly Val Ile Ala Phe Asp
225                 230                 235                 240
Cys Arg Asn Arg Lys Trp Tyr Ile Gln Ala Ala Thr Ser Pro Lys Asp
                245                 250                 255
Val Val Ile Leu Val Asp Val Ser Gly Ser Met Lys Gly Leu Arg Leu
        260                 265                 270
Thr Ile Ala Lys Gln Thr Val Ser Ser Ile Leu Asp Thr Leu Gly Asp
            275                 280                 285
Asp Asp Phe Phe Asn Ile Ile Ala Tyr Asn Glu Glu Leu His Tyr Val
        290                 295                 300
Glu Pro Cys Leu Asn Gly Thr Leu Val Gln Ala Asp Arg Thr Asn Lys
305                 310                 315                 320
Glu His Phe Arg Glu His Leu Asp Lys Leu Phe Ala Lys Gly Ile Gly
                325                 330                 335
Met Leu Asp Ile Ala Leu Asn Glu Ala Phe Asn Ile Leu Ser Asp Phe
            340                 345                 350
Asn His Thr Gly Gln Gly Ser Ile Cys Ser Gln Ala Ile Met Leu Ile
            355                 360                 365
Thr Asp Gly Ala Val Asp Thr Tyr Asp Thr Ile Phe Ala Lys Tyr Asn
        370                 375                 380
Trp Pro Asp Arg Lys Val Arg Ile Phe Thr Tyr Leu Ile Gly Arg Glu
385                 390                 395                 400
Ala Ala Phe Ala Asp Asn Leu Lys Trp Met Ala Cys Ala Asn Lys Gly
                405                 410                 415
Phe Phe Thr Gln Ile Ser Thr Leu Ala Asp Val Gln Glu Asn Val Met
            420                 425                 430
Glu Tyr Leu His Val Leu Ser Arg Pro Lys Val Ile Asp Gln Glu His
            435                 440                 445
Asp Val Val Trp Thr Glu Ala Tyr Ile Asp Ser Thr Leu Thr Asp Asp
        450                 455                 460
Gln Gly Pro Val Leu Met Thr Thr Val Ala Met Pro Val Phe Ser Lys
465                 470                 475                 480
Gln Asn Glu Thr Arg Ser Lys Gly Ile Leu Leu Gly Val Val Gly Thr
                485                 490                 495
Asp Val Pro Val Lys Glu Leu Leu Lys Thr Ile Pro Lys Tyr Lys Leu
            500                 505                 510
Gly Ile His Gly Tyr Ala Phe Ala Ile Thr Asn Asn Gly Tyr Ile Leu
            515                 520                 525
Thr His Pro Glu Leu Arg Leu Leu Tyr Glu Glu Gly Lys Lys Arg Arg
        530                 535                 540
Lys Pro Asn Tyr Ser Ser Val Asp Leu Ser Glu Val Glu Trp Glu Asp
545                 550                 555                 560
Arg Asp Asp Val Leu Arg Asn Ala Met Val Asn Arg Lys Thr Gly Lys
                565                 570                 575
Phe Ser Met Glu Val Lys Lys Thr Val Asp Lys Gly Lys Arg Val Leu
            580                 585                 590
Val Met Thr Asn Asp Tyr Tyr Tyr Thr Asp Ile Lys Gly Thr Pro Phe
        595                 600                 605
Ser Leu Gly Val Ala Leu Ser Arg Gly His Gly Lys Tyr Phe Phe Arg
        610                 615                 620
```

-continued

Gly Asn Val Thr Ile Glu Glu Gly Leu His Asp Leu Glu His Pro Asp
625                 630                 635                 640

Val Ser Leu Ala Asp Glu Trp Ser Tyr Cys Asn Thr Asp Leu His Pro
            645                 650                 655

Glu His Arg His Leu Ser Gln Leu Glu Ala Ile Lys Leu Tyr Leu Lys
        660                 665                 670

Gly Lys Glu Pro Leu Leu Gln Cys Asp Lys Glu Leu Ile Gln Glu Val
            675                 680                 685

Leu Phe Asp Ala Val Ser Ala Pro Ile Glu Ala Tyr Trp Thr Ser
690                 695                 700

Leu Ala Leu Asn Lys Ser Glu Asn Ser Asp Lys Gly Val Glu Val Ala
705                 710                 715                 720

Phe Leu Gly Thr Arg Thr Gly Leu Ser Arg Ile Asn Leu Phe Val Gly
            725                 730                 735

Ala Glu Gln Leu Thr Asn Gln Asp Phe Leu Lys Ala Gly Asp Lys Glu
            740                 745                 750

Asn Ile Phe Asn Ala Asp His Phe Pro Leu Trp Tyr Arg Arg Ala Ala
            755                 760                 765

Glu Gln Ile Pro Gly Ser Phe Val Tyr Ser Ile Pro Phe Ser Thr Gly
770                 775                 780

Pro Val Asn Lys Ser Asn Val Val Thr Ala Ser Thr Ser Ile Gln Leu
785                 790                 795                 800

Leu Asp Glu Arg Lys Ser Pro Val Val Ala Val Gly Ile Gln Met
            805                 810                 815

Lys Leu Glu Phe Phe Gln Arg Lys Phe Trp Thr Ala Ser Arg Gln Cys
            820                 825                 830

Ala Ser Leu Asp Gly Lys Cys Ser Ile Ser Cys Asp Glu Thr Val
            835                 840                 845

Asn Cys Tyr Leu Ile Asp Asn Asn Gly Phe Ile Leu Val Ser Glu Asp
850                 855                 860

Tyr Thr Gln Thr Gly Asp Phe Phe Gly Glu Ile Glu Gly Ala Val Met
865                 870                 875                 880

Asn Lys Leu Leu Thr Met Gly Ser Phe Lys Arg Ile Thr Leu Tyr Asp
                885                 890                 895

Tyr Gln Ala Met Cys Arg Ala Asn Lys Glu Ser Ser Asp Gly Ala His
            900                 905                 910

Gly Leu Leu Asp Pro Tyr Asn Ala Phe Leu Ser Ala Val Lys Trp Ile
            915                 920                 925

Met Thr Glu Leu Val Leu Phe Leu Val Glu Phe Asn Leu Cys Ser Trp
930                 935                 940

Trp His Ser Asp Met Thr Ala Lys Ala Gln Lys Leu Lys Gln Thr Leu
945                 950                 955                 960

Glu Pro Cys Asp Thr Glu Tyr Pro Ala Phe Val Ser Glu Arg Thr Ile
            965                 970                 975

Lys Glu Thr Thr Gly Asn Ile Ala Cys Glu Asp Cys Ser Lys Ser Phe
            980                 985                 990

Val Ile Gln Gln Ile Pro Ser Ser Asn Leu Phe Met Val Val Val Asp
        995                 1000                1005

Ser Ser Cys Leu Cys Glu Ser Val Ala Pro Ile Thr Met Ala Pro Ile
    1010                1015                1020

Glu Ile Arg Tyr Asn Glu Ser Leu Lys Cys Glu Arg Leu Lys Ala Gln
1025                1030                1035                1040

Lys Ile Arg Arg Arg Pro Glu Ser Cys His Gly Phe His Pro Glu Glu
            1045                1050                1055

Asn Ala Arg Glu Cys Gly Gly Ala Pro Ser Leu Gln Ala Gln Thr Val
            1060                1065                1070

Leu Leu Leu Leu Pro Leu Leu Leu Met Leu Phe Ser Arg
            1075                1080                1085

<210> SEQ ID NO 23
<211> LENGTH: 1115
<212> TYPE: PRT
<213> ORGANISM: Homo sapiens
<400> SEQUENCE: 23

Met Ala Val Pro Ala Arg Thr Cys Gly Ala Ser Arg Pro Gly Pro Ala
 1               5                  10                  15

Arg Thr Ala Arg Pro Trp Pro Gly Cys Gly Pro His Pro Gly Pro Gly
            20                  25                  30

Thr Arg Arg Pro Thr Ser Gly Pro Arg Pro Leu Trp Leu Leu Leu
            35                  40                  45

Pro Leu Leu Pro Leu Leu Ala Ala Pro Gly Ala Ser Ala Tyr Ser Phe
 50                  55                  60

Pro Gln Gln His Thr Met Gln His Trp Ala Arg Arg Leu Glu Gln Glu
 65                  70                  75                  80

Val Asp Gly Val Met Arg Ile Phe Gly Gly Val Gln Gln Leu Arg Glu
                85                  90                  95

Ile Tyr Lys Asp Asn Arg Asn Leu Phe Glu Val Gln Glu Asn Glu Pro
            100                 105                 110

Gln Lys Leu Val Glu Lys Val Ala Gly Asp Ile Glu Ser Leu Leu Asp
            115                 120                 125

Arg Lys Val Gln Ala Leu Lys Arg Leu Ala Asp Ala Ala Glu Asn Phe
130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
            195                 200                 205

Gln Ile Pro Thr Asp Ile Tyr Lys Gly Ser Thr Val Ile Leu Asn Glu
            210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Arg Pro Trp Tyr Ile Gln Gly Ala Ser Ser
            275                 280                 285

Pro Lys Asp Met Val Ile Ile Val Asp Val Ser Gly Ser Val Ser Gly
            290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                325                 330                 335

-continued

```
Gln Pro Val Ser Cys Phe Thr His Leu Val Gln Ala Asn Val Arg Asn
            340                 345                 350

Lys Lys Val Phe Lys Glu Ala Val Gln Gly Met Val Ala Lys Gly Thr
            355                 360                 365

Thr Gly Tyr Lys Ala Gly Phe Glu Tyr Ala Phe Asp Gln Leu Gln Asn
            370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                    405                 410                 415

Pro Asn Arg Thr Val Arg Val Phe Thr Phe Ser Val Gly Gln His Asn
            420                 425                 430

Tyr Asp Val Thr Pro Leu Gln Trp Met Ala Cys Ala Asn Lys Gly Tyr
            435                 440                 445

Tyr Phe Glu Ile Pro Ser Ile Gly Ala Ile Arg Ile Asn Thr Gln Glu
            450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
            500                 505                 510

Pro Gly Glu Lys Lys Asn Gln Leu Ile Leu Gly Val Met Gly Ile Asp
            515                 520                 525

Val Ala Leu Asn Asp Ile Lys Arg Leu Thr Pro Asn Tyr Thr Leu Gly
530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
                565                 570                 575

Leu Asp Phe Leu Asp Ala Glu Leu Glu Asp Glu Asn Lys Glu Glu Ile
            580                 585                 590

Arg Arg Ser Met Ile Asp Gly Asn Lys Gly His Lys Gln Ile Arg Thr
            595                 600                 605

Leu Val Lys Ser Leu Asp Glu Arg Tyr Ile Asp Glu Val Thr Arg Asn
            610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
                645                 650                 655

Ile Leu Gln Val Lys Tyr Phe Glu Phe Leu Leu Pro Ser Ser Phe Glu
            660                 665                 670

Ser Glu Gly His Val Phe Ile Ala Pro Arg Glu Tyr Cys Lys Asp Leu
            675                 680                 685

Asn Ala Ser Asp Asn Asn Thr Glu Phe Leu Lys Asn Phe Ile Glu Leu
690                 695                 700

Met Glu Lys Val Thr Pro Asp Ser Lys Gln Cys Asn Asn Phe Leu Leu
705                 710                 715                 720

His Asn Leu Ile Leu Asp Thr Gly Ile Thr Gln Gln Leu Val Glu Arg
                725                 730                 735

Val Trp Arg Asp Gln Asp Leu Asn Thr Tyr Ser Leu Leu Ala Val Phe
            740                 745                 750
```

-continued

```
Ala Ala Thr Asp Gly Gly Ile Thr Arg Val Phe Pro Asn Lys Ala Ala
        755                 760                 765

Glu Asp Trp Thr Glu Asn Pro Glu Pro Phe Asn Ala Ser Phe Tyr Arg
    770                 775                 780

Arg Ser Leu Asp Asn His Gly Tyr Val Phe Lys Pro His Gln Asp
785                 790                 795                 800

Ala Leu Leu Arg Pro Leu Glu Leu Asn Asp Thr Val Gly Ile Leu
                805                 810                 815

Val Ser Thr Ala Val Glu Leu Ser Leu Gly Arg Arg Thr Leu Arg Pro
            820                 825                 830

Ala Val Gly Val Lys Leu Asp Leu Glu Ala Trp Ala Glu Lys Phe
        835                 840                 845

Lys Val Leu Ala Ser Asn Arg Thr His Gln Asp Gln Pro Gln Lys Cys
    850                 855                 860

Gly Pro Asn Ser His Cys Glu Met Asp Cys Glu Val Asn Asn Glu Asp
865                 870                 875                 880

Leu Leu Cys Val Leu Ile Asp Asp Gly Gly Phe Leu Val Leu Ser Asn
                885                 890                 895

Gln Asn His Gln Trp Asp Gln Val Gly Arg Phe Phe Ser Glu Val Asp
            900                 905                 910

Ala Asn Leu Met Leu Ala Leu Tyr Asn Asn Ser Phe Tyr Thr Arg Lys
        915                 920                 925

Glu Ser Tyr Asp Tyr Gln Ala Ala Cys Ala Pro Gln Pro Gly Asn
    930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Trp Ser Leu Phe Gln
                965                 970                 975

Gln Leu Leu Tyr Gly Leu Ile Tyr His Ser Trp Phe Gln Ala Asp Pro
            980                 985                 990

Ala Glu Ala Glu Gly Ser Pro Glu Thr Arg Glu Ser Ser Cys Val Met
        995                 1000                1005

Lys Gln Thr Gln Tyr Tyr Phe Gly Ser Val Asn Ala Ser Tyr Asn Ala
    1010                1015                1020

Ile Ile Asp Cys Gly Asn Cys Ser Arg Leu Phe His Ala Gln Arg Leu
1025                1030                1035                1040

Thr Asn Thr Asn Leu Leu Phe Val Val Ala Glu Lys Pro Leu Cys Ser
                1045                1050                1055

Gln Cys Glu Ala Gly Arg Leu Leu Gln Lys Glu Thr His Cys Pro Ala
            1060                1065                1070

Asp Gly Pro Glu Gln Cys Glu Leu Val Gln Arg Pro Tyr Arg Arg
        1075                1080                1085

Gly Pro His Ile Cys Phe Asp Tyr Asn Ala Thr Glu Asp Thr Ser Asp
    1090                1095                1100

Cys Gly Arg Gly Ala His His His His His
1105                1110                1115
```

<210> SEQ ID NO 24
<211> LENGTH: 1077
<212> TYPE: PRT
<213> ORGANISM: Mus musculus

<400> SEQUENCE: 24

```
Met Ala Gly Pro Gly Ser Leu Cys Cys Ala Ser Arg Gly Ala Ser Ala
1               5                   10                  15
```

```
Leu Leu Ala Thr Ala Leu Leu Tyr Ala Ala Leu Gly Asp Val Val Arg
             20                  25                  30

Ser Glu Gln Gln Ile Pro Leu Ser Val Val Lys Leu Trp Ala Ser Ala
         35                  40                  45

Phe Gly Gly Glu Ile Lys Ser Ile Ala Ala Lys Tyr Ser Gly Ser Gln
     50                  55                  60

Leu Leu Gln Lys Lys Tyr Lys Glu Tyr Glu Lys Asp Val Ala Ile Glu
 65                  70                  75                  80

Glu Ile Asp Gly Leu Gln Leu Val Lys Lys Leu Ala Lys Ile Met Glu
                 85                  90                  95

Glu Met Phe His Lys Lys Ser Glu Ala Val Arg Arg Leu Val Glu Ala
            100                 105                 110

Ala Glu Glu Ala His Leu Lys His Glu Phe Asp Ala Asp Leu Gln Tyr
        115                 120                 125

Glu Tyr Phe Asn Ala Val Leu Ile Asn Glu Arg Asp Lys Asp Gly Asn
    130                 135                 140

Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr
                165                 170                 175

Asn Met Tyr Asn Lys Asp Pro Ala Ile Val Asn Gly Val Tyr Trp Ser
            180                 185                 190

Glu Ser Leu Asn Lys Val Phe Val Asp Asn Phe Asp Arg Asp Pro Ser
        195                 200                 205

Leu Ile Trp Gln Tyr Phe Gly Ser Ala Lys Gly Phe Phe Arg Gln Tyr
    210                 215                 220

Pro Gly Ile Lys Trp Glu Pro Asp Glu Asn Gly Val Ile Ala Phe Asp
225                 230                 235                 240

Cys Arg Asn Arg Lys Trp Tyr Ile Gln Ala Ala Thr Ser Pro Lys Asp
                245                 250                 255

Val Val Ile Leu Val Asp Val Ser Gly Ser Met Lys Gly Leu Arg Leu
            260                 265                 270

Thr Ile Ala Lys Gln Thr Val Ser Ser Ile Leu Asp Thr Leu Gly Asp
        275                 280                 285

Asp Asp Phe Phe Asn Ile Ile Thr Tyr Asn Glu Glu Leu His Tyr Val
    290                 295                 300

Glu Pro Cys Leu Asn Gly Thr Leu Val Gln Ala Asp Arg Thr Asn Lys
305                 310                 315                 320

Glu His Phe Arg Glu His Leu Asp Lys Leu Phe Ala Lys Gly Ile Gly
                325                 330                 335

Met Leu Asp Ile Ala Leu Asn Glu Ala Phe Asn Ile Leu Ser Asp Phe
            340                 345                 350

Asn His Thr Gly Gln Gly Ser Ile Cys Ser Gln Ala Ile Met Leu Ile
        355                 360                 365

Thr Asp Gly Ala Val Asp Thr Tyr Asp Thr Ile Phe Ala Lys Tyr Asn
    370                 375                 380

Trp Pro Asp Arg Lys Val Arg Ile Phe Thr Tyr Leu Ile Gly Arg Glu
385                 390                 395                 400

Ala Ala Phe Ala Asp Asn Leu Lys Trp Met Ala Cys Ala Asn Lys Gly
                405                 410                 415

Phe Phe Thr Gln Ile Ser Thr Leu Ala Asp Val Gln Glu Asn Val Met
            420                 425                 430
```

```
Glu Tyr Leu His Val Leu Ser Arg Pro Lys Val Ile Asp Gln Glu His
            435                 440                 445
Asp Val Val Trp Thr Glu Ala Tyr Ile Asp Ser Thr Leu Pro Gln Ala
        450                 455                 460
Gln Lys Leu Ala Asp Asp Gln Gly Leu Val Leu Met Thr Thr Val Ala
465                 470                 475                 480
Met Pro Val Phe Ser Lys Gln Asn Glu Thr Arg Ser Lys Gly Ile Leu
                485                 490                 495
Leu Gly Val Val Gly Thr Asp Val Pro Val Lys Glu Leu Leu Lys Thr
            500                 505                 510
Ile Pro Lys Tyr Lys Leu Gly Ile His Gly Tyr Ala Phe Ala Ile Thr
        515                 520                 525
Asn Asn Gly Tyr Ile Leu Thr His Pro Glu Leu Arg Pro Leu Tyr Glu
    530                 535                 540
Glu Gly Lys Lys Arg Arg Lys Pro Asn Tyr Ser Ser Val Asp Leu Ser
545                 550                 555                 560
Glu Val Glu Trp Glu Asp Arg Asp Val Leu Arg Asn Ala Met Val
                565                 570                 575
Asn Arg Lys Thr Gly Lys Phe Ser Met Glu Val Lys Lys Thr Val Asp
            580                 585                 590
Lys Gly Lys Arg Val Leu Val Met Thr Asn Asp Tyr Tyr Tyr Thr Asp
        595                 600                 605
Ile Lys Gly Thr Pro Phe Ser Leu Gly Val Ala Leu Ser Arg Gly His
    610                 615                 620
Gly Lys Tyr Phe Phe Arg Gly Asn Val Thr Ile Glu Glu Gly Leu His
625                 630                 635                 640
Asp Leu Glu His Pro Asp Val Ser Leu Ala Asp Glu Trp Ser Tyr Cys
                645                 650                 655
Asn Thr Asp Leu His Pro Glu His Arg His Leu Ser Gln Leu Glu Ala
            660                 665                 670
Ile Lys Leu Tyr Leu Lys Gly Lys Glu Pro Leu Leu Gln Cys Asp Lys
        675                 680                 685
Glu Leu Ile Gln Glu Val Leu Phe Asp Ala Val Ser Ala Pro Ile
    690                 695                 700
Glu Ala Tyr Trp Thr Ser Leu Ala Leu Asn Lys Ser Glu Asn Ser Asp
705                 710                 715                 720
Lys Gly Val Glu Val Ala Phe Leu Gly Thr Arg Thr Gly Leu Ser Arg
                725                 730                 735
Ile Asn Leu Phe Val Gly Ala Glu Gln Leu Thr Asn Gln Asp Phe Leu
            740                 745                 750
Lys Ala Gly Asp Lys Glu Asn Ile Phe Asn Ala Asp His Phe Pro Leu
        755                 760                 765
Trp Tyr Arg Arg Ala Ala Glu Gln Ile Ala Gly Ser Phe Val Tyr Ser
    770                 775                 780
Ile Pro Phe Ser Thr Gly Thr Val Asn Lys Ser Asn Val Val Thr Ala
785                 790                 795                 800
Ser Thr Ser Ile Gln Leu Leu Asp Glu Arg Lys Ser Pro Val Val Ala
                805                 810                 815
Ala Val Gly Ile Gln Met Lys Leu Glu Phe Phe Gln Arg Lys Phe Trp
            820                 825                 830
Thr Ala Ser Arg Gln Cys Ala Ser Leu Asp Gly Lys Cys Ser Ile Ser
        835                 840                 845
Cys Asp Asp Glu Thr Val Asn Cys Tyr Leu Ile Asp Asn Asn Gly Phe
```

```
                    850                 855                 860
Ile Leu Val Ser Glu Asp Tyr Thr Gln Thr Gly Asp Phe Phe Gly Glu
865                 870                 875                 880

Val Glu Gly Ala Val Met Asn Lys Leu Leu Thr Met Gly Ser Phe Lys
                885                 890                 895

Arg Ile Thr Leu Tyr Asp Tyr Gln Ala Met Cys Arg Ala Asn Lys Glu
            900                 905                 910

Ser Ser Asp Ser Ala His Gly Leu Leu Asp Pro Tyr Lys Ala Phe Leu
        915                 920                 925

Ser Ala Ala Lys Trp Ile Met Thr Glu Leu Val Leu Phe Leu Val Glu
    930                 935                 940

Phe Asn Leu Cys Ser Trp Trp His Ser Asp Met Thr Ala Lys Ala Gln
945                 950                 955                 960

Lys Leu Lys Gln Thr Leu Glu Pro Cys Asp Thr Glu Tyr Pro Ala Phe
                965                 970                 975

Val Ser Glu Arg Thr Ile Lys Glu Thr Thr Gly Asn Ile Ala Cys Glu
            980                 985                 990

Asp Cys Ser Lys Ser Phe Val Ile Gln Gln Ile Pro Ser Ser Asn Leu
        995                 1000                1005

Phe Met Val Val Val Asp Ser Ser Cys Leu Cys Glu Ser Val Ala Pro
    1010                1015                1020

Ile Thr Met Ala Pro Ile Glu Ile Arg Tyr Asn Glu Ser Leu Lys Cys
1025                1030                1035                1040

Glu Arg Leu Lys Ala Gln Lys Ile Arg Arg Pro Glu Ser Cys His
                1045                1050                1055

Gly Phe His Pro Glu Glu Asn Ala Arg Glu Cys Gly Gly Ala Ser His
            1060                1065                1070

His His His His His
        1075

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: priner

<400> SEQUENCE: 25
tcgccaccat ggcggtgccg gctc                                          24

<210> SEQ ID NO 26
<211> LENGTH: 49
<212> TYPE: DNA
<213> ORGANISM: Artificial Sequence
<220> FEATURE:
<223> OTHER INFORMATION: Description of Artificial Sequence: priner

<400> SEQUENCE: 26
tcggaattcc tcagtgatgg tgatggtgat gggccccgcg gccacagtc               49

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: priner

<400> SEQUENCE: 27
tcgccaccat ggccgggccg ggc                                           23
```

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: priner

<400> SEQUENCE: 28
tctcagtgat ggtgatggtg atgcgatgca cccccacact ctc        43

<210> SEQ ID NO 29
<211> LENGTH: 3842
<212> TYPE: DNA
<213> ORGANISM: Sus scrofa

<400> SEQUENCE: 29

| | |
|---|---|
| ggggattgat cttcgatcgc gaagatggct gctggctgcc tgctggcctt gactctgaca | 60 |
| cttttccaat ctttgctgat cggtccctca tcgcaggagc cgttcccgtc ggccgtcact | 120 |
| atcaagtcat gggtggataa aatgcaagaa gaccttgtca ccctggcaaa acagcaagt | 180 |
| ggagtcaatc agcttgtcga tatttatgaa aaataccaag atttgtatac tgtggaacca | 240 |
| aataatgcac gccagctggt ggaaattgca gccagggata ttgagaaact tctgagcaac | 300 |
| agatctaaag ccctggtgcg cctagctttg gaagcagaga aggttcaagc agcccaccag | 360 |
| tggagagagg attttgcaag caatgaagtt gtctactaca atgcaaagga tgatctcgat | 420 |
| cctgaaaaaa atgacagtga gccaggcagc cagaggataa aacctgtttt tattgatgat | 480 |
| gctaattttg ggcgacagat atcttatcag catgcagcag tccatattcc caccgacatc | 540 |
| tatgagggct caacaattgt gttaaatgaa ctgaactgga caagtgcctt agatgaagtt | 600 |
| ttcaagaaaa atcgagagga agatccctca ttattgtggc aggtgtttgg cagtgccaca | 660 |
| ggcctggccc ggtattatcc agcttctcca tgggttgata cagtagaac tccaaacaag | 720 |
| attgaccttt atgatgtacg aaggagacca tggtacatcc aaggagctgc atctcctaaa | 780 |
| gatatgctta ttctggtcga cgtgagtgga agtgttagtg gtttgacgct taaactgatc | 840 |
| cgaacatctg tctctgaaat gttggaaacc ctctcagatg acgattttgt gaatgtagct | 900 |
| tcatttaaca gcaatgccca ggatgtaagc tgttttcaac accttgtcca agcaaatgta | 960 |
| agaaataaga aagtgctgaa agatgcagtt aataatatca cagcaaaagg aatcacagat | 1020 |
| tacaagaagg gctttagttt tgcttttgaa caactgctta attataacgt ttctagagcc | 1080 |
| aactgcaata agattatcat gttgttcacc gatggaggag aagagagagc tcaggagata | 1140 |
| tttgccaaat acaacaaaga caaaaagta cgtgtattca cattttcagt tggtcaacat | 1200 |
| aattatgaca gaggacctat tcagtggatg gcctgtgaaa ataaaggtta ttattatgaa | 1260 |
| attccttcca ttggagcaat cagaatcaat actcaggaat atttggatgt tctgggaaga | 1320 |
| ccaatggttt tagcaggaga caaagctaag caagtccagt ggacaaacgt gtacctggat | 1380 |
| gcactggaac tggacttgt cattactgga actcttccgg tcttcaacat aaccggccaa | 1440 |
| aatgaaaata gacgaacttt aaagaaccag ctgattcttg gtgtgatggg agttgatgta | 1500 |
| tctttggaag atattaaaag actgacacca cgttttacac tgtgccccaa tggctattac | 1560 |
| tttgcaattg atcctaatgg ctatgtttta ttacatccaa atcttcagcc aaagaacccc | 1620 |
| aaatctcagg agccagtaac cttggatttc cttgatgcag aattagagaa tgatattaaa | 1680 |
| gtggagatcc gaaataaaat gatagatgga gaaagtggag aaaaaacatt cagaactctg | 1740 |

-continued

```
gttaaatctc aagatgagag atatattgac aaaggaaaca ggacatatac atggactcct    1800
gtcaatggca cagattacag tttggccttg gtattaccaa cctacagttt ttactatata    1860
aaagccaaaa tagaagagac aataactcag gccagatcaa aaaagggcaa atgaaggat     1920 tcagaaacac tgaagcctga taattttgaa gaatctggct atacattcat agcaccaaga    1980
gactactgca atgaccttaa aatatcagat aataataccg aatttctttt aaactttaat    2040
gagtttattg atagaaaaac tccaaacaac ccgtcatgca acacagattt gattaataga    2100
gtcttgctgg atgcgggctt tacaaatgaa cttgtccaaa attactggag taagcagaaa    2160
aacatcaagg gagtgaaagc acggtttgtt gtaactgatg gagggattac cagagtttat    2220
cccaaagagg ctggagaaaa ttggcaagaa aacccagaaa catatgagga cagcttctat    2280
aaaagaagtc tagataacga taactatgtt ttcactgctc cctactttaa caaaagtgga    2340
cctggtgctt atgaatcagg catcatggta agcaaagctg tagaaatata catccaagga    2400
aaacttctta aacctgcagt tgttggaatt aaaattgatg taaattcctg gatagagaat    2460
ttcaccaaaa catcaatcag ggatccgtgt gctggtccag tttgtgattg taaaagaaac    2520
agtgatgtaa tggattgtgt gattctagat gatggtgggt ttcttttgat ggcaaatcat    2580
gatgattata ctaaccagat tggaaggttt tttggagaga ttgacccaag tttgatgaga    2640
cacctggtta atatatcagt ttatgctttt aacaaatctt acgattatca gtcagtgtgt    2700
gagcctggtg ctgcaccaaa acaaggagca ggacatcgct cagcatatgt gccatcaata    2760
gcagacatct tacacattgg ctggtgggcc actgcagctg catggtctat tctacagcag    2820
tttctcttga gtttgacctt tccacgactt cttgaagcag ttgagatgga agatgatgac    2880
tttaccgcct ctctgtcaaa gcagagttgc attactgaac aaacccagta tttctttgat    2940
aatgatagca aatccttcag tggggtcttg gactgtggta actgttccag aatctttcac    3000
gttgaaaaac ttatgaacac caacttaata ttcataatgg ttgagagcaa agggacttgt    3060
ccttgtgaca cacgattgct catacaagct gagcagactt ctgacggtcc agatccttgt    3120
gatatggtta agcaacccag ataccgaaaa gggcctgatg tctgttttga taacaatgcc    3180
ttggaggatt ataccgactg tggtggtgtt tctggattaa atccctccct gtggtccatc    3240
ttcggaatcc agtgtgtttt actttggctt ttatctggca gcagacacta ccagttatga    3300
cccttctaaa accaaatctg catattaaac ttcagaccct gccagaatag gagccctcaa    3360
ttgcattaaa atagggtaaa ctgcagaatc agcagaactc tagctgggcc catcccatgg    3420
catcaatctc agactcataa ggcacccact ggctgcatgt cagggtgtca gatcctgaaa    3480
cttgtgtgaa tgctgcatca tctatgtata acatcagagc aaaattctat acctattcta    3540
ttggaaaatt tgagaatttg ttgttgcatt gttggtgatt acatgtaaaa gggctcccca    3600
cacagttgtg tatgaatcac gcaaattgtc ttgattttga cttgctgcaa tccttgtcct    3660
tttaccaaga aaatctctag agggaaaaaa aaagtctttt ttttccttca ctaattctgc    3720
tacaaattat ttcctgcttg gagtagttat tattaaaaaa tatatatata gagagagaga    3780
gagagaatta acattggtgt aatctgtcaa aatagaaata atggcttatt ttctacaaaa    3840
aa                                                                  3842
```

<210> SEQ ID NO 30
<211> LENGTH: 3057
<212> TYPE: DNA
<213> ORGANISM: Sus scrofa

<400> SEQUENCE: 30

```
atggctgctg gctgcctgct ggccttgact ctgacactt tccaatcttt gctgatcggt      60
ccctcatcgc aggagccgtt cccgtcggcc gtcactatca agtcatgggt ggataaaatg    120
caagaagacc ttgtcaccct ggcaaaaaca gcaagtggag tcaatcagct tgtcgatatt    180
tatgaaaaat accaagattt gtatactgtg aaccaaata atgcacgcca gctggtggaa    240
attgcagcca gggatattga gaaacttctg agcaacagat ctaaagccct ggtgcgccta    300
gctttggaag cagagaaggt tcaagcagcc caccagtgga gagaggattt tgcaagcaat    360
gaagttgtct actacaatgc aaaggatgat ctcgatcctg aaaaaaatga cagtgagcca    420
ggcagccaga ggataaaacc tgttttatt gatgatgcta attttgggcg acagatatct    480
tatcagcatg cagcagtcca tattcccacc gacatctatg agggctcaac aattgtgtta    540
aatgaactga actggacaag tgccttagat gaagttttca gaaaaatcg agaggaagat    600
ccctcattat tgtggcaggt gtttggcagt gccacaggcc tggcccggta ttatccagct    660
tctccatggg ttgataacag tagaactcca acaagattg acctttatga tgtacgaagg    720
agaccatggt acatccaagg agctgcatct cctaaagata tgcttattct ggtcgacgtg    780
agtggaagtg ttagtggttt gacgcttaaa ctgatccgaa catctgtctc tgaaatgttg    840
gaaaccctct cagatgacga ttttgtgaat gtagcttcat ttaacagcaa tgcccaggat    900
gtaagctgtt tcaacaccct tgtccaagca aatgtaagaa ataagaaagt gctgaaagat    960
gcagttaata atatcacagc aaaaggaatc acagattaca agaagggctt tagttttgct   1020
tttgaacaac tgcttaatta taacgtttct agagccaact gcaataagat tatcatgttg   1080
ttcaccgatg gaggagaaga gagagctcag gagatattg ccaaatacaa caaagacaaa   1140
aaagtacgtg tattcacatt ttcagttggt caacataatt atgacagagg acctattcag   1200
tggatggcct gtgaaaataa aggttattat tatgaaattc cttccattgg agcaatcaga   1260
atcaatactc aggaatattt ggatgttctg ggaagaccaa tggttttagc aggagacaaa   1320
gctaagcaag tccagtggac aaacgtgtac ctggatgcac tggaactggg acttgtcatt   1380
actggaactc ttccggtctt caacataacc ggccaaaatg aaaataagac gaacttaaag   1440
aaccagctga ttcttggtgt gatgggagtt gatgtatctt tggaagatat taaaagactg   1500
acaccacgtt ttacactgtg ccccaatggc tattactttg caattgatcc taatggctat   1560
gtttttattac atccaaatct tcagccaaag aaccccaaat ctcaggagcc agtaaccttg   1620
gatttccttg atgcagaatt agagaatgat attaaagtgg agatccgaaa taaaatgata   1680
gatggagaaa gtggagaaaa aacattcaga actctggtta aatctcaaga tgagagatat   1740
attgacaaag gaaacaggac atatacatgg actcctgtca atggcacaga ttacagtttg   1800
gccttggtat taccaaccta cagttttac tatataaaag ccaaaataga agagacaata   1860
actcaggcca gatcaaaaaa gggcaaaatg aaggattcag aaacactgaa gcctgataat   1920
tttgaagaat ctggctatac attcatagca ccaagagact actgcaatga ccttaaaata   1980
tcagataata ataccgaatt tcttttaaac tttaatgagt ttattgatag aaaaactcca   2040
aacaacccgt catgcaacac agattttgatt aatagagtct tgctggatgc gggcttttaca   2100
aatgaacttg tccaaaatta ctggagtaag cagaaaaaca tcaagggagt gaaagcacgg   2160
tttgttgtaa ctgatggagg gattaccaga gtttatccca agaggctgg agaaaattgg   2220
caagaaaacc cagaaacata tgaggacagc ttctataaaa gaagtctaga taacgataac   2280
tatgttttca ctgctcccta ctttaacaaa gtggacctg tgcttatga atcaggcatc   2340
```

-continued

| | |
|---|---|
| atggtaagca aagctgtaga aatatacatc caaggaaaac ttcttaaacc tgcagttgtt | 2400 |
| ggaattaaaa ttgatgtaaa ttcctggata gagaatttca ccaaaacatc aatcagggat | 2460 |
| ccgtgtgctg gtccagtttg tgattgtaaa agaaacagtg atgtaatgga ttgtgtgatt | 2520 |
| ctagatgatg gtgggtttct tttgatggca aatcatgatg attatactaa ccagattgga | 2580 |
| aggttttttg gagagattga cccaagtttg atgagacacc tggttaatat atcagtttat | 2640 |
| gcttttaaca aatcttacga ttatcagtca gtgtgtgagc tggtgctgc accaaaacaa | 2700 |
| ggagcaggac atcgctcagc atatgtgcca tcaatagcag acatcttaca cattggctgg | 2760 |
| tgggccactg cagctgcatg gtctattcta cagcagtttc tcttgagttt gaccttttcca | 2820 |
| cgacttcttg aagcagttga gatggaagat gatgacttta ccgcctctct gtcaaagcag | 2880 |
| agttgcatta ctgaacaaac ccagtatttc tttgataatg atagcaaatc cttcagtggg | 2940 |
| gtcttggact gtggtaactg ttccagaatc tttcacgttg aaaaacttat gaacaccaac | 3000 |
| ttaatattca taatggttga gagcaaaggg acttgtcctt gtgacacacg attgtga | 3057 |

<210> SEQ ID NO 31
<211> LENGTH: 3111
<212> TYPE: DNA
<213> ORGANISM: Sus scrofa

<400> SEQUENCE: 31

| | |
|---|---|
| atggctgctg gctgcctgct ggccttgact ctgacacttt tccaatcttt gctgatcggt | 60 |
| ccctcatcgc aggagccgtt cccgtcggcc gtcactatca agtcatgggt ggataaaatg | 120 |
| caagaagacc ttgtcaccct ggcaaaaaca gcaagtggag tcaatcagct tgtcgatatt | 180 |
| tatgaaaaat accaagatt gtatactgtg gaaccaaata atgcacgcca gctggtggaa | 240 |
| attcagcca gggatattga gaaacttctg agcaacagat ctaaagccct ggtgcgccta | 300 |
| gctttggaag cagagaaggt tcaagcagcc caccagtgga gagaggattt tgcaagcaat | 360 |
| gaagttgtct actacaatgc aaaggatgat ctcgatcctg aaaaaaatga cagtgagcca | 420 |
| ggcagccaga ggataaaaacc tgtttttatt gatgatgcta attttgggcg acagatatct | 480 |
| tatcagcatg cagcagtcca tattcccacc gacatctatg agggctcaac aattgtgtta | 540 |
| aatgaactga actggacaag tgccttagat gaagttttca agaaaaatcg agaggaagat | 600 |
| ccctcattat tgtggcaggt gtttggcagt gccacaggcc tggcccggta ttatccagct | 660 |
| tctccatggg ttgataacag tagaactcca aacaagattg acctttatga tgtacgaagg | 720 |
| agaccatggt acatccaagg agctgcatct cctaaagata tgcttattct ggtcgacgtg | 780 |
| agtggaagtg ttagtggttt gacgcttaaa ctgatccgaa catctgtctc tgaaatgttg | 840 |
| gaaaccctct cagatgacga ttttgtgaat gtagcttcat ttaacagcaa tgcccaggat | 900 |
| gtaagctgtt tcaacaccct tgtccaagca aatgtaagaa ataagaaagt gctgaaagat | 960 |
| gcagttaata atatcacagc aaaaggaatc acagattaca agaagggctt tagttttgct | 1020 |
| tttgaacaac tgcttaatta taacgttttct agagccaact gcaataagat tatcatgttg | 1080 |
| ttcaccgatg gaggagaaga gagagctcag gagatatttg ccaaatacaa caaagacaaa | 1140 |
| aaagtacgtg tattcacatt ttcagttggt caacataatt atgacagagg acctattcag | 1200 |
| tggatggcct gtgaaaataa aggttattat tatgaaattc cttccattgg agcaatcaga | 1260 |
| atcaatactc aggaatattt ggatgttctg ggaagaccaa tggttttagc aggagacaaa | 1320 |
| gctaagcaag tccagtggac aaacgtgtac ctggatgcac tggaactggg acttgtcatt | 1380 |
| actggaactc ttccggtctt caacataacc ggccaaaatg aaaataagac gaacttaaag | 1440 |

-continued

```
aaccagctga ttcttggtgt gatgggagtt gatgtatctt tggaagatat taaaagactg    1500
acaccacgtt ttacactgtg ccccaatggc tattactttg caattgatcc taatggctat    1560
gttttattac atccaaatct tcagccaaag aaccccaaat ctcaggagcc agtaaccttg    1620
gatttccttg atgcagaatt agagaatgat attaaagtgg agatccgaaa taaaatgata    1680
gatggagaaa gtggagaaaa aacattcaga actctggtta aatctcaaga tgagagatat    1740
attgacaaag gaaacaggac atatacatgg actcctgtca atggcacaga ttacagtttg    1800
gccttggtat taccaaccta cagttttttac tatataaaag ccaaaataga gagacaata    1860 actcaggcca gatcaaaaaa gggcaaaatg aaggattcag aaacactgaa gcctgataat    1920
tttgaagaat ctggctatac attcatagca ccaagagact actgcaatga ccttaaaata    1980
tcagataata ataccgaatt tcttttaaac tttaatgagt ttattgatag aaaaactcca    2040
aacaacccgt catgcaacac agatttgatt aatagagtct tgctggatgc gggctttaca    2100
aatgaacttg tccaaaatta ctggagtaag cagaaaaaca tcaagggagt gaaagcacgg    2160
tttgttgtaa ctgatggagg gattaccaga gtttatccca aagaggctgg agaaaaattgg    2220 caagaaaacc cagaaacata tgaggacagc ttctataaaa gaagtctaga taacgataac    2280
tatgttttca ctgctcccta ctttaacaaa agtggacctg tgcttatga atcaggcatc    2340 atggtaagca aagctgtaga aatatacatc caaggaaaac ttcttaaacc tgcagttgtt    2400
ggaattaaaa ttgatgtaaa ttcctggata gagaatttca ccaaaacatc aatcagggat    2460
ccgtgtgctg gtccagtttg tgattgtaaa agaaacagtg atgtaatgga ttgtgtgatt    2520
ctagatgatg gtgggtttct tttgatggca aatcatgatg attatactaa ccagattgga    2580 aggtttttg gagagattga cccaagtttg atgagacacc tggttaatat atcagtttat    2640
gcttttaaca aatcttacga ttatcagtca gtgtgtgagc ctggtgctgc accaaaacaa    2700
ggagcaggac atcgctcagc atatgtgcca tcaatagcag acatcttaca cattggctgg    2760
tgggccactg cagctgcatg gtctattcta cagcagtttc tcttgagttt gacctttcca    2820
cgacttcttg aagcagttga gatggaagat gatgactttta ccgcctctct gtcaaagcag    2880
agttgcatta ctgaacaaac ccagtatttc tttgataatg atagcaaatc cttcagtggg    2940
gtcttggact gtggtaactg ttccagaatc tttcacgttg aaaaacttat gaacaccaac    3000
ttaatattca taatggttga gagcaaaggg acttgtcctt gtgacacacg attgctcata    3060
caagctgagc agacttctga cggtccagat ccttgtgata tggttaagtg a            3111
```

<210> SEQ ID NO 32
<211> LENGTH: 3192
<212> TYPE: DNA
<213> ORGANISM: Sus scrofa

<400> SEQUENCE: 32

```
atggctgctg gctgcctgct ggccttgact ctgacacttt tccaatcttt gctgatcggt      60
ccctcatcgc aggagccgtt cccgtcggcc gtcactatca agtcatgggt ggataaaatg     120
caagaagacc ttgtcaccct ggcaaaaaca gcaagtggag tcaatcagct tgtcgatatt     180
tatgaaaaat accaagattt gtatactgtg gaaccaaata atgcacgcca gctggtggaa     240
attgcagcca gggatattga gaaacttctg agcaacagat ctaaagccct ggtgcgccta     300 gcttttggaag cagagaaggt tcaagcagcc caccagtgga gagaggattt tgcaagcaat     360
gaagttgtct actacaatgc aaaggatgat ctcgatcctg aaaaaaatga cagtgagcca     420
```

-continued

```
ggcagccaga ggataaaacc tgtttttatt gatgatgcta attttgggcg acagatatct    480
tatcagcatg cagcagtcca tattcccacc gacatctatg agggctcaac aattgtgtta    540
aatgaactga actggacaag tgccttagat gaagttttca agaaaaatcg agaggaagat    600
ccctcattat tgtggcaggt gtttggcagt gccacaggcc tggcccggta ttatccagct    660
tctccatggg ttgataacag tagaactcca aacaagattg acctttatga tgtacgaagg    720
agaccatggt acatccaagg agctgcatct cctaaagata tgcttattct ggtcgacgtg    780
agtggaagtg ttagtggttt gacgcttaaa ctgatccgaa catctgtctc tgaaatgttg    840
gaaaccctct cagatgacga ttttgtgaat gtagcttcat ttaacagcaa tgcccaggat    900
gtaagctgtt ttcaacaccct tgtccaagca aatgtaagaa ataagaaagt gctgaaagat    960
gcagttaata atatcacagc aaaaggaatc acagattaca agaagggctt tagttttgct   1020
tttgaacaac tgcttaatta taacgtttct agagccaact gcaataagat tatcatgttg   1080
ttcaccgatg gaggagaaga gagagctcag gagatatttg ccaaatacaa caaagacaaa   1140
aaagtacgtg tattcacatt ttcagttggt caacataatt atgacagagg acctattcag   1200
tggatggcct gtgaaaataa aggttattat tatgaaattc cttccattgg agcaatcaga   1260
atcaatactc aggaatattt ggatgttctg ggaagaccaa tggttttagc aggagacaaa   1320
gctaagcaag tccagtggac aaacgtgtac ctggatgcac tggaactggg acttgtcatt   1380
actggaactc ttccggtctt caacataacc ggccaaaatg aaaataagac gaacttaaag   1440
aaccagctga ttcttggtgt gatgggagtt gatgtatctt tggaagatat taaaagactg   1500
acaccacgtt ttacactgtg ccccaatggc tattactttg caattgatcc taatggctat   1560
gttttattac atccaaatct tcagccaaag aaccccaaat ctcaggagcc agtaaccttg   1620
gatttccttg atgcagaatt agagaatgat attaaagtgg agatccgaaa taaaatgata   1680
gatggagaaa gtggagaaaa acattcaga actctggtta atctcaagca tgagagatat   1740
attgacaaag gaaacaggac atatacatgg actcctgtca atggcacaga ttacagtttg   1800
gccttggtat taccaaccta cagtttttac tatataaaag ccaaaataga agagacaata   1860
actcaggcca gatcaaaaaa gggcaaaatg aaggattcag aaacactgaa gcctgataat   1920
tttgaagaat ctggctatac attcatagca ccaagagact actgcaatga ccttaaaata   1980
tcagataata ataccgaatt tctttttaaac tttaatgagt ttattgatag aaaaactcca   2040
aacaacccgt catgcaacac agatttgatt aatagagtct tgctggatgc gggctttaca   2100
aatgaacttg tccaaaatta ctggagtaag cagaaaaaca tcaagggagt gaaagcacgg   2160
tttgttgtaa ctgatggagg gattaccaga gtttatccca agaggctgg agaaaattgg   2220 caagaaaacc cagaaacata tgaggacagc ttctataaaa gaagtctaga taacgataac   2280
tatgttttca ctgctcccta ctttaacaaa agtggacctg tgcttatga atcaggcatc   2340 atggtaagca aagctgtaga aatatacatc caaggaaaac ttcttaaacc tgcagttgtt   2400
ggaattaaaa ttgatgtaaa ttcctggata gagaatttca ccaaaacatc aatcagggat   2460
ccgtgtgctg gtccagtttg tgattgtaaa agaaacagtg atgtaatgga ttgtgtgatt   2520
ctagatgatg gtgggtttct tttgatggca aatcatgatg attatactaa ccagattgga   2580
aggttttttg gagagattga cccaagtttg atgacacc tggttaatat atcagtttat   2640
gcttttaaca atcttacga ttatcagtca gtgtgtgagc ctggtgctgc accaaaacaa   2700
ggagcaggac atcgctcagc atatgtgcca tcaatagcag acatcttaca cattggctgg   2760
tgggccactg cagctgcatg gtctattcta cagcagtttc tcttgagttt gacctttcca   2820
```

```
cgacttcttg aagcagttga gatggaagat gatgacttta ccgcctctct gtcaaagcag    2880
agttgcatta ctgaacaaac ccagtatttc tttgataatg atagcaaatc cttcagtggg    2940
gtcttggact gtggtaactg ttccagaatc tttcacgttg aaaaacttat gaacaccaac    3000
ttaatattca taatggttga gagcaaaggg acttgtcctt gtgacacacg attgctcata    3060
caagctgagc agacttctga cggtccagat ccttgtgata tggttaagca acccagatac    3120
cgaaaagggc ctgatgtctg ttttgataac aatgccttgg aggattatac cgactgtggt    3180
ggtgtttctt ga                                                         3192
```

<210> SEQ ID NO 33
<211> LENGTH: 1091
<212> TYPE: PRT
<213> ORGANISM: Sus scrofa

<400> SEQUENCE: 33

```
Met Ala Ala Gly Cys Leu Leu Ala Leu Thr Leu Thr Leu Phe Gln Ser
 1               5                  10                  15

Leu Leu Ile Gly Pro Ser Ser Gln Glu Pro Phe Pro Ser Ala Val Thr
             20                  25                  30

Ile Lys Ser Trp Val Asp Lys Met Gln Glu Asp Leu Val Thr Leu Ala
         35                  40                  45

Lys Thr Ala Ser Gly Val Asn Gln Leu Val Asp Ile Tyr Glu Lys Tyr
     50                  55                  60

Gln Asp Leu Tyr Thr Val Glu Pro Asn Asn Ala Arg Gln Leu Val Glu
 65                  70                  75                  80

Ile Ala Ala Arg Asp Ile Glu Lys Leu Leu Ser Asn Arg Ser Lys Ala
                 85                  90                  95

Leu Val Arg Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Asp Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
    290                 295                 300
```

```
Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
                340                 345                 350

Asn Cys Asn Lys Ile Ile Met Leu Phe Thr Asp Gly Gly Glu Glu Arg
                355                 360                 365

Ala Gln Glu Ile Phe Ala Lys Tyr Asn Lys Asp Lys Lys Val Arg Val
370                 375                 380

Phe Thr Phe Ser Val Gly Gln His Asn Tyr Asp Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
                420                 425                 430

Pro Met Val Leu Ala Gly Asp Lys Ala Lys Gln Val Gln Trp Thr Asn
                435                 440                 445

Val Tyr Leu Asp Ala Leu Glu Leu Gly Leu Val Ile Thr Gly Thr Leu
    450                 455                 460

Pro Val Phe Asn Ile Thr Gly Gln Asn Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
                500                 505                 510

Phe Ala Ile Asp Pro Asn Gly Tyr Val Leu Leu His Pro Asn Leu Gln
                515                 520                 525

Pro Lys Asn Pro Lys Ser Gln Glu Pro Val Thr Leu Asp Phe Leu Asp
                530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
                580                 585                 590

Val Asn Gly Thr Asp Tyr Ser Leu Ala Leu Val Leu Pro Thr Tyr Ser
                595                 600                 605

Phe Tyr Tyr Ile Lys Ala Lys Ile Glu Glu Thr Ile Thr Gln Ala Arg
                610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
                660                 665                 670

Glu Phe Ile Asp Arg Lys Thr Pro Asn Asn Pro Ser Cys Asn Thr Asp
                675                 680                 685

Leu Ile Asn Arg Val Leu Leu Asp Ala Gly Phe Thr Asn Glu Leu Val
    690                 695                 700

Gln Asn Tyr Trp Ser Lys Gln Lys Asn Ile Lys Gly Val Lys Ala Arg
705                 710                 715                 720
```

Phe Val Val Thr Asp Gly Gly Ile Thr Arg Val Tyr Pro Lys Glu Ala
        725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
        755                 760                 765

Asn Lys Ser Gly Pro Gly Ala Tyr Glu Ser Gly Ile Met Val Ser Lys
770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
        820                 825                 830

Ser Asp Val Met Asp Cys Val Ile Leu Asp Asp Gly Gly Phe Leu Leu
        835                 840                 845

Met Ala Asn His Asp Asp Tyr Thr Asn Gln Ile Gly Arg Phe Phe Gly
850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Ile
            900                 905                 910

Ala Asp Ile Leu His Ile Gly Trp Trp Ala Thr Ala Ala Trp Ser
        915                 920                 925

Ile Leu Gln Gln Phe Leu Leu Ser Leu Thr Phe Pro Arg Leu Leu Glu
        930                 935                 940

Ala Val Glu Met Glu Asp Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
            980                 985                 990

Val Glu Lys Leu Met Asn Thr Asn Leu Ile Phe Ile Met Val Glu Ser
        995                 1000                1005

Lys Gly Thr Cys Pro Cys Asp Thr Arg Leu Leu Ile Gln Ala Glu Gln
    1010                1015                1020

Thr Ser Asp Gly Pro Asp Pro Cys Asp Met Val Lys Gln Pro Arg Tyr
1025                1030                1035                1040

Arg Lys Gly Pro Asp Val Cys Phe Asp Asn Asn Ala Leu Glu Asp Tyr
                1045                1050                1055

Thr Asp Cys Gly Gly Val Ser Gly Leu Asn Pro Ser Leu Trp Ser Ile
            1060                1065                1070

Phe Gly Ile Gln Cys Val Leu Leu Trp Leu Leu Ser Gly Ser Arg His
        1075                1080                1085

Tyr Gln Leu
    1090

<210> SEQ ID NO 34
<211> LENGTH: 1018
<212> TYPE: PRT
<213> ORGANISM: Sus scrofa

<400> SEQUENCE: 34

```
Met Ala Ala Gly Cys Leu Leu Ala Leu Thr Leu Thr Leu Phe Gln Ser
  1               5                  10                  15

Leu Leu Ile Gly Pro Ser Ser Gln Glu Pro Phe Pro Ser Ala Val Thr
             20                  25                  30

Ile Lys Ser Trp Val Asp Lys Met Gln Glu Asp Leu Val Thr Leu Ala
         35                  40                  45

Lys Thr Ala Ser Gly Val Asn Gln Leu Val Asp Ile Tyr Glu Lys Tyr
     50                  55                  60

Gln Asp Leu Tyr Thr Val Glu Pro Asn Asn Ala Arg Gln Leu Val Glu
 65                  70                  75                  80

Ile Ala Ala Arg Asp Ile Glu Lys Leu Leu Ser Asn Arg Ser Lys Ala
                 85                  90                  95

Leu Val Arg Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
            115                 120                 125

Asp Asp Leu Asp Pro Glu Lys Asn Asp Ser Glu Pro Gly Ser Gln Arg
130                 135                 140

Ile Lys Pro Val Phe Ile Asp Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
            195                 200                 205

Gly Ser Ala Thr Gly Leu Ala Arg Tyr Tyr Pro Ala Ser Pro Trp Val
        210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
            245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Ala Lys Tyr Asn Lys Asp Lys Lys Val Arg Val
        370                 375                 380

Phe Thr Phe Ser Val Gly Gln His Asn Tyr Asp Arg Gly Pro Ile Gln
385                 390                 395                 400

Trp Met Ala Cys Glu Asn Lys Gly Tyr Tyr Tyr Glu Ile Pro Ser Ile
            405                 410                 415
```

-continued

```
Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
    450                 455                 460

Pro Val Phe Asn Ile Thr Gly Gln Asn Glu Asn Lys Thr Asn Leu Lys
465                 470                 475                 480

Asn Gln Leu Ile Leu Gly Val Met Gly Val Asp Val Ser Leu Glu Asp
            485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525

Pro Lys Asn Pro Lys Ser Gln Glu Pro Val Thr Leu Asp Phe Leu Asp
        530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
            565                 570                 575

Asp Glu Arg Tyr Ile Asp Lys Gly Asn Arg Thr Tyr Thr Trp Thr Pro
        580                 585                 590

Val Asn Gly Thr Asp Tyr Ser Leu Ala Leu Val Leu Pro Thr Tyr Ser
            595                 600                 605

Phe Tyr Tyr Ile Lys Ala Lys Ile Glu Glu Thr Ile Thr Gln Ala Arg
        610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
            645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Asn Pro Ser Cys Asn Thr Asp
        675                 680                 685

Leu Ile Asn Arg Val Leu Leu Asp Ala Gly Phe Thr Asn Glu Leu Val
        690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
        755                 760                 765

Asn Lys Ser Gly Pro Gly Ala Tyr Glu Ser Gly Ile Met Val Ser Lys
        770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
        820                 825                 830

Ser Asp Val Met Asp Cys Val Ile Leu Asp Asp Gly Gly Phe Leu Leu
```

-continued

```
                835                 840                 845
Met Ala Asn His Asp Asp Tyr Thr Asn Gln Ile Gly Arg Phe Phe Gly
    850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Ile
            900                 905                 910

Ala Asp Ile Leu His Ile Gly Trp Trp Ala Thr Ala Ala Trp Ser
            915                 920                 925

Ile Leu Gln Gln Phe Leu Leu Ser Leu Thr Phe Pro Arg Leu Leu Glu
    930                 935                 940

Ala Val Glu Met Glu Asp Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
            980                 985                 990

Val Glu Lys Leu Met Asn Thr Asn Leu Ile Phe Ile Met Val Glu Ser
            995                 1000                1005

Lys Gly Thr Cys Pro Cys Asp Thr Arg Leu
    1010                1015

<210> SEQ ID NO 35
<211> LENGTH: 1036
<212> TYPE: PRT
<213> ORGANISM: Sus scrofa

<400> SEQUENCE: 35

Met Ala Ala Gly Cys Leu Leu Ala Leu Thr Leu Thr Leu Phe Gln Ser
1               5                   10                  15

Leu Leu Ile Gly Pro Ser Ser Gln Glu Pro Phe Pro Ser Ala Val Thr
            20                  25                  30

Ile Lys Ser Trp Val Asp Lys Met Gln Glu Asp Leu Val Thr Leu Ala
        35                  40                  45

Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Arg Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Asp Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190
```

```
            Phe Lys Lys Asn Arg Glu Glu Asp Pro Ser Leu Leu Trp Gln Val Phe
                    195                 200                 205

Gly Ser Ala Thr Gly Leu Ala Arg Tyr Tyr Pro Ala Ser Pro Trp Val
                    210                 215                 220

Asp Asn Ser Arg Thr Pro Asn Lys Ile Asp Leu Tyr Asp Val Arg Arg
            225                 230                 235                 240

Arg Pro Trp Tyr Ile Gln Gly Ala Ala Ser Pro Lys Asp Met Leu Ile
                            245                 250                 255

Leu Val Asp Val Ser Gly Ser Val Ser Gly Leu Thr Leu Lys Leu Ile
                        260                 265                 270

Arg Thr Ser Val Ser Glu Met Leu Glu Thr Leu Ser Asp Asp Asp Phe
                    275                 280                 285

Val Asn Val Ala Ser Phe Asn Ser Asn Ala Gln Asp Val Ser Cys Phe
                    290                 295                 300

Gln His Leu Val Gln Ala Asn Val Arg Asn Lys Lys Val Leu Lys Asp
            305                 310                 315                 320

Ala Val Asn Asn Ile Thr Ala Lys Gly Ile Thr Asp Tyr Lys Lys Gly
                            325                 330                 335

Phe Ser Phe Ala Phe Glu Gln Leu Leu Asn Tyr Asn Val Ser Arg Ala
                        340                 345                 350

Asn Cys Asn Lys Ile Ile Met Leu Phe Thr Asp Gly Gly Glu Glu Arg
                    355                 360                 365

Ala Gln Glu Ile Phe Ala Lys Tyr Asn Lys Asp Lys Lys Val Arg Val
                    370                 375                 380

Phe Thr Phe Ser Val Gly Gln His Asn Tyr Asp Arg Gly Pro Ile Gln
            385                 390                 395                 400

Trp Met Ala Cys Glu Asn Lys Gly Tyr Tyr Tyr Glu Ile Pro Ser Ile
                            405                 410                 415

Gly Ala Ile Arg Ile Asn Thr Gln Glu Tyr Leu Asp Val Leu Gly Arg
                        420                 425                 430

Pro Met Val Leu Ala Gly Asp Lys Ala Lys Gln Val Gln Trp Thr Asn
                    435                 440                 445

Val Tyr Leu Asp Ala Leu Glu Leu Gly Leu Val Ile Thr Gly Thr Leu
                    450                 455                 460

Pro Val Phe Asn Ile Thr Gly Gln Asn Glu Asn Lys Thr Asn Leu Lys
            465                 470                 475                 480

Asn Gln Leu Ile Leu Gly Val Met Gly Val Asp Val Ser Leu Glu Asp
                            485                 490                 495

Ile Lys Arg Leu Thr Pro Arg Phe Thr Leu Cys Pro Asn Gly Tyr Tyr
                        500                 505                 510

Phe Ala Ile Asp Pro Asn Gly Tyr Val Leu Leu His Pro Asn Leu Gln
                    515                 520                 525

Pro Lys Asn Pro Lys Ser Gln Glu Pro Val Thr Leu Asp Phe Leu Asp
            530                 535                 540

Ala Glu Leu Glu Asn Asp Ile Lys Val Glu Ile Arg Asn Lys Met Ile
            545                 550                 555                 560

Asp Gly Glu Ser Gly Glu Lys Thr Phe Arg Thr Leu Val Lys Ser Gln
                            565                 570                 575

Asp Glu Arg Tyr Ile Asp Lys Gly Asn Arg Thr Tyr Thr Trp Thr Pro
                        580                 585                 590

Val Asn Gly Thr Asp Tyr Ser Leu Ala Leu Val Leu Pro Thr Tyr Ser
                    595                 600                 605

Phe Tyr Tyr Ile Lys Ala Lys Ile Glu Glu Thr Ile Thr Gln Ala Arg
```

-continued

```
            610                 615                 620
Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
                660                 665                 670

Glu Phe Ile Asp Arg Lys Thr Pro Asn Asn Pro Ser Cys Asn Thr Asp
            675                 680                 685

Leu Ile Asn Arg Val Leu Leu Asp Ala Gly Phe Thr Asn Glu Leu Val
            690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Thr Tyr Glu Asp Ser Phe Tyr
                740                 745                 750

Lys Arg Ser Leu Asp Asn Asp Asn Tyr Val Phe Thr Ala Pro Tyr Phe
            755                 760                 765

Asn Lys Ser Gly Pro Gly Ala Tyr Glu Ser Gly Ile Met Val Ser Lys
770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
                820                 825                 830

Ser Asp Val Met Asp Cys Val Ile Leu Asp Asp Gly Gly Phe Leu Leu
            835                 840                 845

Met Ala Asn His Asp Asp Tyr Thr Asn Gln Ile Gly Arg Phe Phe Gly
            850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Ile
                900                 905                 910

Ala Asp Ile Leu His Ile Gly Trp Trp Ala Thr Ala Ala Trp Ser
            915                 920                 925

Ile Leu Gln Gln Phe Leu Leu Ser Leu Thr Phe Pro Arg Leu Leu Glu
            930                 935                 940

Ala Val Glu Met Glu Asp Asp Phe Thr Ala Ser Leu Ser Lys Gln
945                 950                 955                 960

Ser Cys Ile Thr Glu Gln Thr Gln Tyr Phe Asp Asn Asp Ser Lys
                965                 970                 975

Ser Phe Ser Gly Val Leu Asp Cys Gly Asn Cys Ser Arg Ile Phe His
            980                 985                 990

Val Glu Lys Leu Met Asn Thr Asn Leu Ile Phe Ile Met Val Glu Ser
            995                 1000                1005

Lys Gly Thr Cys Pro Cys Asp Thr Arg Leu Leu Ile Gln Ala Glu Gln
    1010                1015                1020

Thr Ser Asp Gly Pro Asp Pro Cys Asp Met Val Lys
1025                1030                1035
```

<210> SEQ ID NO 36
<211> LENGTH: 1063
<212> TYPE: PRT
<213> ORGANISM: Sus scrofa

<400> SEQUENCE: 36

```
Met Ala Ala Gly Cys Leu Leu Ala Leu Thr Leu Thr Leu Phe Gln Ser
  1               5                  10                  15

Leu Leu Ile Gly Pro Ser Ser Gln Glu Pro Phe Pro Ser Ala Val Thr
             20                  25                  30

Ile Lys Ser Trp Val Asp Lys Met Gln Glu Asp Leu Val Thr Leu Ala
         35                  40                  45

Lys Thr Ala Ser Gly Val Asn Gln Leu Val Asp Ile Tyr Glu Lys Tyr
 50                  55                  60

Gln Asp Leu Tyr Thr Val Glu Pro Asn Asn Ala Arg Gln Leu Val Glu
 65                  70                  75                  80

Ile Ala Ala Arg Asp Ile Glu Lys Leu Leu Ser Asn Arg Ser Lys Ala
                 85                  90                  95

Leu Val Arg Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
130                 135                 140

Ile Lys Pro Val Phe Ile Asp Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Ala Lys Tyr Asn Lys Asp Lys Lys Val Arg Val
```

-continued

```
            370                 375                 380
Phe Thr Phe Ser Val Gly Gln His Asn Tyr Asp Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
450                 455                 460

Pro Val Phe Asn Ile Thr Gly Gln Asn Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525

Pro Lys Asn Pro Lys Ser Gln Glu Pro Val Thr Leu Asp Phe Leu Asp
530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Ile Glu Glu Thr Ile Thr Gln Ala Arg
610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Pro Ser Cys Asn Thr Asp
        675                 680                 685

Leu Ile Asn Arg Val Leu Leu Asp Ala Gly Phe Thr Asn Glu Leu Val
690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
        755                 760                 765

Asn Lys Ser Gly Pro Gly Ala Tyr Glu Ser Gly Ile Met Val Ser Lys
770                 775                 780

Ala Val Glu Ile Tyr Ile Gln Gly Lys Leu Leu Lys Pro Ala Val Val
785                 790                 795                 800
```

-continued

```
Gly Ile Lys Ile Asp Val Asn Ser Trp Ile Glu Asn Phe Thr Lys Thr
            805                 810                 815

Ser Ile Arg Asp Pro Cys Ala Gly Pro Val Cys Asp Cys Lys Arg Asn
        820                 825                 830

Ser Asp Val Met Asp Cys Val Ile Leu Asp Asp Gly Gly Phe Leu Leu
    835                 840                 845

Met Ala Asn His Asp Asp Tyr Thr Asn Gln Ile Gly Arg Phe Gly
850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Ile
            900                 905                 910

Ala Asp Ile Leu His Ile Gly Trp Trp Ala Thr Ala Ala Trp Ser
        915                 920                 925

Ile Leu Gln Gln Phe Leu Leu Ser Leu Thr Phe Pro Arg Leu Leu Glu
    930                 935                 940

Ala Val Glu Met Glu Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
            980                 985                 990

Val Glu Lys Leu Met Asn Thr Asn Leu Ile Phe Ile Met Val Glu Ser
        995                 1000                1005

Lys Gly Thr Cys Pro Cys Asp Thr Arg Leu Leu Ile Gln Ala Glu Gln
    1010                1015                1020

Thr Ser Asp Gly Pro Asp Pro Cys Asp Met Val Lys Gln Pro Arg Tyr
1025                1030                1035                1040

Arg Lys Gly Pro Asp Val Cys Phe Asp Asn Asn Ala Leu Glu Asp Tyr
                1045                1050                1055

Thr Asp Cys Gly Gly Val Ser
        1060

<210> SEQ ID NO 37
<211> LENGTH: 1069
<212> TYPE: PRT
<213> ORGANISM: Sus scrofa

<400> SEQUENCE: 37

Met Ala Ala Gly Cys Leu Leu Ala Leu Thr Leu Thr Leu Phe Gln Ser
1               5                   10                  15

Leu Leu Ile Gly Pro Ser Ser Gln Glu Pro Phe Pro Ser Ala Val Thr
            20                  25                  30

Ile Lys Ser Trp Val Asp Lys Met Gln Glu Asp Leu Val Thr Leu Ala
        35                  40                  45

Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Arg Leu Ala Leu Glu Ala Glu Lys Val Gln Ala Ala His Gln
```

-continued

```
              100                 105                 110
Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
130                 135                 140

Ile Lys Pro Val Phe Ile Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
                180                 185                 190

Phe Lys Lys Asn Arg Glu Glu Asp Pro Ser Leu Leu Trp Gln Val Phe
            195                 200                 205

Gly Ser Ala Thr Gly Leu Ala Arg Tyr Tyr Pro Ala Ser Pro Trp Val
        210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
                260                 265                 270

Arg Thr Ser Val Ser Glu Met Leu Glu Thr Leu Ser Asp Asp Asp Phe
            275                 280                 285

Val Asn Val Ala Ser Phe Asn Ser Asn Ala Gln Asp Val Ser Cys Phe
        290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Ala Lys Tyr Asn Lys Asp Lys Lys Val Arg Val
370                 375                 380

Phe Thr Phe Ser Val Gly Gln His Asn Tyr Asp Arg Gly Pro Ile Gln
385                 390                 395                 400

Trp Met Ala Cys Glu Asn Lys Gly Tyr Tyr Glu Ile Pro Ser Ile
                405                 410                 415

Gly Ala Ile Arg Ile Asn Thr Gln Glu Tyr Leu Asp Val Leu Gly Arg
                420                 425                 430

Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
        450                 455                 460

Pro Val Phe Asn Ile Thr Gly Gln Asn Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
            515                 520                 525
```

```
Pro Lys Asn Pro Lys Ser Gln Glu Pro Val Thr Leu Asp Phe Leu Asp
    530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Ile Glu Glu Thr Ile Thr Gln Ala Arg
    610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Asn Pro Ser Cys Asn Thr Asp
        675                 680                 685

Leu Ile Asn Arg Val Leu Leu Asp Ala Gly Phe Thr Asn Glu Leu Val
    690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
        755                 760                 765

Asn Lys Ser Gly Pro Gly Ala Tyr Glu Ser Gly Ile Met Val Ser Lys
770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
            820                 825                 830

Ser Asp Val Met Asp Cys Val Ile Leu Asp Asp Gly Gly Phe Leu Leu
        835                 840                 845

Met Ala Asn His Asp Asp Tyr Thr Asn Gln Ile Gly Arg Phe Phe Gly
    850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Ile
            900                 905                 910

Ala Asp Ile Leu His Ile Gly Trp Trp Ala Thr Ala Ala Ala Trp Ser
        915                 920                 925

Ile Leu Gln Gln Phe Leu Leu Ser Leu Thr Phe Pro Arg Leu Leu Glu
930                 935                 940
```

-continued

```
Ala Val Glu Met Glu Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
                980                 985                 990

Val Glu Lys Leu Met Asn Thr Asn Leu Ile Phe Ile Met Val Glu Ser
            995                1000                1005

Lys Gly Thr Cys Pro Cys Asp Thr Arg Leu Leu Ile Gln Ala Glu Gln
   1010                1015                1020

Thr Ser Asp Gly Pro Asp Pro Cys Asp Met Val Lys Gln Pro Arg Tyr
1025                1030                1035                1040

Arg Lys Gly Pro Asp Val Cys Phe Asp Asn Asn Ala Leu Glu Asp Tyr
                1045                1050                1055

Thr Asp Cys Gly Gly Val Ser His His His His His His
            1060                1065
```

<210> SEQ ID NO 38
<211> LENGTH: 3055
<212> TYPE: DNA
<213> ORGANISM: Homo sapiens

<400> SEQUENCE: 38

```
atggctgctg gctgcctgct ggccttgact ctgacacttt tccaatcttt gctcatcggc     60
ccctcgtcgg aggagccgtt cccttcggcc gtcactatca aatcatgggt ggataagatg    120
caagaagacc ttgtcacact ggcaaaaaca gcaagtggag tcaatcagct tgttgatatt    180
tatgagaaat atcaagattt gtatactgtg aaccaaata atgcacgcca gctggtagaa    240
attgcagcca gggatattga gaaacttctg agcaacagat ctaaagccct ggtgagcctg    300
gcattggaag cggagaaagt tcaagcagct caccagtgga gagaagattt tgcaagcaat    360
gaagttgtct actacaatgc aaaggatgat ctcgatcctg agaaaatga cagtgagcca    420
ggcagccaga ggataaaaacc tgttttcatt gaagatgcta attttggacg acaaatatct    480
tatcagcacg cagcagtcca tattcctact gacatctatg agggctcaac aattgtgtta    540
aatgaactca actggacaag tgccttagat gaagttttca aaagaatcg cgaggaagac    600
ccttcattat tgtggcaggt ttttggcagt gccactggcc tagctcgata ttatccagct    660
tcaccatggg ttgataatag tagaactcca aataagattg accttttatga tgtacgcaga    720
agaccatggt acatccaagg agctgcatct cctaaagaca tgcttattct ggtggatgtg    780
agtggaagtg ttagtggatt gacacttaaa ctgatccgaa catctgtctc gaaatgtta    840
gaaaccctct cagatgatga tttcgtgaat gtagcttcat taacagcaa tgctcaggat    900
gtaagctgtt ttcagcacct tgtccaagca aatgtaagaa ataaaaaagt gttgaaagac    960
gcggtgaata atatcacagc caaggaatt acagattata gaagggctt tagttttgct   1020
tttgaacagc tgcttaatta taatgtttcc agagcaaact gcaataagat tattatgcta   1080
ttcacggatg aggagaaga gagagcccag gagatattta caaatacaa taagataaa   1140
aaagtacgtg tattcaggtt ttcagttggt caacacaatt atgagagagg acctattcag   1200
tggatggcct gtgaaaacaa aggttattat tatgaaattc cttccattgg tgcaataaga   1260
atcaatactc aggaatatt ggatgttttg ggaagaccaa tggttttagc aggagacaaa   1320
gctaagcaag tccatggac aaatgtgtac ctggatgcat tggaactggg acttgtcatt   1380
actggaactc ttccggtctt caacataacc ggccaatttg aaataagac aaacttaaag   1440
```

-continued

```
aaccagctga ttcttggtgt gatgggagta gatgtgtctt tggaagatat taaaagactg     1500
acaccacgtt ttacactgtg ccccaatggg tattactttg caatcgatcc taatggttat     1560
gttttattac atccaaatct tcagccaaag aacccccaaat ctcaggagcc agtaacattg    1620
gatttccttg atgcagagtt agagaatgat attaaagtgg agattcgaaa taagatgatt     1680 gatgggaaa gtggagaaaa aacattcaga actctggtta aatctcaaga tgagagatat      1740
attgacaaag gaaacaggac atacacatgg acacctgtca atggcacaga ttacagtttg     1800
gccttggtat taccaaccta cagttttttac tatataaaag ccaaactaga agagacaata   1860
actcaggcca gatcaaaaaa gggcaaaatg aaggattcgg aaaccctgaa gccagataat     1920
tttgaagaat ctggctatac attcatagca ccaagagatt actgcaatga cctgaaaata    1980
tcggataata acactgaatt tcttttaaat ttcaacgagt ttattgatag aaaaactcca    2040
aacaacccat catgtaacgc ggatttgatt aatagagtct tgcttgatgc aggctttaca    2100
aatgaacttg tccaaaatta ctggagtaag cagaaaaata tcaagggagt gaaagcacga    2160
tttgttgtga ctgatggtgg gattaccaga gtttatccca aagaggctgg agaaaattgg    2220
caagaaaacc cagagacata tgaggacagc ttctataaaa ggagcctaga taatgataac    2280
tatgttttca ctgctcccta ctttaacaaa agtggacctg tgcctatga atcgggcatt    2340 atggtaagca agctgtaga aatatatatt caagggaaac ttcttaaacc tgcagttgtt    2400
ggaattaaaa ttgatgtaaa ttcctggata gagaatttca ccaaaacctc aatcagagat    2460
ccgtgtgctg gtccagtttg tgactgcaaa agaaacagtg acgtaatgga ttgtgtgatt    2520
ctggatgatg tgggttctct tctgatggca aatcatgatg attatactaa tcagattgga    2580
agattttttg gagagattga tcccagcttg atgagacacc tggttaatat atcagtttat    2640
gcttttaaca aatcttatga ttatcagtca gtatgtgagc ccggtgctgc accaaaacaa    2700
ggagcaggac atcgctcagc atatgtgcca tcagtagcag acatattaca aattggctgg    2760
tgggccactg ctgctgcctg gtctattcta cagcagtttc tcttgagttt gacctttcca    2820
cgactccttg aggcagttga gatggaggat gatgacttca cggcctccct gtccaagcag    2880
agctgcatta ctgaacaaac ccagtatttc ttcgataacg acagtaaatc attcagtggt    2940
gtattagact gtgaaactg ttccagaatc tttcatggag aaaagcttat gaacaccaac    3000
ttaatattca taatggttga gagcaaaggg acatgtccat gtgacacacg actgc         3055
```

<210> SEQ ID NO 39
<211> LENGTH: 3109
<212> TYPE: DNA
<213> ORGANISM: Homo sapiens

<400> SEQUENCE: 39

```
atggctgctg gctgcctgct ggccttgact ctgacacttt tccaatcttt gctcatcggc       60
ccctcgtcgg aggagccgtt cccttcggcc gtcactatca aatcatgggt ggataagatg      120
caagaagacc ttgtcacact ggcaaaaaca gcaagtggag tcaatcagct tgttgatatt      180
tatgagaaat atcaagattt gtatactgtg gaaccaaata tgcacgccca gctggtagaa     240
attgcagcca gggatattga gaaacttctg agcaacagat ctaaagccct ggtgagcctg     300
gcattggaag cggagaaagt tcaagcagct caccagtgga gagaagattt tgcaagcaat    360
gaagttgtct actacaatgc aaaggatgat ctcgatcctg agaaaaatga cagtgagcca    420
ggcagccaga ggataaaacc tgttttcatt gaagatgcta attttggacg acaaatatct    480
```

-continued

```
tatcagcacg cagcagtcca tattcctact gacatctatg agggctcaac aattgtgtta      540
aatgaactca actggacaag tgccttagat gaagttttca aaaagaatcg cgaggaagac      600
ccttcattat tgtggcaggt ttttggcagt gccactggcc tagctcgata ttatccagct      660
tcaccatggg ttgataatag tagaactcca aataagattg acctttatga tgtacgcaga      720
agaccatggt acatccaagg agctgcatct cctaaagaca tgcttattct ggtggatgtg      780
agtggaagtg ttagtggatt gacacttaaa ctgatccgaa catctgtctc cgaaatgtta      840
gaaaccctct cagatgatga tttcgtgaat gtagcttcat ttaacagcaa tgctcaggat      900
gtaagctgtt ttcagcacct tgtccaagca aatgtaagaa ataaaaagt gttgaaagac       960 gcggtgaata atatcacagc caaaggaatt acagattata agaagggctt tagttttgct     1020
tttgaacagc tgcttaatta taatgtttcc agagcaaact gcaataagat tattatgcta     1080
ttcacggatg gaggagaaga gagagcccag gagatattta acaaatacaa taagataaa      1140 aaagtacgtg tattcaggtt ttcagttggt caacacaatt atgagagagg acctattcag     1200
tggatggcct gtgaaaacaa aggttattat tatgaaattc cttccattgg tgcaataaga     1260
atcaatactc aggaatattt ggatgttttg gaagaccaa tggttttagc aggagacaaa      1320
gctaagcaag tccaatggac aaatgtgtac ctggatgcat tggaactggg acttgtcatt     1380
actggaactc ttccggtctt caacataacc ggccaatttg aaaataagac aaacttaaag     1440
aaccagctga ttcttggtgt gatgggagta gatgtgtctt tggaagatat taaaagactg     1500
acaccacgtt ttacactgtg ccccaatggg tattactttg caatcgatcc taatggttat     1560
gttttattac atccaaatct tcagccaaag aaccccaaat ctcaggagcc agtaacattg     1620
gatttccttg atgcagagtt agagaatgat attaaagtgg agattcgaaa taagatgatt     1680
gatggggaaa gtggagaaaa aacattcaga actctggtta aatctcaaga tgagagatat     1740
attgacaaag gaaacaggac atacacatgg acacctgtca atggcacaga ttacagtttg     1800
gccttggtat taccaaccta cagttttttac tatataaaag ccaaactaga agagacaata    1860
actcaggcca gatcaaaaaa gggcaaaatg aaggattcgg aaaccctgaa gccagataat     1920
tttgaagaat ctggctatac attcatagca ccaagagatt actgcaatga cctgaaaata     1980
tcggataata acactgaatt tcttttaaat ttcaacgagt ttattgatag aaaaactcca     2040
aacaacccat catgtaacgc ggatttgatt aatagagtct tgcttgatgc aggctttaca     2100
aatgaacttg tccaaaatta ctggagtaag cagaaaaata tcaagggagt gaaagcacga     2160
tttgttgtga ctgatggtgg gattaccaga gtttatccca aagaggctgg agaaaattgg     2220
caagaaaacc cagagacata tgaggacagc ttctataaaa ggagcctaga taatgataac     2280
tatgttttca ctgctcccta ctttaacaaa agtggacctg tgcctatga atcgggcatt      2340 atggtaagca agctgtaga aatatatatt caagggaaac ttcttaaacc tgcagttgtt      2400
ggaattaaaa ttgatgtaaa ttcctggata gagaatttca ccaaaacctc aatcagagat     2460
ccgtgtgctg gtccagtttg tgactgcaaa agaaacagtg acgtaatgga ttgtgtgatt     2520
ctggatgatg gtgggtttct tctgatggca atcatgatg attatactaa tcagattgga      2580
agattttttg gagagattga tcccagcttg atgagacacc tggttaatat atcagtttat     2640
gcttttaaca aatcttatga ttatcagtca gtatgtgagc ccggtgctgc accaaaacaa     2700
ggagcaggac atcgctcagc atatgtgcca tcagtagcag acatattaca aattggctgg     2760
tgggccactg ctgctgcctg gtctattcta cagcagtttc tcttgagttt gacctttcca     2820
cgactccttg aggcagttga gatggaggat gatgacttca cggcctccct gtccaagcag     2880
```

```
agctgcatta ctgaacaaac ccagtatttc ttcgataacg acagtaaatc attcagtggt    2940
gtattagact gtggaaactg ttccagaatc tttcatggag aaaagcttat gaacaccaac    3000
ttaatattca taatggttga gagcaaaggg acatgtccat gtgacacacg actgctcata    3060
caagcggagc agacttctga cggtccaaat ccttgtgaca tggttaagc                3109
```

<210> SEQ ID NO 40
<211> LENGTH: 3190
<212> TYPE: DNA
<213> ORGANISM: Homo sapiens

<400> SEQUENCE: 40

```
atggctgctg ctgcctgct ggccttgact ctgacacttt tccaatcttt gctcatcggc      60
ccctcgtcgg aggagccgtt cccttcggcc gtcactatca atcatgggt ggataagatg     120 caagaagacc ttgtcacact ggcaaaaaca gcagtggag tcaatcagct tgttgatatt     180
tatgagaaat atcaagattt gtatactgtg aaccaaata atgcacgcca gctggtagaa     240
attgcagcca gggatattga gaaacttctg agcaacagat ctaaagccct ggtgagcctg     300
gcattggaag cggagaaagt tcaagcagct caccagtgga gagaagattt tgcaagcaat    360
gaagttgtct actacaatgc aaaggatgat ctcgatcctg agaaaaatga cagtgagcca    420
ggcagccaga ggataaaacc tgttttcatt gaagatgcta attttggacg acaaatatct    480
tatcagcacg cagcagtcca tattcctact gacatctatg agggctcaac aattgtgtta    540
aatgaactca actggacaag tgccttagat gaagttttca aaaagaatcg cgaggaagac    600
ccttcattat tgtggcaggt ttttggcagt gccactggcc tagctcgata ttatccagct    660
tcaccatggg ttgataatag tagaactcca aataagattc acctttatga tgtacgcaga    720
agaccatggt acatccaagg agctgcatct cctaaagaca tgcttattct ggtggatgtg    780
agtggaagtg ttagtggatt gacacttaaa ctgatccgaa catctgtctc cgaaatgtta    840
gaaaccctct cagatgatga tttcgtgaat gtagcttcat ttaacagcaa tgctcaggat    900
gtaagctgtt ttcagcaccc tgtccaagca aatgtaagaa ataaaaagt gttgaaagac    960 gcggtgaata atatcacagc caaggaatt acagattata gaagggctt tagttttgct    1020 tttgaacagc tgcttaatta taatgttttcc agacaaaact gcaataagat tattatgcta   1080
ttcacggatg gaggagaaga gagagcccag gagatattta caaatacaa taaagataaa    1140 aaagtacgtg tattcaggtt ttcagttggt caacacaatt atgagagagg acctattcag    1200
tggatggcct gtgaaaacaa aggttattat tatgaaattc cttccattgg tgcaataaga    1260
atcaatactc aggaatattt ggatgttttg ggaagaccaa tggttttagc aggagacaaa    1320
gctaagcaag tccaatggac aaatgtgtac ctggatgcat ggaactggg acttgtcatt    1380 actggaactc ttccggtctt caacataacc ggccaatttg aaaataagac aaacttaaag    1440
aaccagctga ttcttggtgt gatgggagta gatgtgtctt ggaagatat taaaagactg    1500 acaccacgtt ttacactgtg ccccaatggg tattactttg caatcgatcc taatggttat    1560
gttttattac atccaaatct tcagccaaag aaccccaaat ctcaggagcc agtaacattg    1620
gatttccttg atgcagagtt agaagatgat ttaaagtgg agattcgaaa taagatgatt    1680
gatggggaaa gtggagaaaa acattcaga actctggtta atctcaaga tgagagatat    1740 attgacaaag gaacaggac atacacatgg acacctgtca atggcacaga ttacagtttg    1800
gccttggtat taccaaccta cagttttac tatataaaag ccaaactaga agagacaata    1860
```

-continued

```
actcaggcca gatcaaaaaa gggcaaaatg aaggattcgg aaaccctgaa gccagataat    1920
tttgaagaat ctggctatac attcatagca ccaagagatt actgcaatga cctgaaaata    1980
tcggataata acactgaatt tcttttaaat ttcaacgagt ttattgatag aaaaactcca    2040
aacaacccat catgtaacgc ggatttgatt aatagagtct tgcttgatgc aggctttaca    2100
aatgaacttg tccaaaatta ctggagtaag cagaaaaata tcaagggagt gaaagcacga    2160
tttgttgtga ctgatggtgg gattaccaga gtttatccca agaggctgg agaaaattgg     2220 caagaaaacc cagagacata tgaggacagc ttctataaaa ggagcctaga taatgataac    2280
tatgttttca ctgctcccta ctttaacaaa agtggacctg gtgcctatga atcgggcatt    2340
atggtaagca agctgtaga aatatatatt caagggaaac ttcttaaacc tgcagttgtt    2400
ggaattaaaa ttgatgtaaa ttcctggata gagaatttca ccaaaacctc aatcagagat    2460
ccgtgtgctg gtccagtttg tgactgcaaa agaaacagtg acgtaatgga ttgtgtgatt    2520
ctggatgatg gtgggtttct tctgatggca aatcatgatg attatactaa tcagattgga    2580
agattttttg gagagattga tcccagcttg atgagacacc tggttaatat atcagtttat    2640
gcttttaaca aatcttatga ttatcagtca gtatgtgagc ccggtgctgc accaaaacaa    2700
ggagcaggac atcgctcagc atatgtgcca tcagtagcag acatattaca aattggctgg    2760
tgggccactg ctgctgcctg gtctattcta cagcagtttc tcttgagttt gacctttcca    2820
cgactccttg aggcagttga gatggaggat gatgacttca cggcctccct gtccaagcag    2880
agctgcatta ctgaacaaac ccagtatttc ttcgataacg acagtaaatc attcagtggt    2940
gtattagact gtggaaactg ttccagaatc tttcatggag aaaagcttat gaacaccaac    3000
ttaatattca taatggttga gagcaaaggg acatgtccat gtgacacacg actgctcata    3060
caagcggagc agacttctga cggtccaaat ccttgtgaca tggttaagca acctagatac    3120
cgaaaagggc ctgatgtctg ctttgataac aatgtcttgg aggattatac tgactgtggt    3180
ggtgtttctg                                                          3190
```

```
<210> SEQ ID NO 41
<211> LENGTH: 1018
<212> TYPE: PRT
<213> ORGANISM: Homo sapiens

<400> SEQUENCE: 41

Met Ala Ala Gly Cys Leu Leu Ala Leu Thr Leu Thr Leu Phe Gln Ser
  1               5                  10                  15

Leu Leu Ile Gly Pro Ser Ser Glu Glu Pro Phe Pro Ser Ala Val Thr
             20                  25                  30

Ile Lys Ser Trp Val Asp Lys Met Gln Glu Asp Leu Val Thr Leu Ala
         35                  40                  45

Lys Thr Ala Ser Gly Val Asn Gln Leu Val Asp Ile Tyr Glu Lys Tyr
     50                  55                  60

Gln Asp Leu Tyr Thr Val Glu Pro Asn Asn Ala Arg Gln Leu Val Glu
 65                  70                  75                  80

Ile Ala Ala Arg Asp Ile Glu Lys Leu Leu Ser Asn Arg Ser Lys Ala
                 85                  90                  95

Leu Val Ser Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
```

-continued

```
            130                 135                 140
Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Asp Pro Ser Leu Leu Trp Gln Val Phe
            195                 200                 205

Gly Ser Ala Thr Gly Leu Ala Arg Tyr Tyr Pro Ala Ser Pro Trp Val
210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Phe
            275                 280                 285

Val Asn Val Ala Ser Phe Asn Ser Asn Ala Gln Asp Val Ser Cys Phe
290                 295                 300

Gln His Leu Val Gln Ala Asn Val Arg Asn Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
            355                 360                 365

Ala Gln Glu Ile Phe Asn Lys Tyr Asn Lys Asp Lys Lys Val Arg Val
            370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
            485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
            515                 520                 525

Pro Lys Asn Pro Lys Ser Gln Glu Pro Val Thr Leu Asp Phe Leu Asp
            530                 535                 540

Ala Glu Leu Glu Asn Asp Ile Lys Val Glu Ile Arg Asn Lys Met Ile
545                 550                 555                 560
```

-continued

```
Asp Gly Glu Ser Gly Glu Lys Thr Phe Arg Thr Leu Val Lys Ser Gln
            565                 570                 575
Asp Glu Arg Tyr Ile Asp Lys Gly Asn Arg Thr Tyr Thr Trp Thr Pro
        580                 585                 590
Val Asn Gly Thr Asp Tyr Ser Leu Ala Leu Val Leu Pro Thr Tyr Ser
    595                 600                 605
Phe Tyr Tyr Ile Lys Ala Lys Leu Glu Thr Ile Thr Gln Ala Arg
610                 615                 620
Ser Lys Lys Gly Lys Met Lys Asp Ser Glu Thr Leu Lys Pro Asp Asn
625                 630                 635                 640
Phe Glu Glu Ser Gly Tyr Thr Phe Ile Ala Pro Arg Asp Tyr Cys Asn
            645                 650                 655
Asp Leu Lys Ile Ser Asp Asn Asn Thr Glu Phe Leu Leu Asn Phe Asn
        660                 665                 670
Glu Phe Ile Asp Arg Lys Thr Pro Asn Asn Pro Ser Cys Asn Ala Asp
    675                 680                 685
Leu Ile Asn Arg Val Leu Leu Asp Ala Gly Phe Thr Asn Glu Leu Val
690                 695                 700
Gln Asn Tyr Trp Ser Lys Gln Lys Asn Ile Lys Gly Val Lys Ala Arg
705                 710                 715                 720
Phe Val Thr Asp Gly Gly Ile Thr Arg Val Tyr Pro Lys Glu Ala
            725                 730                 735
Gly Glu Asn Trp Gln Glu Asn Pro Glu Thr Tyr Glu Asp Ser Phe Tyr
        740                 745                 750
Lys Arg Ser Leu Asp Asn Asp Asn Tyr Val Phe Thr Ala Pro Tyr Phe
    755                 760                 765
Asn Lys Ser Gly Pro Gly Ala Tyr Glu Ser Gly Ile Met Val Ser Lys
770                 775                 780
Ala Val Glu Ile Tyr Ile Gln Gly Lys Leu Leu Lys Pro Ala Val Val
785                 790                 795                 800
Gly Ile Lys Ile Asp Val Asn Ser Trp Ile Glu Asn Phe Thr Lys Thr
            805                 810                 815
Ser Ile Arg Asp Pro Cys Ala Gly Pro Val Cys Asp Cys Lys Arg Asn
        820                 825                 830
Ser Asp Val Met Asp Cys Val Ile Leu Asp Asp Gly Gly Phe Leu Leu
    835                 840                 845
Met Ala Asn His Asp Asp Tyr Thr Asn Gln Ile Gly Arg Phe Gly
850                 855                 860
Glu Ile Asp Pro Ser Leu Met Arg His Leu Val Asn Ile Ser Val Tyr
865                 870                 875                 880
Ala Phe Asn Lys Ser Tyr Asp Tyr Gln Ser Val Cys Glu Pro Gly Ala
            885                 890                 895
Ala Pro Lys Gln Gly Ala Gly His Arg Ser Ala Tyr Val Pro Ser Val
        900                 905                 910
Ala Asp Ile Leu Gln Ile Gly Trp Trp Ala Thr Ala Ala Trp Ser
    915                 920                 925
Ile Leu Gln Gln Phe Leu Leu Ser Leu Thr Phe Pro Arg Leu Leu Glu
930                 935                 940
Ala Val Glu Met Glu Asp Asp Asp Phe Thr Ala Ser Leu Ser Lys Gln
945                 950                 955                 960
Ser Cys Ile Thr Glu Gln Thr Gln Tyr Phe Phe Asp Asn Asp Ser Lys
            965                 970                 975
```

-continued

```
Ser Phe Ser Gly Val Leu Asp Cys Gly Asn Cys Ser Arg Ile Phe His
            980                 985                 990

Gly Glu Lys Leu Met Asn Thr Asn Leu Ile Phe Ile Met Val Glu Ser
            995                 1000                1005

Lys Gly Thr Cys Pro Cys Asp Thr Arg Leu
    1010                1015

<210> SEQ ID NO 42
<211> LENGTH: 1036
<212> TYPE: PRT
<213> ORGANISM: Homo sapiens

<400> SEQUENCE: 42

Met Ala Ala Gly Cys Leu Leu Ala Leu Thr Leu Thr Leu Phe Gln Ser
 1               5                  10                  15

Leu Leu Ile Gly Pro Ser Ser Glu Glu Pro Phe Pro Ser Ala Val Thr
                20                  25                  30

Ile Lys Ser Trp Val Asp Lys Met Gln Glu Asp Leu Val Thr Leu Ala
            35                  40                  45

Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Ser Leu Ala Leu Glu Ala Glu Lys Val Gln Ala Ala His Gln
                100                 105                 110

Trp Arg Glu Asp Phe Ala Ser Asn Glu Val Val Tyr Tyr Asn Ala Lys
            115                 120                 125

Asp Asp Leu Asp Pro Glu Lys Asn Asp Ser Glu Pro Gly Ser Gln Arg
    130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
                180                 185                 190

Phe Lys Lys Asn Arg Glu Glu Asp Pro Ser Leu Leu Trp Gln Val Phe
            195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
                260                 265                 270

Arg Thr Ser Val Ser Glu Met Leu Glu Thr Leu Ser Asp Asp Asp Phe
            275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335
```

```
Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
    370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu His Pro Asn Leu Gln
        515                 520                 525

Pro Lys Asn Pro Lys Ser Gln Glu Pro Val Thr Leu Asp Phe Leu Asp
    530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Leu Glu Glu Thr Ile Thr Gln Ala Arg
    610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Pro Ser Cys Asn Ala Asp
        675                 680                 685

Leu Ile Asn Arg Val Leu Leu Asp Ala Gly Phe Thr Asn Glu Leu Val
    690                 695                 700

Gln Asn Tyr Trp Ser Lys Gln Lys Asn Ile Lys Gly Val Lys Ala Arg
705                 710                 715                 720

Phe Val Val Thr Asp Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750
```

```
Lys Arg Ser Leu Asp Asn Asp Asn Tyr Val Phe Thr Ala Pro Tyr Phe
        755                 760                 765

Asn Lys Ser Gly Pro Gly Ala Tyr Glu Ser Gly Ile Met Val Ser Lys
    770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                    805                 810                 815

Ser Ile Arg Asp Pro Cys Ala Gly Pro Val Cys Asp Cys Lys Arg Asn
                820                 825                 830

Ser Asp Val Met Asp Cys Val Ile Leu Asp Asp Gly Gly Phe Leu Leu
            835                 840                 845

Met Ala Asn His Asp Asp Tyr Thr Asn Gln Ile Gly Arg Phe Gly
        850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Val
                900                 905                 910

Ala Asp Ile Leu Gln Ile Gly Trp Trp Ala Thr Ala Ala Trp Ser
            915                 920                 925

Ile Leu Gln Gln Phe Leu Leu Ser Leu Thr Phe Pro Arg Leu Leu Glu
        930                 935                 940

Ala Val Glu Met Glu Asp Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
                980                 985                 990

Gly Glu Lys Leu Met Asn Thr Asn Leu Ile Phe Ile Met Val Glu Ser
            995                 1000                1005

Lys Gly Thr Cys Pro Cys Asp Thr Arg Leu Leu Ile Gln Ala Glu Gln
    1010                1015                1020

Thr Ser Asp Gly Pro Asn Pro Cys Asp Met Val Lys
1025                1030                1035

<210> SEQ ID NO 43
<211> LENGTH: 1063
<212> TYPE: PRT
<213> ORGANISM: Homo sapiens

<400> SEQUENCE: 43

Met Ala Ala Gly Cys Leu Leu Ala Leu Thr Leu Thr Leu Phe Gln Ser
1               5                   10                  15

Leu Leu Ile Gly Pro Ser Ser Glu Glu Pro Phe Pro Ser Ala Val Thr
                20                  25                  30

Ile Lys Ser Trp Val Asp Lys Met Gln Glu Asp Leu Val Thr Leu Ala
            35                  40                  45

Lys Thr Ala Ser Gly Val Asn Gln Leu Val Asp Ile Tyr Glu Lys Tyr
        50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95
```

-continued

Leu Val Ser Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
            115                 120                 125

Asp Asp Leu Asp Pro Glu Lys Asn Asp Ser Glu Pro Gly Ser Gln Arg
            130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
            195                 200                 205

Gly Ser Ala Thr Gly Leu Ala Arg Tyr Tyr Pro Ala Ser Pro Trp Val
            210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
            275                 280                 285

Val Asn Val Ala Ser Phe Asn Ser Asn Ala Gln Asp Val Ser Cys Phe
            290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
            355                 360                 365

Ala Gln Glu Ile Phe Asn Lys Tyr Asn Lys Asp Lys Lys Val Arg Val
            370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
            450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

-continued

```
Phe Ala Ile Asp Pro Asn Gly Tyr Val Leu His Pro Asn Leu Gln
        515                 520                 525
Pro Lys Asn Pro Lys Ser Gln Glu Pro Val Thr Leu Asp Phe Leu Asp
530                 535                 540
Ala Glu Leu Glu Asn Asp Ile Lys Val Glu Ile Arg Asn Lys Met Ile
545                 550                 555                 560
Asp Gly Glu Ser Gly Glu Lys Thr Phe Arg Thr Leu Val Lys Ser Gln
                565                 570                 575
Asp Glu Arg Tyr Ile Asp Lys Gly Asn Arg Thr Tyr Thr Trp Thr Pro
            580                 585                 590
Val Asn Gly Thr Asp Tyr Ser Leu Ala Leu Val Leu Pro Thr Tyr Ser
        595                 600                 605
Phe Tyr Tyr Ile Lys Ala Lys Leu Glu Thr Ile Thr Gln Ala Arg
    610                 615                 620
Ser Lys Lys Gly Lys Met Lys Asp Ser Glu Thr Leu Lys Pro Asp Asn
625                 630                 635                 640
Phe Glu Glu Ser Gly Tyr Thr Phe Ile Ala Pro Arg Asp Tyr Cys Asn
                645                 650                 655
Asp Leu Lys Ile Ser Asp Asn Asn Thr Glu Phe Leu Leu Asn Phe Asn
            660                 665                 670
Glu Phe Ile Asp Arg Lys Thr Pro Asn Asn Pro Ser Cys Asn Ala Asp
        675                 680                 685
Leu Ile Asn Arg Val Leu Leu Asp Ala Gly Phe Thr Asn Glu Leu Val
    690                 695                 700
Gln Asn Tyr Trp Ser Lys Gln Lys Asn Ile Lys Gly Val Lys Ala Arg
705                 710                 715                 720
Phe Val Val Thr Asp Gly Gly Ile Thr Arg Val Tyr Pro Lys Glu Ala
                725                 730                 735
Gly Glu Asn Trp Gln Glu Asn Pro Glu Thr Tyr Glu Asp Ser Phe Tyr
            740                 745                 750
Lys Arg Ser Leu Asp Asn Asp Asn Tyr Val Phe Thr Ala Pro Tyr Phe
        755                 760                 765
Asn Lys Ser Gly Pro Gly Ala Tyr Glu Ser Gly Ile Met Val Ser Lys
770                 775                 780
Ala Val Glu Ile Tyr Ile Gln Gly Lys Leu Leu Lys Pro Ala Val Val
785                 790                 795                 800
Gly Ile Lys Ile Asp Val Asn Ser Trp Ile Glu Asn Phe Thr Lys Thr
                805                 810                 815
Ser Ile Arg Asp Pro Cys Ala Gly Pro Val Cys Asp Cys Lys Arg Asn
            820                 825                 830
Ser Asp Val Met Asp Cys Val Ile Leu Asp Asp Gly Gly Phe Leu Leu
        835                 840                 845
Met Ala Asn His Asp Asp Tyr Thr Asn Gln Ile Gly Arg Phe Phe Gly
    850                 855                 860
Glu Ile Asp Pro Ser Leu Met Arg His Leu Val Asn Ile Ser Val Tyr
865                 870                 875                 880
Ala Phe Asn Lys Ser Tyr Asp Tyr Gln Ser Val Cys Glu Pro Gly Ala
                885                 890                 895
Ala Pro Lys Gln Gly Ala Gly His Arg Ser Ala Tyr Val Pro Ser Val
            900                 905                 910
Ala Asp Ile Leu Gln Ile Gly Trp Trp Ala Thr Ala Ala Trp Ser
        915                 920                 925
Ile Leu Gln Gln Phe Leu Leu Ser Leu Thr Phe Pro Arg Leu Leu Glu
```

```
                930              935             940
Ala Val Glu Met Glu Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
                980                 985                 990

Gly Glu Lys Leu Met Asn Thr Asn Leu Ile Phe Ile Met Val Glu Ser
                995                1000                1005

Lys Gly Thr Cys Pro Cys Asp Thr Arg Leu Leu Ile Gln Ala Glu Gln
       1010                1015                1020

Thr Ser Asp Gly Pro Asn Pro Cys Asp Met Val Lys Gln Pro Arg Tyr
1025                1030                1035                1040

Arg Lys Gly Pro Asp Val Cys Phe Asp Asn Asn Val Leu Glu Asp Tyr
                1045                1050                1055

Thr Asp Cys Gly Gly Val Ser
                1060

<210> SEQ ID NO 44
<211> LENGTH: 1091
<212> TYPE: PRT
<213> ORGANISM: Homo sapiens

<400> SEQUENCE: 44

Met Ala Ala Gly Cys Leu Leu Ala Leu Thr Leu Thr Leu Phe Gln Ser
  1               5                  10                  15

Leu Leu Ile Gly Pro Ser Ser Glu Glu Pro Phe Pro Ser Ala Val Thr
                 20                  25                  30

Ile Lys Ser Trp Val Asp Lys Met Gln Glu Asp Leu Val Thr Leu Ala
             35                  40                  45

Lys Thr Ala Ser Gly Val Asn Gln Leu Val Asp Ile Tyr Glu Lys Tyr
         50                  55                  60

Gln Asp Leu Tyr Thr Val Glu Pro Asn Asn Ala Arg Gln Leu Val Glu
 65                  70                  75                  80

Ile Ala Ala Arg Asp Ile Glu Lys Leu Leu Ser Asn Arg Ser Lys Ala
                 85                  90                  95

Leu Val Ser Leu Ala Leu Glu Ala Glu Lys Val Gln Ala Ala His Gln
                100                 105                 110

Trp Arg Glu Asp Phe Ala Ser Asn Glu Val Val Tyr Tyr Asn Ala Lys
            115                 120                 125

Asp Asp Leu Asp Pro Glu Lys Asn Asp Ser Glu Pro Gly Ser Gln Arg
        130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
                180                 185                 190

Phe Lys Lys Asn Arg Glu Glu Asp Pro Ser Leu Leu Trp Gln Val Phe
            195                 200                 205

Gly Ser Ala Thr Gly Leu Ala Arg Tyr Tyr Pro Ala Ser Pro Trp Val
        210                 215                 220

Asp Asn Ser Arg Thr Pro Asn Lys Ile Asp Leu Tyr Asp Val Arg Arg
225                 230                 235                 240
```

-continued

```
Arg Pro Trp Tyr Ile Gln Gly Ala Ala Ser Pro Lys Asp Met Leu Ile
            245                 250                 255

Leu Val Asp Val Ser Gly Ser Val Ser Gly Leu Thr Leu Lys Leu Ile
        260                 265                 270

Arg Thr Ser Val Ser Glu Met Leu Glu Thr Leu Ser Asp Asp Asp Phe
    275                 280                 285

Val Asn Val Ala Ser Phe Asn Ser Asn Ala Gln Asp Val Ser Cys Phe
290                 295                 300

Gln His Leu Val Gln Ala Asn Val Arg Asn Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
    370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu His Pro Asn Leu Gln
        515                 520                 525

Pro Lys Asn Pro Lys Ser Gln Glu Pro Val Thr Leu Asp Phe Leu Asp
530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Leu Glu Glu Thr Ile Thr Gln Ala Arg
    610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
```

-continued

```
                660                 665                 670
Glu Phe Ile Asp Arg Lys Thr Pro Asn Pro Ser Cys Asn Ala Asp
        675                 680                 685
Leu Ile Asn Arg Val Leu Leu Asp Ala Gly Phe Thr Asn Glu Leu Val
        690                 695                 700
Gln Asn Tyr Trp Ser Lys Gln Lys Asn Ile Lys Gly Val Lys Ala Arg
705                 710                 715                 720
Phe Val Val Thr Asp Gly Gly Ile Thr Arg Val Tyr Pro Lys Glu Ala
                725                 730                 735
Gly Glu Asn Trp Gln Glu Asn Pro Glu Thr Tyr Glu Asp Ser Phe Tyr
                740                 745                 750
Lys Arg Ser Leu Asp Asn Asp Asn Tyr Val Phe Thr Ala Pro Tyr Phe
                755                 760                 765
Asn Lys Ser Gly Pro Gly Ala Tyr Glu Ser Gly Ile Met Val Ser Lys
                770                 775                 780
Ala Val Glu Ile Tyr Ile Gln Gly Lys Leu Leu Lys Pro Ala Val Val
785                 790                 795                 800
Gly Ile Lys Ile Asp Val Asn Ser Trp Ile Glu Asn Phe Thr Lys Thr
                805                 810                 815
Ser Ile Arg Asp Pro Cys Ala Gly Pro Val Cys Asp Cys Lys Arg Asn
                820                 825                 830
Ser Asp Val Met Asp Cys Val Ile Leu Asp Asp Gly Gly Phe Leu Leu
                835                 840                 845
Met Ala Asn His Asp Asp Tyr Thr Asn Gln Ile Gly Arg Phe Phe Gly
                850                 855                 860
Glu Ile Asp Pro Ser Leu Met Arg His Leu Val Asn Ile Ser Val Tyr
865                 870                 875                 880
Ala Phe Asn Lys Ser Tyr Asp Tyr Gln Ser Val Cys Glu Pro Gly Ala
                885                 890                 895
Ala Pro Lys Gln Gly Ala Gly His Arg Ser Ala Tyr Val Pro Ser Val
                900                 905                 910
Ala Asp Ile Leu Gln Ile Gly Trp Trp Ala Thr Ala Ala Ala Trp Ser
                915                 920                 925
Ile Leu Gln Gln Phe Leu Leu Ser Leu Thr Phe Pro Arg Leu Leu Glu
                930                 935                 940
Ala Val Glu Met Glu Asp Asp Asp Phe Thr Ala Ser Leu Ser Lys Gln
945                 950                 955                 960
Ser Cys Ile Thr Glu Gln Thr Gln Tyr Phe Asp Asn Asp Ser Lys
                965                 970                 975
Ser Phe Ser Gly Val Leu Asp Cys Gly Asn Cys Ser Arg Ile Phe His
                980                 985                 990
Gly Glu Lys Leu Met Asn Thr Asn Leu Ile Phe Ile Met Val Glu Ser
                995                 1000                1005
Lys Gly Thr Cys Pro Cys Asp Thr Arg Leu Leu Ile Gln Ala Glu Gln
    1010                1015                1020
Thr Ser Asp Gly Pro Asn Pro Cys Asp Met Val Lys Gln Pro Arg Tyr
1025                1030                1035                1040
Arg Lys Gly Pro Asp Val Cys Phe Asp Asn Asn Val Leu Glu Asp Tyr
                1045                1050                1055
Thr Asp Cys Gly Gly Val Ser Gly Leu Asn Pro Ser Leu Trp Tyr Ile
                1060                1065                1070
Ile Gly Ile Gln Phe Leu Leu Leu Trp Leu Val Ser Gly Ser Thr His
        1075                1080                1085
```

Arg Leu Leu
 1090

<210> SEQ ID NO 45
<211> LENGTH: 3600
<212> TYPE: DNA
<213> ORGANISM: Homo sapiens

<400> SEQUENCE: 45

| | | | | | |
|---|---|---|---|---|---|
| gcgggggagg | gggcattgat | cttcgatcgc | gaagatggct | gctggctgcc | tgctggcctt | 60 |
| gactctgaca | cttttccaat | ctttgctcat | cggcccctcg | tcggaggagc | cgttcccttc | 120 |
| ggccgtcact | atcaaatcat | gggtggataa | gatgcaagaa | gaccttgtca | cactggcaaa | 180 |
| aacagcaagt | ggagtcaatc | agcttgttga | tatttatgag | aaatatcaag | atttgtatac | 240 |
| tgtggaacca | aataatgcac | gccagctggt | agaaattgca | gccagggata | ttgagaaact | 300 |
| tctgagcaac | agatctaaag | ccctggtgag | cctggcattg | gaagcggaga | agttcaagc | 360 |
| agctcaccag | tggagagaag | attttgcaag | caatgaagtt | gtctactaca | atgcaaagga | 420 |
| tgatctcgat | cctgagaaaa | atgacagtga | gccaggcagc | cagaggataa | aacctgtttt | 480 |
| cattgaagat | gctaattttg | gacgacaaat | atcttatcag | cacgcagcag | tccatattcc | 540 |
| tactgacatc | tatgagggct | caacaattgt | gttaaatgaa | ctcaactgga | caagtgcctt | 600 |
| agatgaagtt | ttcaaaaaga | atcgcgagga | agacccttca | ttattgtggc | aggttttgg | 660 |
| cagtgccact | ggcctagctc | gatattatcc | agcttcacca | tgggttgata | atagtagaac | 720 |
| tccaaataag | attgaccttt | atgatgtacg | cagaagacca | tggtacatcc | aaggagctgc | 780 |
| atctcctaaa | gacatgctta | ttctggtgga | tgtgagtgga | agtgttagtg | gattgacact | 840 |
| taaactgatc | cgaacatctg | tctccgaaat | gttagaaacc | ctctcagatg | atgatttcgt | 900 |
| gaatgtagct | tcatttaaca | gcaatgctca | ggatgtaagc | tgttttcagc | accttgtcca | 960 |
| agcaaatgta | agaaatgaaaa | aagtgttgaa | agacgcggtg | aataatatca | cagccaaagg | 1020 |
| aattacagat | tataagaagg | gctttagttt | tgcttttgaa | cagctgctta | attataatgt | 1080 |
| ttccagagca | aactgcaata | agattattat | gctattcacg | gatggaggag | aagagagagc | 1140 |
| ccaggagata | tttaacaaat | acaataaaga | taaaaagta | cgtgtattca | ggttttcagt | 1200 |
| tggtcaacac | aattatgaga | aggacctat | tcagtggatg | gcctgtgaaa | acaaaggtta | 1260 |
| ttattatgaa | attccttcca | ttggtgcaat | aagaatcaat | actcaggaat | atttggatgt | 1320 |
| tttgggaaga | ccaatggttt | tagcaggaga | caaagctaag | caagtccaat | ggacaaatgt | 1380 |
| gtacctggat | gcattggaac | tgggacttgt | cattactgga | actcttccgg | tcttcaacat | 1440 |
| aaccggccaa | tttgaaaata | agacaaactt | aaagaaccag | ctgattcttg | gtgtgatggg | 1500 |
| agtagatgtg | tctttggaag | atattaaaag | actgacacca | cgttttacac | tgtgccccaa | 1560 |
| tgggtattac | tttgcaatcg | atcctaatgg | ttatgtttta | ttcatccaa | atcttcagcc | 1620 |
| aaagaacccc | aaatctcagg | agccagtaac | attggatttc | cttgatgcag | agttagagaa | 1680 |
| tgatattaaa | gtggagattc | gaaataagat | gattgatggg | gaaagtggag | aaaaaacatt | 1740 |
| cagaactctg | gttaaatctc | aagatgagag | atatattgac | aaaggaaaca | ggacatacac | 1800 |
| atggacacct | gtcaatggca | cagattcag | tttggccttg | gtattaccaa | cctacagttt | 1860 |
| ttactatata | aaagccaaac | tagaagagac | aataactcag | gccagatcaa | aaagggcaa | 1920 |
| aatgaaggat | tcgaaaccc | tgaagccaga | taattttgaa | gaatctggct | atacattcat | 1980 |
| agcaccaaga | gattactgca | atgacctgaa | aatatcggat | aataacactg | aatttctttt | 2040 |

-continued

```
aaatttcaac gagtttattg atagaaaaac tccaaacaac ccatcatgta acgcggattt    2100
gattaataga gtcttgcttg atgcaggctt tacaaatgaa cttgtccaaa attactggag    2160
taagcagaaa aatatcaagg gagtgaaagc acgatttgtt gtgactgatg gtgggattac    2220
cagagtttat cccaaagagg ctggagaaaa ttggcaagaa aacccagaga catatgagga    2280
cagcttctat aaaaggagcc tagataatga taactatgtt ttcactgctc cctactttaa    2340
caaaagtgga cctggtgcct atgaatcggg cattatggta agcaaagctg tagaaatata    2400
tattcaaggg aaacttctta aacctgcagt tgttggaatt aaaattgatg taaattcctg    2460
gatagagaat ttcaccaaaa cctcaatcag agatccgtgt gctggtccag tttgtgactg    2520
caaaagaaac agtgacgtaa tggattgtgt gattctggat gatggtgggt ttcttctgat    2580
ggcaaatcat gatgattata ctaatcagat tggaagattt tttggagaga ttgatcccag    2640
cttgatgaga cacctggtta atatatcagt ttatgctttt aacaaatctt atgattatca    2700
gtcagtatgt gagcccggtg ctgcaccaaa acaaggagca ggacatcgct cagcatatgt    2760
gccatcagta gcagacatat tacaaattgg ctggtgggcc actgctgctg cctggtctat    2820
tctacagcag tttctcttga gtttgacctt tccacgactc cttgaggcag ttgagatgga    2880
ggatgatgac ttcacggcct ccctgtccaa gcagagctgc attactgaac aaacccagta    2940
tttcttcgat aacgacagta aatcattcag tggtgtatta gactgtggaa actgttccag    3000
aatctttcat ggagaaaagc ttatgaacac caacttaata ttcataatgg ttgagagcaa    3060
agggacatgt ccatgtgaca cacgactgct catacaagcg gagcagactt ctgacggtcc    3120
aaatccttgt gacatggtta agcaacctag ataccgaaaa gggcctgatg tctgctttga    3180
taacaatgtc ttggaggatt atactgactg tggtggtgtt tctggattaa atccctccct    3240
gtggtatatc attggaatcc agtttctact actttggctg gtatctggca gcacacaccg    3300
gctgttatga ccttctaaaa accaaatctg catagttaaa ctccagaccc tgccaaaaca    3360
tgagccctgc cctcaattac agtaacgtag ggtcagctat aaaatcagac aaacattagc    3420
tgggcctgtt ccatggcata acactaaggc gcagactcct aaggcaccca ctggctgcat    3480
gtcagggtgt cagatcctta aacgtgtgtg aatgctgcat catctatgtg taacatcaaa    3540
gcaaaatcct atacgtgtcc tctattggaa aatttgggcg tttgttgttg cattgttggt    3600
```

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 46
ggggattgat cttcgatcgc g    21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 47
ctgagatttg gggttctttg g    21

<210> SEQ ID NO 48

-continued

```
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 48
tcgccaccat ggctgctggc tgcctgctg                                     29

<210> SEQ ID NO 49
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 49
tcggaattcc tcagtgatgg tgatggtgat gagaaacacc accacagtcg gt           52

<210> SEQ ID NO 50
<211> LENGTH: 3201
<212> TYPE: DNA
<213> ORGANISM: Homo sapiens

<400> SEQUENCE: 50
ccatgcctgc aactcccaac ttcctcgcaa accccagctc cagcagccgc tggattcccc     60
tccagccaat gcccgtggcc tgggcctttg tgcagaagac ctcggccctc ctgtggctgc    120
tgcttctagg cacctccctg tccctgcgt ggggacaggc caagattcct ctggaaacag    180
tgaagctatg ggctgacacc ttcggcgggg acctgtataa cactgtgacc aaatactcag    240
gctctctctt gctgcagaag aagtacaagg atgtggagtc cagtctgaag atcgaggagg    300
tggatggctt ggagctggtg aggaagttct cagaggacat ggagaacatg ctgcggagga    360
aagtcgaggc ggtccagaat ctggtggaag ctgccgagga ggccgacctg aaccacgaat    420
tcaatgaatc cctggtgttc gactattaca actcggtcct gatcaacgag agggacgaga    480
agggcaactt cgtggagctg gcgccgagt tcctcctgga gtccaatgct cacttcagca    540
acctgccggt gaacacctcc atcagcagcg tgcagctgcc caccaacgtg tacaacaaag    600
acccagatat tttaaatgga gtctacatgt ctgaagcctt gaatgctgtc ttcgtggaga    660
acttccagag agacccaacg ttgacctggc aatattttgg cagtgcaact ggattcttca    720
ggatctatcc aggtataaaa tggacacctg atgagaatgg agtcattact tttgactgcc    780
gaaaccgcgg ctggtacatt caagctgcta cttctcccaa ggacatagtg attttggtgg    840
acgtgagcgg cagtatgaag gggctgagga tgactattgc caagcacacc atcaccacca    900
tcttggacac cctgggggag aatgacttcg ttaatatcat agcgtacaat gactacgtcc    960
attacatcga gccttgtttt aaagggatcc tcgtccaggc ggaccgagac aatcgagagc   1020
atttcaaact gctggtggag gagttgatgg tcaaaggtgt gggggtcgtg gaccaagccc   1080
tgagagaagc cttccagatc ctgaagcagt tccaagaggc caagcaagga agcctctgca   1140
accaggccat catgctcatc agcgacggcg ccgtggagga ctacgagccg gtgtttgaga   1200
agtataactg gccagactgt aaggtccgag ttttcactta cctcattggg agagaagtgt   1260
cttttgctga ccgcatgaag tggattgcat gcaacaacaa aggctactac acgcagatct   1320
caacgctggc ggacacccag gagaacgtga tggaatacct gcacgtgctc agccgcccca   1380
tggtcatcaa ccacgaccac gacatcatct ggacagagg ctacatggac agcaagctcc   1440
tcagctcgca ggctcagagc ctgacactgc tcaccactgt ggccatgcca gtcttcagca   1500
```

```
agaagaacga aacgcgatcc catggcattc tcctgggtgt ggtgggctca gatgtggccc    1560
tgagagagct gatgaagctg gcgccccggt acaagcttgg agtgcacgga tacgcctttc    1620
tgaacaccaa caatggctac atcctctccc atcccgacct ccggcccctg tacagagagg    1680
ggaagaaact aaaacccaaa cctaactaca acagtgtgga tctctccgaa gtggagtggg    1740
aagaccaggc tgaatctctg agaacagcca tgatcaatag ggaaacaggt actctctcga    1800
tggatgtgaa ggttccgatg gataaaggga agcgagttct tttcctgacc aatgactact    1860
tcttcacgga catcagcgac acccctttca gtttggggt ggtgctgtcc cggggccacg    1920
gagaatacat ccttctgggg aacacgtctg tggaagaagg cctgcatgac ttgcttcacc    1980
cagacctggc cctggccggt gactggatct actgcatcac agatattgac ccagaccacc    2040
ggaagctcag ccagctagag gccatgatcc gcttcctcac caggaaggac ccagacctgg    2100
agtgtgacga ggagctggtc cgggaggtgc tgtttgacgc ggtggtgaca gcccccatgg    2160
aagcctactg gacagcgctg gccctcaaca tgtccgagga gtctgaacac gtggtggaca    2220
tggccttcct gggcacccgg gctggcctcc tgagaagcag cttgttcgtg ggctccgaga    2280
aggtctccga gtggcctcct gagaagcagc ttgttcgtgg gctccgagaa ggtctccgac    2340
aggaagttcc tgacacctga ggacgaggcc agcgtgttca ccctggaccg cttcccgctg    2400
tggtaccgcc aggcctcaga gcatcctgct ggcagcttcg tcttcaacct ccgctgggca    2460
gaaggaccag aaagtgcggg tgaacccatg gtggtgacgg caagcacagc tgtggcggtg    2520
accgtggaca agaggacagc cattgctgca gccgcgggcg tccaaatgaa gctggaattc    2580
ctccagcgca aattctgggc ggcaacgcgg cagtgcagca ctgtggatgg gccgtgcaca    2640
cagagctgcg aggacagtga tctggactgc ttcgtcatcg acaacaacgg gttcattctg    2700
atctccaaga ggtcccgaga gacgggaaga tttctggggg aggtggatgg tgctgtcctg    2760
acccagctgc tcagcatggg ggtgttcagc caagtgacta tgtatgacta tcaggccatg    2820
tgcaaaccct cgagtcacca ccacagtgca gcccagcccc tggtcagccc aatttctgcc    2880
ttcttgacgg cgaccaggtg gctgctgcag gagctggtgc tgttcctgct ggagtggagt    2940
gtctggggct cctggtacga cagaggggcc gaggccaaaa gtgtcttcca tcactcccac    3000
aaacacaaga agcaggaccc gctgcagccc tgcgacacgg agtaccccgt gttcgtgtac    3060
cagccggcca tccgggaggc caacgggatc gtggagtgcg ggccctgcca aaggtatttt    3120
gtggtgcagc agattcccaa cagtaacctc ctcctcctgg tgacagaccc cacctgtgac    3180
tgcagcatct tcccaccagt g                                               3201
```

<210> SEQ ID NO 51  
<211> LENGTH: 3209  
<212> TYPE: DNA  
<213> ORGANISM: Homo sapiens

<400> SEQUENCE: 51

```
ccatgcctgc aactcccaac ttcctcgcaa accccagctc cagcagccgc tggattcccc      60
tccagccaat gcccgtggcc tgggcctttg tgcagaagac ctcggccctc ctgtggctgc     120
tgcttctagg cacctccctg tccctgcgt ggggacaggc caagattcct ctggaaacag     180
tgaagctatg ggctgacacc ttcggcgggg acctgtataa cactgtgacc aaatactcag     240
gctctctctt gctgcagaag aagtacaagg atgtggagtc cagtctgaag atcgaggagg     300
tggatggctt ggagctggtg aggaagttct cagaggacat ggaaacatg ctgcggagga     360
```

-continued

| | |
|---|---|
| aagtcgaggc ggtccagaat ctggtggaag ctgccgagga ggccgacctg aaccacgaat | 420 |
| tcaatgaatc cctggtgttc gactattaca actcggtcct gatcaacgag agggacgaga | 480 |
| agggcaactt cgtggagctg ggcgccgagt tcctcctgga gtccaatgct cacttcagca | 540 |
| acctgccggt gaacacctcc atcagcagcg tgcagctgcc caccaacgtg tacaacaaag | 600 |
| acccagatat tttaaatgga gtctacatgt ctgaagcctt gaatgctgtc ttcgtggaga | 660 |
| acttccagag agacccaacg ttgacctggc aatattttgg cagtgcaact ggattcttca | 720 |
| ggatctatcc aggtataaaa tggacacctg atgagaatgg agtcattact tttgactgcc | 780 |
| gaaaccgcgg ctggtacatt caagctgcta cttctcccaa ggacatagtg attttggtgg | 840 |
| acgtgagcgg cagtatgaag gggctgagga tgactattgc caagcacacc atcaccacca | 900 |
| tcttggacac cctgggggag aatgacttcg ttaaatatcat agcgtacaat gactacgtcc | 960 |
| attacatcga gccttgtttt aaagggatcc tcgtccaggc ggaccgagac aatcgagagc | 1020 |
| atttcaaact gctggtggag gagttgatgg tcaaaggtgt ggggtcgtg gaccaagccc | 1080 |
| tgagagaagc cttccagatc ctgaagcagt tccaagaggc caagcaagga agcctctgca | 1140 |
| accaggccat catgctcatc agcgacgcg ccgtggagga ctacgagccg gtgtttgaga | 1200 |
| agtataactg gccagactgt aaggtccgag ttttcactta cctcattggg agagaagtgt | 1260 |
| cttttgctga ccgcatgaag tggattgcat gcaacaacaa aggctactac acgcagatct | 1320 |
| caacgctggc ggacacccag gagaacgtga tggaatacct gcacgtgctc agccgcccca | 1380 |
| tggtcatcaa ccacgaccac gacatcatct ggacagaggc ctacatggac agcaagctcc | 1440 |
| tcagctcgca ggctcagagc ctgacactgc tcaccactgt ggccatgcca gtcttcagca | 1500 |
| agaagaacga aacgcgatcc catggcattc tcctgggtgt ggtgggctca gatgtggccc | 1560 |
| tgagagagct gatgaagctg gcgccccggt acaagcttgg agtgcacgga tacgcctttc | 1620 |
| tgaacaccaa caatggctac atcctctccc atcccgacct ccggcccctg tacagagagg | 1680 |
| ggaagaaact aaaacccaaa cctaactaca acagtgtgga tctctccgaa gtggagtggg | 1740 |
| aagaccaggc tgaatctctg agaacagcca tgatcaatag ggaaacaggt actctctcga | 1800 |
| tggatgtgaa ggttccgatg gataaaggga agcgagttct tttcctgacc aatgactact | 1860 |
| tcttcacgga catcagcgac ccccttttca gtttgggggt ggtgctgtcc cggggccacg | 1920 |
| gagaatacat ccttctgggg aacacgtctg tggaagaagg cctgcatgac ttgcttcacc | 1980 |
| cagacctggc cctggccggt gactggatct actgcatcac agatattgac ccagaccacc | 2040 |
| ggaagctcag ccagctagag gccatgatcc gcttcctcac caggaaggac ccagacctgg | 2100 |
| agtgtgacga ggagctggtc cgggaggtgc tgtttgacgc ggtggtgaca gcccccatgg | 2160 |
| aagcctactg gacagcgctg gccctcaaca tgtccgagga gtctgaacac gtggtggaca | 2220 |
| tggccttcct gggcacccgg gctggcctcc tgagaagcag cttgttcgtg ggctccgaga | 2280 |
| aggtctccga caggaagttc ctgacacctg aggacgaggc agcgtgttc accctggacc | 2340 |
| gcttcccgct gtggtaccgc caggcctcag agcatcctgc tggcagcttc gtcttcaacc | 2400 |
| tccgctgggc agaaggacca gaaagtgcgg gtgaacccat ggtggtgacg gcaagcacag | 2460 |
| ctgtggcggt gaccgtggac aagaggacag ccattgctgc agccgcgggc gtccaaatga | 2520 |
| agctggaatt cctccagcgc aaattctggg cggcaacgcg gcagtgcagc actgtggatg | 2580 |
| ggccgtgcac acagagctgc gaggacagtg atctggactg cttcgtcatc gacaacaacg | 2640 |
| ggttcattct gatctccaag aggtcccgag agacgggaag atttctgggg gaggtggatg | 2700 |
| gtgctgtcct gacccagctg ctcagcatgg gggtgttcag ccaagtgact atgtatgact | 2760 |

-continued

```
atcaggccat gtgcaaaccc tcgagtcacc accacagtgc agcccagccc ctggtcagcc    2820
caatttctgc cttcttgacg gcgaccaggt ggctgctgca ggagctggtg ctgttcctgc    2880
tggagtggag tgtctggggc tcctggtacg acagagggc cgaggccaaa agtgtcttcc     2940
atcactccca caaacacaag aagcaggacc cgctgcagcc ctgcgacacg gagtaccccg    3000
tgttcgtgta ccagccggcc atccgggagg ccaacgggat cgtggagtgc gggccctgcc    3060
agaaggtatt tgtggtgcag cagattccca acagtaacct cctcctcctg gtgacagacc    3120
ccacctgtga ctgcagcatc ttcccaccag tgctgcagga ggcgacagaa gtcaaatata    3180
atgcctctgt caaatgtgac cggatgcgc                                     3209
```

<210> SEQ ID NO 52
<211> LENGTH: 3339
<212> TYPE: DNA
<213> ORGANISM: Homo sapiens

<400> SEQUENCE: 52

```
ccatgcctgc aactcccaac ttcctcgcaa accccagctc cagcagccgc tggattcccc      60
tccagccaat gcccgtggcc tgggcctttg tgcagaagac ctcggccctc ctgtggctgc     120
tgcttctagg caccctcctg tcccctgcgt ggggacaggc caagattcct ctggaaacag     180
tgaagctatg ggctgacacc ttcggcgggg acctgtataa cactgtgacc aaatactcag     240
gctctctctt gctgcagaag aagtacaagg atgtggagtc cagtctgaag atcgaggagg     300
tggatggctt ggagctggtg aggaagttct cagaggacta ggagaacatg ctgcggagga     360
aagtcgaggc ggtccagaat ctggtggaag ctgccgagga ggccgacctg aaccacgaat     420
tcaatgaatc cctggtgttc gactattaca actcggtcct gatcaacgag agggacgaga     480
agggcaactt cgtggagctg ggcgccgagt cctcctggga gtccaatgct cacttcagca     540
acctgccggt gaacacctcc atcagcagcg tgcagctgcc caccaacgtg tacaacaaag     600
acccagatat tttaaatgga gtctacatgt ctgaagcctt gaatgctgtc ttcgtggaga     660
acttccagag agacccaacg ttgacctggc aatattttgg cagtgcaact ggattcttca     720
ggatctatcc aggtataaaa tggacacctg atgagaatgg agtcattact tttgactgcc     780
gaaaccgcgg ctggtacatt caagctgcta cttctcccaa ggacatagtg attttggtgg     840
acgtgagcgg cagtatgaag gggctgagga tgactattgc caagcacacc atcaccacca     900
tcttggacac cctgggggag aatgacttcg ttaatatcat agcgtacaat gactacgtcc     960
attacatcga gccttgtttt aaagggatcc tcgtccaggc ggaccgagac aatcgagagc    1020
atttcaaact gctggtggag gagttgatgg tcaaaggtgt ggggtcgtg gaccaagccc    1080 tgagagaagc cttccagatc ctgaagcagt tccaagaggc caagcaagga agcctctgca    1140
accaggccat catgctcatc agcgacgcg ccgtggagga ctacgagccg gtgtttgaga    1200
agtataactg gccagactgt aaggtccgag ttttcactta cctcattggg agagaagtgt    1260
cttttgctga ccgcatgaag tggattgcat gcaacaacaa aggctactac acgcagatct    1320
caacgctggc ggacacccag gagaacgtga tggaatacct gcacgtgctc agccgcccca    1380
tggtcatcaa ccacgaccac gacatcatct ggacagaggc ctacatggac agcaagctcc    1440
tcagctcgca ggctcagagc ctgacactgc tcaccactgt ggccatgcca gtcttcagca    1500
agaagaacga aacgcgatcc catggcattc tcctgggtgt ggtgggctca gatgtggccc    1560
tgagagagct gatgaagctg gcgccccggt acaagcttgg agtgcacgga tacgcctttc    1620
```

```
tgaacaccaa caatggctac atcctctccc atcccgacct ccggcccctg tacagagagg   1680
ggaagaaact aaacccaaa cctaactaca acagtgtgga tctctccgaa gtggagtggg    1740
aagaccaggc tgaatctctg agaacagcca tgatcaatag ggaaacaggt actctctcga   1800
tggatgtgaa ggttccgatg gataaaggga agcgagttct tttcctgacc aatgactact   1860
tcttcacgga catcagcgac accccttca gtttgggggt ggtgctgtcc cggggccacg    1920
gagaatacat ccttctgggg aacacgtctg tggaagaagg cctgcatgac ttgcttcacc   1980
cagacctggc cctggccggt gactggatct actgcatcac agatattgac ccagaccacc   2040
ggaagctcag ccagctagag gccatgatcc gcttcctcac caggaaggac ccagacctgg   2100
agtgtgacga ggagctggtc cgggaggtgc tgtttgacgc ggtggtgaca gcccccatgg   2160
aagcctactg gacagcgctg gccctcaaca tgtccgagga gtctgaacac gtggtggaca   2220
tggccttcct gggcacccgg gctggcctcc tgagaagcag cttgttcgtg gctccgaga    2280
aggtctccga gtggcctcct gagaagcagc ttgttcgtgg ctccgagaa ggtctccgac    2340
aggaagttcc tgacacctga ggacgaggcc agcgtgttca ccctggaccg cttcccgctg   2400
tggtaccgcc aggcctcaga gcatcctgct ggcagcttcg tcttcaacct ccgctgggca   2460
gaaggaccag aaagtgcggg tgaacccatg gtggtgacgg caagcacagc tgtggcggtg   2520
accgtggaca agaggacagc cattgctgca gccgcgggcg tccaaatgaa gctggaattc   2580
ctccagcgca aattctgggc ggcaacgcgg cagtgcagca ctgtggatgg gccgtgcaca   2640
cagagctgcg aggacagtga tctggactgc ttcgtcatcg acaacaacgg gttcattctg   2700
atctccaaga ggtcccgaga gacgggaaga tttctggggg aggtggatgg tgctgtcctg   2760
acccagctgc tcagcatggg ggtgttcagc caagtgacta tgtatgacta tcaggccatg   2820
tgcaaaccct cgagtcacca ccacagtgca gcccagcccc tggtcagccc aatttctgcc   2880
ttcttgacgg cgaccaggtg gctgctgcag gagctggtgc tgttcctgct ggagtggagt   2940
gtctggggct cctggtacga cagaggggcc gaggccaaaa gtgtcttcca tcactcccac   3000
aaacacaaga agcaggaccc gctgcagccc tgcgacacgg agtacccgt gttcgtgtac    3060
cagccggcca tccgggaggc caacgggatc gtggagtgcg ggccctgcca gaaggtattt   3120
gtggtgcagc agattcccaa cagtaacctc ctcctcctgg tgacagaccc cacctgtgac   3180
tgcagcatct tcccaccagt gctgcaggag gcgacagaag tcaaatataa tgcctctgtc   3240
aaatgtgacc ggatgcgctc ccagaagctc cgccggcgac cagactcctg ccacgccttc   3300
catccagagg agaatgccca ggactgcggc ggcgcctcg                          3339
```

<210> SEQ ID NO 53
<211> LENGTH: 1050
<212> TYPE: PRT
<213> ORGANISM: Homo sapiens

<400> SEQUENCE: 53

Met Pro Ala Thr Pro Asn Phe Leu Ala Asn Pro Ser Ser Ser Arg
 1               5                  10                  15

Trp Ile Pro Leu Gln Pro Met Pro Val Ala Trp Ala Phe Val Gln Lys
            20                  25                  30

Thr Ser Ala Leu Leu Trp Leu Leu Leu Leu Gly Thr Ser Leu Ser Pro
        35                  40                  45

Ala Trp Gly Gln Ala Lys Ile Pro Leu Glu Thr Val Lys Leu Trp Ala
    50                  55                  60

Asp Thr Phe Gly Gly Asp Leu Tyr Asn Thr Val Thr Lys Tyr Ser Gly

-continued

```
                65                  70                  75                  80
Ser Leu Leu Gln Lys Lys Tyr Lys Asp Val Glu Ser Ser Leu Lys
                        85                  90                  95

Ile Glu Glu Val Asp Gly Leu Glu Leu Val Arg Lys Phe Ser Glu Asp
                100                 105                 110

Met Glu Asn Met Leu Arg Arg Lys Val Glu Ala Val Gln Asn Leu Val
                115                 120                 125

Glu Ala Ala Glu Ala Asp Leu Asn His Glu Phe Asn Glu Ser Leu
        130                 135                 140

Val Phe Asp Tyr Tyr Asn Ser Val Leu Ile Asn Glu Arg Asp Glu Lys
145                 150                 155                 160

Gly Asn Phe Val Glu Leu Gly Ala Glu Phe Leu Leu Glu Ser Asn Ala
                165                 170                 175

His Phe Ser Asn Leu Pro Val Asn Thr Ser Ile Ser Ser Val Gln Leu
                180                 185                 190

Pro Thr Asn Val Tyr Asn Lys Asp Pro Asp Ile Leu Asn Gly Val Tyr
                195                 200                 205

Met Ser Glu Ala Leu Asn Ala Val Phe Val Glu Asn Phe Gln Arg Asp
        210                 215                 220

Pro Thr Leu Thr Trp Gln Tyr Phe Gly Ser Ala Thr Gly Phe Phe Arg
225                 230                 235                 240

Ile Tyr Pro Gly Ile Lys Trp Thr Pro Asp Glu Asn Gly Val Ile Thr
                245                 250                 255

Phe Asp Cys Arg Asn Arg Gly Trp Tyr Ile Gln Ala Ala Thr Ser Pro
                260                 265                 270

Lys Asp Ile Val Ile Leu Val Asp Val Ser Gly Ser Met Lys Gly Leu
                275                 280                 285

Arg Met Thr Ile Ala Lys His Thr Ile Thr Thr Ile Leu Asp Thr Leu
        290                 295                 300

Gly Glu Asn Asp Phe Val Asn Ile Ile Ala Tyr Asn Asp Tyr Val His
305                 310                 315                 320

Tyr Ile Glu Pro Cys Phe Lys Gly Ile Leu Val Gln Ala Asp Arg Asp
                325                 330                 335

Asn Arg Glu His Phe Lys Leu Leu Val Glu Glu Leu Met Val Lys Gly
                340                 345                 350

Val Gly Val Val Asp Gln Ala Leu Arg Glu Ala Phe Gln Ile Leu Lys
                355                 360                 365

Gln Phe Gln Glu Ala Lys Gln Gly Ser Leu Cys Asn Gln Ala Ile Met
        370                 375                 380

Leu Ile Ser Asp Gly Ala Val Glu Asp Tyr Glu Pro Val Phe Glu Lys
385                 390                 395                 400

Tyr Asn Trp Pro Asp Cys Lys Val Arg Val Phe Thr Tyr Leu Ile Gly
                405                 410                 415

Arg Glu Val Ser Phe Ala Asp Arg Met Lys Trp Ile Ala Cys Asn Asn
                420                 425                 430

Lys Gly Tyr Tyr Thr Gln Ile Ser Thr Leu Ala Asp Thr Gln Glu Asn
                435                 440                 445

Val Met Glu Tyr Leu His Val Leu Ser Arg Pro Met Val Ile Asn His
        450                 455                 460

Asp His Asp Ile Ile Trp Thr Glu Ala Tyr Met Asp Ser Lys Leu Leu
465                 470                 475                 480

Ser Ser Gln Ala Gln Ser Leu Thr Leu Leu Thr Thr Val Ala Met Pro
                485                 490                 495
```

```
Val Phe Ser Lys Lys Asn Glu Thr Arg Ser His Gly Ile Leu Leu Gly
            500                 505                 510

Val Val Gly Ser Asp Val Ala Leu Arg Glu Leu Met Lys Leu Ala Pro
            515                 520                 525

Arg Tyr Lys Leu Gly Val His Gly Tyr Ala Phe Leu Asn Thr Asn Asn
            530                 535                 540

Gly Tyr Ile Leu Ser His Pro Asp Leu Arg Pro Leu Tyr Arg Glu Gly
545                 550                 555                 560

Lys Lys Leu Lys Pro Lys Pro Asn Tyr Asn Ser Val Asp Leu Ser Glu
                565                 570                 575

Val Glu Trp Glu Asp Gln Ala Glu Ser Leu Arg Thr Ala Met Ile Asn
            580                 585                 590

Arg Glu Thr Gly Thr Leu Ser Met Asp Val Lys Val Pro Met Asp Lys
            595                 600                 605

Gly Lys Arg Val Leu Phe Leu Thr Asn Asp Tyr Phe Phe Thr Asp Ile
610                 615                 620

Ser Asp Thr Pro Phe Ser Leu Gly Val Val Leu Ser Arg Gly His Gly
625                 630                 635                 640

Glu Tyr Ile Leu Leu Gly Asn Thr Ser Val Glu Gly Leu His Asp
                645                 650                 655

Leu Leu His Pro Asp Leu Ala Leu Ala Gly Asp Trp Ile Tyr Cys Ile
                660                 665                 670

Thr Asp Ile Asp Pro Asp His Arg Lys Leu Ser Gln Leu Glu Ala Met
                675                 680                 685

Ile Arg Phe Leu Thr Arg Lys Asp Pro Asp Leu Glu Cys Asp Glu Glu
            690                 695                 700

Leu Val Arg Glu Val Leu Phe Asp Ala Val Val Thr Ala Pro Met Glu
705                 710                 715                 720

Ala Tyr Trp Thr Ala Leu Ala Leu Asn Met Ser Glu Glu Ser Glu His
                725                 730                 735

Val Val Asp Met Ala Phe Leu Gly Thr Arg Ala Gly Leu Leu Arg Ser
            740                 745                 750

Ser Leu Phe Val Gly Ser Glu Lys Val Ser Asp Arg Lys Phe Leu Thr
            755                 760                 765

Pro Glu Asp Glu Ala Ser Val Phe Thr Leu Asp Arg Phe Pro Leu Trp
            770                 775                 780

Tyr Arg Gln Ala Ser Glu His Pro Ala Gly Ser Phe Val Phe Asn Leu
785                 790                 795                 800

Arg Trp Ala Glu Gly Pro Glu Ser Ala Gly Glu Pro Met Val Val Thr
            805                 810                 815

Ala Ser Thr Ala Val Ala Val Thr Val Asp Lys Arg Thr Ala Ile Ala
            820                 825                 830

Ala Ala Ala Gly Val Gln Met Lys Leu Glu Phe Leu Gln Arg Lys Phe
            835                 840                 845

Trp Ala Ala Thr Arg Gln Cys Ser Thr Val Asp Gly Pro Cys Thr Gln
850                 855                 860

Ser Cys Glu Asp Ser Asp Leu Asp Cys Phe Val Ile Asp Asn Asn Gly
865                 870                 875                 880

Phe Ile Leu Ile Ser Lys Arg Ser Arg Glu Thr Gly Arg Phe Leu Gly
                885                 890                 895

Glu Val Asp Gly Ala Val Leu Thr Gln Leu Leu Ser Met Gly Val Phe
            900                 905                 910
```

```
Ser Gln Val Thr Met Tyr Asp Tyr Gln Ala Met Cys Lys Pro Ser Ser
        915                 920                 925

His His His Ser Ala Ala Gln Pro Leu Val Ser Pro Ile Ser Ala Phe
        930                 935                 940

Leu Thr Ala Thr Arg Trp Leu Leu Gln Glu Leu Val Leu Phe Leu Leu
945                 950                 955                 960

Glu Trp Ser Val Trp Gly Ser Trp Tyr Asp Arg Gly Ala Glu Ala Lys
                965                 970                 975

Ser Val Phe His His Ser His Lys His Lys Gln Asp Pro Leu Gln
        980                 985                 990

Pro Cys Asp Thr Glu Tyr Pro Val Phe Val Tyr Gln Pro Ala Ile Arg
        995                 1000                1005

Glu Ala Asn Gly Ile Val Glu Cys Gly Pro Cys Gln Lys Val Phe Val
        1010                1015                1020

Val Gln Gln Ile Pro Asn Ser Asn Leu Leu Leu Val Thr Asp Pro
1025                1030                1035                1040

Thr Cys Asp Cys Ser Ile Phe Pro Pro Val
                1045                1050

<210> SEQ ID NO 54
<211> LENGTH: 1069
<212> TYPE: PRT
<213> ORGANISM: Homo sapiens

<400> SEQUENCE: 54

Met Pro Ala Thr Pro Asn Phe Leu Ala Asn Pro Ser Ser Ser Ser Arg
1               5                   10                  15

Trp Ile Pro Leu Gln Pro Met Pro Val Ala Trp Ala Phe Val Gln Lys
                20                  25                  30

Thr Ser Ala Leu Leu Trp Leu Leu Leu Gly Thr Ser Leu Ser Pro
        35                  40                  45

Ala Trp Gly Gln Ala Lys Ile Pro Leu Glu Thr Val Lys Leu Trp Ala
    50                  55                  60

Asp Thr Phe Gly Gly Asp Leu Tyr Asn Thr Val Thr Lys Tyr Ser Gly
65                  70                  75                  80

Ser Leu Leu Leu Gln Lys Lys Tyr Lys Asp Val Glu Ser Ser Leu Lys
                85                  90                  95

Ile Glu Glu Val Asp Gly Leu Glu Leu Val Arg Lys Phe Ser Glu Asp
                100                 105                 110

Met Glu Asn Met Leu Arg Arg Lys Val Glu Ala Val Gln Asn Leu Val
        115                 120                 125

Glu Ala Ala Glu Glu Ala Asp Leu Asn His Glu Phe Asn Glu Ser Leu
    130                 135                 140

Val Phe Asp Tyr Tyr Asn Ser Val Leu Ile Asn Glu Arg Asp Glu Lys
145                 150                 155                 160

Gly Asn Phe Val Glu Leu Gly Ala Glu Phe Leu Leu Glu Ser Asn Ala
                165                 170                 175

His Phe Ser Asn Leu Pro Val Asn Thr Ser Ile Ser Val Gln Leu
        180                 185                 190

Pro Thr Asn Val Tyr Asn Lys Asp Pro Asp Ile Leu Asn Gly Val Tyr
        195                 200                 205

Met Ser Glu Ala Leu Asn Ala Val Phe Val Glu Asn Phe Gln Arg Asp
    210                 215                 220

Pro Thr Leu Thr Trp Gln Tyr Phe Gly Ser Ala Thr Gly Phe Phe Arg
225                 230                 235                 240
```

-continued

```
Ile Tyr Pro Gly Ile Lys Trp Thr Pro Asp Glu Asn Gly Val Ile Thr
                245                 250                 255

Phe Asp Cys Arg Asn Arg Gly Trp Tyr Ile Gln Ala Ala Thr Ser Pro
            260                 265                 270

Lys Asp Ile Val Ile Leu Val Asp Val Ser Gly Ser Met Lys Gly Leu
        275                 280                 285

Arg Met Thr Ile Ala Lys His Thr Ile Thr Thr Ile Leu Asp Thr Leu
    290                 295                 300

Gly Glu Asn Asp Phe Val Asn Ile Ile Ala Tyr Asn Asp Tyr Val His
305                 310                 315                 320

Tyr Ile Glu Pro Cys Phe Lys Gly Ile Leu Val Gln Ala Asp Arg Asp
                325                 330                 335

Asn Arg Glu His Phe Lys Leu Leu Val Glu Glu Leu Met Val Lys Gly
            340                 345                 350

Val Gly Val Val Asp Gln Ala Leu Arg Glu Ala Phe Gln Ile Leu Lys
        355                 360                 365

Gln Phe Gln Glu Ala Lys Gln Gly Ser Leu Cys Asn Gln Ala Ile Met
    370                 375                 380

Leu Ile Ser Asp Gly Ala Val Glu Asp Tyr Glu Pro Val Phe Glu Lys
385                 390                 395                 400

Tyr Asn Trp Pro Asp Cys Lys Val Arg Val Phe Thr Tyr Leu Ile Gly
                405                 410                 415

Arg Glu Val Ser Phe Ala Asp Arg Met Lys Trp Ile Ala Cys Asn Asn
            420                 425                 430

Lys Gly Tyr Tyr Thr Gln Ile Ser Thr Leu Ala Asp Thr Gln Glu Asn
        435                 440                 445

Val Met Glu Tyr Leu His Val Leu Ser Arg Pro Met Val Ile Asn His
    450                 455                 460

Asp His Asp Ile Ile Trp Thr Glu Ala Tyr Met Asp Ser Lys Leu Leu
465                 470                 475                 480

Ser Ser Gln Ala Gln Ser Leu Thr Leu Leu Thr Thr Val Ala Met Pro
                485                 490                 495

Val Phe Ser Lys Lys Asn Glu Thr Arg Ser His Gly Ile Leu Leu Gly
            500                 505                 510

Val Val Gly Ser Asp Val Ala Leu Arg Glu Leu Met Lys Leu Ala Pro
        515                 520                 525

Arg Tyr Lys Leu Gly Val His Gly Tyr Ala Phe Leu Asn Thr Asn Asn
    530                 535                 540

Gly Tyr Ile Leu Ser His Pro Asp Leu Arg Pro Leu Tyr Arg Glu Gly
545                 550                 555                 560

Lys Lys Leu Lys Pro Lys Pro Asn Tyr Asn Ser Val Asp Leu Ser Glu
                565                 570                 575

Val Glu Trp Glu Asp Gln Ala Glu Ser Leu Arg Thr Ala Met Ile Asn
            580                 585                 590

Arg Glu Thr Gly Thr Leu Ser Met Asp Val Lys Val Pro Met Asp Lys
        595                 600                 605

Gly Lys Arg Val Leu Phe Leu Thr Asn Asp Tyr Phe Phe Thr Asp Ile
    610                 615                 620

Ser Asp Thr Pro Phe Ser Leu Gly Val Val Leu Ser Arg Gly His Gly
625                 630                 635                 640

Glu Tyr Ile Leu Leu Gly Asn Thr Ser Val Glu Glu Gly Leu His Asp
                645                 650                 655
```

```
Leu Leu His Pro Asp Leu Ala Leu Ala Gly Asp Trp Ile Tyr Cys Ile
            660                 665                 670

Thr Asp Ile Asp Pro Asp His Arg Lys Leu Ser Gln Leu Glu Ala Met
            675                 680                 685

Ile Arg Phe Leu Thr Arg Lys Asp Pro Asp Leu Glu Cys Asp Glu Glu
            690                 695                 700

Leu Val Arg Glu Val Leu Phe Asp Ala Val Thr Ala Pro Met Glu
705                 710                 715                 720

Ala Tyr Trp Thr Ala Leu Ala Leu Asn Met Ser Glu Glu Ser Glu His
                725                 730                 735

Val Val Asp Met Ala Phe Leu Gly Thr Arg Ala Gly Leu Leu Arg Ser
                740                 745                 750

Ser Leu Phe Val Gly Ser Glu Lys Val Ser Asp Arg Lys Phe Leu Thr
                755                 760                 765

Pro Glu Asp Glu Ala Ser Val Phe Thr Leu Asp Arg Phe Pro Leu Trp
            770                 775                 780

Tyr Arg Gln Ala Ser Glu His Pro Ala Gly Ser Phe Val Phe Asn Leu
785                 790                 795                 800

Arg Trp Ala Glu Gly Pro Glu Ser Ala Gly Glu Pro Met Val Val Thr
                805                 810                 815

Ala Ser Thr Ala Val Ala Val Thr Val Asp Lys Arg Thr Ala Ile Ala
                820                 825                 830

Ala Ala Ala Gly Val Gln Met Lys Leu Glu Phe Leu Gln Arg Lys Phe
                835                 840                 845

Trp Ala Ala Thr Arg Gln Cys Ser Thr Val Asp Gly Pro Cys Thr Gln
            850                 855                 860

Ser Cys Glu Asp Ser Asp Leu Asp Cys Phe Val Ile Asp Asn Asn Gly
865                 870                 875                 880

Phe Ile Leu Ile Ser Lys Arg Ser Arg Glu Thr Gly Arg Phe Leu Gly
                885                 890                 895

Glu Val Asp Gly Ala Val Leu Thr Gln Leu Leu Ser Met Gly Val Phe
                900                 905                 910

Ser Gln Val Thr Met Tyr Asp Tyr Gln Ala Met Cys Lys Pro Ser Ser
                915                 920                 925

His His His Ser Ala Ala Gln Pro Leu Val Ser Pro Ile Ser Ala Phe
            930                 935                 940

Leu Thr Ala Thr Arg Trp Leu Leu Gln Glu Leu Val Leu Phe Leu Leu
945                 950                 955                 960

Glu Trp Ser Val Trp Gly Ser Trp Tyr Asp Arg Gly Ala Glu Ala Lys
                965                 970                 975

Ser Val Phe His His Ser His Lys His Lys Gln Asp Pro Leu Gln
            980                 985                 990

Pro Cys Asp Thr Glu Tyr Pro Val Phe Val Tyr Gln Pro Ala Ile Arg
            995                1000                1005

Glu Ala Asn Gly Ile Val Glu Cys Gly Pro Cys Gln Lys Val Phe Val
            1010                1015                1020

Val Gln Gln Ile Pro Asn Ser Asn Leu Leu Leu Val Thr Asp Pro
1025                1030                1035                1040

Thr Cys Asp Cys Ser Ile Phe Pro Pro Val Leu Gln Glu Ala Thr Glu
                1045                1050                1055

Val Lys Tyr Asn Ala Ser Val Lys Cys Asp Arg Met Arg
            1060                1065
```

-continued

```
<210> SEQ ID NO 55
<211> LENGTH: 1097
<212> TYPE: PRT
<213> ORGANISM: Homo sapiens

<400> SEQUENCE: 55
```

| | | | | | | | | | | | | | | | |
|---|---|---|---|---|---|---|---|---|---|---|---|---|---|---|---|
| Met | Pro | Ala | Thr | Pro | Asn | Phe | Leu | Ala | Asn | Pro | Ser | Ser | Ser | Arg | |
| 1 | | | | 5 | | | | | 10 | | | | | 15 | |
| Trp | Ile | Pro | Leu | Gln | Pro | Met | Pro | Val | Ala | Trp | Ala | Phe | Val | Gln | Lys |
| | | | 20 | | | | | 25 | | | | | 30 | | |
| Thr | Ser | Ala | Leu | Leu | Trp | Leu | Leu | Leu | Gly | Thr | Ser | Leu | Ser | Pro | |
| | | 35 | | | | | 40 | | | | | 45 | | | |
| Ala | Trp | Gly | Gln | Ala | Lys | Ile | Pro | Leu | Glu | Thr | Val | Lys | Leu | Trp | Ala |
| | 50 | | | | | 55 | | | | | 60 | | | | |
| Asp | Thr | Phe | Gly | Gly | Asp | Leu | Tyr | Asn | Thr | Val | Thr | Lys | Tyr | Ser | Gly |
| 65 | | | | | 70 | | | | | 75 | | | | | 80 |
| Ser | Leu | Leu | Leu | Gln | Lys | Lys | Tyr | Lys | Asp | Val | Glu | Ser | Ser | Leu | Lys |
| | | | | 85 | | | | | 90 | | | | | 95 | |
| Ile | Glu | Glu | Val | Asp | Gly | Leu | Glu | Leu | Val | Arg | Lys | Phe | Ser | Glu | Asp |
| | | | 100 | | | | | 105 | | | | | 110 | | |
| Met | Glu | Asn | Met | Leu | Arg | Arg | Lys | Val | Glu | Ala | Val | Gln | Asn | Leu | Val |
| | | 115 | | | | | 120 | | | | | 125 | | | |
| Glu | Ala | Ala | Glu | Glu | Ala | Asp | Leu | Asn | His | Glu | Phe | Asn | Glu | Ser | Leu |
| | 130 | | | | | 135 | | | | | 140 | | | | |
| Val | Phe | Asp | Tyr | Tyr | Asn | Ser | Val | Leu | Ile | Asn | Glu | Arg | Asp | Glu | Lys |
| 145 | | | | | 150 | | | | | 155 | | | | | 160 |
| Gly | Asn | Phe | Val | Glu | Leu | Gly | Ala | Glu | Phe | Leu | Leu | Glu | Ser | Asn | Ala |
| | | | | 165 | | | | | 170 | | | | | 175 | |
| His | Phe | Ser | Asn | Leu | Pro | Val | Asn | Thr | Ser | Ile | Ser | Ser | Val | Gln | Leu |
| | | | 180 | | | | | 185 | | | | | 190 | | |
| Pro | Thr | Asn | Val | Tyr | Asn | Lys | Asp | Pro | Asp | Ile | Leu | Asn | Gly | Val | Tyr |
| | | 195 | | | | | 200 | | | | | 205 | | | |
| Met | Ser | Glu | Ala | Leu | Asn | Ala | Val | Phe | Val | Glu | Asn | Phe | Gln | Arg | Asp |
| | 210 | | | | | 215 | | | | | 220 | | | | |
| Pro | Thr | Leu | Thr | Trp | Gln | Tyr | Phe | Gly | Ser | Ala | Thr | Gly | Phe | Phe | Arg |
| 225 | | | | | 230 | | | | | 235 | | | | | 240 |
| Ile | Tyr | Pro | Gly | Ile | Lys | Trp | Thr | Pro | Asp | Glu | Asn | Gly | Val | Ile | Thr |
| | | | | 245 | | | | | 250 | | | | | 255 | |
| Phe | Asp | Cys | Arg | Asn | Arg | Gly | Trp | Tyr | Ile | Gln | Ala | Ala | Thr | Ser | Pro |
| | | | 260 | | | | | 265 | | | | | 270 | | |
| Lys | Asp | Ile | Val | Ile | Leu | Val | Asp | Val | Ser | Gly | Ser | Met | Lys | Gly | Leu |
| | | 275 | | | | | 280 | | | | | 285 | | | |
| Arg | Met | Thr | Ile | Ala | Lys | His | Thr | Ile | Thr | Thr | Ile | Leu | Asp | Thr | Leu |
| | 290 | | | | | 295 | | | | | 300 | | | | |
| Gly | Glu | Asn | Asp | Phe | Val | Asn | Ile | Ile | Ala | Tyr | Asn | Asp | Tyr | Val | His |
| 305 | | | | | 310 | | | | | 315 | | | | | 320 |
| Tyr | Ile | Glu | Pro | Cys | Phe | Lys | Gly | Ile | Leu | Val | Gln | Ala | Asp | Arg | Asp |
| | | | | 325 | | | | | 330 | | | | | 335 | |
| Asn | Arg | Glu | His | Phe | Lys | Leu | Leu | Val | Glu | Glu | Leu | Met | Val | Lys | Gly |
| | | | 340 | | | | | 345 | | | | | 350 | | |
| Val | Gly | Val | Val | Asp | Gln | Ala | Leu | Arg | Glu | Ala | Phe | Gln | Ile | Leu | Lys |
| | | 355 | | | | | 360 | | | | | 365 | | | |
| Gln | Phe | Gln | Glu | Ala | Lys | Gln | Gly | Ser | Leu | Cys | Asn | Gln | Ala | Ile | Met |
| | 370 | | | | | 375 | | | | | 380 | | | | |

```
Leu Ile Ser Asp Gly Ala Val Glu Asp Tyr Glu Pro Val Phe Glu Lys
385                 390                 395                 400

Tyr Asn Trp Pro Asp Cys Lys Val Arg Val Phe Thr Tyr Leu Ile Gly
            405                 410                 415

Arg Glu Val Ser Phe Ala Asp Arg Met Lys Trp Ile Ala Cys Asn Asn
        420                 425                 430

Lys Gly Tyr Tyr Thr Gln Ile Ser Thr Leu Ala Asp Thr Gln Glu Asn
            435                 440                 445

Val Met Glu Tyr Leu His Val Leu Ser Arg Pro Met Val Ile Asn His
        450                 455                 460

Asp His Asp Ile Ile Trp Thr Glu Ala Tyr Met Asp Ser Lys Leu Leu
465                 470                 475                 480

Ser Ser Gln Ala Gln Ser Leu Thr Leu Leu Thr Thr Val Ala Met Pro
                485                 490                 495

Val Phe Ser Lys Lys Asn Glu Thr Arg Ser His Gly Ile Leu Leu Gly
            500                 505                 510

Val Val Gly Ser Asp Val Ala Leu Arg Glu Leu Met Lys Leu Ala Pro
        515                 520                 525

Arg Tyr Lys Leu Gly Val His Gly Tyr Ala Phe Leu Asn Thr Asn Asn
530                 535                 540

Gly Tyr Ile Leu Ser His Pro Asp Leu Arg Pro Leu Tyr Arg Glu Gly
545                 550                 555                 560

Lys Lys Leu Lys Pro Lys Pro Asn Tyr Asn Ser Val Asp Leu Ser Glu
            565                 570                 575

Val Glu Trp Glu Asp Gln Ala Glu Ser Leu Arg Thr Ala Met Ile Asn
        580                 585                 590

Arg Glu Thr Gly Thr Leu Ser Met Asp Val Lys Val Pro Met Asp Lys
            595                 600                 605

Gly Lys Arg Val Leu Phe Leu Thr Asn Asp Tyr Phe Phe Thr Asp Ile
        610                 615                 620

Ser Asp Thr Pro Phe Ser Leu Gly Val Val Leu Ser Arg Gly His Gly
625                 630                 635                 640

Glu Tyr Ile Leu Leu Gly Asn Thr Ser Val Glu Glu Gly Leu His Asp
                645                 650                 655

Leu Leu His Pro Asp Leu Ala Leu Ala Gly Asp Trp Ile Tyr Cys Ile
            660                 665                 670

Thr Asp Ile Asp Pro Asp His Arg Lys Leu Ser Gln Leu Glu Ala Met
        675                 680                 685

Ile Arg Phe Leu Thr Arg Lys Asp Pro Asp Leu Glu Cys Asp Glu Glu
690                 695                 700

Leu Val Arg Glu Val Leu Phe Asp Ala Val Val Thr Ala Pro Met Glu
705                 710                 715                 720

Ala Tyr Trp Thr Ala Leu Ala Leu Asn Met Ser Glu Glu Ser Glu His
            725                 730                 735

Val Val Asp Met Ala Phe Leu Gly Thr Arg Ala Ser Gly Leu Leu Arg
        740                 745                 750

Ser Ser Leu Phe Val Gly Ser Glu Lys Val Ser Asp Arg Lys Phe Leu
            755                 760                 765

Thr Pro Glu Asp Glu Ala Ser Val Phe Thr Leu Asp Arg Phe Pro Leu
        770                 775                 780

Trp Tyr Arg Gln Ala Ser Glu His Pro Ala Gly Ser Phe Val Phe Asn
785                 790                 795                 800

Leu Arg Trp Ala Glu Gly Pro Glu Ser Ala Gly Glu Pro Met Val Val
```

-continued

```
              805                 810                 815
Thr Ala Ser Thr Ala Val Ala Val Thr Val Asp Lys Arg Thr Ala Ile
            820                 825                 830
Ala Ala Ala Ala Gly Val Gln Met Lys Leu Glu Phe Leu Gln Arg Lys
            835                 840                 845
Phe Trp Ala Ala Thr Arg Gln Cys Ser Thr Val Asp Gly Pro Cys Thr
        850                 855                 860
Gln Ser Cys Glu Asp Ser Asp Leu Asp Cys Phe Val Ile Asp Asn Asn
865                 870                 875                 880
Gly Phe Ile Leu Ile Ser Lys Arg Ser Arg Glu Thr Gly Arg Phe Leu
                885                 890                 895
Gly Glu Val Asp Gly Ala Val Leu Thr Gln Leu Leu Ser Met Gly Val
            900                 905                 910
Phe Ser Gln Val Thr Met Tyr Asp Tyr Gln Ala Met Cys Lys Pro Ser
            915                 920                 925
Ser His His His Ser Ala Ala Gln Pro Leu Val Ser Pro Ile Ser Ala
    930                 935                 940
Phe Leu Thr Ala Thr Arg Trp Leu Leu Gln Glu Leu Val Leu Phe Leu
945                 950                 955                 960
Leu Glu Trp Ser Val Trp Gly Ser Trp Tyr Asp Arg Gly Ala Glu Ala
                965                 970                 975
Lys Ser Val Phe His Ser His Lys His Lys Lys Gln Asp Pro Leu
                980                 985                 990
Gln Pro Cys Asp Thr Glu Tyr Pro Val Phe Val Tyr Gln Pro Ala Ile
        995                 1000                1005
Arg Glu Ala Asn Gly Ile Val Glu Cys Gly Pro Cys Gln Lys Val Phe
    1010                1015                1020
Val Val Gln Gln Ile Pro Asn Ser Asn Leu Leu Leu Leu Val Thr Asp
1025                1030                1035                1040
Pro Thr Cys Asp Cys Ser Ile Phe Pro Pro Val Leu Gln Glu Ala Thr
                1045                1050                1055
Glu Val Lys Tyr Asn Ala Ser Val Lys Cys Asp Arg Met Arg Ser Gln
            1060                1065                1070
Lys Leu Arg Arg Arg Pro Asp Ser Cys His Ala Phe His Pro Glu Glu
        1075                1080                1085
Asn Ala Gln Asp Cys Gly Gly Ala Ser
1090                1095
```